United States Patent
Mueller et al.

(10) Patent No.: US 9,102,722 B2
(45) Date of Patent: *Aug. 11, 2015

(54) COMPOSITION AND METHOD FOR THE DIAGNOSIS AND TREATMENT OF DISEASES ASSOCIATED WITH NEURITE DEGENERATION

(71) Applicants: AbbVie Deutschland GmbH & Co. KG, Wiesbaden (DE); AbbVie Inc., North Chicago, IL (US)

(72) Inventors: Bernhard Mueller, Neustadt-gimmeldingen (DE); Lili Huang, Westford, MA (US); Philip D. Bardwell, Boston, MA (US); Yuliya Kutskova, Northborough, MA (US); John Memmott, Framingham, MA (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/033,707

(22) Filed: Sep. 23, 2013

(65) Prior Publication Data

US 2014/0023659 A1 Jan. 23, 2014

Related U.S. Application Data

(63) Continuation of application No. 13/750,846, filed on Jan. 25, 2013.

(60) Provisional application No. 61/591,324, filed on Jan. 27, 2012.

(51) Int. Cl.
| | |
|---|---|
| *C07K 16/22* | (2006.01) |
| *C07K 16/18* | (2006.01) |
| *A61K 39/395* | (2006.01) |
| *C07K 16/28* | (2006.01) |
| *A61K 39/00* | (2006.01) |

(52) U.S. Cl.
CPC .............. *C07K 16/22* (2013.01); *C07K 16/18* (2013.01); *C07K 16/28* (2013.01); *A61K 2039/505* (2013.01); *C07K 2317/21* (2013.01); *C07K 2317/24* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,394,448 A | 7/1983 | Szoka, Jr. et al. |
| 4,399,216 A | 8/1983 | Axel et al. |
| 4,510,245 A | 4/1985 | Cousens et al. |
| 4,526,938 A | 7/1985 | Churchill et al. |
| 4,554,101 A | 11/1985 | Hopp |
| 4,634,665 A | 1/1987 | Axel et al. |
| 4,704,692 A | 11/1987 | Ladner |
| 4,816,397 A | 3/1989 | Boss et al. |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,241,070 A | 8/1993 | Law |
| 5,258,498 A | 11/1993 | Huston et al. |
| 5,290,540 A | 3/1994 | Prince et al. |
| 5,294,404 A | 3/1994 | Grandone et al. |
| 5,304,489 A | 4/1994 | Rosen |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,480,792 A | 1/1996 | Buechler et al. |
| 5,496,925 A | 3/1996 | Mattingly |
| 5,516,637 A | 5/1996 | Huang et al. |
| 5,525,490 A | 6/1996 | Erickson et al. |
| 5,525,524 A | 6/1996 | Buechler et al. |
| 5,530,101 A | 6/1996 | Queen et al. |

(Continued)

FOREIGN PATENT DOCUMENTS

| | | |
|---|---|---|
| DE | 102008014880 A1 | 9/2009 |
| EA | 008253 B1 | 4/2007 |

(Continued)

OTHER PUBLICATIONS

MacCallum et al., "Antibody-antigen Interaction: Contact Analysis and Binding Site topography", J. Mol. biol. 262:732-745, 1996.*
De Pascalis et al., "Grafting of "abbreviated" complementarity-determining regions containing specificity-determining residues essential for ligand contact to engineer a less immunogenic humanized monoclonal antibody.", J. Immunol., 169:3076-3084, 2002.*
Hermanson G.T., "Antibody Modification and Conjugation," in: Bioconjugate Techniques, 1996, Chapter 10, Academic Press, pp. 456-493.
Singer M., et al. Genes and Genomes, A Changing Perspective, University science Books, California, 1991, pp. 68-69.

(Continued)

*Primary Examiner* — Ronald Schwadron
(74) *Attorney, Agent, or Firm* — Lisa V. Mueller; Michael Best & Friedrich LLP

(57) ABSTRACT

Provided herein are antibodies that bind to Repulsive Guidance Molecule a (RGMa) and methods of using the antibodies to treat and diagnose neurite degenerative diseases and disorders.

5 Claims, 24 Drawing Sheets

(56) References Cited

U.S. PATENT DOCUMENTS

| | | |
|---|---|---|
| 5,541,109 A | 7/1996 | Searfoss, III et al. |
| 5,543,524 A | 8/1996 | Mattingly et al. |
| 5,545,806 A | 8/1996 | Lonberg et al. |
| 5,565,332 A | 10/1996 | Hoogenboom et al. |
| 5,565,352 A | 10/1996 | Hochstrasser et al. |
| 5,565,362 A | 10/1996 | Rosen |
| 5,569,825 A | 10/1996 | Lonberg et al. |
| 5,571,698 A | 11/1996 | Ladner et al. |
| 5,573,904 A | 11/1996 | Mattingly |
| 5,580,717 A | 12/1996 | Dower et al. |
| 5,580,859 A | 12/1996 | Felgner et al. |
| 5,585,089 A | 12/1996 | Queen et al. |
| 5,593,896 A | 1/1997 | Adamczyk et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,679,377 A | 10/1997 | Bernstein et al. |
| 5,679,526 A | 10/1997 | Buechler et al. |
| 5,693,762 A | 12/1997 | Queen et al. |
| 5,698,426 A | 12/1997 | Huse |
| 5,714,350 A | 2/1998 | Co et al. |
| 5,714,352 A | 2/1998 | Jakobovits |
| 5,723,323 A | 3/1998 | Kauffman et al. |
| 5,733,743 A | 3/1998 | Johnson et al. |
| 5,747,262 A | 5/1998 | Hinck et al. |
| 5,750,753 A | 5/1998 | Kimae et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,780,225 A | 7/1998 | Wigler et al. |
| 5,783,699 A | 7/1998 | Mattingly et al. |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,824,799 A | 10/1998 | Buechler et al. |
| 5,827,690 A | 10/1998 | Meade et al. |
| 5,833,985 A | 11/1998 | Ball et al. |
| 5,837,243 A | 11/1998 | Deo et al. |
| 5,837,500 A | 11/1998 | Ladner et al. |
| 5,849,992 A | 12/1998 | Meade et al. |
| 5,851,776 A | 12/1998 | Valkirs |
| 5,855,913 A | 1/1999 | Hanes et al. |
| 5,874,064 A | 2/1999 | Edwards et al. |
| 5,877,397 A | 3/1999 | Lonberg et al. |
| 5,885,527 A | 3/1999 | Buechler |
| 5,885,793 A | 3/1999 | Griffiths et al. |
| 5,912,015 A | 6/1999 | Bernstein et al. |
| 5,916,597 A | 6/1999 | Lee et al. |
| 5,916,771 A | 6/1999 | Hori et al. |
| 5,922,615 A | 7/1999 | Nowakowski et al. |
| 5,922,845 A | 7/1999 | Deo et al. |
| 5,934,272 A | 8/1999 | Lloyd et al. |
| 5,939,272 A | 8/1999 | Buechler et al. |
| 5,939,598 A | 8/1999 | Kucherlapati et al. |
| 5,947,124 A | 9/1999 | Buechler et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,579 A | 11/1999 | Buechler et al. |
| 5,985,615 A | 11/1999 | Jakobovits et al. |
| 5,989,463 A | 11/1999 | Tracy et al. |
| 5,994,616 A | 11/1999 | Rosen |
| 5,994,619 A | 11/1999 | Stice et al. |
| 5,998,209 A | 12/1999 | Jokobovits et al. |
| 6,004,746 A | 12/1999 | Brent et al. |
| 6,017,517 A | 1/2000 | Park |
| 6,019,944 A | 2/2000 | Buechler |
| 6,019,968 A | 2/2000 | Platz et al. |
| 6,075,181 A | 6/2000 | Kucherlapati et al. |
| 6,087,326 A | 7/2000 | Hinck et al. |
| 6,091,001 A | 7/2000 | Jakobovits et al. |
| 6,096,311 A | 8/2000 | Fanger et al. |
| 6,111,166 A | 8/2000 | Van De Winkel |
| 6,113,855 A | 9/2000 | Buechler |
| 6,114,598 A | 9/2000 | Kucherlapati et al. |
| 6,130,364 A | 10/2000 | Jakobovits et al. |
| 6,143,576 A | 11/2000 | Buechler |
| 6,180,370 B1 | 1/2001 | Queen et al. |
| 6,204,023 B1 | 3/2001 | Robinson et al. |
| 6,270,765 B1 | 8/2001 | Deo et al. |
| 6,303,755 B1 | 10/2001 | Deo et al. |
| 6,350,861 B1 | 2/2002 | Co et al. |
| 6,365,116 B1 | 4/2002 | Barham et al. |
| 6,410,690 B1 | 6/2002 | Deo et al. |
| 6,632,926 B1 | 10/2003 | Chen et al. |
| 6,660,843 B1 | 12/2003 | Feige et al. |
| 6,682,928 B2 | 1/2004 | Keler et al. |
| 6,699,658 B1 | 3/2004 | Wittrup et al. |
| 6,864,239 B2 | 3/2005 | Peri et al. |
| 6,890,763 B2 | 5/2005 | Jackowski et al. |
| 6,914,128 B1 | 7/2005 | Salfeld et al. |
| 6,925,389 B2 | 8/2005 | Hitt et al. |
| 6,984,720 B1 | 1/2006 | Korman et al. |
| 6,989,100 B2 | 1/2006 | Norton |
| 7,094,761 B2 | 8/2006 | Peri et al. |
| 7,265,212 B2 | 9/2007 | Babcook et al. |
| 7,288,253 B2 | 10/2007 | Roskos et al. |
| 7,368,531 B2 | 5/2008 | Rosen et al. |
| 7,439,063 B2 | 10/2008 | Digicaylioglu et al. |
| 7,498,034 B2 | 3/2009 | Bicknell et al. |
| 7,504,225 B2 | 3/2009 | Ring et al. |
| 7,524,492 B2 | 4/2009 | Sharma |
| 7,582,440 B2 | 9/2009 | Bicknell et al. |
| 7,612,181 B2 | 11/2009 | Wu et al. |
| 7,612,183 B2 | 11/2009 | Ellis et al. |
| 7,659,370 B2 | 2/2010 | Woolf et al. |
| 7,696,155 B2 | 4/2010 | Woolf et al. |
| 7,696,156 B2 | 4/2010 | Woolf et al. |
| 7,771,952 B2 | 8/2010 | Strittmatter et al. |
| 7,951,369 B2 | 5/2011 | Goldenberg et al. |
| 7,968,091 B2 | 6/2011 | Woolf et al. |
| 7,968,520 B2 | 6/2011 | Woolf et al. |
| 7,981,415 B2 | 7/2011 | Staunton et al. |
| 7,981,416 B2 | 7/2011 | Hardy et al. |
| 7,981,420 B2 | 7/2011 | Mueller et al. |
| 7,999,072 B2 | 8/2011 | Plouet et al. |
| 8,017,115 B2 | 9/2011 | Irving et al. |
| 2002/0110804 A1 | 8/2002 | Stanton et al. |
| 2002/0136725 A1 | 9/2002 | Blackburn et al. |
| 2002/0137134 A1 | 9/2002 | Gerngross |
| 2003/0009152 A1 | 1/2003 | O'hara et al. |
| 2003/0087394 A1 | 5/2003 | Sharma |
| 2003/0170881 A1 | 9/2003 | Davis et al. |
| 2003/0186374 A1 | 10/2003 | Hufton et al. |
| 2003/0212001 A1 | 11/2003 | Peri et al. |
| 2003/0235584 A1 | 12/2003 | Kloetzer et al. |
| 2004/0009491 A1 | 1/2004 | Birse et al. |
| 2004/0018577 A1 | 1/2004 | Emerson et al. |
| 2004/0018590 A1 | 1/2004 | Gerngross et al. |
| 2004/0038292 A1 | 2/2004 | Burslem et al. |
| 2004/0071711 A1 | 4/2004 | Bicknell et al. |
| 2004/0092444 A1 | 5/2004 | Digicaylioglu et al. |
| 2004/0102376 A1 | 5/2004 | Mueller et al. |
| 2005/0013809 A1 | 1/2005 | Owens et al. |
| 2005/0042664 A1 | 2/2005 | Wu et al. |
| 2005/0054078 A1 | 3/2005 | Miller et al. |
| 2005/0058649 A1 | 3/2005 | Landes et al. |
| 2005/0059604 A1 | 3/2005 | Peri et al. |
| 2005/0142137 A1 | 6/2005 | Gallo et al. |
| 2005/0197284 A9 | 9/2005 | Digicaylioglu et al. |
| 2006/0003391 A1 | 1/2006 | Ring et al. |
| 2006/0063208 A1 | 3/2006 | Woolf et al. |
| 2006/0104968 A1 | 5/2006 | Bookbinder et al. |
| 2006/0160164 A1 | 7/2006 | Miller et al. |
| 2006/0252101 A1 | 11/2006 | Strittmatter et al. |
| 2006/0292613 A1 | 12/2006 | Peri et al. |

(56) References Cited

U.S. PATENT DOCUMENTS

| | | |
|---|---|---|
| 2007/0025913 A1 | 2/2007 | Bicknell et al. |
| 2007/0071675 A1 | 3/2007 | Wu et al. |
| 2007/0122491 A1 | 5/2007 | Lyons et al. |
| 2007/0155687 A1 | 7/2007 | Lyons et al. |
| 2007/0166711 A1 | 7/2007 | Samuels et al. |
| 2007/0253946 A1 | 11/2007 | Yamashita et al. |
| 2008/0004255 A1 | 1/2008 | Lyons et al. |
| 2008/0008692 A1 | 1/2008 | Lyons et al. |
| 2008/0020401 A1 | 1/2008 | Grenier et al. |
| 2008/0081337 A1 | 4/2008 | Sharma |
| 2008/0105705 A1 | 5/2008 | Schmidt |
| 2008/0135582 A1 | 6/2008 | Schmidt |
| 2008/0145359 A1 | 6/2008 | Bicknell et al. |
| 2008/0160034 A1 | 7/2008 | Brennan et al. |
| 2008/0181897 A1 | 7/2008 | Ni et al. |
| 2008/0213791 A1 | 9/2008 | Freije et al. |
| 2008/0219924 A1 | 9/2008 | Bicknell et al. |
| 2008/0248493 A1 | 10/2008 | Mattingly et al. |
| 2008/0274045 A9 | 11/2008 | Bicknell et al. |
| 2008/0279859 A1 | 11/2008 | Mezler et al. |
| 2009/0012628 A1 | 1/2009 | Shortkroff et al. |
| 2009/0017039 A1 | 1/2009 | Mi et al. |
| 2009/0028852 A1 | 1/2009 | Herrera et al. |
| 2009/0054984 A1 | 2/2009 | Shortkroff et al. |
| 2009/0069903 A1 | 3/2009 | Shortkroff et al. |
| 2009/0093409 A1 | 4/2009 | Digicaylioglu et al. |
| 2009/0123413 A1 | 5/2009 | Hardy et al. |
| 2009/0191118 A1 | 7/2009 | Young et al. |
| 2009/0191572 A1 | 7/2009 | Bicknell et al. |
| 2009/0220588 A1 | 9/2009 | Edelman et al. |
| 2009/0220589 A1 | 9/2009 | Trieu et al. |
| 2009/0227502 A1 | 9/2009 | Goldberg et al. |
| 2009/0252742 A1 | 10/2009 | Bergstein |
| 2009/0252748 A1 | 10/2009 | Mi et al. |
| 2009/0269356 A1 | 10/2009 | Epstein et al. |
| 2009/0280116 A1 | 11/2009 | Smith et al. |
| 2009/0297527 A1 | 12/2009 | Muller et al. |
| 2009/0304693 A1 | 12/2009 | Ghayur et al. |
| 2009/0311253 A1 | 12/2009 | Ghayur et al. |
| 2010/0004431 A1 | 1/2010 | Bernett et al. |
| 2010/0015665 A1 | 1/2010 | Latham et al. |
| 2010/0028340 A1 | 2/2010 | Mueller et al. |
| 2010/0036091 A1 | 2/2010 | Robinson et al. |
| 2010/0036502 A1 | 2/2010 | Svrluga et al. |
| 2010/0041139 A1 | 2/2010 | Goldberg |
| 2010/0047239 A1 | 2/2010 | Wu et al. |
| 2010/0068803 A1 | 3/2010 | Goldberg |
| 2010/0099103 A1 | 4/2010 | Hsieh et al. |
| 2010/0105569 A1 | 4/2010 | Hsieh et al. |
| 2010/0111967 A1 | 5/2010 | Baehner et al. |
| 2010/0150918 A1 | 6/2010 | Kufer et al. |
| 2010/0168393 A1 | 7/2010 | Clube et al. |
| 2010/0183588 A1 | 7/2010 | Plouet et al. |
| 2010/0183608 A1 | 7/2010 | Woolf et al. |
| 2010/0183631 A1 | 7/2010 | Rothe et al. |
| 2010/0184033 A1 | 7/2010 | West et al. |
| 2010/0249039 A1 | 9/2010 | Zangemeister-Wittke et al. |
| 2010/0254979 A1 | 10/2010 | Staunton et al. |
| 2010/0286048 A1 | 11/2010 | Rosen et al. |
| 2010/0297121 A1 | 11/2010 | Mi |
| 2010/0310573 A1 | 12/2010 | Nakagawa et al. |
| 2010/0322948 A1 | 12/2010 | Mueller et al. |
| 2010/0330076 A1* | 12/2010 | Georgiou et al. .......... 424/131.1 |
| 2011/0003971 A1 | 1/2011 | Strittmatter et al. |
| 2011/0020221 A1 | 1/2011 | Berman et al. |
| 2011/0070156 A1 | 3/2011 | Govindan et al. |
| 2011/0110852 A1 | 5/2011 | Miller et al. |
| 2011/0110936 A1 | 5/2011 | Nam et al. |
| 2011/0112280 A1 | 5/2011 | Mueller et al. |
| 2011/0117085 A1 | 5/2011 | Rotem-Yehudar et al. |
| 2011/0135657 A1 | 6/2011 | Hu et al. |
| 2011/0135664 A1 | 6/2011 | Mueller |
| 2011/0171126 A1 | 7/2011 | Burton et al. |
| 2011/0183924 A1 | 7/2011 | Mintz et al. |
| 2011/0195021 A1 | 8/2011 | Deckert et al. |
| 2011/0206671 A1 | 8/2011 | Yamashita et al. |
| 2011/0212107 A1 | 9/2011 | Goldberg et al. |
| 2011/0243841 A1 | 10/2011 | Chang et al. |
| 2011/0263827 A1 | 10/2011 | Ghayur et al. |
| 2011/0293526 A1 | 12/2011 | Plikus et al. |

FOREIGN PATENT DOCUMENTS

| | | |
|---|---|---|
| EP | 239400 A2 | 9/1987 |
| EP | 321201 A2 | 6/1989 |
| EP | 360257 A2 | 3/1990 |
| EP | 0368684 A1 | 5/1990 |
| EP | 404097 A2 | 12/1990 |
| EP | 0471293 A2 | 2/1992 |
| EP | 0519596 A1 | 12/1992 |
| EP | 229246 B1 | 8/1993 |
| EP | 368684 B1 | 3/1994 |
| EP | 592106 A1 | 4/1994 |
| EP | 239400 B1 | 8/1994 |
| EP | 291533 B1 | 10/1995 |
| EP | 0963376 A1 | 12/1999 |
| EP | 1176195 A1 | 1/2002 |
| EP | 1347046 A1 | 9/2003 |
| EP | 1396543 A2 | 3/2004 |
| EP | 1440981 A2 | 7/2004 |
| EP | 592106 B1 | 11/2004 |
| EP | 519596 B1 | 2/2005 |
| EP | 1677113 A1 | 7/2006 |
| EP | 1733737 A1 | 12/2006 |
| EP | 2033971 A1 | 3/2009 |
| EP | 2260055 A1 | 12/2010 |
| GB | 2456390 A | 7/2009 |
| JP | 2010065045 A | 3/2010 |
| KR | 20080058021 A | 6/2008 |
| RU | 2212241 C2 | 9/2003 |
| RU | 2362780 C2 | 7/2009 |
| WO | 9002809 A1 | 3/1990 |
| WO | 9005144 A1 | 5/1990 |
| WO | 9005370 A1 | 5/1990 |
| WO | 9014424 A1 | 11/1990 |
| WO | 9014430 A1 | 11/1990 |
| WO | 9014443 A1 | 11/1990 |
| WO | 9105548 A1 | 5/1991 |
| WO | 9105939 A1 | 5/1991 |
| WO | 9109630 A1 | 7/1991 |
| WO | 9109967 A1 | 7/1991 |
| WO | 9110737 A1 | 7/1991 |
| WO | 9110741 A1 | 7/1991 |
| WO | 9117271 A1 | 11/1991 |
| WO | 9201047 A1 | 1/1992 |
| WO | 9202551 A1 | 2/1992 |
| WO | 9209690 A2 | 6/1992 |
| WO | 9215679 A1 | 9/1992 |
| WO | 9218619 A1 | 10/1992 |
| WO | 9219244 A2 | 11/1992 |
| WO | 9220791 A1 | 11/1992 |
| WO | 9222324 A1 | 12/1992 |
| WO | 9301288 A1 | 1/1993 |
| WO | 9306213 A1 | 4/1993 |
| WO | 9311236 A1 | 6/1993 |
| WO | 9401234 A2 | 1/1994 |
| WO | 9402602 A1 | 2/1994 |
| WO | 9429469 A2 | 12/1994 |
| WO | 9515982 A2 | 6/1995 |
| WO | 9520401 A1 | 8/1995 |
| WO | WO-96013518 A1 | 5/1996 |
| WO | 9618978 A1 | 6/1996 |
| WO | 9620698 A2 | 7/1996 |
| WO | 9633735 A1 | 10/1996 |
| WO | 9634096 A1 | 10/1996 |
| WO | 9700957 A1 | 1/1997 |
| WO | 9708320 A1 | 3/1997 |
| WO | 97029131 A1 | 8/1997 |
| WO | 9732572 A2 | 9/1997 |
| WO | 9744013 A1 | 11/1997 |
| WO | 97044013 A1 | 11/1997 |
| WO | 9816280 A1 | 4/1998 |
| WO | 9816654 A1 | 4/1998 |
| WO | 9824893 A2 | 6/1998 |

(56) References Cited

FOREIGN PATENT DOCUMENTS

| | | |
|---|---|---|
| WO | 9825947 A1 | 6/1998 |
| WO | 9831346 A1 | 7/1998 |
| WO | 9831700 A1 | 7/1998 |
| WO | 9847343 A2 | 10/1998 |
| WO | 9849286 A2 | 11/1998 |
| WO | 9850433 A2 | 11/1998 |
| WO | 9901047 A1 | 1/1999 |
| WO | 9911274 A1 | 3/1999 |
| WO | 9915154 A1 | 4/1999 |
| WO | 9920253 A1 | 4/1999 |
| WO | 9925044 A1 | 5/1999 |
| WO | 9936569 A1 | 7/1999 |
| WO | 9945031 A2 | 9/1999 |
| WO | 9945962 A1 | 9/1999 |
| WO | 9951741 A2 | 10/1999 |
| WO | 9953049 A1 | 10/1999 |
| WO | 9954342 A1 | 10/1999 |
| WO | 9966903 A2 | 12/1999 |
| WO | 0002911 A2 | 1/2000 |
| WO | 0005410 A2 | 2/2000 |
| WO | 0009560 A2 | 2/2000 |
| WO | 0014271 A1 | 3/2000 |
| WO | 0017221 A1 | 3/2000 |
| WO | 0037504 A2 | 6/2000 |
| WO | 0056772 A1 | 9/2000 |
| WO | 0073801 A2 | 12/2000 |
| WO | 0154708 A1 | 8/2001 |
| WO | 0158956 A2 | 8/2001 |
| WO | 0183525 A2 | 11/2001 |
| WO | 0190304 A2 | 11/2001 |
| WO | 0202773 A2 | 1/2002 |
| WO | 02051438 A2 | 7/2002 |
| WO | 02072636 A2 | 9/2002 |
| WO | 03004615 A2 | 1/2003 |
| WO | 03016466 A2 | 2/2003 |
| WO | 03031462 A2 | 4/2003 |
| WO | 03035835 A2 | 5/2003 |
| WO | 03089608 A2 | 10/2003 |
| WO | 2004003150 A2 | 1/2004 |
| WO | 2004005457 A2 | 1/2004 |
| WO | 2004067561 A1 | 8/2004 |
| WO | 2004078140 A2 | 9/2004 |
| WO | 2004092405 A2 | 10/2004 |
| WO | 2005016955 A2 | 2/2005 |
| WO | 2005061554 A1 | 7/2005 |
| WO | 2005087268 A1 | 9/2005 |
| WO | 2005100584 A2 | 10/2005 |
| WO | 2006054000 A2 | 5/2006 |
| WO | 2006066171 A1 | 6/2006 |
| WO | 2006088972 A2 | 8/2006 |
| WO | 2006094724 A2 | 9/2006 |
| WO | 2006127861 A2 | 11/2006 |
| WO | 2007024715 A2 | 3/2007 |
| WO | 2007024715 A9 | 3/2007 |
| WO | 2007039256 A2 | 4/2007 |
| WO | 2007058671 A1 | 5/2007 |
| WO | 2007062852 A2 | 6/2007 |
| WO | 2007106507 A2 | 9/2007 |
| WO | 2007141258 A2 | 12/2007 |
| WO | 2008013492 A1 | 1/2008 |
| WO | 2008038599 A1 | 4/2008 |
| WO | 2008073919 A2 | 6/2008 |
| WO | 2008073923 A2 | 6/2008 |
| WO | 2008082651 A2 | 7/2008 |
| WO | 2008085797 A2 | 7/2008 |
| WO | 2008087224 A2 | 7/2008 |
| WO | 2009002386 A2 | 12/2008 |
| WO | 2009006543 A1 | 1/2009 |
| WO | 2009026392 A1 | 2/2009 |
| WO | 2009030500 A1 | 3/2009 |
| WO | 2009092032 A1 | 7/2009 |
| WO | 2009094592 A2 | 7/2009 |
| WO | 2009106356 A1 | 9/2009 |
| WO | 2009140383 A2 | 11/2009 |
| WO | 2009149185 A2 | 12/2009 |
| WO | 2010006060 A2 | 1/2010 |
| WO | 2010007144 A2 | 1/2010 |
| WO | WO-2010006184 A2 | 1/2010 |
| WO | WO-2010006189 A2 | 1/2010 |
| WO | 2010017451 A2 | 2/2010 |
| WO | WO-2010021696 A1 | 2/2010 |
| WO | 2010044506 A2 | 4/2010 |
| WO | WO-2010062914 A1 | 6/2010 |
| WO | 2010088688 A2 | 8/2010 |
| WO | 2010105298 A1 | 9/2010 |
| WO | 2010127284 A2 | 11/2010 |
| WO | 2011039289 A1 | 4/2011 |
| WO | 2011039734 A2 | 4/2011 |
| WO | 2011068839 A1 | 6/2011 |
| WO | 2011070045 A1 | 6/2011 |
| WO | 2011071059 A1 | 6/2011 |

OTHER PUBLICATIONS

Adamczyk M., et al., "Chemiluminescent N-Sulfonylacridinium-9-Carboxamides and Their Application in Clinical Assays," Luminescence Biotechnology: Instruments and Applications, CRC Press LLC, Florida, Chapter 5, 2002, pp. 77-105.

Alberts et al., Molecular Biology of the Cell, Chapter 23: The Immune System, Garland Science, New York, Third Edition, 1994, pp. 1216-1221.

Ausubel F.M., et al., in: Current Protocols in Molecular Biology, Greene Publishing Associates and Wiley-Interscience, New York, 1987, Table of Contents.

Capelli L.P., et al., "Deletion of the RMGA and CHD2 Genes in a Child with Epilepsy and Mental Deficiency," European Journal of Medical Genetics, 2012, pp. 1-3, article in press.

Casset, F., et al., "A Peptide Mimetic of an Anti-CD4 Monoclonal Antibody by Rational Design," Biochemical and Biophysical Research Communications, 2003, vol. 307 (1), pp. 198-205.

GenomeQuest—Sequence Search Report 'result Feb. 15 11:32 am (redo 1), NP_001159755.1, dated Feb. 15, 2010.

Graham D.I., et al., Trauma, Chapter 5 in Greenfield's Neuropathology, Oxford University Press, 1996, pp. 197-262.

Halbrooks P.J., et al., "Role of RGM Coreceptors in Bone Morphogenetic Protein Signaling," Journal of Molecular Signaling, 2007, vol. 2:4, 10 pages, open access.

Harlow E., et al., Antibodies: A Laboratory Manual, Cold Spring Harbor Laboratory Press, New York, 1988, pp. 555-561, 578-582 and 591-592.

Mattingly P.G., et al., In Instruments and Applications Luminescence: Instruments and Applications, Dyke K.V., Ed., CRC Press, Florida, 2002, pp. 77-105.

Pauwels R., "Pharmacokinetics of Inhaled Drugs" in: Aerosols in Medicine: Principles, Diagnosis and Therapy, Moren F., et al., eds., Elsevier, Chapter 8, 1985, p. 219-224.

Puchtler H., et al., "Some commnets on the Ninhydrin-Schiff reaction," Journal of Histochemistry & Cytochemistry, 1962, vol. 10, pp. 365.

Yamashita T., RGMa Modulates T Cell Responses and is Involved in Autoimmune Encephalomyelitis, Supplementary Text & figures Information Titles, Nature Medicine (2011) 19 pages.

Abstracts of the XIIth International Symposium on Bioluminescence and Chemiluminescence to be Held at Robinson College, University of cambridge, England, Apr. 5-9, 2002, Luminescence, 2002, vol. 17, pp. 77-115.

Adamczyk M., et al., "Chemiluminescence Quenching of Pteroic Aacid-N-sulfonyl-acridinium-9-carboxamide Conjugates by Folate Binding Protein," Bioorganic and Medicinal Chemistry Letters, 2004, vol. 14 (9), pp. 2313-2317.

Adamczyk M., et al., "Chemiluminescent Acridinium-9-Carboxamide Boronic Acid Probes: Application to a Homogeneous Glycated Hemoglobin Assay," Bioorganic & Medicinal Chemistry Letters, 2006, vol. 16 (5), pp. 1324-1328.

Adamczyk M., et al., "Homogeneous Chemiluminescent Assays for Free Choline in Human Plasma and Whole Blood," Analytica Chimica Acta, 2006, vol. 579 (1), pp. 61-67.

(56) References Cited

OTHER PUBLICATIONS

Adamczyk M., et al., "Intrinsic Factor-Mediated Modulation of Cyanocobalamin-N-sulfonylacridinium-9-carboxamide Chemiluminescence," Bioorganic and Medicinal Chemistry Letters, 2004, vol. 14 (15), pp. 3917-3921.
Adamczyk M., et al., "Linker-Medicated Modulation of the Cheiluminescent Signal from N10-(3-Sulfopropyl)-N-Sulfonylacridinium-9-carboxamide Tracers ," Bioconjugate Chemistry, 2000, vol. 11 (5), pp. 714-724.
Adamczyk M., et al., "Modulation of the Chemiluminescent Signal from N10-(3-Sulfopropyl)-N- Sulfonylacridinium-9-carboxamides ," Tetrahedron, 1999, vol. 55, pp. 10899-10914.
Adamczyk M., et al., "Neopentyl 3-Triflyloxypropanesulfaonate Areactive Sulfopropylation Reagent for the Preparation of Chemiluminescent Labels ," Journal of Organic Chemistry, 1998, vol. 63, pp. 5636-5639.
Adamczyk M., et al., "Regiodependent Luminescence Quenching of Biotinylated N-Sulfonyl-acridinium-9-carboxamides by Avidin ," Organic Letters, 2003, vol. 5 (21), pp. 3779-3782.
Adamczyk M., et al., "Synthesis of a Chemiluminescent Acridinium Hydroxylamine (AHA) for the Direct Detection of Abasic Sites in DNA," Organic Letters , 1999, vol. 1 (5), pp. 779-781.
Albert S.E., et al., "Time-Dependent Induction of Protective Anti-Influenza Immune Responses in Human Peripheral Blood Lymphocyte/SCID Mice," Journal of Immunology, 1997, vol. 159 (3), pp. 1393-1403.
Amann E., et al., "Tightly Regulated Tac Promoter Vectors Useful for the Expression of Unfused and Fused Proteins in *Escherichia coli*," Gene, 1988, vol. 69 (2), pp. 301-315.
Ames R.S., et al., "Conversion of Murine Fabs Isolated from a Combinatorial Phage Display Library to Full Length Immunoglobulins," Journal of Immunological Methods , 1995, vol. 184 (2), pp. 177-186.
Anderson W.F., "Human Gene Therapy," Science, 1992, vol. 256 (5058), pp. 808-813.
Ara J., et al., "Bone Morphogenetic Proteins 4, 6, and 7 are Up-Regulated in Mouse Spinal Cord during Experimental Autoimmune Encephalomyelitis," Journal of Neuroscience Research, 2008, vol. 86 (1), pp. 125-135.
Arai K., et al., "An ELISA to Determine the Biodistribution of Human Monoclonal Antibody in Tumor-Xenografted SCID Mice," Journal of Immunological Methods , 1998, vol. 217 (1-2), pp. 79-85.
Azzazy H.M., et al., "Phage Display Technology: Clinical Applications and Recent Innovations," Clinical Biochemistry, 2002, vol. 35 (6), pp. 425-445.
Babcook J.S., et al., "A Novel Strategy for Generating Monoclonal Antibodies from Single, Isolated Lymphocytes Producing Antibodies of Defined Specificities," Proceedings of the National Academy of Sciences, 1996, vol. 93 (15), pp. 7843-7848.
Babitt J.L., et al. "Bone Morphogenetic Protein Signaling by Hemojuvelin Regulates Hepcidin Expression, XP002476347," Nature Genetics, 2006, vol. 38 (5), pp. 531-539.
Babitt J.L., et al., "Modulation of Bone Morphogenetic Protein Signaling in Vivo Regulates Systemic Iron Balance," The Journal of Clinical Investigation, 2007, vol. 117 (7), pp. 1933-1939.
Babitt J.L., et al. "Repulsive Guidancemolecule (RGMa), a Dragon Homologue, is Abone Morphogenetic Protein Co-receptor," Journal of Biological Chemistry, 2005, vol. 280 (33), pp. 29820-29827.
Bagnard D., et al., "Semaphorins act as Attractive and Repulsive Guidance Signals during the Development of Cortical Projections ," Development, 1998, vol. 125 (24), pp. 5043-5053.
Baldari C., et al., "A Novel Leader Peptide Which Allows Efficient Secretion of a Fragment of Human Interleukin 1 Beta in *Saccharomyces cerevisiae*," The EMBO Journal, 1987, vol. 6 (1), pp. 229-234.
Barbas C.F., et al., "In Vitro Evolution of a Neutralizing Human Antibody to Human Immunodeficiency Virus Type 1 to Enhance Affinity and Broaden Strain Cross-Reactivity," Proceedings of the National Academy of Sciences, 1994, vol. 91 (9), pp. 3809-3813.
Barbas C.F., et al., "Assembly of Combinatorial Antibody Libraries on Phage Surfaces: The Gene III Site," Proceedings of the National Academy of Sciences, 1991, vol. 88 (18), pp. 7978-7982.
Beaud, M.L. et al., "Anti-Nogo-A antibody treatment does not prevent cell body shrinkage in the motor cortex in adult monkeys subjected to unilateral cervical cord lesion," BMC Neuroscience, vol. 9 (5), pp. 1-11, 2008.
Becker D., et al., "New Plant Binary Vectors with Selectable Markers Located Proximal to the Left T-DNA Border," Plant Molecular Biology, 1992, vol. 20 (6), pp. 1195-1197.
Berrar D., et al., "Survival Trees for Analyzing Clinical Outcome in Lung Adenocarcinomas Based on Gene Expression Profiles: Identification of Neogenin and Diacylglycerol Kinase Alpha Expression as Critical Factors," Journal of Computational Biology, 2005, vol. 12 (5), pp. 534-544.
Berzofsky J.A., "Intrinsic and Extrinsic Factors in Protein Antigenic Structure," Science, 1985, vol. 229 (4717), pp. 932-940.
Beschorner R., et al., "Long-term Expression of Heme Oxygenase-1 (HO-1, HSP-32) Following Focal Cerebral Infarctions and Traumatic Brain Injury in Humans," Acta Neuropathologica, 2000, vol. 100 (4), pp. 377-384.
Better M., et al. "*Escherichia coli* Secretion of an Active Chimeric Antibody Fragment," Science, 1988, vol. 240 (4855), pp. 1041-1043.
Bevan M., "Binary Agrobacterium Vectors for Plant Transformation," Nucleic Acids Research, 1984, vol. 12 (22), pp. 8711-8721.
Bird R.E., et al., "Single-Chain Antigen-Binding Proteins," Science, 1988, vol. 242 (4877), pp. 423-426.
Blomer U., et al., "Highly Efficient and Sustained Gene Transfer in Adult Neurons with a Lentivirus Vector ," Journal of Virology, 1997, vol. 71 (9), pp. 6641-6649.
Bocher W.O., et al, "Antigen-specific B and T cells in Human/mouse Radiation Chimera Following Immunization in Vivo," Immunology, 1999, vol. 96 (4), pp. 634-641.
Bodanszky M., et al., "Active Esters and Resins in Peptide Synthesis," Chemistry and Industry, 1966, vol. 38, pp. 1597-1598.
Bombil F., et al., "A Promising Model of Primary Human Immunization in Human-Scid Mouse ," Immunobiology, 1996, vol. 195 (3), pp. 360-375.
Bonhoeffer F., et al., "How do Retinal Axons Find their Targets on the Tectum," Trends in Neurosciences, 1984, vol. 7, pp. 378-381.
Bork P., et al., "Go Hunting in Sequence Databases but Watch out for the Traps ," Trends in Genetics, 1996, vol. 12 (10), pp. 425-427.
Bork P., "Powers and Pitfalls in Sequence Analysis: The 70% Hurdle ," Genome Research, 2000, vol. 10 (4), pp. 398-400.
Boss M.A., et al., "Genetically Engineered Antibodies," Immunology Today, 1985, vol. 6 (1), pp. 12-13.
Bossers K., et al., "Analysis of Gene Expression in Parkinson's Disease: Possible Involvement of Neurotrophic Support and Axon Guidance in Dopaminergic Cell Death," Brain Pathology, 2009, vol. 19 (1), pp. 91-107.
Bowie J.U., et al., "Deciphering the Message in Protein Sequences: Tolerance to Amino Acid Substitutions," Science, 1990, vol. 247 (4948), pp. 1306-1310.
Braisted J.E., et al., "Netrin-1 Promotes Thalamic Axon Growth and is Required for Proper Development of the Thalamocortical Projection," The Journal of Neuroscience, 2000, vol. 20 (15), pp. 5792-5801.
Brawn A., et al., "Topographic Mapping From the Retina to the Midbrain is Controlled by Relative but not Absolute Levels of EphA Receptor Signaling," Cell, 2000, vol. 102 (1), pp. 77-88.
Brenner S.E., "Errors in Genome Annotation ," Trends in Genetics, 1999, vol. 15 (4), pp. 132-133.
Brinkmann U., et al., "Phage Display of Disulfide-stabilized Fv Fragments," Journal of Immunological Methods , 1995, vol. 182 (1), pp. 41-50.
Brinks H., et al., "The Repulsive Guidance Molecule RGMa is Involved in the Formation of Afferent Connections in the Dentate Gyrus," The Journal of Neuroscience, 2004, vol. 24 (15), pp. 3862-3869.
Brown J.P., et al., "Protein Antigens of Normal and Malignant Human Cells identified by Immunoprecipitatin with Monoclonal Antibodies ," The Journal of Biological Chemistry, 1980, vol. 255 (11), pp. 4980-4983.

(56) References Cited

OTHER PUBLICATIONS

Brown J.P., et al., "Structural Characterization of Human Melanoma-Associated Antigen p97 with Monoclonal Antibodies," The Journal of Immunology, 1981, vol. 127 (2), pp. 539-546.
Buchwald H., et al., "Long-term, Continuous Intravenous Heparin Administration by an Implantable Infusion Pump in Ambulatory Patients with Recurrent Venous Thrombosis," Surgery, 1980, vol. 88 (4), pp. 507-516.
Burgess W.H., et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 1990, vol. 111 (5 Pt 1), pp. 2129-2138.
Burton D.R., et al., "Human Antibodies from Combinatorial Libraries," Advances in Immunology, 1994, vol. 57, pp. 191-280.
Burtrum D., et al., "A Fully Human Monoclonal Antibody to the Insulin-Like Growth Factor I Receptor Blocks Ligand-Dependent Signaling and Inhibits Human Tumor Growth in Vivo," Cancer Research, 2003, vol. 63 (24), pp. 8912-8921.
Camus L., et al., "Molecular Evolution of Hemojuvelin and the Repulsive Guidance Molecule Family," Journal of Molecular Evolution, 2007, vol. 107 (2), pp. 428-431.
Camus L.M., et al., "Molecular Evolution of Hemojuvelin and the Repulsive Guidance Molecule Family," Journal of Molecular Evolution, 2007, vol. 65 (1), pp. 68-81.
Caroni P., et al., "Antibody Against Myelin-associated Inhibitor of Neurite Growth Neutralizes Nonpermissive Substrate Properties of CNS White Matter," Neuron, 1988, vol. 1 (1), pp. 85-96.
Caroni P., et al., "Two Membrane Protein Fractions from Rat Central Myelin with Inhibitory Properties for Neurite Growth and Fibroblast Spreading," Journal of Cell Biology, 1988, vol. 106 (4), pp. 1281-1288.
Carter P., et al., "Humanization of an Anti-p185 HER2 Antibody for Human Cancer Therapy," Proceedings of the National Academy of Sciences, 1992, vol. 89 (10), pp. 4285-4289.
Casadevall A., et al., "Immunoglobulin Isotype Influences Affinity and Specificity," Proceedings of the National Academy of Sciences, 2012, vol. 109 (31), pp. 12272-12273.
Chamat S., et al., "Human Monoclonal Antibodies Isolated from Spontaneous Epstein-Barr Virus-Transformed Tumors of Hu-SPL-SCID Mice and Specific for Fusion Protein Display Broad Neutralizing Activity Toward Respiratory Syncytial Virus," The Journal of Infectious Diseases, 1999, vol. 180 (2), pp. 268-277.
Charron G., et al., "Neuron Specificity of the Neurofilament Light Promoter in Transgenic Mice Requires the Presence of DNA Unwinding Elements," The Journal of Biological Chemistry, 1995, vol. 270 (43), pp. 25739-25745.
Chen M.S., et al., "Nogo-A is a Myelin-associated Neurite Outgrowth Inhibitor and an Antigen for Monoclonal Antibody IN-1," Nature, 2000, vol. 403 (6768), pp. 434-439.
Chen Y., et al., "Selection and Analysis of an Optimized Anti-VEGF Antibody: Crystal Structure of an Affinity-Matured Fab in Complex with Antigen," Journal of Molecular Biology, 1999, vol. 293 (4), pp. 865-881.
Cheng H.J., et al., "Identification and Cloning of ELF-1, a Developmentally Expressed Ligand for the Mek4 and Sek Receptor Tyrosine Kinases," Cell, 1994, vol. 79 (1), pp. 157-168.
Cheng P.P., et al., "Hepcidin Expression in Anemia of Chronic Disease and Concomitant Iron-deficiency Anemia," Clinical and Experimental Medicine, 2011, vol. 11 (1), pp. 33-42.
Chothia C., et al., "Canonical Structures for the Hypervariable Regions of Immunoglobulins," Journal of Molecular Biology, 1987, vol. 196 (4), pp. 901-917.
Chothia C., et al., "Conformations of Immunoglobulin Hypervariable Regions," Nature, 1989, vol. 342 (6252), pp. 877-883.
Chothia C., et al., "Structural Repertoire of the Human VH Segments," Journal of Molecular Biology, 1992, vol. 227 (3), pp. 799-817.
Clackson T., et al., "Making Antibody Fragments Using Phage Display Libraries," Nature, 1991, vol. 352 (6336), pp. 624-628.
Cleek R.L., et al., "Biodegradable Polymeric Carriers for a bFGF Antibody for Cardiovascular Application," Proc. Intl. Symp. Control. Rel. Bioact. Mater., 1997, vol. 24, pp. 853-854.
Co M.S., et al., "Genetically Engineered Deglycosylation of the Variable Domain Increases the Affinity of an Anti-CD33 Monoclonal Antibody," Molecular Immunology, 1993, vol. 30 (15), pp. 1361-1367.
Conrad S., et al., "Neogenin-RGMa Signaling at the Growth Cone is Bone Morphogenetic Protein-independent and Involves RhoA, ROCK, and PKC," The Journal of Biological Chemistry, 2007, vol. 282 (22), pp. 16423-16433.
Conrad U., et al., "Compartment-specific Accumulation of Recombinant Immunoglobulins in Plant Cells: An Essential Tool for Antibody Production and Immunomodulation of Physiological Functions and Pathogen Activity," Plant Molecular Biology, 1998, vol. 38 (1-2), pp. 101-109.
Corder E.H., et al., "Gene Dose of Apolipoprotein E Type 4 Allele and the Risk of Alzheimer'S Disease in Late Onset Families," Science, 1993, vol. 261 (5123), pp. 921-923.
Cox E.C., et al., "Axonal Guidance in the Chick Visual System: Posterior Tectal Membranes Induce Collapse of Growth Cones from the Temporal Retina," Neuron, 1990, vol. 4 (1), pp. 31-37.
Cramer C.L., et al., "Transgenic Plants for Therapeutic Proteins: Linking Upstream and Downstream Strategies," Current Topics in Microbiology and Immunology, 1999, vol. 240, pp. 95-118.
David S., et al., "Axonal Elongation into Peripheral Nervous System "Bridges" After Central Nervous System Injury in Adult Rats," Science, 1981, vol. 214 (4523), pp. 931-933.
Davis S., et al., "Ligands for EPH-Related Receptor Tyrosine Kinases that Require Membrane Attachment or Clustering for Activity," Science, 1994, vol. 266 (5186), pp. 816-819.
De Pascalis R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunological Methods, 2002, vol. 169 (6), pp. 3076-3084.
Divry P., "Histochemical Study of the Senile Plates," Journal De Neurologie Et De Psychiatrie, 1927, vol. 27, pp. 643-657.
Doerks T., et al., "Protein Annotation: Detective work for Function Prediction," Trends in Genetics, 1998, vol. 14 (6), pp. 248-250.
Drescher U., et al., "In Vitro Guidance of Retinal Ganglion Cell Axons by RAGS, a 25 kDa Tectal Protein Related to Ligands for Eph Receptor Tyrosine Kinases," Cell, 1995, vol. 82 (3), pp. 359-370.
During M. J., et al., "Controlled Release of Dopamine from a Polymeric Brain Implant: In Vivo Characterization," Annals of Neurology, 1989, vol. 25 (4), pp. 351-356.
Elmer L.W., et al., "The Increasing Role of Monoamine Oxidase Type B Inhibitors in Parkinson's Disease Therapy," Expert Opinion on Pharmacotherapy, 2008, vol. 9 (16), pp. 2759-2772.
Eren R., et al., "Human Monoclonal Antibodies Specific to Hepatitis B Virus Generated in a Human/mouse Radiation Chimera: the Trimera System," Immunology, 1998, vol. 93 (2), pp. 154-161.
Famulok M., et al., "Oligonucleotide Libraries—Variatio Delectat," Current Opinion in Chemical Biology, 1998, vol. 2 (3), pp. 320-327.
Fanger M.W., et al., "Production and Use of Anti-FcR Bispecific Antibodies," Immunomethods, 1994, vol. 4 (1), pp. 72-81.
Fazeli A., et al., "Phenotype of Mice Lacking Functional Deleted in Colorectal Cancer (Dcc) Gene," Nature, 1997, vol. 386 (6627), pp. 796-804.
Feldheim D.A., et al., "Genetic Analysis of Ephrin-A2 and Ephrin-A5 Shows their Requirement in Multiple Aspects of Retinocollicular Mapping," Neuron, 2000, vol. 25 (3), pp. 563-574.
Feldheim D.A., et al., "Topographic Guidance Labels in a Sensory Projection to the Forebrain," Neuron, 1998, vol. 21 (6), pp. 1303-1313.
Feys T., et al., "A Detailed Inventory of DNA Copy Number Alterations in Four Commonly used Hodgkin's Lymphoma Cell Lines," Haematologica, 2007, vol. 92 (7), pp. 913-920.
Fishwild D.M., et al., "High-Avidity Human IgGK Monoclonal Antibodies from a Novel Strain of Minilocus Transgenic Mice," Nature Biotech, 1996, vol. 14 (7), pp. 845-851.

(56) References Cited

OTHER PUBLICATIONS

Fitzgerald D.P., et al., "Characterization of Neogenin-expressing Neural Progenitor Populations and Migrating Neuroblasts in the Embryonic Mouse Forebrain," Neuroscience, 2006, vol. 142 (3), pp. 703-716.
Fitzgerald D.P., et al., "Neogenin is Expressed on Neurogenic and Gliogenic Progenitors in the Embryonic and Adult Central Nervous System," Gene Expression Patterns, 2007, vol. 7 (7), pp. 784-792.
Flanagan J.G., et al., "The Ephrins and Eph Receptors in Neural Development," Annual Review Neuroscience, 1998, vol. 21, pp. 309-345.
Foote J., et al., "Antibody Framework Residues Affecting the Conformation of the Hypervariable Loops," Journal of Molecular Biology, 1992, vol. 224 (2), pp. 487-499.
Fournier A.E., et al., "Identification of a Receptor Mediating Nogo-66 Inhibition of Axonal Regeneration," Nature, 2001, vol. 409 (6818), pp. 341-346.
Frisen J., et al., "Ephrin-a5 (al-1/rags) is Essential for Proper Retinal Axon Guidance and Topographic Mapping in the Mammalian Visual System," Neuron, 1998, vol. 20 (2), pp. 235-243.
Frohman E.M., et al., "Modeling Axonal Degeneration within the Anterior Visual System: Implications for Demonstrating Neuroprotection in Multiple Sclerosis," Archives of neurology, 2008, vol. 65 (1), pp. 26-35.
Fuchs P., et al., "Targeting Recombinant Antibodies to the Surface of *Escherichia coli*: Fusion to a Peptidoglycan Associated Lipoprotein," BioTechnology, 1991, vol. 9 (12), pp. 1369-1372.
Funaro A., et al., "Generation of Potent Neutralizing Human Monoclonal Antibodies Against Cytomegalovirus Infection from Immune B Cells," BMC Biotechnol, 2008, vol. 8:85, 10 pages.
Galfre G., et al., "Antibodies to Major Histocompatibility Antigens Produced by Hybrid Cell Lines," Nature, 1977, vol. 266 (5602), pp. 550-552.
Gallo M.L., et al., "The Human Immunoglobulin Loci Introduced into Mice: V (D) and J Gene Segment Usage Similar to that of Adult Humans," European Journal of Immunology, 2000, vol. 30 (2), pp. 534-540.
Ganz T., "Hepcidin and Iron Regulation, 10 Years Later," Blood, 2011, vol. 117 (17), pp. 4425- 4433.
Garrard L.J., et al., "Fab Assembly and Enrichment in a Monovalent Phage Display System," BioTechnology, 1991, vol. 9 (12), pp. 1373-1377.
Gavilondo J.V., et al., "Antibody Engineering at the Millennium," Biotechniques, 2000, vol. 29 (1), pp. 128-145.
Geddes B.J., et al., "Assessing Viral Gene Therapy in Neuroendocrine Models," Front in Neuroendocrinology, 1999, vol. 20 (4), pp. 296-316.
Geddes B.J., et al., "Long-term Gene Therapy in the CNS: Reversal of Hypothalamic Diabetes Insipidus in the Brattleboro Rat by using an Adenovirus Expressing Arginine Vasopressin," Nature Medicine, 1997, vol. 3 (12), pp. 1402-1404.
Gefter M.L., et al., "A Simple Method for Polyethylene Glycol-Promoted Hybridization of Mouse Myeloma Cells," Somatic Cell Genetics, 1997, vol. 3 (2), pp. 231-236.
Geisbrecht B.V., et al., "Netrin Binds Discrete Subdomains of DCC and UNC5 and Mediates Interactions between DCC and Heparin," The Journal of Biological Chemistry, 2003, vol. 278 (35), pp. 32561-32568.
Genbank, "Hemojuvelin Isoform a Precursor [*Homo sapiens*]", Accession No. NP_998818.1, Jun. 30, 2012.
Genbank, "*Homo sapiens* RGM Domain Family, Member A (RGMA), Transcript Variant 4, mRNA", Accession No. NM_020211.2, Jun. 29, 2012.
Genbank, "Repulsive Guidance Molecule A Isoform 3 [*Homo sapiens*]", Accession No. NP_064596.2, Jun. 29, 2012.
Genbank, "RGM Domain Family Member B [*Homo sapiens*]", Accession No. NP_001012779.2, Jul. 1, 2012.
Gennaro A.R., ed., Remington: The Science and Practice of Pharmacy, 19th Edition, Mack Publishing, 1995, Table of Contents.

Gheith M.E., et al., "Managing Refractory Glaucoma with a Fixed Combination of Bimatoprost (0.03%) and Timolol (0.5%)," Clinical Ophthalmology, 2008, vol. 2 (1), pp. 15-20.
Giege R., et al., "An Introduction to the Crystallogenesis of Biological Macromolecules" in: Crystallization of Nucleic Acids and Proteins, Chapter 1, 2nd Edition, Ducruix A., et al., Eds., Oxford University Press, 1999, pp. 1-16.
Gierer A., "Directional Cues for Growing Axons Forming the Retinotectal Projection," Development, 1987, vol. 101 (3), pp. 479-489.
Giger R.J., et al., "Mechanisms of CNS Myelin Inhibition: Evidence for Distinct and Neuronal Cell Type Specific Receptor Systems, "Restorative Neurology and Neuroscience, 2008, vol. 26 (2-3), pp. 97-115.
Gillies S.D., et al., "High-Level Expression of Chimeric Antibodies Using Adapted cDNA Variable Region Cassettes," Journal of Immunological Methods, 1989, vol. 125 (1-2), pp. 191-202.
Giordano F.J., et al., "Intracoronary Gene Transfer of Fibroblast Growth Factor-5 Increases Blood Flow and Contractile Function in an Ischemic Region of the Heart," Nature Medicine, 1996, vol. 2 (5), pp. 534-539.
Gisin., "The Preparation of Merrifield-Resins through Total Esterification with Cesium Salts," Helvetica Chimica Acta, 1973, vol. 56, pp. 1476-1482.
Glenner G.G., "Amyloid Deposits and Amyloidosis. The Beta-Fibrilloses (First of Two Parts)," The New England Journal of Medicine, 1980, vol. 302 (23), pp. 1283-1292.
Gnana-Prakasam J.P., et al., "Iron-mediated Retinal Degeneration in Haemojuvelin-knockout Mice," The Biochemical Journal, 2012, vol. 441 (3), pp. 599-608.
Goeddel D.V., "Systems for Heterologous Gene Expression," Methods in Enzymology, 1990, vol. 185, pp. 3-7.
Gold L., et al., "Diversity of Oligonucleotide Functions," Annual Review of Biochemistry, 1995, vol. 64, pp. 763-797.
Goldspiel B.R., et al., "Human Gene therapy," Clinical Pharmacy, 1993, vol. 12 (7), pp. 488-505.
Goodhill G.J., "Dating Behavior of the Retinal Ganglion Cell," Neuron, 2000, vol. 25 (3), pp. 501-503.
Goodman C.S., "Mechanisms and Molecules that Control Growth Cone Guidance," Annual Review of Neuroscience, 1996, vol. 19, pp. 341-377.
Goodson J.M., "Dental Applications" in: Medical Applications of Controlled Release, vol. 2, Chapter 6, Langer R.S., et al., eds., CRC Press, 1984, pp. 115-138.
Gram H., et al., "In Vitro Selection and Affinity Maturation of Antibodies from a Naïve Combinatorial Immunoglobulin Library," Proceedings of the National Academy of Sciences, 1992, vol. 89 (8), pp. 3576-3580.
Grandpre T., et al., "Identification of the Nogo Inhibitor of Axon Regeneration as a Reticulon Protein," Nature, 2000, vol. 403 (6768), pp. 439-444.
Gray F., et al., "Secretion Capture and Report Web: use of Affinity Derivatized Agarose Microdroplets for the Selection of Hybridoma Cells," Journal of Immunological Methods, 1995, vol. 182 (2), pp. 155-163.
Green L. L., et al., "Regulation of B Cell Development by Variable Gene Complexity in Mice Reconstituted with Human Immunoglobulin Yeast Artificial Chromosomes," Journal of Experimental Medicine, 1998, vol. 188 (3), pp. 483-495.
Green L.L., "Antibody Engineering via Genetic Engineering of the Mouse: XenoMouse Strains are a Vehicle for the Facile Generation of Therapeutic Human Monoclonal Antibodies," Journal of Immunological Methods, 1999, vol. 231 (1-2), pp. 11-23.
Green L.L., et al., "Antigen-Specific Human Monoclonal Antibodies from Mice Engineered with Human Ig Heavy and Light Chain YACs," Nature Genetics, 1994, vol. 7 (1), pp. 13-21.
Griffiths A.D., et al., "Human Anti-Self Antibodies with High Specificity from Phage Display Libraries," European Molecular Biology Organization, 1993, vol. 12 (2), pp. 725-734.
Hall A.K., et al., "Emerging Roles for Bone Morphogenetic Proteins in Central Nervous System Glial Biology," Journal of Neuroscience Research, 2004, vol. 76 (1), pp. 1-8.

(56) References Cited

OTHER PUBLICATIONS

Hammerling G.J., et al., Eds., Monoclonal Antibodies and T-Cell Hybridomas : Perspectives and Technical Advances, Elsevier/North-Holland Biomedical Press, 1981, Appendix, pp. 563-587.
Hanes J., et al., "In Vitro Selection and Evolution of Functional Proteins by using Ribosome Display," Proceedings of the National Academy of Sciences, 1997, vol. 94 (10), pp. 4937-4942.
Hanes J., et al., "Ribosome Display Efficiently Selects and Evolves High-Affinity Antibodies in Vitro from Immune Libraries," Proceedings of the National Academy of Sciences, 1998, vol. 95 (24), pp. 14130-14135.
Hanson L.R., et al., "Intranasal Delivery Bypasses the Blood-Brain Barrier to Target Therapeutic Agents to the Central Nervous System and Treat Neurodegenerative Disease," BMC Neuroscience, 2008, vol. 9 (Suppl 3), pp. S5.
Harding F.A., et al., "Class Switching in Human Immunoglobulin Transgenic Mice," Annals New York Academy of Sciences, 1995, vol. 764, pp. 536-546.
Harel N.Y., et al., "Can Regenerating Axons Recapitulate Developmental Guidance During Recovery from Spinal Cord Injury," Nature Reviews Neuroscience, 2006, vol. 7 (8), pp. 603-616.
Harlow, et al., "Production of Antibody-Producing Hybridomas in the Rodent Systems," Monoclonal Antibod. And T-Cell Hybrid., pp. 563-681, 1989.
Hata K., et al., "RGMa Inhibition Promotes Axonal Growth and Recovery After Spinal Cord Injury," Journal of Cell Biology, 2006, vol. 173 (1), pp. 47-58.
Hawkins R.E., et al., "Selection of Phage Antibodies by Binding Affinity Mimicking Affinity Maturation," Journal of Molecular Biology, 1992, vol. 226 (3), pp. 889-896.
Hay B.N., et al., "Bacteriophage Cloning and *Escherichia coli* Expression of a Human IgM Fab," Human Antibodies and Hybridomas, 1992, vol. 3 (2), pp. 81-85.
Heard C., et al., "Two Neutralizing Human Anti-RSV Antibodies: Cloning, Expression, and Characterization," Molecular Medicine, 1999, vol. 5 (1), pp. 35-45.
Hentze M.W., et al., "Two to Tango: Regulation of Mammalian Iron Metabolism," Cell, 2010, vol. 142 (1), pp. 24-38.
Herz U. et al., "The Humanized (Hu-Pbmc) Scid Mouse as an in vivo Model for Human Ige Production and Allergic Inflammation of the Skin," International Archives of Allergy and Immunology, 1997, vol. 113 (1-3), 150-152.
Heukeshoven J., et al., "Improved Silver Staining Procedure for Fast Staining in Phastsystem Development Unit .I. Staining of Sodium Dodecyl Sulfate Gels," Electrophoresis, 1988, vol. 9 (1), pp. 28-32.
Heukeshoven J., et al., "Increased Sensitivity for Coomassie Staining of Sodium Dodecyl Sulfate-Polyacrylamide Gels Using Phastsystem Development Unit," Electrophoresis, 1988, vol. 9 (1), pp. 60-61.
Higgins D.G., et al., "Fast and Sensitive Multiple Sequence Alignments on a Microcomputer," Computer Applications in the Biosciences, 1989, vol. 5 (2), pp. 151-153.
Holliger P., et al., ""Diabodies": Small Bivalent and Bispecific Antibody Fragments," Proceedings of the National Academy of Sciences, 1993, vol. 90 (14), pp. 6444-6448.
Hong K., et al., "A Ligand-Gated Association Between Cytoplasmic Domains of Unc5 and Dcc Family Receptors Converts Netrin-Induced Growth Cone Attraction to Repulsion," Cell, 1999, vol. 97 (7), pp. 927-941.
Hood E.E., et al., "Molecular Farming of Industrial Proteins from Transgenic Maize," Advances in Experimental Medicine and Biology, 1999, vol. 464, pp. 127-147.
Hoogenboom H.R., et al., "Designing and Optimizing Library Selection Strategies for Generating High-Affinity Antibodies," Trends in Biotechnology, 1997, vol. 15 (2), pp. 62-70.
Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.
Hoogenboom H.R., et al., "Natural and Designer Binding Sites Made by Phage Display Technology," Immunology Today, 2000, vol. 21 (8), pp. 371-378.
Horsley M.B., et al., "Retinal Nerve Fiber Layer Thickness in Patients Receiving Chronic Anti-Vascular Endothelial Growth Factor Therapy," American Journal of Ophthalmology, 2010, vol. 150 (4), pp. 558-561.
Howard M.A., et al., "Intracerebral Drug Delivery in Rats with Lesion-Induced Memory Deficits," Journal of Neurosurgery, 1989, vol. 71 (1), pp. 105-112.
Hu Y.C., et al., "Identification of Differentially Expressed Genes in Esophageal Squamous Cell Carcinoma (Escc) by Cdna Expression Array: Overexpression of Fra-1, Neogenin, Id-1, and Cdc25b Genes in Escc," Clinical Cancer Research, 2001, vol. 7 (8), pp. 2213-2221.
Huang FW., et al., "A Mouse Model of Juvenile Hemochromatosis," The Journal of Clinical Investigation, 2005, vol. 115 (8), pp. 2187-2191.
Hunt D., et al., "The Nogo Receptor, its Ligands and Axonal Regeneration in the Spinal Cord; A Review", Journal of Neurocytology, 2002, vol. 31 (2), pp. 93-120.
Hurrell., G.R., ed., "Monoclonal Hybridoma Antibodies" in: Techniques and Applications, CRC Press Inc., Boco Raron, FL, 1982, Table of Contents.
Huse W.D., et al., "Generation of a Large Combinatorial Library of the Immunoglobulin Repertoire in Phage Lambda," Science, 1989, vol. 246 (4935), pp. 1275-1281.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences, 1988, vol. 85 (16), pp. 5879-5883.
Huston J.S., et al., "Protein Engineering of Single-Chain Fv Analogs and Fusion Proteins," Methods in Enzymology, 1991, vol. 203, pp. 46-88.
Hutchins W.A., et al., "Human Immune Response to a Peptide Mimic of *Neisseria meningititis* Serogroup C in hu-PBMC-SCID Mice," Hybridoma, 1999, vol. 18 (2), pp. 121-129.
Ike Y., et al., "Solid Phase Synthesis of Polynucleotides. VIII. Synthesis of Mixed Oligodeoxyribonucleotides by the Phosphotriester Solid Phase Method", Nucleic Acids Research, 1983, vol. 11 (2), pp. 477-488.
Ilan E., et al., "The Hepatitis B Virus-Trimera Mouse: A Model for Human HBV Infectoin and Evaluation of Anti-HBV Therapeutic Agents," Hepatology, 1999, vol. 29 (2), pp. 553-562.
Iseda T., et al., "Single, High-Dose Intraspinal Injection of Chondroitinase Reduces Glycosaminoglycans in Injured Spinal Cord and Promotes Corticospinal Axonal Regrowth after Hemisection but Not Contusion," Journal of Neurotrauma, 2008, vol. 25 (4), pp. 334-349.
Isner J.M., et al., "Clinical Evidence of Angiogenesis after Arterial Gene Transfer of phVEGF165 in Patient with Ischaemic Limb," Lancet, 1996, vol. 348 (9024), pp. 370-374.
Itakura K., et al., "Expression in *Escherichia coli* of a Chemically Synthesized Gene for the Hormone Somatostatin", Science, 1984, vol. 198 (4321), pp. 1056-1063.
Itakura K., et al., "Synthesis and Use of Synthetic Oligonucleotides," Annual Review of Biochemistry, 1984, vol. 53, pp. 323-356.
Itokazu T., et al., "Identification of the Neogenin-Binding Site on the Repulsive Guidance Molecule A," PLoS One, 2012, vol. 7 (3), pp. e32791.
Jackson J.R., et al., "In Vitro Antibody Maturation Improvement of a High Affinity, Neutralizing Antibody Against IL-1β," The Journal of Immunology, 1995, vol. 154 (7), pp. 3310-3319.
Jefferis R., "Glycosylation of Recombinant Antibody Therapeutics," Biotechnology Program, 2005, vol. 21 (1), pp. 11-16.
Johnsson B., et al., "Comparison of Methods for Immobilization to Carboxymethyl Dextran Sensor Surfaces by Analysis of the Specific Activity of Monoclonal Antibodies," Journal of Molecular Recognition, 1995, vol. 8 (1-2), pp. 125-131.
Johnsson B., et al., "Immobilization of Proteins to a Carboxymethyldextran-Modified Gold Surface for Biospecific Interaction Analysis in Surface Plasmon Resonance Sensors," Analytical Biochemistry, 1991, vol. 198 (2), pp. 268-277.

(56) References Cited

OTHER PUBLICATIONS

Joliot A., et al., "Antennapedia Homeobox Peptide Regulates Neural Morphogenesis," Proceedings of the National Academy of Sciences, 1991, vol. 88 (5), pp. 1864-1868.
Jones P.T., et al., "Replacing the Complementarity-Determining Regions in a Human Antibody with those from a Mouse," Nature, 1986, vol. 321 (6069), pp. 522-525.
Jonsson U., et al., "Introducing a Biosensor Based Technology for Real-Time Biospecific Interaction Analysis," Annales de Biologie Clinique, 1993, vol. 51 (1), pp. 19-26.
Jonsson U., et al., "Real-Time Biospecific Interaction Analysis Using Surface Plasmon Resonance and a Sensor Chip Technology," Biotechniques, 1991, vol. 11 (5), pp. 620-627.
Jost W.H., et al., "Initial Experience with Ropinirole PR (Prolonged Release)," Journal of Neurology, 2008, vol. 255 (Suppl 5), pp. 60-63.
Kabat E.A., et al., "Attempts to Locate Complementarity—Determining Residues in the variable Positions of Light and Heavy Chains," Annals New York Academy of Sciences, 1971, vol. 190, pp. 382-393.
Kalimo H., et al., "Vascular Diseases", in: Greenfield's Neuropathology, Chapter 7, Graham D.I., et al., eds., Oxford University Press, 1997, pp. 315-396.
Kasus-Jacobi A., et al., "Evidence for an Interaction Between the Insulin Receptor and Grb7. A Role for Two of Its Binding Domains, PIR and SH2," Oncogene, 2000, vol. 19 (16), pp. 2052-2059.
Kato H., et al., "The Initiation of the Microglial Response," Brain Pathology, 2000, vol. 10 (1), pp. 137-143.
Kaufman R. J., et al., Translational Efficiency of Polycistronic mRNAs and their Utilization to Express Heterologous Genes in Mammalian Cells, EMBO, 1987, vol. 6 (1), pp. 187-193.
Kaufman R.J., et al., "Amplification and Expression of Sequences Cotransfected with a Modular Dihydrofolate Reductase Complementary DNA Gene," Journal of Molecular Biology, 1982, vol. 159 (4), pp. 601-621.
Keeling S.L., et al., "Mouse Neogenin, a DCC-like molecule, has Four Splice Variants and is Expressed widely in the Adult Mouse and during Embryogenesis," Oncogene, 1997, vol. 15 (6), pp. 691-700.
Keino-Masu K., et al., "Deleted in Colorectal Cancer (DCC) Encodes a Netrin Receptor," Cell, 1996, vol. 87 (2), pp. 175-185.
Kellermann S.A., et al., "Antibody Discovery: The Use of Transgenic Mice to Generate Human Monoclonal Antibodies for Therapeutics," Current Opinion in Biotechnology, 2002, vol. 13 (6), pp. 593-597.
Kenney J.S., et al., "Production of Monoclonal Antibodies using a Secretion Capture Report Web," Biotechnology, 1995, vol. 13 (8), pp. 787-790.
Kettleborough C.A., et al., "Isolation of Tumor Cell-specific Single-chain Fv from Immunized Mice using Phage-antibody Libraries and the Re-construction of Whole Antibodies from these Antibody Fragments," European Journal of Immunology, 1994, vol. 24 (4), pp. 952-958.
Khachaturian Z.S., "Diagnosis of Alzheimer's Disease," Archives of Neurology, 1985, vol. 42, pp. 1097-1105.
Khor S.P., et al., "The Pharmacokinetics and Pharmacodynamics of Levodopa in the Treatment of Parkinson's Disease," Current Clinical Pharmacology, 2007, vol. 2 (3), pp. 234-243.
Kipriyanov S.M., et al., "Single-Chain Antibody Streptavidin Fusions: Tetrameric Bifunctional scFv-Complexes with Biotin Binding Activity and Enhanced Affinity to Antigen," Human Antibodies and Hybridomas, 1995, vol. 6 (3), pp. 93-101.
Kipriyanov S.M., et al., "Recombinant Single-Chain Fv Fragments Carrying C-Terminal Cysteine Residues: Production of Bivlent and Biotinylated Miniantibodies," Molecular Immunology, 1994, vol. 31 (14), pp. 1047-1058.
Kirschner D.A., et al., "X-Ray Diffraction from Intraneuronal Paired Helical Filaments and Extraneuronal Amyloid Fibers in Alzheimer Disease Indicates Cross-Beta Conformation," Proceedings of the National Academy of Sciences, 1986, vol. 83 (2), pp. 503-507.
Kitayama M., et al., "Activated Microglia Inhibit Axonal Growth through RGMa," PLoS One, 2011, vol. 6 (9), pp. e25234.

Knappik A., et al., "Fully Synthetic Human Combinatorial Antibody Libraries (hUCAL)Based on Modular Consensus Frameworks and CDRs Randomized with Trinucleotides," Journal of Molecular Biology, 2000, vol. 296 (1), pp. 57-86.
Knoll B., et al., "Stripe Assay to Examine Axonal Guidance and Cell Migration," Nature Protocols, 2007, vol. 2 (5), pp. 1216-1224.
Koeberle P.D., et al., "The Repulsive Guidance Molecule, RGMa, Promotes Retinal Ganglion Cell Survival in Vitro and in Vivo," Neuroscience, 2010, vol. 169 (1), pp. 495-504.
Kohler G., et al., "Continuous Cultures of Fused Cells Secreting Antibody of Predefined Specificity ," Nature, 1975, vol. 256 (5517), pp. 495-497.
Kolodkin A.L., et al., "The Semaphorin Genes Encode a Family of Transmembrane and Secreted Growth Cone Guidance Molecules," Cell, 1993, vol. 75 (7), pp. 1389-1399.
Konig K., et al., "The Axonal Guidance Receptor Neogenin Promotes Acute Inflammation," PLoS One, 2012, vol. 7 (3), pp. e32145.
Korchynskyi O., et al., "Identification and Functional Characterization of Distinct Critically Important Bone Morphogenetic Protein-Specific Response Elements in the Id1 Promoter," Journal of Biological Chemistry, 2002, vol. 277 (7), pp. 4883-4891.
Kubo T., et al., "Crosstalk Between the Immune and Central Nervous Systems with Special Reference to Drug Development", Chapter 14, 2011, pp. 365-380.
Kuby J., Immunoglobulins: Structure and Function, Immunology, 3rd Edition, 1997, W.H. Freeman and Company, New York, pp. 131-134.
Kurjan J., et al., "Structure of a Yeast Pheromone Gene (MF Alpha): A Putative Alpha-Factor Precursor Contains Four Tandem Copies of Mature Alpha-Factor," Cell, 1982, vol. 30 (3), pp. 933-943.
Kyoto A., et al., "Synapse Formation of the Cortico-Spinal Axons is Enhanced by RGMa Inhibition after Spinal Cord Injury," Brain Research, 2007, vol. 1186, pp. 74-86.
Kyte J., et al., "A Simple Method for Displaying the Hydropathic Character of a Protein," Journal of Molecular Biology, 1982, vol. 157 (1), pp. 105-132.
Lah G.J., et al., "Dual Roles of the Chemorepellent Axon Guidance Molecule RGMA in Establishing Pioneering Axon Tracts and Neural Fate Decisions in Embryonic Vertebrate Forebrain," Developmental Neurobiology, 2012.
Lah G.J., et al., "Novel Roles of the Chemorepellent Axon Guidance Molecule Rgma in Cell Migration and Adhesion," Molecular and Cellular Biology, 2012, vol. 32 (5), pp. 968-980.
Lai M., et al., "Focal Brain Injury Increases Activin BetaA mRNA Expression in Hippocampal Neurons," Neuroreport, 1997, vol. 8 (12), pp. 2691-2694.
Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.
Lamminmaki U., et al., "Crystal Structure of a Recombinant Anti-Estradiol Fab Fragment in Complex with 17beta -Estradiol," The Journal of Biological Chemistry, 2001, vol. 276 (39), pp. 36687-36694.
Langer R., et al., "Chemical and Physical Structure of Polymers as Carriers for Controlled Rlease of Bioactive Agents: A Review," Journal of Macromolecular Science—Reviews in Macromolecular Chemistry & Physics, 1983, vol. C23 (1), pp. 61-126.
Langer R., "New Methods of Drug Delivery," Science, 1990, vol. 249 (4976), pp. 1527-1533.
Langer R.S., et al., eds., Medical Applications of Controlled Release: Applications and Evaluation, vol. 2, CRC Press, 1984, pp. 113-138.
Leader K.A., et al., "Antibody Responses to the Blood Group Antigen D in SCID Mice Reconstituted with Human Blood Mononuclear Cells," Immunology, 1992, vol. 76 (2), pp. 229-234.
Lerner E.A., "How to Make a Hybridoma," The Yale Journal of Biology & Medicine, 1981, vol. 54 (5), pp. 387-402.
Levy R.D., et al., "Inhibition of Calcification of Bioprosthetic Heart Valves by Local Controlled-Release Diphosphonate," Science, 1985, vol. 228 (4696), pp. 190-192.
Li J., et al., "Potential Prognostic Value of Repulsive Guidance Molecules in Breast Cancer," Anticancer Research, 2011, vol. 31 (5), pp. 1703-1711.

(56) References Cited

OTHER PUBLICATIONS

Li J., et al., "Repulsive Guidance Molecule B (RGMB) Plays Negative Roles in Breast Cancer by Coordinating BMP Signaling," Journal of Cellular Biochemistry, 2012, vol. 113 (7), pp. 2523-2531.
Li J., et al., "Repulsive Guidance Molecules, Novel Bone Morphogenetic Protein Co-Receptors, are Key Regulators of the Growth and Aggressiveness of Prostate Cancer Cells," International Journal of Oncology, 2012, vol. 40 (2), pp. 544-550.
Liang B.A., et al., "Review of Tissue Plasminogen Activator, Ischemic Stroke, and Potential Legal Issues," Archives of Neurology, 2008, vol. 65 (11), pp. 1429-1433.
Lingor P., et al., "Inhibition of Rho Kinase (Rock) Increases Neurite Outgrowth on Chondroitin Sulphate Proteoglycan in Vitro and Axonal Regeneration in the Adult Optic Nerve in Vivo," Journal of Neurochemistry, 2007, vol. 103 (1), pp. 181-189.
Little M., et al., "Of Mice and Men: Hybridoma and Recombinant Antibodies," Immunology Today, 2000, vol. 21 (8), pp. 364-370.
Logeart-Avramoglou D., et al., "An Assay for the Determination of Biologically Active Bone Morphogenetic Proteins Using Cells Transfected with an Inhibitor of Differentiation Promoter-luciferase Construct," Analytical Biochemistry, 2006, vol. 349 (1), pp. 78-86.
Lonberg N., et al., "Antigen-Specific Human Antibodies From Mice Comprising Four Distinct Genetic Modifications," Nature, 1994, vol. 368, pp. 856-859.
Lonberg N., et al., "Human Antibodies from Transgenic Mice," International Reviews of Immunology, 1995, vol. 13 (1), pp. 65-93.
Lories R.J., et al., "Bone Morphogenetic Protein Signaling in Joint Homeostasis and Disease," Cytokine and Growth Factor, 2005, vol. 16 (3), pp. 287-298.
Luciani N., et. al., "Hemojuvelin: A New Link Between Obesity and Iron Homeostasis," Obesity, 2011, vol. 19 (8), pp. 1545-1551.
Luckow V. A., et al., "High Level Expression of Nonfused Foreign Genes with Autographa Californica Nuclear Polyhedrosis Virus Expression Vectors," Virology, 1989, vol. 170 (1), pp. 31-39.
Lund J., et al., "Human Fc Gamma Rl and Fc Gamma RII Interact with Distinct but Overlapping Sites on Human IgG," Journal of Immunology, 1991, vol. 147 (8), pp. 2657-2662.
Lunn M.P., et al., "High-Affinity Anti-Ganglioside IgG Antibodies Raised in Complex Ganglioside Knockout Mice: Reexamination of GDIa Immunolocalization," Journal of Neurochemistry, 2000, vol. 75 (1), pp. 404-412.
Ma C.H., et al., "The BMP Coreceptor RGMb Promotes While the Endogenous BMP Antagonist Noggin Reduces Neurite Outgrowth and Peripheral Nerve Regeneration by Modulating BMP Signaling," The Journal of Neuroscience, 2011, vol. 31 (50), pp. 18391-18400.
MacCallum R.M., et al., "Antibody-Antigen Interactions: Contact Analysis and Binding Site Topography," Journal of Molecular Biology, 1996, vol. 262 (5), pp. 732-745.
Macquitty J.J., et al., "GenPharm's Knockout Mice," Science, 1992, vol. 257 (5074), pp. 1188.
Mann D.M., et al., "The Pattern of Acquisition of Plaques and Tangles in the Brains of Patients Under 50 Years of Age with Down's Syndrome.," Journal of the Neurological Sciences, 1989, vol. 89 (2-3), pp. 169-179.
Mann D.M, "The Neuropathology of Alzheimer's Disease: A Review with Pathogenetic, Aetiological and Therapeutic Considerations," Mechanisms of Ageing and Development, 1985, vol. 31 (3), pp. 213-255.
Marchalonis J.J., et al., "Evolutionary Factors in the Emergence of the Combinatorial Germline Antibody Repertoire," Advances in Experimental Medicine and Biology, 2001, vol. 484, pp. 13-30.
Marks J.D., et al., "By-Passing Immunization: Building High Affinity Human Antibodies by Chain Shuffling," Biotechnology, 1992, vol. 10 (7), pp. 779-783.
Martinez G., et al., "Expression of Bone Morphogenetic Protein-6 and Transforming Growth Factor-Beta1 in the Rat Brain after a Mild and Reversible Ischemic Damage," Brain Research, 2001, vol. 894 (1), pp. 1-11.

Matsunaga E., et al., "Repulsive Guidance Molecule Plays Multiple Roles in Neuronal Differentiation and Axon Guidance," The Journal of Neuroscience, 2006, vol. 26 (22), pp. 6082- 6088.
Matsunaga E., et al., "Repulsive Guidance molecule/neogenin: a Novel Ligand-receptor System Playing Multiple Roles in Neural Development," Development, Growth & Differentiation, 2004, vol. 46 (6), pp. 481-486.
Matsunaga E., et al., "RGM and its Receptor Neogenin Regulate Neuronal Survival," Nature Cell Biology, 2004, vol. 6 (8), pp. 749-755.
Matsuura I., et al., "BMP Inhibits Neurite Growth by a Mechanism Dependent on LIM-Kinase," Biochemical and Biophysical Research Communications, 2007, vol. 360 (4), pp. 868-873.
Mattingly P.G., "Chemiluminescent 10-Methyl-Acridinium-9(N-Sulphonylcarboxamide) Salts. Synthesis and Kinetics of Light Emission ," Journal of Bioluminescence and Chemiluminescence, 1991, vol. 6 (2), pp. 107-114.
Mautes A.E., et al., "Vascular Events After Spinal Cord Injury: Contribution to Secondary Pathogenesis," Physical Therapy, 2000, vol. 80 (7), pp. 673-687.
McCafferty J., et al., "Phage Antibodies: Filamentous Phage Displaying Antibody Variable Domains," Nature, 1990, vol. 348 (6301), pp. 552-554.
McCapra F., et al., "Chemiluminescence Involving Peroxide Decompositions 5" Photochemistry and Photobiology, 1965, vol. 4 (6), pp. 1111-1121.
McNamara J.O., "Emerging Insights into the Genesis of Epilepsy.," Nature, 1999, vol. 399 (6738 Suppl.), pp. A15-A22.
Meier J., et al., "Extra Neruofilament NF-L Submits Rescue Motor Neuron Disease Caused by Overexpression of the Human NF-H Gene in Mice," Journal of Neuropathology and Experimental neurology, 1999, vol. 58 (10), pp. 1099-1110.
Mendez M.J., et al., "Functional Transplant of Megabase Human Immunoglobulin Loci Recapitulates Human Antibody Response in Mice," Nature Genetics, 1997, vol. 15 (2), pp. 146-156.
Merrifield R.B., et al., "Solid Phase Peptide Synthesis. I. The Synthesis of a Tetrapeptide," Journal of the American Chemical Society, 1963, vol. 85, pp. 2149-2154.
Mey J., et al., "Development of the Visual System of the Chick—A Review," Journal Fur Hirnforschung, 1992, vol. 33 (6), pp. 673-702.
Meyerhardt J.A., et al., "Identification and Characterization of Neogenin, a DCC-Related Gene," Oncogene, 1997, vol. 14 (10), pp. 1129-1136.
Mills C.D., et al., "Strain and Model Differences in Behavioral Outcomes After Spinal Cord Injury in Rat," Journal of Neurotrauma, 2001, vol. 18 (8), pp. 743-756.
Milstein C., et al, "Hybrid Hybridomas and their use in Immunohistochemistry," Nature, 1983, vol. 305 (5934), pp. 537-540.
Mimms L.T., et al., "Discrimination of Hepatitis B Virus (HBV) Subtypes using Monoclonal Antibodies to the PreS1 and PreS2 Domains of the Viral Envelope," Virology, 1990, vol. 176 (2), pp. 604-619.
Ming G.L., et al., "cAMP-Dependent Growth Cone Guidance by Netrin-1," Neuron, 1997, vol. 19 (6), pp. 1225-1235.
Mirakaj V., et al., "Repulsive Guidance Molecule-A (Rgm-A) Inhibits Leukocyte Migration and Mitigates Inflammation," Proceedings of the National Academy of Sciences, 2011, vol. 108 (16), pp. 6555-6560.
Mirakaj V., et al., "The Guidance Receptor Neogenin Promotes Pulmonary Inflammation During Lung Injury," The FASEB Journal, 2012, vol. 26 (4), pp. 1549-1558.
Monahan M.W., et al., "A Rapid Method for the Preparation of Amino Acid Resin Esters for Merrifield Solid-phase Peptide Synthesis," Biopolymers, 1973, vol. 12 (11), pp. 2513-2519.
Monnier P.P., et al., "Rgm is a Repulsive Guidance Molecule for Retinal Axons," Nature, 2002, vol. 419 (6905), pp. 392-395.
Monschau B., et al., "Shared and Distinct Functions of RAGS and ELF-1 in Guiding Retinal Axons," EMBO Journal, 1997, vol. 16 (16), pp. 1258-1267.
Morgan R.A., et al., "Human Gene Therapy," Annual Review of Biochemistry, 1993, vol. 62, 191-217.

(56) References Cited

OTHER PUBLICATIONS

Mori H., et al., "Mass Spectrometry of Purified Amyloid Beta Protein in Alzheimer's Disease," The Journal of Biological Chemistry, 1992, vol. 267 (24), pp. 17082-17086.
Morrison S.L., "Transfectomas Provide Novel Chimeric Antibodies," Science, 1985, vol. 229 (4719), pp. 1202-1207.
Mueller B.K., et al., "The Role of Repulsive Guidance Molecules in the Embryonic and Adult Vertebrate Central Nervous System," Philosophical Transactions of the Royal Society, 2006, vol. 361 (1473), pp. 1513-1529.
Mueller B.K., "Growth Cone Guidance: First Steps Towards a Deeper Understanding," Annual Review of Neuroscience, 1999, vol. 22, pp. 351-388.
Mueller B.K., "RGM, a Repulsive Guidance Molecule, is Involved in Retinal Axon Guidance in Vitro" in: Molecular Basis of Axon Growth and Nerve Pattern Formation, vol. 20, Fujisawa H., ed., Japan Scientific Societies Press, 1997, pp. 215-229.
Muhlhauser J., et al., "VEGF165 Expressed by a Replication-Deficient Recombinant Adenovirus Vector Induces Angiogenesis in Vivo," Circulation Research, 1995, vol. 77 (6), pp. 1077-1086.
Muller B.K., et al., "Chromophore-Assisted Laser Inactivation of a Repulsive Axonal Guidance Molecule," Current Biology : CB, 1996, vol. 6 (11), pp. 1497-1502.
Muller B.K., et al., "In Vitro Experiments on Axonal Guidance and Growth-Cone Collapse," The Journal of Experimental Biology, 1990, vol. 153, pp. 29-46.
Muller B.K., et al., "Molecular inactivation. Spatially and Temporally Defined Molecular Knockouts," Current Biology, 1995, vol. 5 (11), pp. 1255-1256.
Muller B.K., et al., "Novel Gene Families Involved in Neural Pathfinding," Current Opinion in Genetics & Development, 1996, vol. 6 (4), pp. 469-474.
Mulligan R.C., "The Basic Science of Gene Therapy," Science, 1993, vol. 260 (5110), pp. 926-932.
Mullinax R.L., et al., "Expressoin of a Heterodimeric Fab Antibody Protein in One Cloning Step," Bio Techniques 1992, vol. 12 (6), pp. 864-869.
Muramatsu R, "Rgma Modulates T Cell Responses and is Involved in Autoimmune Encephalomyelitis," Nature Medicine, 2011, vol. 17 (4), pp. 488-494.
Murphy W.J., et al., "CD40 Stimulation Promotes Human Secondary Immunoglobulin Responses in HuPBL-SCID Chimeras," Clinical Immunology, 1999, vol. 90 (1), pp. 22-27.
Murphy W.J., et al., "The HuPBL-SCID Mouse as a Means to Examine Human Immune Function in Vivo," Seminars in Immunology, 1996, vol. 8 (4), pp. 233-241.
Nagata A., et al., "In Vivo Quantitative Evaluation of the Rat Retinal Nerve Fiber Layer with Pptical Coherence Tomography," Investigative Ophthalmology & Visual Science, 2009, vol. 50 (6), pp. 2809-2815.
Nakamoto M., et al., "Topographically Specific Effects of Elf-1 on Retinal Axon Guidance in Vitro and Retinal Axon Mapping in Vivo," Cell, 1996, vol. 86 (5), pp. 755-766.
Narang S.A., Tetrahedron, 1983, vol. 39 (1), pp. 3-22.
Nemeth E., et al., "Hepcidin, a Putative Mediator of Anemia of Inflammation, is a Type Ii Acute-Phase Protein," Blood, 2003, vol. 101 (7), pp. 2461-2463.
Neuberger M.S., et al., "Recombinant Antibodies Possessing Novel Effector Functions," Nature, 1984, vol. 312 (5995), pp. 604-608.
Ngo J.T., et al., "Computational Complexity, Protein Structure Prediction, and the Levinthal Paradox," 1994, pp. 491-495.
Nguyen H., et al., "Production of Human Monoclonal Antibodies in SCID Mouse," Microbiology and Immunology, 1997, vol. 41 (12), pp. 901-907.
Niederkofler V., et al., "Hemojuvelin is Essential for Dietary Iron Sensing, and its Mutation Leads to Severe Iron Overload," The Journal of Clinical Investigation, 2005, vol. 115 (8), pp. 2180-2186.
Niederkofler V., et al., "Repulsive Guidance Molecule (Rgm) Gene Function is Required for Neural Tube Closure but not Retinal Topography in the Mouse Visual System," the Journal of Neuroscience : The Official Journal of the Society for Neuroscience, 2004, vol. 24 (4), pp. 808-818.
Nielsen P.E., et al., "Sequence-Selective Recognition of DNA by Strand Displacement with a Thymine-substituted Polyamide," Science, vol. 254 (5037), pp. 1497-1500, 1991.
Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.
Oi V.T., et al., "Chimeric Antibodies,"Bio Techniques, 1986, vol. 4 (3), pp. 314-221.
Oldekamp J., et al., "Expression Pattern of the Repulsive Guidance Molecules RGM A, B and C During Mouse Development," Gene Expression Patterns, 2004, vol. 4 (3), pp. 283-288.
Padlan E.A., "A Possible Procedure for Recucing the Immunogenicity of Antibody Variable Domains While Preserving Their Ligand-Binding Properties," Molecular Immunology, 1991, vol. 28 (4-5), pp. 489-498.
Padlan E.A., et al., "Identification of Specificity-determining Residues in Antibodies," FASEB Journal, 1995, vol. 9 (1), pp. 133-139.
Padlan E.A., et al., "Structure of an Antibody-antigen Complex: Crystal Structure of the HyHEL-10 Fab-lysozyme Complex," Proceedings of the National Academy of Sciences, 1989, vol. 86 (15), pp. 5938-5942.
Papanikolaou G., et al., "Hepcidin in Iron Overload Disorders," Blood, 2005, vol. 105 (10), pp. 4103-4105.
Papanikolaou G., et al., "Mutations in Hfe2 Cause Iron Overload in Chromosome 1q-Linked Juvenile Hemochromatosis," Nature Genetics, 2004, vol. 36 (1), pp. 77-82.
Pawson T., et al., "Assembly of Cell Regulatory Systems through Protein Interaction Domains," Science, 2003, vol. 300 (5618), pp. 445-452.
Pearson W.R., et al., "Improved Tools for Biological Sequence Comparison," Proceedings of the National Academy of Sciences, 1988, vol. 85 (8), pp. 2444-2448.
Persic L., et al., "An Integrated Vector System for the Eukaryotic Expression of Antibodies or their Fragments After Selection from Phage Display Libraries," Gene, 1997, vol. 187 (1), pp. 9-18.
Picker A., et al., "Requirement for the Zebrafish Mid-Hindbrain Boundary in Midbrain Polarisation, Mapping and Confinement of the Retinotectal Projection," Development, 1999, vol. 26 (13), pp. 2967-2978.
Pietrangelo A., "Hepcidin in Human Iron Disorders: Therapeutic Implications," Journal of Hepatology, 2011, vol. 54 (1), pp. 173-181.
Pietta P.G., et al., "Amide Protection and Amide Supports in Solid-phase Peptide Synthesis," Chemical Communications, 1970, pp. 650-651.
Poljak R.J., "Production and Structure of Diabodies," Structure, 1994, vol. 2 (12), pp. 1121-1123.
Postler E., et al., "Expression of the S-100 Proteins MRP-8 and -14 in Ischemic Brain Lesions," Glia, 1997, vol. 19 (1), pp. 27-34.
Powell K.T., et al., "Gel Microdroplets and Flow Cytometry Rapid Determination of Antibody Secretion by Individual Cells within a Cell Population," Biotechnology, 1990, vol. 8 (4), pp. 333-337.
Presta L.G., et al., "Humanization of an Antibody Directed Against IgE," Journal of Immunology, 1993, vol. 151 (5), pp. 2623-2632.
Puschel A.W., et al., "Murine Semaphorin D/collapsin is a Member of a Diverse Gene Family and Creates Domains Inhibitory for Axonal Extension," Neuron, 1995, vol. 14 (5), pp. 941-948.
Rajagopalan S., et al., "Neogenin Mediates the Action of Repulsive Guidance Molecule," Nature Cell Biology, 2004, vol. 6 (8), pp. 756-762.
Raper J.A., et al., "The Enrichment of a Neuronal Growth Cone Collapsing Activity from Embryonic Chick Brain," Neuron, vol. 4 (1), pp. 21-29, 1990.
Razavi Z., et al., "Stable and Versatile Active Acridinium Esters I ," Luminescence, 2000, vol. 15 (4), pp. 239-244.
Razavi Z., et al., "Stable and Versatile Active Acridinium Esters II ," Luminescence, 2000, vol. 15, pp. 245-249.

(56) References Cited

OTHER PUBLICATIONS

Reifers F., et al., "FGF8 is Mutated in Zebrafish Acerebellar (ACE) Mutants and is Required for Maintenance of Midbrain-Hindbrain Boundary Development and Somitogenesis," Development, 1998, vol. 125 (13), pp. 2381-2395.
Reisner Y., et al., "The Trimera Mouse: Generating Human Monoclonal Antibodies and an Animal Model for Human Diseases," Trends in Biotechnology, 1998, vol. 16 (6), pp. 242-246.
Resch E., et al., "Long Signal Peptides of RGMa and DCBLD2 are Dissectible into Subdomains According to the NtraC Model," Molecular BioSystems, 2011, vol. 7 (3), pp. 942-951.
Riechmann L., et al., "Reshaping Human Antibodies for Therapy," Nature, 1988, vol. 332 (6162), pp. 323-327.
Roberts R.W., et al., "RNA-peptide Fusions for the in Vitro Selection of Peptides and Proteins," Proceedings of the National Academy of Sciences, 1997, vol. 94 (23), pp. 12297-12302.
Robinson C., "Gene Therapy—Proceeding from Laboratory to Clinic," Tibtech, 1993, vol. 11 (5), pp. 155.
Robinson J.R., Sustained and Controlled Release Drug Delivery Systems, Marcel Dekker, Inc., 1978, Table of Contents.
Roes J., et al., "Mouse Anti-mouse IgD Monoclonal Antibodies Generated in IgD-deficient Mice," Journal of Immunological Methods, 1995, vol. 183 (2), pp. 231-237.
Roguska M.A., et al., "Humanization of Murine Monoclonal Antibodies through Variable Domain Resurfacing," Proceedings of the National Academy of Sciences, 1994, vol. 91 (3), pp. 969-973.
Rosen C.A., Therapeuticprotein HARMJ38—Seq ID No. 1853 Database EMBL/GENBANK/DDBJ Jun. 15, 2006, XP002468529.
Routbort M.J., et al., "Seizures, Cell Death, and Mossy Fiber Sprouting in Kainic Acid-Treated organotypic Hippocampal Cultures," Neuroscience, 1999, vol. 94 (3), pp. 755-765.
Rudikoff S., et al., "Single Amino Acid Substitution Altering Antigen-Binding Specificity," Proceedings of the National Academy of Sciences of the United States of America, 1982, vol. 79 (6), pp. 1979-1983.
Ruoslahti E., "RGD and Other Recognition Sequences for Integrins," Annual Review of Cell and Developmental Biology, 1996, vol. 12, pp. 697-715.
Saeed O., et al., "Pharmacological Suppression of Hepcidin Increases Macrophage Cholesterol Efflux and Reduces Foam Cell Formation and Atherosclerosis," Arteriosclerosis, Thrombosis, and Vascular Biology, 2012, vol. 32 (2), pp. 299-307.
Saltzman W.M., et al., "Transport Rates of Proteins in Porous Materials with Known Microgeometry," Biophysical Journal, 1989, vol. 55 (1), pp. 163-171.
Samad T.A., et al., "Dragon, a Bonemorphogenetic Protein Co-Receptor," Journal of Biological Chemistry, 2005, vol. 280 (14), pp. 14122-14129.
Sambrook J., "Expression of Cloned Genes in *Escherichia coli*" in: Molecular Cloning, 2nd Edition, Cold Spring Harbor Laboratory Press, 1989, Chap. 17.2-17.9.
Sandhu J.S., et al., "The use of SCID Mice in Biotechnology and as a Model for Human Disease," Critical Reviews in Biotechnology, 1996, vol. 16 (1), pp. 95-118.
Santoro S.W., et al., "A General Purpose RNA-Cleaving Dna Enzyme," Proceedings of the National Academy of Sciences, 1997, vol. 94 (9), pp. 4262-4266.
Saudek C.D., et al., "A Preliminary Trial of the Programmable Implantable Medication System for Insulin Delivery," The New England Journal of Medicine, 1989, vol. 321 (9), pp. 574-579.
Sawai H., et al., "Direct Production of the Fab Fragment Derived from the Sperm Immobilizing Antibody using Polymerase Chain Reaction and Cdna Expression Vectors," American Journal of Reproductive Immunology, 1995, vol. 34 (1), pp. 26-34.
Schaffar G., et al., "Lim-only Protein 4 Interacts Directly with the Repulsive Guidance Molecule a Receptor Neogenin," Journal of Neurochemistry, 2008, vol. 107 (2), pp. 418-431.
Schaper W., et al., "Molecular Mechanisms of Coronary Collateral Vessel Growth," Circulation Research, 1996, vol. 79 (5), pp. 911-919.
Schaper W., et al., "Therapeutic Targets in Cardiovascular Disorders," Current Opinion in Biotechnology, 1996, vol. 7 (6), pp. 635-640.
Schier R., et al., "Identification of Functional and Structural Amino-Acid Residues by Parsimonious Mutagenesis," Gene, 1996, vol. 169 (2), 147-155.
Schmidtmer J., et al., "Isolation and Expression Pattern of Three Mouse Homologues of Chick Rgm," Gene Expression Patterns, 2004, vol. 4 (1), pp. 105-110.
Schnell L., et al., "Axonal Regeneration in the Rat Spinal Cord Produced by an Antibody Against Myelin-Associated Neurite Growth Inhibitors," Nature, 1990, vol. 343 (6255), pp. 269-272.
Schnichels S., et al., "Gene Expression of the Repulsive Guidance Molecules/Neogenin in the Developing and Mature Mouse Visual System: C57BL/6J vs. the Glaucoma Model DBA/2J," Gene Expression Patterns, 2007, vol. 8 (1), pp. 1-11.
Schnichels S., et al., "RGMA and Neogenin Protein Expression are influenced by Lens Injury following Optic Nerve Crush in the Rat Retina," Graefe's Archive for Clinical and Experimental Ophthalmology, 2012, vol. 250 (1), pp. 39-50.
Schultz L.D., et al., "Expression and Secretion in Yeast of a 400-kDa Envelope Glycoprotein Derived from Epstein-Barr Virus," Gene, 1987, vol. 54 (1), pp. 113-123.
Schwab J.M., et al., "Central Nervous System Injury-Induced Repulsive Guidance Molecule Expression in the Adult Human Brain," Archives of Neurology, 2005, vol. 62 (10), pp. 1561-1568.
Schwab J.M., et al., "Selective Accumulation of Cyclooxygenase-1-Expressing Microglial Cells/Macrophages in Lesions of Human Focal Cerebral Ischemia," Acta Neuropathology, 2000, vol. 99 (6), pp. 609-614.
Schwab J.M., et al., "Spinal Cord Injury-Induced Lesional Expression of the Repulsive Guidance Molecule (RGM)," The European Journal of Neuroscience, 2005, vol. 21 (6), pp. 1569-1576.
Seed B., "An LFA-3 cDNA Encodes a Phospholipid-Linked Membrane Protein Homologous to its Receptor CD2," Nature, 1997, vol. 329 (6142), pp. 840-842.
Sefton M.V., et al., "Implantable Pumps," Critical Reviews in Biomedical Engineering, 1987, vol. 14 (3), pp. 201-240.
Serafini T., et al., "Netrin-1 Is Required for Commissural Axon Guidance in the Developing Vertebrate Nervous System," Cell, 1996, vol. 87 (6), pp. 1001-1014.
Setoguchi T., et al., "Treatment of Spinal Cord Injury by Transplantation of Fetal Neural Precursor Cells Engineered to Express BMP inhibitor," Experimental Neurology, 2004, vol. 189 (1), pp. 33-44.
Severyn C.J., et al., "Molecular Biology, Genetics and Biochemistry of the Repulsive Guidance Molecule Family," Biochemical Journal, 2009, vol. 422 (3), pp. 393-403.
Shapiro G.S., et al., "DNA Target Motifs of Somatic Mutagenesis in Antibody Genes," Critical Reviews in Immunology, 2002, vol. 22 (3), pp. 183-200.
Sharp P.A., "RNAi and Double-Strand RNA," Genes & Development, 1999, vol. 13 (2), pp. 139-141.
Sherwood J.K., et al., "Controlled Antibody Delivery Systems," Biotechnology, 1992, vol. 10 (11), pp. 1446-1449.
Shields R.L., et al., "Lack of Fucose on Human IgG1 N-Linked Oligosaccharide Improves Binding to Human Fcgamma RIII and Antibody-Dependent Cellular Toxicity," The Journal of Biological Chemistry, 2002, vol. 277 (30), pp. 26733-26740.
Shoemaker L.D., et al., "Identification of Differentially Expressed Proteins in Murine Embryonic and Postnatal Cortical Neural Progenitors," PLoS One, 2010, vol. 5 (2), pp. e9121.
Shu L., et al., "Secretion of a Single-Gene-Encoded Immunoglobulin from Myeloma Cells," Proceedings of the National Academy of Sciences, 1993, vol. 90 (17), pp. 7995-7999.
Sims M.J., et al., "A Humanized CD18 Antibody can Block Function without Cell Destruction," Journal of Immunology, 1993, vol. 151 (4), pp. 2296-2308.
Skerra A., et al., "Assembly of a Functional Immunoglobulin Fv Fragment in *Escherichia coli*," Science, 1988, vol. 240 (4855), pp. 1038-1041.
Skolnick J., et al., "From Genes to Protein Structure and Function: Novel Applications of Computational Approaches in the Genomic Era," Trends in Biotechnology, 2000, vol. 18 (1), pp. 34-39.

(56) References Cited

OTHER PUBLICATIONS

Smith D.B., et al., "Single-Step Purification of Polypeptides Expressed in *Escherichia coli* as Fusions with Glutathione S-Transferase," Gene, 1988, vol. 67 (1), pp. 31-40.
Smith G. E., et al., "Production of human beta interferon in insect cells infected with a baculovirus expression vector", Mol Cell Biol., 1983, 3 (12), 2156-2165.
Smith T.F., et al., "The Challenges of Genome Sequence Annotation or "The Devil Is in the Details"," Nature Biotechnology, 1997, vol. 15 (12), pp. 1222-1223.
Smithson S.L., et al., "Molecular Analysis of the Heavy Chain of Antibodies that Recognize the Capsular Polysaccharide of Neisseria Meningitidis in hu-PBMC Reconstituted SCID Mice and in the Immunized Human Donor," Molecular Immunology, 1999, vol. 36 (2), pp. 113-124.
Song Y.K., et al., "Antibody Mediated Lung Targeting of Long-Circulating Emulsions," PDA Journal of Pharmaceutical Science & Technology, 1995, vol. 50 (6), pp. 372-377.
Sperry R.W., "Chemoaffinity in the orderly Growth of Nerve Fiber Patterns and Connections," Proceedings of the National Academy of Sciences, 1963, vol. 50, pp. 703-710.
Staerz U.D., et al., "Hybrid Antibodies Can Target Sites for Attack by T Cells," Nature, 1985, vol. 314 (6012), pp. 628-631.
Stahl B., et al., "Biochemical Characterization of a Putative Axonal Guidance Molecule of the Chick Visual System," Neuron, 1990, vol. 5 (5), pp. 735-743.
Steenbakkers P.G., et al., "Efficient Generation of Monoclonal Antibodies from Preselected Antigen-Specific B Cells. Efficient Immortalization of Preselected B Cells," Molecular Biology Reports, 1994, vol. 19 (2), pp. 125-134.
Steinecke P., et al., "Ribozymes," Methods in Cell Biology, 1995, vol. 50, pp. 449-460.
Steward O., et al., "A Re-assessment of the Effects of a Nogo-66 Receptor Antagonist on Regenerative Growth of Axons and Locomotor Recovery After Spinal Cord Injury in Mice," Experimental Neurology, 2008, vol. 209 (2), pp. 446-468.
Stokes B.T., et al., "Experimental Modelling of Human Spinal Cord Injury: a Model that Crosses the Species Barrier and Mimics the Spectrum of Human Cytopathology," Spinal Cord, 2002, vol. 40 (3), pp. 101-109.
Stoll G., et al., "Inflammation and Glial Responses in Ischemic Brain Lesions," Progress in Neurobiology, 1998, vol. 56 (2), pp. 149-171.
Streit W.J., et al., "'Reactive Microgliosis," Progress in Neurobiology, 1999, vol. 57 (6), pp. 563-581.
Studier F.W., et al., "Use of T7 RNA Polymerase to Direct Expression of Cloned Genes," Methods in Enzymology, 1990, vol. 185, pp. 60-89.
Studnicka G.M., et al., "Human-Engineered Monoclonal Antibodies Retain Full Specific Binding Activity by Preserving Non-CDR Complementarity-Modulating Residues," Protein Engineering, 1994, vol. 7 (6), pp. 805-814.
Suda M., et al., "Peptides Derived from Repulsive Guidance Molecule Act As Antagonists," Biochemical and Biophysical Research Communications, 2008, vol. 371 (3), pp. 501-504.
Sutcliffe J.G., et al., "Antibodies that React with Predetermined Sites on Proteins," Science, 1983, vol. 219 (4585), pp. 660-666.
Takeda S., et al., "Construction of Chimaeric Processed Immunoglobulin Genes Containing Mouse Variable and Human Constant Region Sequences," Nature, 1985, vol. 314 (6010), pp. 452-454.
Talac R., et al., "Animal Models of Spinal Cord Injury for Evaluation of Tissue Engineering Treatment Strategies," Biomaterials, 2004, vol. 25 (9), pp. 1505-1510.
Tanelian D.L., et al., "Semaphorin III Can Repulse and Inhibit Adult Sensory Afferents in Vivo," Nature Medicine, 1997, vol. 3 (12), pp. 1398-1401.
Tassew N.G., et al., "Intraretinal RGMa is Involved in Retino-Tectal Mapping," Molecular and Cellular Neuroscience, 2008, vol. 37 (4), pp. 761-769.
Tassew N.G., et al., "Sustained in Vivo Inhibition of Protein Domains Using Single-Chain Fv Recombinant Antibodies and its Application to Dissect RGMa Activity on Axonal Outgrowth," Journal of Neuroscience, 2009, vol. 29 (4), pp. 1126-1131.
Taylor L.D., et al., "A Transgenic Mouse that Expresses a Diversity of Human Sequence Heavy and Light Chain Immunoglobulins," Nucleic Acids Research, 1992, vol. 20 (23), pp. 6287-6295.
Terry R.D., et al., "Senile Dementia of the Alzheimer Type Without Neocortical Neurofibrillary Tangles," Journal of Neuropathology & Experimental Neurology, 1987, vol. 46 (3), pp. 262-268.
Tessier-Lavigne M., et al., "The Molecular Biology of Axon Guidance," Science, 1996, vol. 274 (5290), pp. 1123-1133.
Tolstoshev P., "Gene Therapy, Concepts, Current Trials and Future Directions," Annual Review of Pharmacology and Toxicology, 1993, vol. 32, pp. 573-596.
Umana P., et al., "Engineered Glycoforms of an Antineuroblastoma IgG1 with Optimized Antibody-dependent Cellular Cytotoxic Activity," Nature Biotechnology, 1999, vol. 17 (2), pp. 176-180.
Uniport, "A1L187_HUMAN", Accession No. A1L187, Feb. 6, 2007.
Uniport, Hemojuvelin Variant (R326X), EBI Accession No. ADU04761, Jan. 13, 2005.
Uniport, Human Polypeptide Seq ID No. 1934, EBI Accession No. ABB89558, May 24, 2002.
Uniport, Novel Protein Sequence #944, EBI Accession No. ADQ65971, Oct. 7, 2004.
Uniprpot, Human Protein Encoded by Full Length cDNA Clone Seq ID No. 3867, EBI Accession No. ADL31834, May 20, 2004.
Urist M.R., et al., "Osteoporosis: A Bone Morphogenetic Protein Auto-Immune Disorder," Progress in Clinical and Biological Research, 1985, vol. 187, pp. 77-96.
Urlaub G., et al., "Isolation of Chinese Hamster Cell Mutants Deficient in Dihydrofolate Reductase Activity," Proceedings of the National Academy of Sciences, 1980, vol. 77 (7), pp. 4216-4220.
Vajdos F.F., et al., "Comprehensive Functional Maps of the Antigen-binding Site of an Anti-ErbB2 Antibody Obtained with Shotgun Scanning Mutagenesis," Journal of Molecular Biology, 2002, vol. 320 (2), pp. 415-428.
Van Den Hondel., "Gene Transfer Systems and Vector Development for Filamentous Fungi" in: Applied Molecular Genetics of Fungi, J.F. Peberdy et al., eds., C.A.M.J.J. & Punt, P.J., 1991, pp. 1-28.
Verhoeyen M., et al., "Reshaping Human Antibodies: Grafting an Antilysozyme Activity ," Science, 1988, vol. 239, pp. 1534-1536.
Verma I.M., et al., "Gene Therapy—Promises, Problems and Prospects," Nature, 1997, vol. 389 (6648), pp. 239-242.
Vielmetter J., et al., "In Vitro Assay to Test Differential Substrate Affinities of Growing Axons and Migratory Cells," Experimental Brain Research, 1990, vol. 81 (2), pp. 283-287.
Vielmetter J., et al., "Neogenin, An Avian Cell Surface Protein Expressed During Terminal Neuronal Differentiation, Is Closely Related to the Human Tumor Suppressor Molecule Deleted in Colorectal Cancer," The Journal of Cell Biology, 1994, vol. 127 (6 Pt 2), pp. 2009-2020.
Voet., Biochemistry, Second Edition, John Wiley & Sons, Inc, 1995, pp. 1361.
Wahl J., et al., "Ephrin-A5 Induces Collapse of Growth Cones by Activating Rho and Rho Kinase," Journal of Cell Biology, 2000, vol. 149 (2), pp. 263-270.
Wallemacq P.E., et al., "Evaluation of the New AxSYM Cyclosporine Assay: Comparison with TDx Monoclonal Whole Blood and Emit Cyclosporine Assays," Clinical Chemistry, 1999, vol. 45 (3), pp. 432-435.
Wallick S.C., et al., "Glycosylation of a VH Residue of a Monoclonal Antibody against Alpha (1-6) Dextran Increases its Affinity for Antigen," Journal of Experimental Medicine, 1988, vol. 168 (3), pp. 1099-1109.
Walter J., et al., "Avoidance of Posterior Tectal Membranes by Temporal Retinal Axons," Development, 1987, vol. 101 (4), pp. 909-913.
Walter J., et al., "Axonal Guidance by an Avoidance Mechanism," Journal de Physiologie, 1990, vol. 84 (1), pp. 104-110.
Walter J., et al., "Recognition of Position-Specific Properties of Tectal Cell Membranes by Retinal Axons in Vitro," Development, 1987, vol. 101 (4), pp. 685-696.

(56) References Cited

OTHER PUBLICATIONS

Wang H., et al., "Netrin-3, A Mouse Homolog of Human NTN2L, is Highly Expressed in Sensory Ganglia and Shows Differential Binding to Netrin Receptors," The Journal of Neuroscience, 1999, vol. 19 (12), pp. 4938-4947.
Wang Q., et al., "Second-Generation Adenovirus Vectors," Nature Medicine, 1996, vol. 2 (6), pp. 714-716.
Ward E.S., et al., "Binding Activities of a Repertoire of Single Immunoglobulin Variable Domains Secreted from *Escherichia coli*," Nature, 1989, vol. 341 (6242), pp. 544-546.
Weinstein D.A., et al., "Inappropriate Expression of Hepcidin is Associated with Iron Refractory Anemia: Implications for the Anemia of Chronic Disease," Blood, 2002, vol. 100 (10), pp. 3776-3778.
Weiss G., et al., "Anemia of Chronic Disease," The New England Journal of Medicine, 2005, vol. 352 (10), pp. 1011-1023.
Wells D.A., et al., "High Throughput Bioanalytical Sample Preparation Methods and Automation Strategies," Progress in Pharmaceutical and Biomedical Analysis, 2003, Table of Contents.
Wells J.A., "Additivity of Mutational Effects in Proteins," Biochemistry, 1990, vol. 29 (37), pp. 8509-8517.
Wen L., et al., "Limiting Dilution Assay for Human B Cells Based on their Activation by Mutant EL4 Thymoma Cells: Total and Antimalaria Responder B Cell Frequencies," European Journal of Immunology, 1987, vol. 17 (6), pp. 887-892.
Wilbur W.J., et al., "Rapid Similarity Searches of Nucleic Acid and Protein Data Banks," Proceedings of the National Academy of Sciences, 1983, vol. 80 (3), pp. 726-730.
Wilm M., et al., "Analytical Properties of the Nanoelectrospray Ion Source," Analytical Chemistry, 1996, vol. 68 (1), pp. 1-8.
Wilm M., et al., "Femtomole Sequencing of Proteins from Polyacrylamide Gels by Nano-Electrospray Mass Spectrometry," Nature, 1996, vol. 379 (6564), pp. 466-469.
Winnaker E.L., From Genes to Clones: Introduction to Gene Technology, VCH Publishers, 1987, Table of Contents.
Wisniewski H.M., et al., "Reexamination of the Pathogenesis of the Senile Plaque", in: Progress in Neuropathology, Grupe and Stratton, N.Y, Zimmerman H.M., ed., vol. 2, 1973, pp. 1-26.
Wright A., et al., "Antibody Variable Region Glycosylation: Position Effects on Antigen Binding and Carbohydrate Structure," The EMBO Journal, 1991, vol. 10 (10), pp. 2717-2723.
Wu C., et al., "Simultaneous Targeting of Multiple Disease Mediators by a Dual-Variable-Domain Immunoglobulin," Nature Biotechnology, 2007, vol. 25 (11), pp. 1290-1297.
Wu G., et al., "Delivery Systems for Gene Therapy," Biotherapy, 1991, vol. 3 (1), pp. 87-95.
Wu G.Y., et al., "Receptor-mediated in Vitro Gene Transformation by a Soluble DNA Carrier System," Journal of Biological Chemistry, 1987, vol. 262 (10), pp. 4429-4432.
Wu H., et al., "Humanization of a Murine Monoclonal Antibody by Simultaneous Optimization of Framework and Cdr Residues," Journal of Molecular Biology, 1999, vol. 294 (1), pp. 151-162.
Xia Y., et al., "Dragon (Repulsive Guidance Molecule B) Inhibits IL-6 Expression in Macrophages," Journal of Immunology, 2011, vol. 186 (3), pp. 1369-1376.
Xia Y., et al., "Localization and Action of Dragon (repulsive guidance molecule b), a Novel Bone Morphogenetic Protein Coreceptor, throughout the Reproductive Axis," Endocrinology, 2005, vol. 146 (8), pp. 3614-3621.
Xia Y., et al., "Repulsive Guidance Molecule RGMa Alters Utilization of Bone Morphogenetic Protein (BMP) Type II Receptors by BMP2 and BMP4," Journal of Biological Chemistry, 2007, vol. 282 (25), pp. 18129-18140.
Yamashita T., et al., "Neogenin and Repulsive Guidance Molecule Signaling in the Central Nervous System," Current Opinion in Neurobiology, 2007, vol. 17 (1), pp. 29-34.
Yang X.D., et al., "Fully Human Anti-Interleukin-8 Monoclonal Antibodies: Potential Therapeutics for the Treatment of Inflammatory Disease States," Journal of Leukocyte Biology, 1999, vol. 66 (3), pp. 401-410.
Yatscoff R.W., et al., "Abbott TDx Monoclonal Antibody Assay Evaluated for Measuring Cyclosporine in Whole Blood," Clinical Chemistry, 1990, vol. 36 (11), pp. 1969-1973.
Yeh M.Y., et al., "A Cell-surface Antigen Which is Present in the Ganglioside Fraction and Shared by Human Melanomas," International Journal of Cancer, 1982, vol. 29 (3), pp. 269-275.
Yeh M.Y., et al., "Cell Surface Antigens of Human Melanoma Identified by Monoclonal Antibody," Proceedings of the National Academy of Sciences, 1979, vol. 76 (6), pp. 2927-2931.
Yelton D.E., et al., "Affinity Maturation of the BR96 Anti-Carcinoma Antibody by Codon-Based Mutagenesis," The Journal of Immunology, 1995, vol. 155 (4), pp. 1994-2004.
Yoshinari K., et al., "Differential Effects of Immunosuppressants and Antibiotics on Human Monoclonal Antibody Production is SCID Mouse Ascites by Five Heterohybridomas," Hybridoma, 1998, vol. 17 (1), pp. 41-45.
Yu T.W., et al., "Dynamic Regulation of Axon Guidance," Nature Neuroscience, 2001, Suppl. 4, pp. 1169-1176.
Zapata G., et al., "Engineering Linear F(ab')2 Fragments for Efficient Production in *Escherichia coli* and Enhanced Antiproliferative Activity," Protein Engineering, 1995, vol. 8 (10), pp. 1057-1062.
Zhang G., et al., "Electrical Stimulation of Olfactory Bulb Downregulates RGMa Expression After Ischemia/Reperfusion Injury in Rats," Brain Research Bulletin, 2011, vol. 86 (3-4), pp. 254-261.

\* cited by examiner

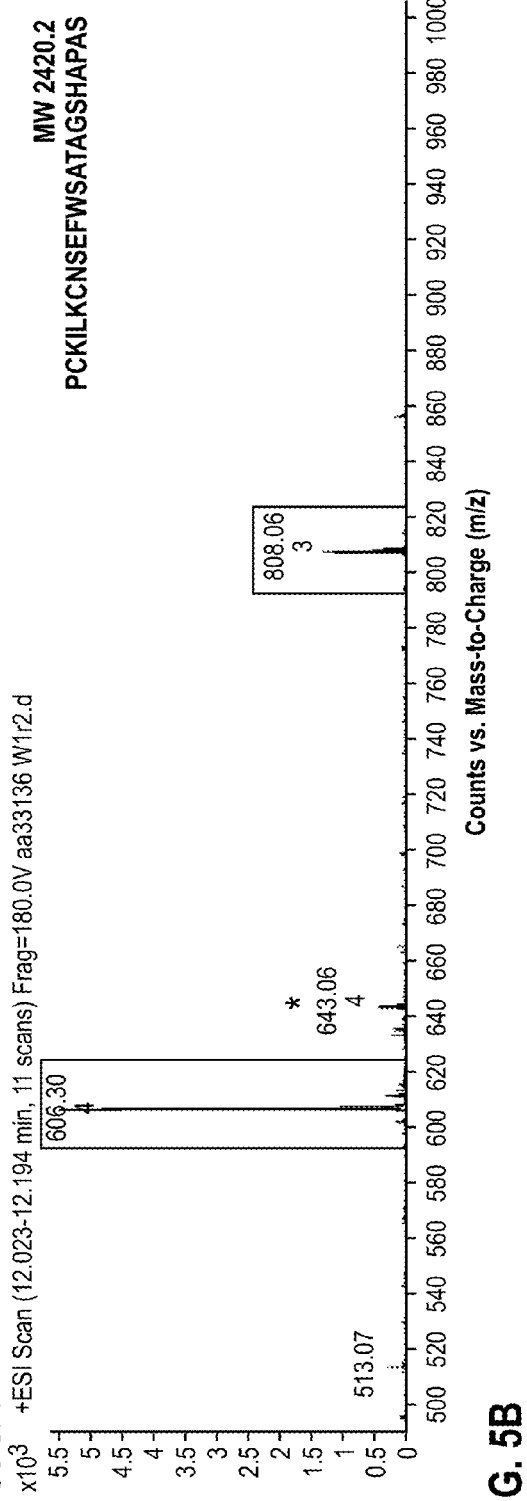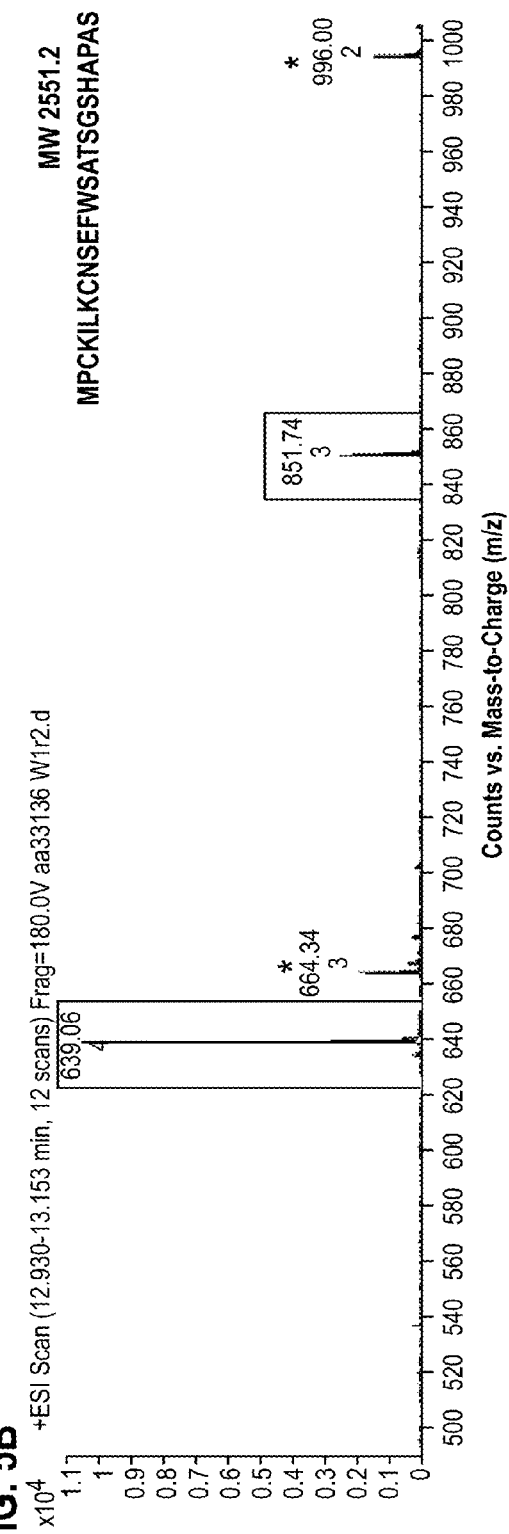

hIgG 10 mg/kg brain →

AE12-1 1 mg/kg brain → h5F9.23 1 mg/kg brain →

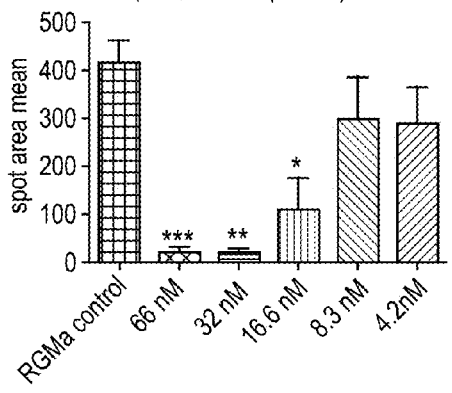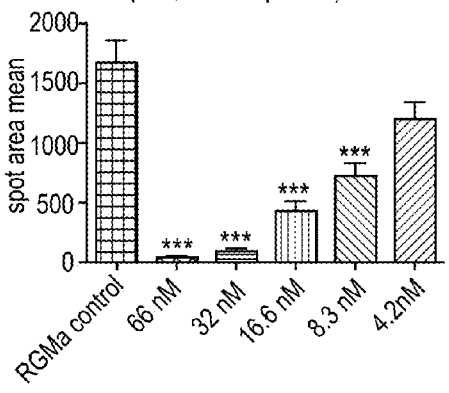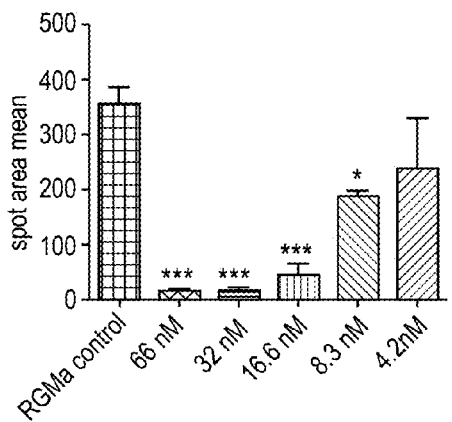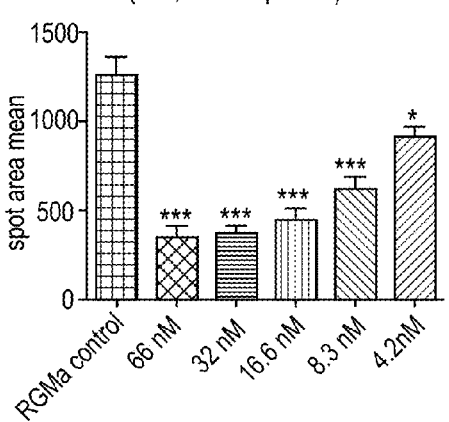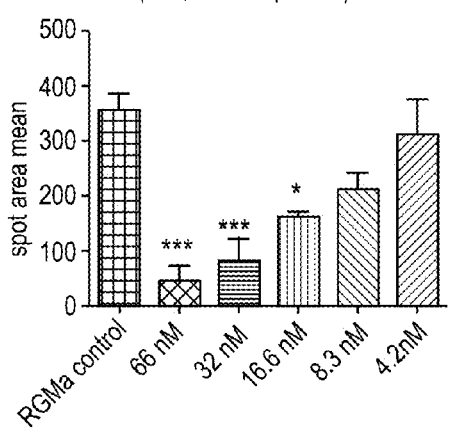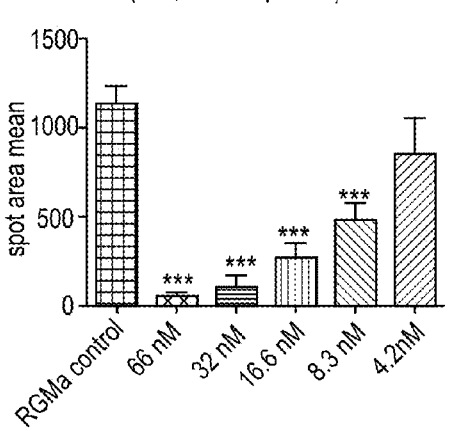

RGMa-Fc binding on SH-SY5Y cells
AE 12-1
2011-12-21

RGMa-Fc binding on SH-SY5Y cells
AE 12-1 F
2011-12-21

RGMa-Fc binding on SH-SY5Y cells
AE 12-1 H
2011-12-21

RGMa-Fc binding on SH-SY5Y cells
AE 12-1 I
2011-12-21

RGMa-Fc binding on SH-SY5Y cells
AE 12-1 L
2011-12-21

RGMa-Fc binding on SH-SY5Y cells
AE 12-1 K
2011-12-21

RGMa-Fc binding on SH-SY5Y cells
AE 12-1 V
2011-12-21

RGMa-Fc binding on SH-SY5Y cells
AE 12-1 Y
2011-12-06

RGMA-(47-127)
rat Hc neurons 3DIV
(2011-09-23)
r5F9

RGMA-(47-127)
rat Hc neurons 3DIV
(2011-09-23)
AE 12-1

RGMA-(47-127)
rat Hc neurons 3DIV
(2011-09-23)
AE 12-6

Regeneration
GAP-43**

Reyellination
MBP**

Inflammation
CD68**

COMPOSITION AND METHOD FOR THE DIAGNOSIS AND TREATMENT OF DISEASES ASSOCIATED WITH NEURITE DEGENERATION

CROSS-REFERENCE TO RELATED APPLICATIONS

This is a continuation of U.S. patent application Ser. No. 13/750,846, filed on Jan. 25, 2013. U.S. patent application Ser. No. 13/750,846 claims priority to U.S. Provisional Patent Application No. 61/591,324, filed on Jan. 27, 2012, and incorporates the entire contents by reference.

SEQUENCE LISTING

The instant application contains a Sequence Listing which has been submitted in ASCII format via EFS-Web and is hereby incorporated by reference in its entirety. Said ASCII copy, created on Jan. 25, 2013, is named 11423USO.txt and is 100,936 bytes in size.

FIELD OF THE INVENTION

The present invention relates to antibodies and methods of using the antibodies to treat and diagnose diseases associated with neurite degeneration, such as multiple sclerosis.

BACKGROUND

The early stages of many neurodegenerative diseases are characterized by neurite damage and compromised synaptic function. Neurite degeneration often leads to neuronal cell death and can impair the conduction of signals in the affected nerves, causing impairment in sensation, movement, cognition, or other functions depending on which nerves are involved. Neurite degeneration is also a pathological hallmark of multiple sclerosis ("MS"). MS is an autoimmune, neurodegenerative disease that affects about 350,000 people in the United States and is a major cause of nervous system disability or death in young adults. A common clinical condition in humans afflicted with MS is the degenerative formation of neural lesions resulting from extensive degradation of the myelin sheaths surrounding the axons of the neurons, and eventual degradation of the axons themselves. The demyelination that occurs in MS is believed to be initiated by the attack of protease enzymes on three major neurological proteins: myelin basic protein (MBP), proteo-lipid protein (PLP) and myelin oligodendrocyte glycoprotein (MOG). Mechanistically, MS is an inflammatory demyelinating disease that is at least partially caused by an autoimmune response to myelin degradation products. Recent studies have emphasized the role of neurite and axonal injury in addition to the well known demyelation and inflammatory mechanisms.

Patients typically are diagnosed as having a neurite degenerative disease based on a combination of patient history and neurologic examination, including magnetic resonance imaging (MRI) of the brain and spinal cord, electrodiagnostic procedures (e.g., evoked potential tests such as visual evoked potentials, brain stem auditory evoked potentials, or somatosensory evoked potentials), and lumbar puncture to look for evidence of immunoglobulin synthesis in the cerebrospinal fluid.

Currently, there is no cure for diseases associated with neurite degeneration, so treatment typically involves management of symptoms and treatment of the frequency and severity of relapses.

SUMMARY OF THE INVENTION

In one aspect, the present invention is directed to an isolated antibody or antibody fragment thereof which binds to Repulsive Guidance Molecule a ("RGMa"). The antibody comprises a domain or region selected from (a) a variable heavy domain region comprising the amino acid sequence of SEQ ID NO:1, (b) a variable light domain region comprising the amino acid sequence of SEQ ID NO:5, (c) a variable heavy domain region comprising the amino acid sequence of SEQ ID NO:9, (d) a variable light domain region comprising the amino acid sequence of SEQ ID NO:13, (e) a variable heavy domain region comprising the amino acid sequence of SEQ ID NO:17, (f) a variable light domain region comprising the amino acid sequence of SEQ ID NO:21, (g) a variable heavy domain region comprising the amino acid sequence of SEQ ID NO:25, (h) a variable light domain region comprising the amino acid sequence of SEQ ID NO:29, (i) a variable heavy domain region comprising the amino acid sequence of SEQ ID NO:33, (j) a variable light domain region comprising the amino acid sequence of SEQ ID NO:37; (k) a variable heavy domain region comprising the amino acid sequence of SEQ ID NO:41; (l) a variable light domain region comprising the amino acid sequence of SEQ ID NO:45; (m) a variable heavy domain region comprising the amino acid sequence of SEQ ID NO:49; (n) a variable light domain region comprising the amino acid sequence of SEQ ID NO:53, (o) a variable heavy domain region comprising the amino acid sequence of SEQ ID NO:57, (p) a variable light domain region comprising the amino acid sequence of SEQ ID NO:61, (q) a variable heavy domain region comprising the amino acid sequence of SEQ ID NO:152, (r) a variable light domain region comprising the amino acid sequence of SEQ ID NO:95, (s) a variable heavy domain region comprising the amino acid sequence of SEQ ID NO:99, (t) a variable light domain region comprising the amino acid sequence of SEQ ID NO:103, (u) a variable heavy domain region comprising the amino acid sequence of SEQ ID NO:107, (v) a variable light domain region comprising the amino acid sequence of SEQ ID NO:111, (w) a variable heavy domain region comprising the amino acid sequence of SEQ ID NO:115, (x) a variable light domain region comprising the amino acid sequence of SEQ ID NO:119, (y) a variable heavy domain region comprising the amino acid sequence of SEQ ID NO:123, (z) a variable light domain region comprising the amino acid sequence of SEQ ID NO:127, (aa) a variable heavy domain region comprising the amino acid sequence of SEQ ID NO:131, (bb) a variable light domain region comprising the amino acid sequence of SEQ ID NO:135, (cc) a variable light domain region comprising the amino acid sequence of SEQ ID NO:67, (dd) a variable light domain region comprising the amino acid sequence of SEQ ID NO:68, (ee) a variable light domain region comprising the amino acid sequence of SEQ ID NO:69 (ff) a variable light domain region comprising the amino acid sequence of SEQ ID NO:70, (gg) a variable light domain region comprising the amino acid sequence of SEQ ID NO:71, (hh) a variable light domain region comprising the amino acid sequence of SEQ ID NO:72, (ii) a variable light domain region comprising the amino acid sequence of SEQ ID NO:73, (jj) a variable heavy domain comprising the amino acid sequence of SEQ ID NO:1 and a variable light domain region comprising the amino acid sequence of SEQ ID NO:5, (kk) a variable heavy domain comprising the amino acid sequence of SEQ ID NO:9 and a variable light domain region comprising the amino acid sequence of SEQ ID NO:13, (ll) a variable heavy domain comprising the amino acid sequence of SEQ ID NO:17 and a variable light domain region comprising the amino acid sequence of SEQ ID NO:21, (mm) a variable heavy domain comprising the amino acid sequence of SEQ ID NO:25 and a variable light domain region comprising the amino acid sequence of SEQ ID NO:29, (nn) a variable heavy domain comprising the amino acid sequence of SEQ ID NO:33 and a variable light domain region comprising the amino acid sequence of SEQ ID NO:37, (oo) a variably heavy domain comprising the amino acid sequence of SEQ ID NO:41 and a variable light domain region comprising the amino acid sequence of SEQ ID NO:45, (pp) a variable heavy domain comprising the amino acid sequence of SEQ ID NO:49 and a variable light domain region comprising the amino acid sequence of SEQ ID NO:53, (qq) a variable heavy domain comprising the amino acid sequence of SEQ ID NO:57 and a variable light domain region comprising the amino acid sequence of SEQ ID NO:61, (rr) a variable heavy domain region comprising the amino acid sequence of SEQ ID NO:152 and a variable light domain region comprising the amino acid sequence of SEQ ID NO:95, (ss) a variable heavy domain region comprising the amino acid sequence of SEQ ID NO:99 and a variable light domain region comprising the amino acid sequence of SEQ ID NO:103, (tt) a variable heavy domain region comprising the amino acid sequence of SEQ ID NO:107 and a variable light domain region comprising the amino acid sequence of SEQ ID NO:111, (uu) a variable heavy domain region comprising the amino acid sequence of SEQ ID NO:115 and a variable light domain region comprising the amino acid sequence of SEQ ID NO:119, (vv) a variable heavy domain region comprising the amino acid sequence of SEQ ID NO:123 and a variable light domain region comprising the amino acid sequence of SEQ ID NO:127, (ww) a variable heavy domain region comprising the amino acid sequence of SEQ ID NO:131 and a variable light domain region comprising the amino acid sequence of SEQ ID NO:135, (xx) a variable heavy chain comprising a complementarity determining region (CDR)1 comprising the amino acid sequence of SEQ ID NO:2, a CDR2 comprising the amino acid sequence of SEQ ID NO:3, and a CDR3 comprising the amino acid sequence of SEQ ID NO:4, (yy) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8, (zz) a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12, (aaa) a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16, (bbb) a variable heavy chain comprising a CDR1 comprising the amino acid sequence of SEQ ID NO:18, a CDR2 comprising the amino acid sequence of SEQ ID NO:19, and a CDR3 comprising the amino acid sequence of SEQ ID NO:20, (ccc) a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24, (ddd) a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (eee) a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32, (fff) a variable heavy chain comprising a CDR1 comprising the amino acid sequence of SEQ ID NO:34, a CDR2 comprising the amino acid sequence of SEQ ID NO:35, and a CDR3 comprising the amino acid sequence of SEQ ID NO:36, (ggg) a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40, (hhh) a variable heavy chain comprising a CDR1 comprising the amino acid sequence of SEQ ID NO:42, a CDR2 comprising the amino acid sequence of SEQ ID NO:43, and CDR3 comprising the amino acid sequence of SEQ ID NO:44; (iii) a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; (jjj) a variable heavy chain comprising a CDR1 comprising the amino acid sequence of SEQ ID NO:50, a CDR2 comprising the amino acid sequence of SEQ ID NO:51, and a CDR3 comprising the amino acid sequence of SEQ ID NO:52 and a variable light chain comprising a CDR1 comprising the amino acid sequence of SEQ ID NO:54, a CDR2 comprising the amino acid sequence of SEQ ID NO:55, and a CDR3 comprising the amino acid sequence of SEQ ID NO:56, (kick) a variable heavy chain comprising a CDR1 comprising the amino acid sequence of SEQ ID NO:58, a CDR2 comprising the amino acid sequence of SEQ ID NO:59, and a CDR3 comprising the amino acid sequence of SEQ ID NO:60, (lll) a variable light chain comprising a CDR1 comprising the amino acid sequence of SEQ ID NO:62, a CDR2 comprising the amino acid sequence of SEQ ID NO:63, and a CDR3 comprising the amino acid sequence of SEQ ID NO:64, (mmm) a variable heavy chain comprising a CDR1 comprising the amino acid sequence of SEQ ID NO:92 or 153, a CDR2 comprising the amino acid sequence of SEQ ID NO:93 or 154, and a CDR3 comprising the amino acid sequence of SEQ ID NO:94 or 155, (nnn) a variable light chain comprising a CDR1 comprising the amino acid sequence of SEQ ID NO:96 or 156, a CDR2 comprising the amino acid sequence of SEQ ID NO:97 or 157, and a CDR3 comprising the amino acid sequence of SEQ ID NO:98 or 158, (ooo) a variable heavy chain comprising a CDR1 comprising the amino acid sequence of SEQ ID NO:100, a CDR2 comprising the amino acid sequence of SEQ ID NO:101, and a CDR3 comprising the amino acid sequence of SEQ ID NO:102, (ppp) a variable light chain comprising a CDR1 comprising the amino acid sequence of SEQ ID NO:104, a CDR2 comprising the amino acid sequence of SEQ ID NO:105, and a CDR3 comprising the amino acid sequence of SEQ ID NO:106, (qqq) a variable heavy chain comprising a CDR1 comprising the amino acid sequence of SEQ ID NO:108, a CDR2 comprising the amino acid sequence of SEQ ID NO:109, and a CDR3 comprising the amino acid sequence of SEQ ID NO:110, (rrr) a variable light chain comprising a CDR1 comprising the amino acid sequence of SEQ ID NO:112, a CDR2 comprising the amino acid sequence of SEQ ID NO:113, and a CDR3 comprising the amino acid sequence of SEQ ID NO:114, (sss) a variable heavy chain comprising a CDR1 comprising the amino acid sequence of SEQ ID NO:116, a CDR2 comprising the amino acid sequence of SEQ ID NO:117, and a CDR3 comprising the amino acid sequence of SEQ ID NO:118, (ttt) a variable light chain comprising a CDR1 comprising the amino acid sequence of SEQ ID NO:120, a CDR2 comprising the amino acid sequence of SEQ ID NO:121, and a CDR3 comprising the amino acid sequence of SEQ ID NO:122, (uuu) a variable heavy chain comprising a CDR1 comprising the amino acid sequence of SEQ ID NO:124, a CDR2 comprising the amino acid sequence of SEQ ID NO:125, and a CDR3 comprising the amino acid sequence of SEQ ID NO:126, (vvv) a variable light chain comprising a CDR1 comprising the amino acid sequence of SEQ ID NO:128, a CDR2 comprising the amino acid sequence of SEQ ID NO:129, and a CDR3 comprising the amino acid sequence of SEQ ID NO:130, (www) a variable heavy chain comprising a CDR1 comprising the amino acid sequence of SEQ ID NO:132, a CDR2 comprising the amino acid sequence of SEQ ID NO:133, and a CDR3 comprising the amino acid sequence of SEQ ID NO:134, (xxx) a variable light chain comprising a CDR1 comprising the amino acid sequence of SEQ ID NO:136, a CDR2 comprising the amino acid sequence of SEQ ID NO:137, and a CDR3 comprising the amino acid sequence of SEQ ID NO:138, (yyy) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:67, (zzz) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:68, (aaaa) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:69, (bbbb) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:70, (cccc) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:71, (dddd) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:72, (eeee) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:73, (ffff) a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4 and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8, (gggg) a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4 and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:67, (hhhh) a variable heavy chain comprising a CDR1 comprising the amino acid sequence of SEQ ID NO:92 or 153, a CDR2 comprising the amino acid sequence of SEQ ID NO:93 or 154, and a CDR3 comprising the amino acid sequence of SEQ ID NO:94 or 155 and a variable light chain comprising a CDR1 comprising the amino acid sequence of SEQ ID NO:96 or 156, a CDR2 comprising the amino acid sequence of SEQ ID NO:97 or 157, and a CDR3 comprising the amino acid sequence of SEQ ID NO:98 or 158, (iiii) a variable heavy chain comprising a CDR1 comprising the amino acid sequence of SEQ ID NO:100, a CDR2 comprising the amino acid sequence of SEQ ID NO:101, and a CDR3 comprising the amino acid sequence of SEQ ID NO:102 and a variable light chain comprising a CDR1 comprising the amino acid sequence of SEQ ID NO:104, a CDR2 comprising the amino acid sequence of SEQ ID NO:105, and a CDR3 comprising the amino acid sequence of SEQ ID NO:106, (jjjj) a variable heavy chain comprising a CDR1 comprising the amino acid sequence of SEQ ID NO:108, a CDR2 comprising the amino acid sequence of SEQ ID NO:109, and a CDR3 comprising the amino acid sequence of SEQ ID NO:110 and a variable light chain comprising a CDR1 comprising the amino acid sequence of SEQ ID NO:112, a CDR2 comprising the amino acid sequence of SEQ ID NO:113, and a CDR3 comprising the amino acid sequence of SEQ ID NO:114, (kkkk) a variable heavy chain comprising a CDR1 comprising the amino acid sequence of SEQ ID NO:116, a CDR2 comprising the amino acid sequence of SEQ ID NO:117, and a CDR3 comprising the amino acid sequence of SEQ ID NO:118 and a variable light chain comprising a CDR1 comprising the amino acid sequence of SEQ ID NO:120, a CDR2 comprising the amino acid sequence of SEQ ID NO:121, and a CDR3 comprising the amino acid sequence of SEQ ID NO:122, (1111) a variable heavy chain comprising a CDR1 comprising the amino acid sequence of SEQ ID NO:124, a CDR2 comprising the amino acid sequence of SEQ ID NO:125, and a CDR3 comprising the amino acid sequence of SEQ ID NO:126 and a variable light chain comprising a CDR1 comprising the amino acid sequence of SEQ ID NO:128, a CDR2 comprising the amino acid sequence of SEQ ID NO:129, and a CDR3 comprising the amino acid sequence of SEQ ID NO:130, (mmmm) a variable heavy chain comprising a CDR1 comprising the amino acid sequence of SEQ ID NO:132, a CDR2 comprising the amino acid sequence of SEQ ID NO:133, and a CDR3 comprising the amino acid sequence of SEQ ID NO:134 and a variable light chain comprising a CDR1 comprising the amino acid sequence of SEQ ID NO:136, a CDR2 comprising the amino acid sequence of SEQ ID NO:137, and a CDR3 comprising the amino acid sequence of SEQ ID NO:138, (nnnn) a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4 and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:68, (oooo) a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:69, (pppp) a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:70, (qqqq) a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:71, (rrrr) a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:72, (ssss) a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:73, (tttt) a variable heavy chain comprising a CDR 1 comprising the amino acid sequence of SEQ ID NO:10, a CDR2 comprising the amino acid sequence of SEQ ID NO:11, and a CDR3 comprising the amino acid sequence of SEQ ID NO:12, and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16, (uuuu) a variable heavy chain comprising a CDR 1 comprising the amino acid sequence of SEQ ID NO:18, a CDR2 comprising the amino acid sequence of SEQ ID NO:19, and a CDR3 comprising the amino acid sequence of SEQ ID NO:20, and a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24, (vvvv) a variable heavy chain comprising a CDR 1 comprising the amino acid sequence of SEQ ID NO:26, a CDR2 comprising the amino acid sequence of SEQ ID NO:27, and a CDR3 comprising the amino acid sequence of SEQ ID NO:28, and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32, (wwww) a variable heavy chain comprising a CDR 1 comprising the amino acid sequence of SEQ ID NO:34, a CDR2 comprising the amino acid sequence of SEQ ID NO:35, and a CDR3 comprising the amino acid sequence of SEQ ID NO:36, and a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40, (xxxx) a variable heavy domain chain comprising a CDR1 comprising the amino acid sequence of SEQ ID NO:42, a CDR2 comprising the amino acid sequence of SEQ ID NO:43, and a CDR comprising the amino acid sequence of SEQ ID NO:44, and a variable light domain chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; (yyyy) a variable heavy chain comprising a CDR 1 comprising the amino acid sequence of SEQ ID NO:50, a CDR2 comprising the amino acid sequence of SEQ ID NO:51, and a CDR3 comprising the amino acid sequence of SEQ ID NO:52, and a variable light chain comprising a CDR1 comprising the amino acid sequence of SEQ ID NO:54, a CDR2 comprising the amino acid sequence of SEQ ID NO:55, and a CDR3 comprising the amino acid sequence of SEQ ID NO:56, (zzzz) a variable heavy chain comprising a CDR 1 comprising the amino acid sequence of SEQ ID NO:58, a CDR2 comprising the amino acid sequence of SEQ ID NO:59, and a CDR3 comprising the amino acid sequence of SEQ ID NO:60, and a variable light chain comprising a CDR1 comprising the amino acid sequence of SEQ ID NO:62, a CDR2 comprising the amino acid sequence of SEQ ID NO:63, and a CDR3 comprising the amino acid sequence of SEQ ID NO:64.

The isolated antibody or antibody fragment may be a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multi-specific antibody, a Fab, a dual specific antibody, a DVD, a Fab', a bispecific antibody, a F(ab')2, or a Fv. The antibody or antibody fragment may be human. The antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, or a human IgA constant domain. The human IgG1 constant domain may comprise, or consist of, SEQ ID NO:140.

The antibody or fragment thereof may comprise a variable heavy region comprising a sequence selected from the group consisting of SEQ ID NO:1, SEQ ID NO:9, SEQ ID NO:17, SEQ ID NO:25, SEQ ID NO:33, SEQ ID NO:41, SEQ ID NO:49, SEQ ID NO:57, SEQ ID NO:91, SEQ ID NO:99, SEQ ID NO:107, SEQ ID NO:115, SEQ ID NO:123, and SEQ ID NO:131.

The isolated antibody or antibody fragment may comprise a variable light region comprising a sequence selected from the group consisting of SEQ ID NO:5, SEQ ID NO:13, SEQ ID NO:21, SEQ ID NO:29, SEQ ID NO:37, SEQ ID NO:45, SEQ ID NO:53, SEQ ID NO:61, SEQ ID NO:95, SEQ ID NO:103, SEQ ID NO:111, SEQ ID NO:119, SEQ ID NO:127, and SEQ ID NO:135.

The isolated antibody or antibody fragment may comprise a variable light domain that comprises complementarity-determining region (CDR) residues SEQ ID NO:6, SEQ ID NO:7, and SEQ ID NO:8, or SEQ ID NO:6, SEQ ID NO:7, and SEQ ID NO:67, SEQ ID NO:6, SEQ ID NO:7, and SEQ ID NO:68, or SEQ ID NO:6, SEQ ID NO:7, and SEQ ID NO:69, or SEQ ID NO:6, SEQ ID NO:7, and SEQ ID NO:70, or SEQ ID NO:6, SEQ ID NO:7, and SEQ ID NO:71, or SEQ ID NO:6, SEQ ID NO:7, and SEQ ID NO:72 or SEQ ID NO:6, SEQ ID NO:7, and SEQ ID NO:73, or SEQ ID NO:14, SEQ ID NO:15, and SEQ ID NO:16, or SEQ ID NO:22, SEQ ID NO:23, and SEQ ID NO:24, or SEQ ID NO:30, SEQ ID NO:31, and SEQ ID NO:32, or SEQ ID NO:38, SEQ ID NO:39, and SEQ ID NO:40, or SEQ ID NO:54, SEQ ID NO:55, and SEQ ID NO:56, or SEQ ID NO:62, SEQ ID NO:63, and SEQ ID NO:64, or SEQ ID NO:46, SEQ ID NO:47, and SEQ ID NO:48, SEQ ID NO:96, SEQ ID NO:97, and SEQ ID NO:98, SEQ ID NO:104, SEQ ID NO:105, and SEQ ID NO:106, SEQ ID NO:112, SEQ ID NO:113, and SEQ ID NO:114, SEQ ID NO:120, SEQ ID NO:121, and SEQ ID NO:122, SEQ ID NO:128, SEQ ID NO:129, and SEQ ID NO:130, SEQ ID NO:136, SEQ ID NO:137, and SEQ ID NO:138, and SEQ ID NO: 156, and SEQ ID NO: 157, and SEQ ID NO: 158.

The isolated antibody or antibody fragment may comprise a variable heavy domain that comprises complementarity-determining region (CDR) residues SEQ ID NO:2, SEQ ID NO:3, and SEQ ID NO:4, or SEQ ID NO:10, SEQ ID NO:11, and SEQ ID NO:12, or SEQ ID NO:18, SEQ ID NO:19, and SEQ ID NO:20, or SEQ ID NO:26, SEQ ID NO:27, and SEQ ID NO:28, or SEQ ID NO:34, SEQ ID NO:35, and SEQ ID NO:36, or SEQ ID NO:50, SEQ ID NO:51, and SEQ ID NO:52, or SEQ ID NO:58, SEQ ID NO:59, and SEQ ID NO:60, SEQ ID NO:42, SEQ ID NO:43, and SEQ ID NO:44, SEQ ID NO:92, SEQ ID NO:93, and SEQ ID NO:94, SEQ ID NO:100, SEQ ID NO:101, and SEQ ID NO:102, SEQ ID NO:108, SEQ ID NO:109, and SEQ ID NO:110, SEQ ID NO:116, SEQ ID NO:117, and SEQ ID NO:118, SEQ ID NO:124, SEQ ID NO:125, and SEQ ID NO:126, SEQ ID NO:132, SEQ ID NO:133, and SEQ ID NO:134, SEQ ID NO: 153, and SEQ ID NO: 154, and SEQ ID NO: 155.

The isolated antibody or antibody fragment may comprise a variable heavy domain that comprises complementarity-determining region (CDR) residues SEQ ID NO:2, SEQ ID NO:3, and SEQ ID NO:4, and a variable light domain that comprises complementarity-determining region (CDR) residues SEQ ID NO:6, SEQ ID NO:7, and SEQ ID NO:8.

The isolated antibody or antibody fragment may comprise a variable heavy domain that comprises complementarity-determining region (CDR) residues SEQ ID NO:10, SEQ ID NO:11, and SEQ ID NO:12, and a variable light domain that comprises complementarity-determining region (CDR) residues SEQ ID NO:14, SEQ ID NO:15, and SEQ ID NO:16.

The isolated antibody or antibody fragment may comprise a variable heavy domain that comprises complementarity-determining region (CDR) residues SEQ ID NO:18, SEQ ID NO:19, and SEQ ID NO:20, and a variable light domain that comprises complementarity-determining region (CDR) residues SEQ ID NO:22, SEQ ID NO:23, and SEQ ID NO:24.

The isolated antibody or antibody fragment may comprise a variable heavy domain that comprises complementarity-determining region (CDR) residues SEQ ID NO:26, SEQ ID NO:27, and SEQ ID NO:28, and a variable light domain that comprises complementarity-determining region (CDR) residues SEQ ID NO:30, SEQ ID NO:31, and SEQ ID NO:32.

The isolated antibody or antibody fragment may comprise a variable heavy domain that comprises complementarity-determining region (CDR) residues SEQ ID NO:34, SEQ ID NO:35, and SEQ ID NO:36, and a variable light domain that comprises complementarity-determining region (CDR) residues SEQ ID NO:38, SEQ ID NO:39, and SEQ ID NO:40.

The isolated antibody or antibody fragment may comprise a variable heavy domain that comprises complementarity-determining region (CDR) residues SEQ ID NO:50, SEQ ID NO:51, and SEQ ID NO:52, and a variable light domain that comprises complementarity-determining region (CDR) residues SEQ ID NO:54, SEQ ID NO:55, and SEQ ID NO:56.

The isolated antibody or antibody fragment may comprise a variable heavy domain that comprises complementarity-determining region (CDR) residues SEQ ID NO:58, SEQ ID NO:59, and SEQ ID NO:60, and a variable light domain that comprises complementarity-determining region (CDR) residues SEQ ID NO:62, SEQ ID NO:63, and SEQ ID NO:64.

The isolated antibody or antibody fragment may comprise a variable heavy domain that comprises complementarity-determining region (CDR) residues SEQ ID NO:42, SEQ ID NO:43, and SEQ ID NO:44, and a variable light domain that comprises complementarity-determining region (CDR) residues SEQ ID NO:46, SEQ ID NO:47, and SEQ ID NO:48.

The isolated antibody or antibody fragment may comprise a variable heavy domain that comprises complementarity-determining region (CDR) residues SEQ ID NO:92 or 153, SEQ ID NO:93 or 154, and SEQ ID NO:94 or 155, and a variable light domain that comprises complementarity-determining region (CDR) residues SEQ ID NO:96 or 156, SEQ ID NO:97 or 157, and SEQ ID NO:98 or 158.

The isolated antibody or antibody fragment may comprise a variable heavy domain that comprises complementarity-determining region (CDR) residues SEQ ID NO:100, SEQ ID NO:101, and SEQ ID NO:102, and a variable light domain that comprises complementarity-determining region (CDR) residues SEQ ID NO:104, SEQ ID NO:105, and SEQ ID NO:106.

The isolated antibody or antibody fragment may comprise a variable heavy domain that comprises complementarity-determining region (CDR) residues SEQ ID NO:108, SEQ ID NO:109, and SEQ ID NO:110, and a variable light domain that comprises complementarity-determining region (CDR) residues SEQ ID NO:112, SEQ ID NO:113, and SEQ ID NO:114.

The isolated antibody or antibody fragment may comprise a variable heavy domain that comprises complementarity-determining region (CDR) residues SEQ ID NO:116, SEQ ID NO:117, and SEQ ID NO:118, and a variable light domain that comprises complementarity-determining region (CDR) residues SEQ ID NO:120, SEQ ID NO:121, and SEQ ID NO:122.

The isolated antibody or antibody fragment may comprise a variable heavy domain that comprises complementarity-determining region (CDR) residues SEQ ID NO:124, SEQ ID NO:125, and SEQ ID NO:126, and a variable light domain that comprises complementarity-determining region (CDR) residues SEQ ID NO:128, SEQ ID NO:129, and SEQ ID NO:130.

The isolated antibody or antibody fragment may comprise a variable heavy domain that comprises complementarity-determining region (CDR) residues SEQ ID NO:132, SEQ ID NO:133, and SEQ ID NO:134, and a variable light domain that comprises complementarity-determining region (CDR) residues SEQ ID NO:136, SEQ ID NO:137, and SEQ ID NO:138.

The isolated antibody or antibody fragment may comprise an agent selected from the group consisting of: an immunoadhesion molecule, an imaging agent, and a therapeutic agent. The imaging agent may be a radiolabel, an enzyme, a fluorescent label, a luminescent label, a bioluminescent label, a magnetic label, or biotin. The radiolabel may be 3H, 14C, 35S, 90Y, 99Tc, 111In, 125I, 131I, 177Lu, 166Ho, or 153Sm.

In another aspect, the present invention is directed to an antibody, or fragment thereof, that binds to the RGMa epitope PCKILKCNSEFWSATSGSHAPAS (hRGMa 47-69) (SEQ ID NO:79). The antibody that binds to the RGMa epitope PCKILKCNSEFWSATSGSHAPAS (hRGMa 47-69) (SEQ ID NO:79), may comprise a variable heavy domain that comprises complementarity-determining region (CDR) residues SEQ ID NO:2, SEQ ID NO:3, and SEQ ID NO:4, and a variable light domain that comprises complementarity-determining region (CDR) residues SEQ ID NO:6, SEQ ID NO:7, and SEQ ID NO:8.

In another aspect, the present invention is directed to an isolated antibody or antibody fragment thereof which binds to Repulsive Guidance Molecule a ("RGMa"). The antibody or antibody fragment comprises a variable heavy domain that comprises three complementarity-determining regions (CDR—H1, H2, and H3) corresponding to the following formulas, respectively:

Xaa1-Xaa2-Xaa3-Xaa4-Xaa5     (Formula 1—CDR-H1), wherein Xaa1 is an amino acid selected from the group consisting of S, D, E, N, G, and T; Xaa2 is an amino acid selected from the group consisting of H, Y, L, S, and Q; Xaa3 is an amino acid selected from the group consisting of G, D, A, T, and Y; Xaa4 is an amino acid selected from the group consisting of I, M, and W; and Xaa5 is an amino acid sequence from the group consisting of S, N, H, A, T, and Q;

Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-(Xaa)$n$ (Formula 2—CDR-H2), wherein n is 0 or 1, and wherein Xaa1 is an amino acid selected from the group consisting of W, V, A, G, L, E, S, and N; Xaa2 is an amino acid selected from the group consisting of I, M, and F; Xaa3 is an amino acid selected from the group consisting of S, N, D, F, and Y; Xaa4 is an amino acid selected from the group consisting of P, Y, G, W, H, A, and S; Xaa5 is an amino acid selected from the group consisting of Y, N, D, E, S, K, G, and T; Xaa6 is an amino acid selected from the group consisting of S, G, D, T, and N; Xaa7 is an amino acid selected from the group consisting of G, S, I, E, N, and R; Xaa8 is an amino acid selected from the group consisting of N, L, R, S, T, and Y; Xaa9 is an amino acid selected from the group consisting of T, K, G, N, I, and Y; Xaa10 is an amino acid selected from the group consisting of N, G, Y, T, and K; Xaa11 is an amino acid selected from the group consisting of Y, F, N, and H; Xaa12 is an amino acid selected from the group consisting of A, T, V, P, L, and S; Xaa13 is an amino acid selected from the group consisting of Q, D, P, and S; Xaa14 is an amino acid selected from the group consisting of K, S, N, and L; Xaa15 is an amino acid selected from the group consisting of L, F, V, K, and R; Xaa16 is an amino acid selected from the group consisting of Q, K, R, and S; and Xaa17 is a glycine; and Xaa1-Xaa2-Xaa3-Xaa4-Xaa5-Xaa6-(Xaa)$n$ (Formula 3—CDR-H3), wherein n is 0-11, and
wherein Xaa1 is an amino acid selected from the group consisting of V, S, E, N, L, D, Q, and A; Xaa2 is an amino acid selected from the group consisting of G, T, R, Y, L, I, D, and S; Xaa3 is an amino acid selected from the group consisting of S, V, D, G, F, Y, P, M, C, L, and A; Xaa4 is an amino acid selected from the group consisting of G, L, Y, N, E, K, A, and F; Xaa5 is an amino acid selected from the group consisting of P, S, Y, A, V, G, T, E, and W; Xaa6 is an amino acid selected from the group consisting of Y, V, S, L, D, G, H, and P; Xaa7 is an amino acid selected from the group consisting of Tyr, Asp, Gly, Ser, Phe, Leu, and Cys; Xaa8 is an amino acid selected from the group consisting of Tyr, Lys, Asp, Ala, and Gln; Xaa9 is an amino acid selected from the group consisting of Met, Glu, Phe, Leu, Ser, Thr, Pro, and Tyr; Xaa10 is an amino acid selected from the group consisting of Asp, Gly, Tyr, Ser, Leu, His, and Phe; Xaa11 is an amino acid selected from the group consisting of Val, Tyr, Leu, His, Gly, Trp, and Asp; Xaa12 is an amino acid selected from the group consisting of Tyr and Phe; Xaa13 is an amino acid selected from the group consisting of Tyr, Gly, and Asp; Xaa14 is an amino acid selected from the group consisting of Ala, Leu, Pro, and Tyr; Xaa15 is an amino acid selected from the group consisting of Met, Leu, and Phe; Xaa16 is an amino acid selected from the group consisting of Asp and Gly; and Xaa17 is an amino acid selected from the group consisting of an Val, Asp, and Tyr.

In another aspect, the present invention is directed to an isolated antibody or antibody fragment thereof which binds to Repulsive Guidance Molecule a ("RGMa"). The antibody or antibody fragment comprises a variable light domain that comprises three complementarity-determining regions (CDR-L1, L2 and L3) corresponding to the following formulas, respectively:

Xaa1-Xaa2-Xaa3-Xaa4-Xaa5-Xaa6-Xaa7-Xaa8-Xaa9-Xaa10-Xaa11-(Xaa)$n$ (Formula 1—CDR-L1), wherein n is 0-3, and
wherein Xaa1 is an amino acid selected from the group consisting of T, S, R, G, and Q; Xaa2 is an amino acid selected from the group consisting of G, L, and A; Xaa3 is an amino acid selected from the group consisting of T, D, S, N and A; Xaa4 is an amino acid selected from the group consisting of S, K, G, Q, N, and E; Xaa5 is an amino acid sequence from the group consisting of S, L, G, I, D, and P; Xaa6 is an amino acid selected from the group consisting of S, G, N, H, and I; Xaa7 is an amino acid selected from the group consisting of V, D, I, S, G and H; Xaa8 is an amino acid selected from the group consisting of G, K, A, S, I, N, T, and D; Xaa9 is an amino acid selected from the group consisting of D, Y, A, C, S, and F; Xaa10 is an amino acid selected from the group consisting of S, A, G, L, V, and N; Xaa11 is an amino acid selected from the group consisting of I, C, Y, H, R, N, and S; Xaa12 is an amino acid selected from the group consisting of Tyr, Gly, Ala, and Val; Xaa13 is an amino acid selected from the group consisting of Val, and Asn; and Xaa14 is an amino acid selected from the group consisting of Ser and His;

Xaa1-Xaa2-Xaa3-Xaa4-Xaa5-Xaa6-Xaa7-(Xaa)$n$ (Formula 2—CDR-L2), wherein n is 0-4, and wherein Xaa1 is an amino acid selected from the group consisting of D, Q, G, V, Y, S and E; Xaa2 is an amino acid selected from the group consisting of V, D, N, and A; Xaa3 is an amino acid selected from the group consisting of T, S, Y, N, and K; Xaa4 is an amino acid selected from the group consisting of K, N, D, Q and T; Xaa5 is an amino acid selected from the group consisting of R, G, S, and L; Xaa6 is an amino acid selected from the group consisting of P, S, I, and E; Xaa7 is an amino acid selected from the group consisting of S, H, I, and T; Xaa8 is Asn; Xaa9 is Lys; and Xaa10 is Gly; Xaa11 is Asp; and Xaa1-Xaa2-Xaa3-Xaa4-Xaa5-Xaa6-Xaa7-Xaa8-Xaa9-(Xaa)$n$ (Formula 3—CDR-L3), wherein n is 0-2, and wherein Xaa1 is an amino acid selected from the group consisting of C, Q, H, F, H, L, V, I, K, Y, and A; Xaa2 is an amino acid selected from the group consisting of S, A, T, Q, and V; Xaa3 is an amino acid selected from the group consisting of Y, W, and S; Xaa4 is an amino acid selected from the group consisting of A, D, G, S, H and Y; Xaa5 is an amino acid selected from the group consisting of G, S, N, P, D, V, and T; Xaa6 is an amino acid selected from the group consisting of I, T, S, G, L, F and Y; Xaa7 is an amino acid selected from the group consisting of D, T, L, I, P, and S; Xaa8 is an amino acid selected from the group consisting of T, G, R, Y, D, N, W, L, F and P; Xaa9 is an amino acid selected from the group consisting of L, V, G, T, and H; Xaa10 is an amino acid selected from the group consisting of Val, Tyr, and His; Xaa11 is Leu or Val.

In another aspect, the present invention is directed to an isolated antibody or antibody fragment thereof which binds to Repulsive Guidance Molecule a ("RGMa"), wherein the antibody or antibody fragment comprises a variable heavy domain that comprises three complementarity-determining regions (CDR-H1, H2, and H3) corresponding to the following formulas, respectively:

Xaa1-Xaa2-Xaa3-Xaa4-Xaa5 (Formula 1—CDR-H1), wherein Xaa1 is an amino acid selected from the group consisting of S, D, E, N, G, and T; Xaa2 is an amino acid selected from the group consisting of H, Y, L, S, and Q; Xaa3 is an amino acid selected from the group consisting of G, D, A, T, and Y; Xaa4 is an amino acid selected from the group consisting of I, M, and W; and Xaa5 is an amino acid sequence from the group consisting of S, N, H, A, T, and Q;

Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-(Xaa)$n$     (Formula 2—CDR-H2), wherein n is 0 or 1, and wherein Xaa1 is an amino acid selected from the group consisting of Y, V, A, G, L, G, S, and N; Xaa2 is an amino acid selected from the group consisting of I, M, and F; Xaa3 is an amino acid selected from the group consisting of S, N, D, F, and Y; Xaa4 is an amino acid selected from the group consisting of P, Y, G, W, H, A, and S; Xaa5 is an amino acid selected from the group consisting of Y, N, D, E, S, K, G, and T; Xaa6 is an amino acid selected from the group consisting of S, G, D, T, and N; Xaa7 is an amino acid selected from the group consisting of G, S, I, E, N, and R; Xaa8 is an amino acid selected from the group consisting of N, L, R, S, T, and Y; Xaa9 is an amino acid selected from the group consisting of T, K, G, N, I, and Y; Xaa10 is an amino acid selected from the group consisting of N, G, Y, T, and K; Xaa11 is an amino acid selected from the group consisting of Y, F, N, and H; Xaa12 is an amino acid selected from the group consisting of A, T, V, P, L, and S; Xaa13 is an amino acid selected from the group consisting of Q, D, P, and S; Xaa14 is an amino acid selected from the group consisting of K, S, N, and L; Xaa15 is an amino acid selected from the group consisting of L, F, V, K, and R; Xaa16 is an amino acid selected from the group consisting of Q, K, R, and S; and Xaa17 is a glycine; and Xaa1-Xaa2-Xaa3-Xaa4-Xaa5-Xaa6-(Xaa)$n$     (Formula 3—CDR-H3), wherein n is 0-11, and wherein Xaa1 is an amino acid selected from the group consisting of V, S, E, N, L, D, Q, and A; Xaa2 is an amino acid selected from the group consisting of G, T, R, Y, L, I, D, and S; Xaa3 is an amino acid selected from the group consisting of S, V, D, G, F, Y, P, M, C, L, and A; Xaa4 is an amino acid selected from the group consisting of G, L, Y, N, E, K, A, and F; Xaa5 is an amino acid selected from the group consisting of P, S, Y, A, V, G, T, E, and W; Xaa6 is an amino acid selected from the group consisting of Y, V, S, L, D, G, H, and P; Xaa7 is an amino acid selected from the group consisting of Tyr, Asp, Gly, Ser, Phe, Leu, and Cys; Xaa8 is an amino acid selected from the group consisting of Tyr, Lys, Asp, Ala, and Gln; Xaa9 is an amino acid selected from the group consisting of Met, Glu, Phe, Leu, Ser, Thr, Pro, and Tyr; Xaa10 is an amino acid selected from the group consisting of Asp, Gly, Tyr, Ser, Leu, His, and Phe; Xaa11 is an amino acid selected from the group consisting of Val, Tyr, Leu, His, Gly, Trp, and Asp; Xaa12 is an amino acid selected from the group consisting of Tyr and Phe; Xaa13 is an amino acid selected from the group consisting of Tyr, Gly, and Asp; Xaa14 is an amino acid selected from the group consisting of Ala, Leu, Pro, and Tyr; Xaa15 is an amino acid selected from the group consisting of Met, Leu, and Phe; Xaa16 is an amino acid selected from the group consisting of Asp and Gly; and Xaa17 is an amino acid selected from the group consisting of an Val, Asp, and Tyr; and wherein the antibody or antibody fragment also comprises a variable light domain that comprises three complementarity-determining regions (CDR-L1, L2, and L3) corresponding to the following formulas, respectively:

Xaa1-Xaa2-Xaa3-Xaa4-Xaa5-Xaa6-Xaa7-Xaa8-Xaa9-Xaa10-Xaa11-(Xaa)$n$     (Formula 1—CDR-L1), wherein n is 0-3, and wherein Xaa1 is an amino acid selected from the group consisting of T, S, R, G, and Q; Xaa2 is an amino acid selected from the group consisting of G, L, and A; Xaa3 is an amino acid selected from the group consisting of T, D, S, N and A; Xaa4 is an amino acid selected from the group consisting of S, K, G, Q, N, and E; Xaa5 is an amino acid sequence from the group consisting of S, L, G, I, D, and P; Xaa6 is an amino acid selected from the group consisting of S, G, N, H, and I; Xaa7 is an amino acid selected from the group consisting of V, D, I, S, G and H; Xaa8 is an amino acid selected from the group consisting of G, K, A, S, I, N, T, and D; Xaa9 is an amino acid selected from the group consisting of D, Y, A, C, S, and F; Xaa10 is an amino acid selected from the group consisting of S, A, G, L, V, and N; Xaa11 is an amino acid selected from the group consisting of I, C, Y, H, R, N, and S; Xaa12 is an amino acid selected from the group consisting of Tyr, Gly, Ala, and Val; Xaa13 is an amino acid selected from the group consisting of Val, and Asn; and Xaa14 is an amino acid selected from the group consisting of Ser and His;

Xaa1-Xaa2-Xaa3-Xaa4-Xaa5-Xaa6-Xaa7-(Xaa)$n$     (Formula 2—CDR-L2), wherein n is 0-4, and wherein Xaa1 is an amino acid selected from the group consisting of D, Q, G, V, Y, S and E; Xaa2 is an amino acid selected from the group consisting of V, D, N, and A; Xaa3 is an amino acid selected from the group consisting of T, S, Y, N, and K; Xaa4 is an amino acid selected from the group consisting of K, N, D, Q and T; Xaa5 is an amino acid selected from the group consisting of R, G, S, and L; Xaa6 is an amino acid selected from the group consisting of P, S, I, and E; Xaa7 is an amino acid selected from the group consisting of S, H, I, and T; Xaa8 is Asn; Xaa9 is Lys; and Xaa10 is Gly; Xaa11 is Asp; and Xaa1-Xaa2-Xaa3-Xaa4-Xaa5-Xaa6-Xaa7-Xaa8-Xaa9-(Xaa)$n$     (Formula 3—CDR-L3), wherein n is 0-2, and wherein Xaa1 is an amino acid selected from the group consisting of C, Q, H, F, H, L, V, I, K, Y, and A; Xaa2 is an amino acid selected from the group consisting of S, A, T, Q, and V; Xaa3 is an amino acid selected from the group consisting of Y, W, and S; Xaa4 is an amino acid selected from the group consisting of A, D, G, S, H and Y; Xaa5 is an amino acid selected from the group consisting of G, S, N, P, D, V, and T; Xaa6 is an amino acid selected from the group consisting of I, T, S, G, L, F and Y; Xaa7 is an amino acid selected from the group consisting of D, T, L, I, P, and S; Xaa8 is an amino acid selected from the group consisting of T, G, R, Y, D, N, W, L, F and P; Xaa9 is an amino acid selected from the group consisting of L, V, G, T, and H; Xaa10 is an amino acid selected from the group consisting of Val, Tyr, and His; Xaa11 is Leu or Val.

In another aspect, the present invention is directed to a pharmaceutical composition that comprises the herein described antibody, antibody fragment, or mixture or derivative thereof.

In another aspect, the present invention is directed to a method of treating, preventing, modulating, or attenuating a disease or disorder associated with neurite degeneration, comprising administering to a subject in need thereof a therapeutically effective amount of the herein described antibody. The neurite degenerative disorder may be multiple sclerosis, Parkinson's disease; Alzheimer's disease; Huntington's disease; amyotrophic lateral sclerosis and other motoneuron diseases; Tay-Sachs disease; Niemann-Pick disease; Gaucher's disease; Hurler's syndrome; idiopathic inflammatory demyelinating diseases; vitamin B12 deficiency; central pontine myelinolysis; tabes dorsalis; transverse myelitis; Devic's disease, progressive multifocal leukoencephalopathy; optic neuritis; traumatic injury to the CNS; ischemic cerebral stroke; a retinopathy; such as glaucoma, diabetic retinopathy or age-dependent macular degeneration; and a leukodystrophy.

In another aspect, the present invention is directed to a method for determining whether a subject has a neurite degenerative disorder. The method may comprise measuring the level of RGMa in a sample from the subject; and comparing the level of RGMa in the sample with a normal control. An altered level of RGMa indicates that the subject has a neurite degenerative disorder. An increased level of RGMa as compared to the normal control, indicates that the subject has neurite degenerative disorder. The sample may be a blood sample or a serum sample or a cerebrospinal fluid sample. The step of measuring the level of RGMa in a sample, may be conducted with an immunoassay. The immunoassay may be an enzyme-linked immunosorbent assay (ELISA). The ELISA may be a sandwich ELISA.

In another aspect, the present invention is directed to an isolated antibody or antibody fragment comprising SEQ ID NOs:1-7 and 67.

In another aspect, the present invention is directed to an isolated antibody or antibody fragment comprising SEQ ID NOs:1-7 and 68.

In another aspect, the present invention is directed to an isolated antibody or antibody fragment comprising SEQ ID NOs:1-7 and 69.

In another aspect, the present invention is directed to an isolated antibody or antibody fragment comprising SEQ ID NOs:1-7 and 70.

In another aspect, the present invention is directed to an isolated antibody or antibody fragment comprising SEQ ID NOs:1-7 and 71.

In another aspect, the present invention is directed to an isolated antibody or antibody fragment comprising SEQ ID NOs:1-7 and 72.

In another aspect, the present invention is directed to an isolated antibody or antibody fragment comprising SEQ ID NOs:1-7 and 73.

In another aspect, the present invention is directed to an isolated monoclonal antibody or antibody fragment comprising SEQ ID NOs:1-7 and 67, 68, 69, 70, 71, 72, or 73, that binds to the RGMa epitope PCKILKCNSEFWSATSGSHAPAS (hRGMa 47-69) (SEQ ID NO:79).

BRIEF DESCRIPTION OF THE DRAWINGS

FIGS. 5A-5B show MS spectra from the reduced E1 fraction of trypsin/Asp-N excised *E. coli* hRGMa with AE12-1 mAb showing the +3 and +4 charge states (boxed) of two peptides corresponding to the sequences (SEQ ID NOS 74 and 80, respectively, in order of appearance) shown on the spectra. The peaks labeled with * are peptides that could not be assigned to the hRGMa antigen and may be related to the antibody.

FIGS. 13A-13F show the results of an RGMa binding assay on SH-SY5Y cells and primary neurons (HCA High Content Analysis) using AE12-6, AE12-15 and AE12-23.

DETAILED DESCRIPTION

Figure 1:
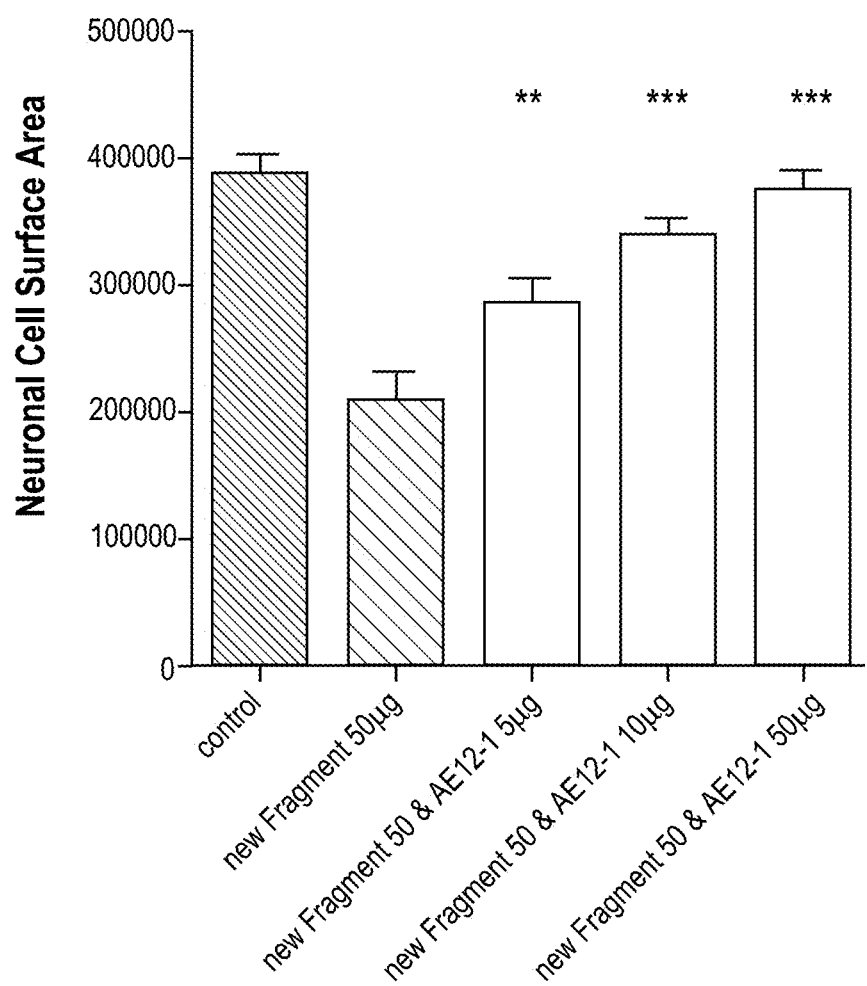
FIG. 1 shows testing results from a neurite outgrowth assay using 50 µg/ml of a hRGMa fragment. This fragment encompasses the N-terminal amino acids 47-127 of SEQ ID NO:65 (See SEQ ID NO:139) and contains both high affinity neogenin- and the bone morphogenetic protein-interaction domains.

The inventors have discovered new antibodies that bind to Repulsive Guidance Molecule a ("RGMa") and may be used to treat diseases related to neurite degeneration. Provided herein are specific and non-specific antibodies that are capable of attenuating clinical signs associated with diseases related to neurite degeneration.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

a. About

"About" as used herein may refer to approximately a +/−10% variation from the stated value. It is to be understood that such a variation is always included in any given value provided herein, whether or not specific reference is made to it.

b. Affinity Matured Antibody

"Affinity Matured Antibody" is used herein to refer to an antibody with one or more alterations in one or more CDRs, which result in an improvement in the affinity (i.e. $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies are known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

c. Antibody and Antibodies

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11): 1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA and IgY), class (for example, IgG1, IgG2, IgG3, IgG4, IgA1 and IgA2) or subclass. For simplicity sake, an antibody against an analyte is frequently referred to herein as being either an "anti-analyte antibody," or merely an "analyte antibody" (e.g., an anti-RGMa antibody or an RGMa antibody).

d. Antibody Fragment

"Antibody fragment" as used herein refers to a portion of an intact antibody comprising the antigen-binding site or variable region. The portion does not include the constant heavy chain domains (i.e. CH2, CH3 or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

e. Binding Constants

"Binding Constants" are described herein. The term "association rate constant," "$k_{on}$" or "$k_a$" as used herein, refers to the value indicating the binding rate of an antibody to its target antigen or the rate of complex formation between an antibody and antigen as shown by the equation below:

The term "dissociation rate constant," "$k_{off}$" or "$k_d$" as used interchangeably herein, refers to the value indicating the dissociation rate of an antibody from its target antigen or separation of Ab–Ag complex over time into free antibody and antigen as shown by the equation below:

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "equilibrium dissociation constant" or "$K_D$" as used interchangeably, herein, refers to the value obtained by dividing the dissociation rate ($k_{off}$) by the association rate ($k_{on}$). The association rate, the dissociation rate and the equilibrium dissociation constant are used to represent the binding affinity of an antibody to an antigen.

f. Binding Protein

"Binding Protein" is used herein to refer to a monomeric or multimeric protein that binds to and forms a complex with a binding partner, such as, for example, a polypeptide, an antigen, a chemical compound or other molecule, or a substrate of any kind A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody, a tetrameric immunoglobulin, an IgG molecule, an IgG$_1$ molecule, a monoclonal antibody, a chimeric antibody, a CDR-grafted antibody, a humanized antibody, an affinity matured antibody, and fragments of any such antibodies that retain the ability to bind to an antigen.

g. Bispecific Antibody

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds.

h. CDR

"CDR" is used herein to refer to the "complementarity determining region" within an antibody variable sequence. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

i. Component or Components

"Component," "components," or "at least one component," refer generally to a capture antibody, a detection or conjugate calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

j. Consensus or Consensus Sequence

"Consensus" or "Consensus Sequence" as used herein refers to a synthetic nucleic acid sequence, or corresponding polypeptide sequence, constructed based on analysis of an alignment of multiple subtypes of a particular antigen. The sequence may be used to induce broad immunity against multiple subtypes or serotypes of a particular antigen. Synthetic antigens, such as fusion proteins, may be manipulated to consensus sequences (or consensus antigens).

k. Control

"Control" as used herein refers to a composition known to not contain an analyte of interest ("negative"), e.g., RGMa (such as membrane-associated RGMa, soluble RGMa, fragments of membrane-associated RGMa, fragments of soluble RGMa, variants of RGMa (membrane-associated or soluble RGMa) or any combinations thereof), or to contain an analyte of interest ("positive control"), e.g., RGMa (such as membrane-associated RGMa, soluble RGMa, fragments of membrane-associated RGMa, fragments of soluble RGMa, variants of RGMa (membrane-associated or soluble RGMa) or any combinations thereof). A positive control can comprise a known concentration of RGMa. "Control," "positive control," and "calibrator" may be used interchangeably herein to refer to a composition comprising a known concentration of RGMa. A "positive control" can be used to establish assay performance characteristics and is a useful indicator of the integrity of reagents (e.g., analytes). A "normal control" may refer to a sample or a subject that is free from an iron-related disease or disorder.

l. Derivative

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains or fragments of antibodies. The derivative may also comprise at least one further compound, e.g. a protein domain, said protein domain being linked by covalent or non-covalent bonds. The linkage can be based on genetic fusion according to the methods known in the art. The additional domain present in the fusion protein comprising the antibody employed in accordance with the invention may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g. a cytokine or growth hormone), a chemical agent, a peptide, a protein or a drug, for example.

m. Dual-Specific Antibody

"Dual-specific antibody" is used herein to refer to a full-length antibody that can bind two different antigens (or epitopes) in each of its two binding arms (a pair of HC/LC) (see PCT publication WO 02/02773). Accordingly a dual-specific binding protein has two identical antigen binding arms, with identical specificity and identical CDR sequences, and is bivalent for each antigen to which it binds.

n. Dual Variable Domain

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig". Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., Nature Biotech., 25: 1290-1297 (2007). A preferred example of such DVD-Ig molecules comprises a heavy chain that comprises the structural formula VD1-(X1)$_n$-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C—(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein according to the invention not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of RGMa. Non-limiting examples of a DVD-Ig binding protein include a DVD-Ig binding protein that binds one or more epitopes of RGMa, a DVD-Ig binding protein that binds an epitope of a human RGMa and an epitope of a RGMa of another species (for example, mouse), and a DVD-Ig binding protein that binds an epitope of a human RGMa and an epitope of another target molecule (for example, VEGFR2 or VEGFR1).

o. Epitope or Epitopes

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

p. Framework or Framework Sequence

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol:// vbase.mrc-cpe.cam.ac.uk/) or in the international ImMuno-GeneTics® (IMGT®) information system (hypertext transfer protocol://imgt.cines.fr/texts/IMGTrepertoire/Locus-Genes/).

q. Functional Antigen Binding Site

"Functional antigen binding site" as used herein may mean a site on a binding protein (e.g. an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

r. Human Antibody

"Human antibody" as used herein may include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

s. Humanized Antibody

"Humanized antibody" is used herein to describe an antibody that comprises heavy and light chain variable region sequences from a non-human species (e.g. a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

t. Identical or Identity

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

u. Isolated Polynucleotide

"Isolated polynucleotide" as used herein may mean a polynucleotide (e.g. of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

v. Label and Detectable Label

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as $^{3}H$, $^{125}I$, $^{35}S$, $^{14}C$, $^{32}P$, and $^{33}P$), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997); and in Haugland, *Handbook of Fluorescent Probes and Research Chemicals* (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In one aspect, the acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In *Luminescence Biotechnology: Instruments and Applications*; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

w. Linking Sequence and Linking Peptide Sequence

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine (His) tags, such as a 6×His tag (SEQ ID NO: 148), which has an amino acid sequence of HHHHHH (SEQ ID NO:148), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO:149) and derivatives thereof (e.g., ADDDDK (SEQ ID NO:150), etc.); (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

x. Multivalent Binding Protein

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

y. Predetermined Cutoff and Predetermined Level

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). The present disclosure provides exemplary predetermined levels. However, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

z. Pretreatment Reagent

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., RGMa (such as membrane-associated RGMa, soluble RGMa, fragments of membrane-associated RGMa, fragments of soluble RGMa, variants of RGMa (membrane-associated or soluble RGMa) or any combinations thereof)) entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

aa. Quality Control Reagents

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

bb. Recombinant Antibody and Recombinant Antibodies

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multivalent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

cc. Sample, Test Sample, and Patient Sample

"Sample," "test sample," and "patient sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

dd. Series of Calibrating Compositions

"Series of calibrating compositions" refers to a plurality of compositions comprising a known concentration of Cys-CRGMa, wherein each of the compositions differs from the other compositions in the series by the concentration of Cys-CRGMa.

ee. Solid Phase

"Solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

ff. Specific Binding

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

gg. Specific Binding Partner

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

hh. Stringent Conditions

"Stringent conditions" is used herein to describe hybridization to filter-bound DNA in 6× sodium chloride/sodium citrate (SSC) at about 45° C. followed by one or more washes in 0.2×SSC/0.1% SDS at about 50-65° C. The term "under highly stringent conditions", refers to hybridization to filter-bound nucleic acid in 6×SSC at about 45° C. followed by one or more washes in 0.1×SSC/0.2% SDS at about 68° C., or under other stringent hybridization conditions. See, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3.

ii. Treat, Treating or Treatment

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

jj. Tracer

"Tracer" as used herein refers to an analyte or analyte fragment conjugated to a label, such as Cys-CRGMa conjugated to a fluorescein moiety, wherein the analyte conjugated to the label can effectively compete with the analyte for sites on an antibody specific for the analyte.

kk. Variant

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-RGMa antibody that differs from the corresponding fragment of anti-RGMa antibody in amino acid sequence but is still antigenically reactive and can compete with the corresponding fragment of anti-RGMa antibody for binding with RGMa. "Variant" also can be used to describe a polypeptide or a fragment thereof that has been differentially processed, such as by proteolysis, phosphorylation, or other post-translational modification, yet retains its antigen reactivity.

ll. Vector

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Anti-RGMA Antibodies

Provided herein are antibodies for use in methods of treating neurite degenerative diseases and disorders. Several of the herein described antibodies have been selected for binding to RGMa, while minimizing or eliminating reactivity with Repulsive Guidance Molecule c ("RGMc"). For example, see Table 4, wherein the PROfusion-derived monoclonal antibody AE12-1 and AE12-1 variants (AE12-1F, AE12-1H, AE12-1L, AE12-1V, AE12-1I, AE12-1K, and AE12-1Y) exhibit RGMa neutralizing activity without (low detection) cross reacting with RGMc. Because antibodies raised against RGMa can often cross-react with RGMc and, at high intravenous doses may result in iron accumulation in hepatocytes, the specific binding of the herein described antibodies for RGMa is of therapeutic benefit. Further, the high selectivity of these antibodies offers large therapeutic dose windows or ranges for treatment.

a. RGMa

Human RGMa, which can exist as a 450 amino acid protein with a predicted N-terminal signal peptide of 47 amino acids and a C-terminal GPI-attachment signal, was first proposed to regulate the guidance of retinal axons by binding to neogenin, a transmembrane protein that is also a receptor for netrins, which are secreted molecules that play a role in neuronal development and cell survival. In addition to regulating retinal axonal guidance, RGMa has been shown to inhibit axon growth in adult rats. See Yamashita et al., Current Opinion in Neurobiology (2007)17:1-6. Consistent with these mechanisms, RGMa expression increases after an injury to the spinal cord, during which time inhibition of RGMa enhances axonal growth. See Kitayama et al., PLoS One, (2011) Vol. 6 (9), pages 1-9; and Hata et al., J. Cell Biol. (2006)173:47-58. RGMa expression is also upregulated at the lesion site and in scar tissue of humans suffering from focal cerebral ischemia or traumatic brain injury. See Yamashita et al., Current Opinion in Neurobiology (2007)17:1-6; Schwab et al., Arch Neurol (2005)22:2134-2144; and Muramatsu et al., Nat. Medicine (2011) 17:488-94.

RGMa may have the following amino acid sequence:

(SEQ ID NO: 65)

MQPPRERLVV TGRAGWMGMG RGAGRSALGF WPTLAFLLCS FPAATSPCKI

LKCNSEFWSA TSGSHA PASDDTPEFC AALRSYALCT RRTARTCRGD LAYHSAVHGI

EDLMSQHNCS KDGPTSQPRL RTLPPAGDSQ ERSDSPEICH YEKSFHKHSA

TPNYTHCGLF GDPHLRTFTD RFQTCKVQGA WPLIDNNYLN VQVTNTPVLP

GSAATATSKL TIIFKNFQEC VDQKVYQAEM DELPAAFVDG SKNGGDKHGA

NSLKITEKVS GQHVEIQAKY IGTTIVVRQV GRYLTFAVRM PEEVVNAVED

WDSQGLYLCL RGCPLNQQID FQAFHTNAEG TGARRLAAAS PAPTAPETFP

YETAVAKCKE KLPVEDLYYQ ACVFDLLTTG DVNFTLAAYY ALEDVKMLHS

NKDKLHLYER TRDLPGRAAA GLPLAPRPLL GALVPLLALL PVFC.

The RGMa may be a fragment or variant of SEQ ID NO:65. The fragment of RGMa may be between 5 and 425 amino acids, between 10 and 400 amino acids, between 50 and 350 amino acids, between 100 and 300 amino acids, between 150 and 250 amino acids, between 200 and 300 amino acids, or between 75 and 150 amino acids in length. The fragment may comprise a contiguous number of amino acids from SEQ ID NO:65.

The fragment of RGMa may have the following amino acid sequence:
PCKI LKCNSEFWSA TSGSHA PASDDTPEFC AALRSYALCT RRTARTCRGD LAYHSAVHGI EDLMSQHNCS KDGPTSQPRL RTLPPAGDSQ ERSDSPEICH YEKSFHKHSA TPNYTHCGLF GD (SEQ ID NO:66), which corresponds to amino acids 47-168 of SEQ ID NO:65. The RGMa fragment may be a fragment of SEQ ID NO:66. The RGMa fragment may be a variant of SEQ ID NO:66. The RGMa fragment may have the following RGMa sequence: PCKILKCNSEFWSATSGSHAPAS (SEQ ID NO:74).

RGMa may exist as a cell membrane bound form and/or as a soluble form.

b. RGMa—Recognizing Antibody

The antibody is an antibody that binds to RGMa, a fragment thereof, or a variant thereof. The antibody may be a fragment of the anti-RGMa antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise F(ab')$_2$, Fv or scFv fragments. The antibody derivatives can be produced by peptidomimetics. Further, techniques described for the production of single chain antibodies can be adapted to produce single chain antibodies.

Human antibodies may be derived from phage-display technology or from transgenic mice that express human immunoglobulin genes. The human antibody may be generated as a result of a human in vivo immune response and isolated. See, for example, Funaro et al., BMC Biotechnology, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-RGMa antibodies. For example, libraries of naïve human single chain variable fragments (scFv) may be used to select human anti-RGMa antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art. For example, not only do the antibodies of the invention recognize and bind RGMa, they are further characterized by having an additional biological activity, for example, the ability to attenuate clinical signs associated with diseases related to neurite degeneration.

The antibody may specifically bind to RGMa. The RGMa-specific RGMa antibody may comprise SEQ ID NOs:1 and 5; SEQ ID NOs:2-4 and 6-8; SEQ ID NOs:2-4,6,7, and 67; SEQ ID NOs:2-4,6,7, and 68; SEQ ID NOs:2-4,6,7, and 69; SEQ ID NOs:2-4,6,7, and 70; SEQ ID NOs:2-4,6,7, and 71; SEQ ID NOs:2-4,6,7, and 72; or SEQ ID NOs:2-4,6,7, and 73. The antibody may bind to SEQ ID NO:65, SEQ ID NO:66, SEQ ID NO:74, or a fragment or variant thereof. The antibody may recognize and specifically bind an epitope present on a RGMa polypeptide or a variant as described above. The epitope may be SEQ ID NO:66, SEQ ID NO:74, or a variant thereof (1) Antibody Binding Characteristics The antibody may immunospecifically bind to RGMa (SEQ ID NO:65), SEQ ID NO:66, SEQ ID NO:74, a fragment thereof, or a variant thereof and may have a $k_{off}$ (or $k_d$) of at least $1.0 \times 10^{-3}$ s$^{-1}$, of at least $1.0 \times 10^{-4}$ s$^{-1}$, of at least $1.0 \times 10^{-5}$ s$^{-1}$, of at least $1.0 \times 10^{-6}$ s$^{-1}$ or has a $k_{off}$ (or $k_d$) ranging from $1.0 \times 10^{-3}$ s$^{-1}$ to $1.0 \times 10^{-6}$ s$^{-1}$, from $1.0 \times 10^{-3}$ s$^{-1}$ to $1.0 \times 10^{-5}$ s$^{-1}$ or from $1.0 \times 10^{-3}$ s$^{1}$ to $1.0 \times 10^{-4}$ s$^{-1}$. The fragment may be SEQ ID NO:66 or SEQ ID NO:74.

The antibody may immunospecifically bind to RGMa (SEQ ID NO:65), SEQ ID NO:66, SEQ ID NO:74, a fragment thereof, or a variant thereof and has a $k_{on}$ (or $k_a$) of at least $2.4 \times 10^4$ M$^{-1}$s$^{-1}$, of at least about $2.5 \times 10^4$ M$^{-1}$s$^{-1}$, of at least about $3.3 \times 10^4$ M$^{-1}$s$^{-1}$, of at least about $5.0 \times 10^4$ M$^{-1}$s$^{-1}$, of at least about $1.25 \times 10^6$ M$^{-1}$s$^{-1}$ of at least about $1.35 \times 10^6$ M$^{-1}$s$^{-1}$, of at least about $1.0 \times 10^6$ M$^{-1}$s$^{-1}$, of at least about $1.0 \times 10^7$ M$^{-1}$s$^{-1}$, or has a $k_{on}$ (or $k_a$) ranging from about $5.0 \times 10^4$ M$^{-1}$s$^{-1}$ to about $1.0 \times 10^8$ M$^{-1}$s$^{-1}$, from about $3.3 \times 10^4$ M$^{-1}$s$^{-1}$ to about $1.0 \times 10^9$ M$^{-1}$s$^{-1}$, from about $2.5 \times 10^4$ M$^{-1}$s$^{-1}$ to about $1.25 \times 10^6$ M$^{-1}$s$^{-1}$, from about $2.4 \times 10^4$ M$^{-1}$s$^{-1}$ to about $1.35 \times 10^7$ M$^{-1}$s$^{-1}$. The fragment may be SEQ ID NO:66 or SEQ ID NO:74.

(2) Antibody Structure (a) Heavy Chain and Light Chain CDRs

The antibody may immunospecifically bind to RGMa (SEQ ID NO:65), SEQ ID NO:66, SEQ ID NO:74, a fragment thereof, or a variant thereof and comprise a variable heavy chain and/or variable light chain shown in Table 1. The antibody may immunospecifically bind to RGMa, a fragment thereof, or a variant thereof and comprise one or more of the heavy chain or light chain CDR sequences also shown in Table 1. The light chain of the antibody may be a kappa chain or a lambda chain. For example, see Table 1.

Provided herein is an isolated nucleic acid encoding an antibody that immunospecifically binds to RGMa, a fragment thereof, or a variant thereof. The isolated nucleic acid may comprise a nucleotide sequence that hybridizes, under stringent conditions, to the nucleic acid molecule that encodes an antibody comprising the heavy chain or light chain CDR sequences shown in Table 1.

TABLE 1

List of Amino Acid Sequences of VH and VL Regions of Fully Human Anti-RGMa Monoclonal Antibodies (AE12-1 to AE12-8, AE12-13, AE12-15, AE12-20, AE12-21, AE12-23, and AE12-24)

| PROTEIN REGION | SEQ ID NO. | SEQUENCE |
| --- | --- | --- |
| AE12-1 (VH) | 1 | EVQLVQSGAEVKKPGASVKVSCKAS GYTFTSHGISWVRQAPGQGLDWMG WISPYSGNTNYAQKLQGRVTMTTD TSTSTAYMELSSLRSEDTAVYYCAR VGSGPYYYMDVWGQGTLVTVSS |
| AE12-1 (VH) CDR-H1 | 2 | SHGIS |
| AE12-1 (VH) CDR-H2 | 3 | WISPYSGNTNYAQKLQG |
| AE12-1 (VH) CDR-H3 | 4 | VGSGPYYYMDV |
| AE12-1 (VL) (Lambda chain) | 5 | QSALTQPRSVSGSPGQSVTISCTG TSSSVGDSIYVSWYQQHPGKAPK LMLYDVTKRPSGVPDRFSGSKSG NTASLTISGLQAEDEADYYCCSY AGTDTLFGGGTKVTVL |
| AE12-1 (VL) CDR-L1 | 6 | TGTSSSVGDSIYVS |
| AE12-1 (VL) CDR-L2 | 7 | DVTKRPS |
| AE12-1 (VL) CDR-L3 | 8 | CSYAGTDTL |
| AE12-2 (VH) | 9 | EVQLVQSGAEVKKPGASVKVSC KASGYTFTSYDINWVRQATGQG LEWMGWMNPNSGNTGYAQKFQ |

TABLE 1-continued

List of Amino Acid Sequences of VH and VL Regions of Fully Human Anti-RGMa Monoclonal Antibodies (AE12-1 to AE12-8, AE12-13, AE12-15, AE12-20, AE12-21, AE12-23, and AE12-24)

| PROTEIN REGION | SEQ ID NO. | SEQUENCE |
| --- | --- | --- |
| | | GRVTMTRNTSISTAYMELSSLRSEDTAVYYCARSTSLSVWGQGTLVTVSS |
| AE12-2 (VH) CDR-H1 | 10 | SYDIN |
| AE12-2 (VH) CDR-H2 | 11 | WMNPNSGNTGYAQKFQG |
| AE12-2 (VH) CDR-H3 | 12 | STSLSV |
| AE12-2 (VL) (Lambda chain) | 13 | SYELTQPPSVSVSPGQTASITCSGDKLGDKYACWYQQKPGQSPVLVIYQDSKRPSGIPKRFSGSNSGDTATLTISGTQAMDEADYYCQAWDSSTGVFGPGTKVTVL |
| AE12-2 (VL) CDR-L1 | 14 | SGDKLGDKYAC |
| AE12-2 (VL) CDR-L2 | 15 | QDSKRPS |
| AE12-2 (VL) CDR-L3 | 16 | QAWDSSTGV |
| AE12-3 (VH) | 17 | EVQLVESGGGLVQPGRSLRLSCAASGFTFDDYAMHWVRQAPGKGLEWVAVISYDGSNKYYADSVKGRFTISRDNSKNTLYLQMNSLRAEDTAVYYCARERVYSSGKEGYYYGMDVWGQGTMVTVSS |
| AE12-3 (VH) CDR-H1 | 18 | DYAMH |
| AE12-3 (VH) CDR-H2 | 19 | VISYDGSNKYYADSVKG |
| AE12-3 (VH) CDR-H3 | 20 | ERVYSSGKEGYYYGMDV |
| AE12-3 (VL) (Lambda chain) | 21 | QSGLTQPPSVSAAPGQRVTISCTGSGSNIGAGYGVHWYQQLPATAPKILIYGDYNRPSGVPDRFSGSRSGTSASLTITGLQAEDEADYYCQSYDNSLRGVLFGGGTKLTVL |
| AE12-3 (VL) CDR-L1 | 22 | TGSGSNIGAGYGVH |
| AE12-3 (VL) CDR-L2 | 23 | GDYNRPS |
| AE12-3 (VL) CDR-L3 | 24 | QSYDNSLRGVL |
| AE12-4 (VH) | 25 | EVQLVESGGGVVQPGTSLRLSCAASGFPFSSYGMHWVRQAPGKGLEWVAAISGDGILKYYTDSVKGRFTISRDNSKNTLYLQMNNLSGEDTGLYYCARNYDNSLDYWGQGTLVTVSS |
| AE12-4 (VH) CDR-H1 | 26 | SYGMH |
| AE12-4 (VH) CDR-H2 | 27 | AISGDGILKYYTDSVKG |
| AE12-4 (VH) CDR-H3 | 28 | NYDNSLDY |
| AE12-4 (VL) (Lambda chain) | 29 | QPVLTQSPSVSASLGASVKVTCTLSSGHSAYAIAWHQQQPEKGPRYLMKVNSDGSHNKGDGVPDRFSGSSSGAERYLIISGLQSEDEADYYCQTWGPGIRVFGGGTKLTVL |
| AE12-4 (VL) CDR-L1 | 30 | TLSSGHSAYAIA |
| AE12-4 (VL) CDR-L2 | 31 | VNSDGSHNKGD |
| AE12-4 (VL) CDR-L3 | 32 | QTWGPGIRV |

TABLE 1-continued

List of Amino Acid Sequences of VH and VL Regions of Fully Human Anti-RGMa Monoclonal Antibodies (AE12-1 to AE12-8, AE12-13, AE12-15, AE12-20, AE12-21, AE12-23, and AE12-24)

| PROTEIN REGION | SEQ ID NO. | SEQUENCE |
|---|---|---|
| AE12-5 (VH) | 33 | EVQLVQSGAEVKKPGASVKVSCKVSGHSLSELTIHWVRQAPGKGLEWMGGFDPEDGRGTYAPNFRGRVTMTEDTSTDTAYMELSGLRSEDAAVYCATLLGEYDSYFDLWGRGTLVTVSS |
| AE12-5 (VH) CDR-H1 | 34 | ELTIH |
| AE12-5 (VH) CDR-H2 | 35 | GFDPEDGRGTYAPNFRG |
| AE12-5 (VH) CDR-H3 | 36 | LLGEYDSYFDL |
| AE12-5 (VL) (Kappa chain) | 37 | DVVMTQSPDFQSVTPEDKVTITCRASQSIGSCLHWYQQKPDQSPKLLIKYASQSISGVPSRFSGSGSGTDFTLTINSLEAEDAATYYCHQSSSLPYTFGQGTKLEIK |
| AE12-5 (VL) CDR-L1 | 38 | RASQSIGSCLH |
| AE12-5 (VL) CDR-L2 | 39 | YASQSIS |
| AE12-5 (VL) CDR-L3 | 40 | HQSSSLPYT |
| AE12-6 (VH) | 41 | EVQLVQSGAEVKKPGASVKVSCKASGYIFTNYDIAWVRQAPGQGLEWMGWMNPDSGNTGFVQKFKGRVTATSNTDITTAYMELSSLTSEDTAVYYCARDRFGSGYDLDHWGQGTLVTVSS |
| AE12-6 (VH) CDR-H1 | 42 | NYDIA |
| AE12-6 (VH) CDR-H2 | 43 | WMNPDSGNTGFVQKFKG |
| AE12-6 (VH) CDR-H3 | 44 | DRFGSGYDLDH |
| AE12-6 (VL) (Lambda chain) | 45 | SYELTQPPSVSVAPGQTARITCGGNNIGSKSVHWYQQKPGQAPVLVVYDDSDRPSGIPERFSGSNSGNTATLTISRVEAGDEADYYCQVWGSSSDHYVFGTGTKVTVL |
| AE12-6 (VL) CDR-L1 | 46 | GGNNIGSKSVH |
| AE12-6 (VL) CDR-L2 | 47 | DDSDRPS |
| AE12-6 (VL) CDR-L3 | 48 | QVWGSSSDHYV |
| AE12-7 (VH) | 49 | EVQLVESGGGLVQPGGSLRLSCAASGFTSSSYAMTWVRQAPGKGLEWVSGISGSGESTYYADSVKGRFTISRDNSKNTLYLQMNSLRVEDTAIYYCARQGYGAHDYWGQGTLVTVSS |
| AE12-7 (VH) CDR-H1 | 50 | SYAMT |
| AE12-7 (VH) CDR-H2 | 51 | GISGSGESTYYADSVKG |
| AE12-7 (VH) CDR-H3 | 52 | QGYGAHDY |
| AE12-7 (VL) (Lambda chain) | 53 | QSVLTQPPSASGTPGQRVTISCSGASSNVGSNRVNWYQQFPGMAPKLLIYSNNQRPSGVPDRFSGSKSGTSASLAISGLQSEDEADYYCAAWDDSLNGYVFGTGTKVTVL |
| AE12-7 (VL) CDR-L1 | 54 | SGASSNVGSNRVN |
| AE12-7 (VL) CDR-L2 | 55 | SNNQRPS |
| AE12-7 (VL) CDR-L3 | 56 | AAWDDSLNGYV |

TABLE 1-continued

List of Amino Acid Sequences of VH and VL Regions of Fully Human Anti-RGMa Monoclonal Antibodies (AE12-1 to AE12-8, AE12-13, AE12-15, AE12-20, AE12-21, AE12-23, and AE12-24)

| PROTEIN REGION | SEQ ID NO. | SEQUENCE |
|---|---|---|
| AE12-8 (VH) | 57 | EVQLLESGGGLVKPGGSLRLSCAASGFTFD DYAMHWVRQAPGKGLEWVSLISWDGG STYYADSVKGRFTISRDNSKNSLYLQMN SLRAEDTALYYCAKDIPKVGGYSYGYG ALGYWGQGTPVTVSS |
| AE12-8 (VH) CDR-H1 | 58 | DYAMH |
| AE12-8 (VH) CDR-H2 | 59 | LISWDGGSTYYADSVKG |
| AE12-8 (VH) CDR-H3 | 60 | DIPKVGGYSYGYGALGY |
| AE12-8 (VL) (Lambda chain) | 61 | SYELTQPPSVSVAPGQTARITCGGNNIGD ISVHWYQQKSGQAPMLVVHDDSDRPSG IPERFSGSNSGSSATLTISRVEAGDEAD YHCQVWDSGSGHHVFGTGTKVTVL |
| AE12-8 (VL) CDR-L1 | 62 | GGNNIGDISVH |
| AE12-8 (VL) CDR-L2 | 63 | DDSDRPS |
| AE12-8 (VL) CDR-L3 | 64 | QVWDSGSGHHV |
| AE12-13 (VH) | 91 | EVQLQESGAGLLKPSETLSLTCAVYGG SFSGYYWSWIRQPPGKGLEWIGEINHS GSTNYNPSLKSRVTISVDTSKNQFSLKL SSVTAADTAVYYCARDDGAGVFDLW GRGTLVTVSS |
| AE12-13 (VH) CDR-H1 | 92 | GYYWS |
| AE12-13 (VH) CDR-H2 | 93 | EINHSGSTNYNPSLKS |
| AE12-13 (VH) CDR-H3 | 94 | DDGAGVFDL |
| AE12-13 (VL) (Kappa chain) | 95 | DIQLTQSPSSLSASVGDGVTITCQASQ DISNYLNWYQQKPGKAPKLLIYDASN LETGVPSRFSGSGSGTFFTLTINNLQPE DFATYYCQQSGNTPWTFGQGTKVEINR |
| AE12-13 (VL) CDR-L1 | 96 | QASQDISNYLN |
| AE12-13 (VL) CDR-L2 | 97 | DASNLET |
| AE12-13 (VL) CDR-L3 | 98 | QQSGNTPWT |
| AE12-15 (VH) | 99 | EVQLVQSGAEVKEPGASVKVSCKA SGYTFTDYYIQWVRQAPGHGLEWM GWINPKTGGTNYLQKFQGRVTMTR DTSTRTAYMELSSLRSDDTAFYYCV REDMNTVLATSWFDPWGQGTLVTVSS |
| AE12-15 (VH) CDR-H1 | 100 | DYYIQ |
| AE12-15 (VH) CDR-H2 | 101 | WINPKTGGTNYLQKFQG |
| AE12-15 (VH) CDR-H3 | 102 | EDMNTVLATSWFDP |
| AE12-15 (VL) (Lambda chain) | 103 | SYELTQPPSVSVSPGQTARITCSGNQ LGHKFASWYQQKPGQSPVVVIYED KKRPSGIPERFSGSNSGNTATLTISG TQAMDEADYYCQVWDVITDHYVF GTGTKVTVLG |
| AE12-15 (VL) CDR-L1 | 104 | SGNQLGHKFAS |
| AE12-15 (VL) CDR-L2 | 105 | EDKKRPS |
| AE12-15 (VL) CDR-L3 | 106 | QVWDVITDHYV |
| AE12-20 (VH) | 107 | EVQLVQSGSEVKKPGASVKLSCKT SGYTFTNSAIHWVRQAPGQRLEWM |

TABLE 1-continued

List of Amino Acid Sequences of VH and VL Regions of Fully Human Anti-RGMa Monoclonal Antibodies (AE12-1 to AE12-8, AE12-13, AE12-15, AE12-20, AE12-21, AE12-23, and AE12-24)

| PROTEIN REGION | SEQ ID NO. | SEQUENCE |
|---|---|---|
| | | GWINAGNGNTKYSQKFQGRVTITR DTSASTAYMELSSLRSEDTAVYYCA WAYCGGDCYSLDYWGQGTLVTVSS |
| AE12-20 (VH) CDR-H1 | 108 | NSAIH |
| AE12-20 (VH) CDR-H2 | 109 | WINAGNGNTKYSQKFQG |
| AE12-20 (VH) CDR-H3 | 110 | AYCGGDCYSLDY |
| AE12-20 (VL) (Kappa chain) | 111 | DIQVTQSPSSLAASVGDRVTITCQAS QDISNYLNWYQQRPGKAPKLLIYDA SNLETGVPPRFSGDGSTHFSFTITNV QPEDVGTYYCQQYDSLPLTFGQGTR LEIKR |
| AE12-20 (VL) CDR-L1 | 112 | QASQDISNYLN |
| AE12-20 (VL) CDR-L2 | 113 | DASNLET |
| AE12-20 (VL) CDR-L3 | 114 | QQYDSLPLT |
| AE12-21 (VH) | 115 | EVQLLESGGDLVRPGGSLRLTCEGSG FNFFTQTIHWVRQAPGKGLEWVASIS SDSNYIYHADSLKGRFTVSRDNAQDS VFLQMNSLRVEDTAVYYCARDILLEP LAPHYYYGLDVWGQGTTVTVSS |
| AE12-21 (VH) CDR-H1 | 116 | TQTIH |
| AE12-21 (VH) CDR-H2 | 117 | SISSDSNYIYHADSLKG |
| AE12-21 (VH) CDR-H3 | 118 | DILLEPLAPHYYYGLDV |
| AE12-21 (VL) (Kappa chain) | 119 | DIQVTQSPSSLSASVGDRVTITCRAS QPISTYVNWYQQKPGKAPKLLIYDA STLEIGVPSRISGSGSGTDFTFTISSLQ PEDIATYYCQQYDNFPLTFGGGTKV DIKR |
| AE12-21 (VL) CDR-L1 | 120 | RASQPISTYVN |
| AE12-21 (VL) CDR-L2 | 121 | DASTLEI |
| AE12-21 (VL) CDR-L3 | 122 | QQYDNFPLT |
| AE12-23 (VH) | 123 | EVQLQESGPGLVKPSETLSLTCTVSG GSISGYYWSWIRQSPGKGLEWIGEIFH TGRTYYNPSLRSRLTISVDTSKNQFSL KLSSLTAADTAVYYCARDSAFGSFD YWGQGTLVTVSS |
| AE12-23 (VH) CDR-H1 | 124 | GYYWS |
| AE12-23 (VH) CDR-H2 | 125 | EIFHTGRTYYNPSLRS |
| AE12-23 (VH) CDR-H3 | 126 | DSAFGSFDY |
| AE12-23 (VL) (Kappa chain) | 127 | DIRVTQSPSSLSASVGDRVTITCQAN EDISIYLNWYQQRPGKAPKLLIYDA SNLETGVPSRFSGSGSGTDFTFTISS LQPEDFATYYCQQYHTYPFTFGGGT KVDIKR |
| AE12-23 (VL) CDR-L1 | 128 | QANEDISIYLN |
| AE12-23 (VL) CDR-L2 | 129 | DASNLET |
| AE12-23 (VL) CDR-L3 | 130 | QQYHTYPFT |
| AE12-24 (VH) | 131 | EVQLQESGPGLVKPSETLSLTCNVSG GSISSYYWSWIRQPPGKGLEWIGNIYY SGSTNYNPSLKSRVTISVDTSKSQFSLK |

TABLE 1-continued

List of Amino Acid Sequences of VH and VL Regions of Fully Human Anti-RGMa Monoclonal Antibodies (AE12-1 to AE12-8, AE12-13, AE12-15, AE12-20, AE12-21, AE12-23, and AE12-24)

| PROTEIN REGION | SEQ ID NO. | SEQUENCE |
|---|---|---|
| | | LSSVTAADTAVYYCARALDFWSGQY FDYWGQGTLVTVSS |
| AE12-24 (VH) CDR-H1 | 132 | SYYWS |
| AE12-24 (VH) CDR-H2 | 133 | NIYYSGSTNYNPSLKS |
| AE12-24 (VH) CDR-H3 | 134 | ALDFWSGQYFDY |
| AE12-24 (VL) (Kappa chain) | 135 | DIVMTQTPSSLSASVGDRVTITCQASQD ISDYLNWYQQKPGKAPKLLIYDASTLE SGVPSRFSGSGSGTDFTLTISGLQPEDF ATYYCQQSYSIPPTFGPGTRLEIKR |
| AE12-24 (VL) CDR-L1 | 136 | QASQDISDYLN |
| AE12-24 (VL) CDR-L2 | 137 | DASTLES |
| AE12-24 (VL) CDR-L3 | 138 | QQSYSIPPT |

The antibody or variant or derivative thereof may contain one or more amino acid sequences that are greater than 95%, 90%, 85%, 80%, 75%, 70%, 65%, 60%, 55%, or 50% identical to one or more of SEQ ID NOs:1-64 and 67-73. The antibody or variant or derivative thereof may be encoded by one or more nucleic acid sequences that are greater than 95%, 90%, 85%, 80%, 75%, 70%, 65%, 60%, 55%, or 50% identical to one or more of SEQ ID NOs:1-64 and 67-73. Polypeptide identity and homology can be determined, for example, by the algorithm described in the report: Wilbur, W. J. and Lipman, D. J. Proc. Natl. Acad. Sci. USA 80, 726-730 (1983).

The herein described antibody, variant or derivative thereof may be encoded by a nucleic acid that hybridizes under stringent conditions with the complement of one or more of SEQ ID NOs:3-42. The herein described antibody, variant or derivative thereof may be encoded by a nucleic acid that hybridizes under highly stringent conditions with the complement of one or more nucleic acids that encode one or more of SEQ ID NOs:1-64 and 67-73.

The antibody may comprise SEQ ID NO:8, wherein the Cys residue of SEQ ID NO:8 is substituted for another amino acid. The antibody may comprise SEQ ID NOs:1 and 5, or 2-4 and 6-8, wherein the Cys residue of SEQ ID NO:8 is substituted for another amino acid, or wherein the Cys residue at position 91 of SEQ ID NO:5 is substituted with another amino acid. The Cys residue at position 91 of SEQ ID NO:5 may be substituted with a phenylalanine, a histidine, a leucine, a valine, an isoleucine, a lysine, or a tyrosine, for example. The Cys residue of SEQ ID NO:8 may be substituted with a phenylalanine (see SEQ ID NO:67), a histidine (see SEQ ID NO:68), a leucine (see SEQ ID NO:69), a valine (see SEQ ID NO:70), an isoleucine (see SEQ ID NO:71), a lysine (see SEQ ID NO:72), or a tyrosine (see SEQ ID NO:73), for example. See Table 2.

The antibody may be an IgG, IgE, IgM, IgD, IgA and IgY molecule class (for example, IgG1, IgG2, IgG3, IgG4, IgA1 and IgA2) or subclass. For example, the antibody may be an IgG1 molecule having the following constant region sequence:

(SEQ ID NO: 140)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPEAAG

GPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVD

KSRWQQGNVFSCSVMHEALHNHYTQKSLSLSPGK.

The above constant region in SEQ ID NO:140 contains two (2) mutations of the wildtype constant region sequence at positions 234 and 235. Specifically, these mutations are leucine to alanine changes at each of positions 234 and 235 (which are referred to as the "LLAA" mutations). These mutations are shown above in bold and underlining. The purpose of these mutations is to eliminate the effector function.

Alternatively, an IgG1 molecule can have the above constant region sequence (SEQ ID NO:140) containing one or more mutations. For example, the constant region sequence of SEQ ID NO:140 may containing a mutation at amino acid 250 where threonine is replaced with glutamine (SEQ ID NO:141), a mutation at amino acid 428 where methionine is replaced with leucine (SEQ ID NO:142) or mutations at amino acid 250 where threonine is replaced with glutamine and a mutation at amino acid 428 where methionine is replaced with leucine (SEQ ID NO:143) as shown below in Table 2A.

Alternatively, an IgG1 molecule can contain a heavy chain comprising: AE12-1 (VH) CDR-H1 (SEQ ID NO:2), AE12-1 (VH) CDR-H2 (SEQ ID NO:3), AE12-1 (VH) CDR-H3 (SEQ ID NO:4) and a light chain comprising: AE12-1 (VL) CDR-L1 (SEQ ID NO:6), AE12-1 (VL) CDR-L2 (SEQ ID NO:7) and AE12-1-V (VL) CDR-L3 (SEQ ID NO:70) and a constant sequence of SEQ ID NO:143 as shown below in Table 2B (this antibody is referred to as AE12-1V-QL and has a light chain sequence of SEQ ID NO:144 and a heavy chain sequence of SEQ ID NO: 145).

Alternatively, an IgG1 molecule can contain a heavy chain comprising: AE12-1 (VH) CDR-H1 (SEQ ID NO:2), AE12-1 (VH) CDR-H2 (SEQ ID NO:3), AE12-1 (VH) CDR-H3 (SEQ ID NO:4) and a light chain comprising: AE12-1 (VL) CDR-L1 (SEQ ID NO:6), AE12-1 (VL) CDR-L2 (SEQ ID NO:7) and AE12-1-Y (VL) CDR-L3 (SEQ ID NO:73) and a constant sequence of SEQ ID NO:143 as shown below in Table 2B (this antibody is referred to as AE12-1Y-QL and has a light chain sequence of SEQ ID NO:146 and a heavy chain sequence of SEQ ID NO: 147).

TABLE 2

| PROTEIN REGION | SEQ ID NO. | SEQUENCE |
| --- | --- | --- |
| AE12-1-F (VL) CDR-L3 | 67 | FSYAGTDTL |
| AE12-1-H (VL) CDR-L3 | 68 | HSYAGTDTL |
| AE12-1-L (VL) CDR-L3 | 69 | LSYAGTDTL |
| AE12-1-V (VL) CDR-L3 | 70 | VSYAGTDTL |
| AE12-1-I (VL) CDR-L3 | 71 | ISYAGTDTL |
| AE12-1-K (VL) CDR-L3 | 72 | KSYAGTDTL |
| AE12-1-Y (VL) CDR-L3 | 73 | YSYAGTDTL |

TABLE 2A

| Amino acid Mutation | SEQ ID NO: | SEQUENCE |
| --- | --- | --- |
| None | 140 | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLTCL VKGFYPSDIAVEWESNGQPENNYKTTPPVLDSDGSFFLYSKL TVDKSRWQQGNVFSCSVMHEALHNHYTQKSLSLSPGK |
| T250Q | 141 | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPEAAGGPSVFLFP PKPKDQLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLTCL VKGFYPSDIAVEWESNGQPENNYKTTPPVLDSDGSFFLYSKL TVDKSRWQQGNVFSCSVMHEALHNHYTQKSLSLSPGK |
| M428L | 142 | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPEAAGGPSVFLFP PKPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLTCL VKGFYPSDIAVEWESNGQPENNYKTTPPVLDSDGSFFLYSKL TVDKSRWQQGNVFSCSVLHEALHNHYTQKSLSLSPGK |
| T250Q and M428L | 143 | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPEAAGGPSVFLFP PKPKDQLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLTCL VKGFYPSDIAVEWESNGQPENNYKTTPPVLDSDGSFFLYSKL TVDKSRWQQGNVFSCSVLHEALHNHYTQKSLSLSPGK |

TABLE 2B

| PROTEIN REGION | SEQ ID NO: | SEQUENCE |
| --- | --- | --- |
| AE12-1V-QL Light chain (CDR's underlined | 144 | QSALTQPRSVSGSPGQSVTISC<u>TGTSSSVGDSIYVS</u>WYQQHPGKAPK LMLY<u>DVTKRPS</u>GVPDRFSGSKSGNTASLTISGLQAEDEADYYC<u>VSYA GTDTL</u>FGGGTKVTVLGQPKAAPSVTLFPPSSEELQANKATLVCLISDF YPGAVTVAWKADSSPVKAGVETTTPSKQSNNKYAASSYLSLTPEQWKS HRSYSCQVTHEGSTVEKTVAPTECS* |

TABLE 2B-continued

| PROTEIN REGION | SEQ ID NO: | SEQUENCE |
|---|---|---|
| AE12-1V-QL Heavy chain (CDR's underlined and mutations bolded) | 145 | EVQLVQSGAEVKKPGASVKVSCKASGYTFT<u>SHGI</u>SWVRQAPGQGLDW MG<u>WISPYSGNTNYAQKLQG</u>RVTMTTDTSTSTAYMELSSLRSEDTAVY YCAR<u>VGSGPYYYMDV</u>WGQGTLVTVSSASTKGPSVFPLAPSSKSTSGG TAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPEA AGGPSVFLFPPKPKDQLMISRTPEVTCVVVDVSHEDPEVKFNWYVDGV EVHNAKTKPREEQYNSTYRVVSVLTVLHQDWLNGKEYKCKVSNKALPA PIEKTISKAKGQPREPQVYTLPPSREEMTKNQVSLTCLVKGFYPSDIA VEWESNGQPENNYKTTPPVLDSDGSFFLYSKLTVDKSRWQQGNVFSCS VLHEALHNHYTQKSLSLSPGK* |
| AE12-1Y-QL Light chain (CDR's underlined and mutations bolded) | 146 | QSALTQPRSVSGSPGQSVTISC<u>TGTSSSVGDSIYVS</u>WYQQHPGKAP KLMLY<u>DVTKRPS</u>GVPDRFSGSKSGNTASLTISGLQAEDEADYYC<u>YS YAGTDTLF</u>GGGTKVTVLGQPKAAPSVTLFPPSSEELQANKATLVCLI SDFYPGAVTVAWKADSSPVKAGVETTTPSKQSNNKYAASSYLSLTPE QWKSHRSYSCQVTHEGSTVEKTVAPTECS* |
| AE12-1Y-QL Heavy chain (CDR's underlined and mutations bolded) | 147 | EVQLVQSGAEVKKPGASVKVSCKASGYTFT<u>SHGI</u>SWVRQAPGQGLDWM G<u>WISPYSGNTNYAQKLQG</u>RVTMTTDTSTSTAYMELSSLRSEDTAVYYC AR<u>VGSGPYYYMDV</u>WGQGTLVTVSSASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPEAAGGPSVF LFPPKPKDQLMISRTPEVTCVVVDVSHEDPEVKFNWYVDGVEVHNAKTKP REEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNY KTTPPVLDSDGSFFLYSKLTVDKSRWQQGNVFSCSVLHEALHNHYTQKSL SLSPGK* |

The antibody or antibody fragment may comprise a variable heavy domain that comprises three complementarity-determining regions (CDR-H1, H2, and H3) corresponding to the following formulas, respectively:

Xaa1-Xaa2-Xaa3-Xaa4-Xaa5 (Formula 1—CDR-H1), wherein Xaa1 is an amino acid selected from the group consisting of S, D, E, N, G, and T; Xaa2 is an amino acid selected from the group consisting of H, Y, L, S, and Q; Xaa3 is an amino acid selected from the group consisting of G, D, A, T, and Y; Xaa4 is an amino acid selected from the group consisting of I, M, and W; and Xaa5 is an amino acid sequence from the group consisting of S, N, H, A, T, and Q;

Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-(Xaa)n (Formula 2—CDR-H2), wherein n is 0 or 1, and
wherein Xaa1 is an amino acid selected from the group consisting of W, V, A, G, L, E, S, and N; Xaa2 is an amino acid selected from the group consisting of I, M, and F; Xaa3 is an amino acid selected from the group consisting of S, N, D, F, and Y; Xaa4 is an amino acid selected from the group consisting of P, Y, G, W, H, A, and S; Xaa5 is an amino acid selected from the group consisting of Y, N, D, E, S, K, G, and T; Xaa6 is an amino acid selected from the group consisting of S, G, D, T, and N; Xaa7 is an amino acid selected from the group consisting of G, S, I, E, N, and R; Xaa8 is an amino acid selected from the group consisting of N, L, R, S, T, and Y; Xaa9 is an amino acid selected from the group consisting of T, K, G, N, I, and Y; Xaa10 is an amino acid selected from the group consisting of N, G, Y, T, and K; Xaa11 is an amino acid selected from the group consisting of Y, F, N, and H; Xaa12 is an amino acid selected from the group consisting of A, T, V, P, L, and S; Xaa13 is an amino acid selected from the group consisting of Q, D, P, and S; Xaa14 is an amino acid selected from the group consisting of K, S, N, and L; Xaa15 is an amino acid selected from the group consisting of L, F, V, K, and R; Xaa16 is an amino acid selected from the group consisting of Q, K, R, and S; and Xaa17 is a glycine; and Xaa1-Xaa2-Xaa3-Xaa4-Xaa5-Xaa6-(Xaa)n (Formula 3—CDR-H3), wherein n is 0-11, and
wherein Xaa1 is an amino acid selected from the group consisting of V, S, E, N, L, D, Q, and A; Xaa2 is an amino acid selected from the group consisting of G, T, R, Y, L, I, D, and S; Xaa3 is an amino acid selected from the group consisting of S, V, D, G, F, Y, P, M, C, L, and A; Xaa4 is an amino acid selected from the group consisting of G, L, Y, N, E, K, A, and F; Xaa5 is an amino acid selected from the group consisting of P, S, Y, A, V, G, T, E, and W; Xaa6 is an amino acid selected from the group consisting of Y, V, S, L, D, G, H, and P; Xaa7 is an amino acid selected from the group consisting of Tyr, Asp, Gly, Ser, Phe, Leu, and Cys; Xaa8 is an amino acid selected from the group consisting of Tyr, Lys, Asp, Ala, and Gln; Xaa9 is an amino acid selected from the group consisting of Met, Glu, Phe, Leu, Ser, Thr, Pro, and Tyr; Xaa10 is an amino acid selected from the group consisting of Asp, Gly, Tyr, Ser, Leu, His, and Phe; Xaa11 is an amino acid selected from the group consisting of Val, Tyr, Leu, His, Gly, Trp, and Asp; Xaa12 is an amino acid selected from the group consisting of Tyr and Phe; Xaa13 is an amino acid selected from the group consisting of Tyr, Gly, and Asp; Xaa14 is an amino acid selected from the group consisting of Ala, Leu, Pro, and Tyr; Xaa15 is an amino acid selected from the group consisting of Met, Leu, and Phe; Xaa16 is an amino acid selected from the group consisting of Asp and Gly; and Xaa17 is an amino acid selected from the group consisting of an Val, Asp, and Tyr.

The isolated antibody or antibody fragment thereof may comprise a variable light domain that comprises three complementarity-determining regions (CDR-L1, L2, and L3) corresponding to the following formulas, respectively:

Xaa1-Xaa2-Xaa3-Xaa4-Xaa5-Xaa6-Xaa7-Xaa8-Xaa9-Xaa10-Xaa11-(Xaa)$n$  (Formula 1—CDR-L1), wherein n is 0-3, and
wherein Xaa1 is an amino acid selected from the group consisting of T, S, R, G, and Q; Xaa2 is an amino acid selected from the group consisting of G, L, and A; Xaa3 is an amino acid selected from the group consisting of T, D, S, N and A; Xaa4 is an amino acid selected from the group consisting of S, K, G, Q, N, and E; Xaa5 is an amino acid sequence from the group consisting of S, L, G, I, D, and P; Xaa6 is an amino acid selected from the group consisting of S, G, N, H, and I; Xaa7 is an amino acid selected from the group consisting of V, D, I, S, G and H; Xaa8 is an amino acid selected from the group consisting of G, K, A, S, I, N, T, and D; Xaa9 is an amino acid selected from the group consisting of D, Y, A, C, S, and F; Xaa10 is an amino acid selected from the group consisting of S, A, G, L, V, and N; Xaa11 is an amino acid selected from the group consisting of I, C, Y, H, R, N, and S; Xaa12 is an amino acid selected from the group consisting of Tyr, Gly, Ala, and Val; Xaa13 is an amino acid selected from the group consisting of Val, and Asn; and Xaa14 is an amino acid selected from the group consisting of Ser and His;

Xaa1-Xaa2-Xaa3-Xaa4-Xaa5-Xaa6-Xaa7-(Xaa)$n$  (Formula 2—CDR-L2), wherein n is 0-4, and wherein Xaa1 is an amino acid selected from the group consisting of D, Q, G, V, Y, S and E; Xaa2 is an amino acid selected from the group consisting of V, D, N, and A; Xaa3 is an amino acid selected from the group consisting of T, S, Y, N, and K; Xaa4 is an amino acid selected from the group consisting of K, N, D, Q and T; Xaa5 is an amino acid selected from the group consisting of R, G, S, and L; Xaa6 is an amino acid selected from the group consisting of P, S, I, and E; Xaa7 is an amino acid selected from the group consisting of S, H, I, and T; Xaa8 is Asn; Xaa9 is Lys; and Xaa10 is Gly; Xaa11 is Asp; and Xaa1-Xaa2-Xaa3-Xaa4-Xaa5-Xaa6-Xaa7-Xaa8-Xaa9-(Xaa)$n$  (Formula 3—CDR-L3), wherein n is 0-2, and
wherein Xaa1 is an amino acid selected from the group consisting of C, Q, H, F, H, L, V, I, K, Y, and A; Xaa2 is an amino acid selected from the group consisting of S, A, T, Q, and V; Xaa3 is an amino acid selected from the group consisting of Y, W, and S; Xaa4 is an amino acid selected from the group consisting of A, D, G, S, H and Y; Xaa5 is an amino acid selected from the group consisting of G, S, N, P, D, V, and T; Xaa6 is an amino acid selected from the group consisting of I, T, S, G, L, F and Y; Xaa7 is an amino acid selected from the group consisting of D, T, L, I, P, and S; Xaa8 is an amino acid selected from the group consisting of T, G, R, Y, D, N, W, L, F and P; Xaa9 is an amino acid selected from the group consisting of L, V, G, T, and H; Xaa10 is an amino acid selected from the group consisting of Val, Tyr, and His; Xaa11 is Leu or Val.

The antibody or antibody fragment comprises a variable heavy domain that comprises three complementarity-determining regions (CDR-H1, H2, and H3) corresponding to the following formulas, respectively:

Xaa1-Xaa2-Xaa3-Xaa4-Xaa5  (Formula 1—CDR-H1), wherein Xaa1 is an amino acid selected from the group consisting of S, D, E, N, G, and T; Xaa2 is an amino acid selected from the group consisting of H, Y, L, S, and Q; Xaa3 is an amino acid selected from the group consisting of G, D, A, T, and Y; Xaa4 is an amino acid selected from the group consisting of I, M, and W; and Xaa5 is an amino acid sequence from the group consisting of S, N, H, A, T, and Q;

Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-(Xaa)$n$  (Formula 2—CDR-H2), wherein n is 0 or 1, and
wherein Xaa1 is an amino acid selected from the group consisting of Y, V, A, G, L, G, S, and N; Xaa2 is an amino acid selected from the group consisting of I, M, and F; Xaa3 is an amino acid selected from the group consisting of S, N, D, F, and Y; Xaa4 is an amino acid selected from the group consisting of P, Y, G, W, H, A, and S; Xaa5 is an amino acid selected from the group consisting of Y, N, D, E, S, K, G, and T; Xaa6 is an amino acid selected from the group consisting of S, G, D, T, and N; Xaa7 is an amino acid selected from the group consisting of G, S, I, E, N, and R; Xaa8 is an amino acid selected from the group consisting of N, L, R, S, T, and Y; Xaa9 is an amino acid selected from the group consisting of T, K, G, N, I, and Y; Xaa10 is an amino acid selected from the group consisting of N, G, Y, T, and K; Xaa11 is an amino acid selected from the group consisting of Y, F, N, and H; Xaa12 is an amino acid selected from the group consisting of A, T, V, P, L, and S; Xaa13 is an amino acid selected from the group consisting of Q, D, P, and S; Xaa14 is an amino acid selected from the group consisting of K, S, N, and L; Xaa15 is an amino acid selected from the group consisting of L, F, V, K, and R; Xaa16 is an amino acid selected from the group consisting of Q, K, R, and S; and Xaa17 is a glycine; and Xaa1-Xaa2-Xaa3-Xaa4-Xaa5-Xaa6-(Xaa)$n$  (Formula 3—CDR-H3), wherein n is 0-11, and
wherein Xaa1 is an amino acid selected from the group consisting of V, S, E, N, L, D, Q, and A; Xaa2 is an amino acid selected from the group consisting of G, T, R, Y, L, I, D, and S; Xaa3 is an amino acid selected from the group consisting of S, V, D, G, F, Y, P, M, C, L, and A; Xaa4 is an amino acid selected from the group consisting of G, L, Y, N, E, K, A, and F; Xaa5 is an amino acid selected from the group consisting of P, S, Y, A, V, G, T, E, and W; Xaa6 is an amino acid selected from the group consisting of Y, V, S, L, D, G, H, and P; Xaa7 is an amino acid selected from the group consisting of Tyr, Asp, Gly, Ser, Phe, Leu, and Cys; Xaa8 is an amino acid selected from the group consisting of Tyr, Lys, Asp, Ala, and Gln; Xaa9 is an amino acid selected from the group consisting of Met, Glu, Phe, Leu, Ser, Thr, Pro, and Tyr; Xaa10 is an amino acid selected from the group consisting of Asp, Gly, Tyr, Ser, Leu, His, and Phe; Xaa11 is an amino acid selected from the group consisting of Val, Tyr, Leu, His, Gly, Trp, and Asp; Xaa12 is an amino acid selected from the group consisting of Tyr and Phe; Xaa13 is an amino acid selected from the group consisting of Tyr, Gly, and Asp; Xaa14 is an amino acid selected from the group consisting of Ala, Leu, Pro, and Tyr; Xaa15 is an amino acid selected from the group consisting of Met, Leu, and Phe; Xaa16 is an amino acid selected from the group consisting of Asp and Gly; and Xaa17 is an amino acid selected from the group consisting of an Val, Asp, and Tyr; and
wherein the antibody or antibody fragment also comprises a variable light domain that comprises three complementarity-determining regions (CDR-L1, L2, and L3) corresponding to the following formulas, respectively:

Xaa1-Xaa2-Xaa3-Xaa4-Xaa5-Xaa6-Xaa7-Xaa8-
    Xaa9-Xaa10-Xaa11-(Xaa)$n$     (Formula 1—CDR-L1), wherein n is 0-3, and wherein Xaa1 is an amino acid selected from the group consisting of T, S, R, G, and Q; Xaa2 is an amino acid selected from the group consisting of G, L, and A; Xaa3 is an amino acid selected from the group consisting of T, D, S, N and A; Xaa4 is an amino acid selected from the group consisting of S, K, G, Q, N, and E; Xaa5 is an amino acid sequence from the group consisting of S, L, G, I , D, and P; Xaa6 is an amino acid selected from the group consisting of S, G, N, H, and I; Xaa7 is an amino acid selected from the group consisting of V, D, I, S, G and H; Xaa8 is an amino acid selected from the group consisting of G, K, A, S, I, N, T, and D; Xaa9 is an amino acid selected from the group consisting of D, Y, A, C, S, and F; Xaa10 is an amino acid selected from the group consisting of S, A, G, L, V, and N; Xaa11 is an amino acid selected from the group consisting of I, C, Y, H, R, N, and S; Xaa12 is an amino acid selected from the group consisting of Tyr, Gly, Ala, and Val; Xaa13 is an amino acid selected from the group consisting of Val, and Asn; and Xaa14 is an amino acid selected from the group consisting of Ser and His;

Xaa1-Xaa2-Xaa3-Xaa4-Xaa5-Xaa6-Xaa7-(Xaa)$n$     (Formula 2—CDR-L2), wherein n is 0-4, and wherein Xaa1 is an amino acid selected from the group consisting of D, Q, G, V, Y, S and E; Xaa2 is an amino acid selected from the group consisting of V, D, N, and A; Xaa3 is an amino acid selected from the group consisting of T, S, Y, N, and K; Xaa4 is an amino acid selected from the group consisting of K, N, D, Q and T; Xaa5 is an amino acid selected from the group consisting of R, G, S, and L; Xaa6 is an amino acid selected from the group consisting of P, S, I, and E; Xaa7 is an amino acid selected from the group consisting of S, H, I, and T; Xaa8 is Asn; Xaa9 is Lys; and Xaa10 is Gly; Xaa11 is Asp; and Xaa1-Xaa2-Xaa3-Xaa4-Xaa5-Xaa6-Xaa7-Xaa8-
    Xaa9-(Xaa)$n$     (Formula 3—CDR-L3), wherein n is 0-2, and
wherein Xaa1 is an amino acid selected from the group consisting of C, Q, H, F, H, L, V, I, K, Y, and A; Xaa2 is an amino acid selected from the group consisting of S, A, T, Q, and V; Xaa3 is an amino acid selected from the group consisting of Y, W, and S; Xaa4 is an amino acid selected from the group consisting of A, D, G, S, H and Y; Xaa5 is an amino acid selected from the group consisting of G, S, N, P, D, V, and T; Xaa6 is an amino acid selected from the group consisting of I, T, S, G, L, F and Y; Xaa7 is an amino acid selected from the group consisting of D, T, L, I, P, and S; Xaa8 is an amino acid selected from the group consisting of T, G, R, Y, D, N, W, L, F and P; Xaa9 is an amino acid selected from the group consisting of L, V, G, T, and H; Xaa10 is an amino acid selected from the group consisting of Val, Tyr, and His; Xaa11 is Leu or Val.

In Formula 1—CDR-L1, if n is 1, then the formula will be as follows:

Xaa1-Xaa2-Xaa3-Xaa4-Xaa5-Xaa6-Xaa7-Xaa8-
    Xaa9-Xaa10-Xaa11-Xaa12.

In Formula 1—CDR-L1, if n is 2, then the formula will be as follows:

Xaa1-Xaa2-Xaa3-Xaa4-Xaa5-Xaa6-Xaa7-Xaa8-
    Xaa9-Xaa10-Xaa11-Xaa12-Xaa13.

In Formula 1-CDR-L1, if n is 3, then the formula will be as follows:

Xaa1-Xaa2-Xaa3-Xaa4-Xaa5-Xaa6-Xaa7-Xaa8-
    Xaa9-Xaa10-Xaa11-Xaa12-Xaa13-Xaa14.

In Formula 2—CDR-L2, if n is 1, then the formula will be as follows:

Xaa1-Xaa2-Xaa3-Xaa4-Xaa5-Xaa6-Xaa7-Xaa8.

In Formula 2—CDR-L2, if n is 2, then the formula will be as follows:

Xaa1-Xaa2-Xaa3-Xaa4-Xaa5-Xaa6-Xaa7-Xaa8-
    Xaa9.

In Formula 2—CDR-L2, if n is 3, then the formula will be as follows:

Xaa1-Xaa2-Xaa3-Xaa4-Xaa5-Xaa6-Xaa7-Xaa8-
    Xaa9-Xaa10.

In Formula 2—CDR-L2, if n is 4, then the formula will be as follows:

Xaa1-Xaa2-Xaa3-Xaa4-Xaa5-Xaa6-Xaa7-Xaa8-
    Xaa9-Xaa10-Xaa11.

In Formula 3—CDR-L3, if n is 1, then the formula will be as follows:

Xaa1-Xaa2-Xaa3-Xaa4-Xaa5-Xaa6-Xaa7-Xaa8-
    Xaa9-Xaa10.

In Formula 3—CDR-L3, if n is 2, then the formula will be as follows:

Xaa1-Xaa2-Xaa3-Xaa4-Xaa5-Xaa6-Xaa7-Xaa8-
    Xaa9-Xaa10-Xaa11.

In Formula 2—CDR-H2, if n is 1, then the formula will be as follows:

Xaa1-Xaa2-Xaa3-Xaa4-Xaa5-Xaa6-Xaa7-Xaa8-
    Xaa9-Xaa10-Xaa11-Xaa12-Xaa13-Xaa14-
    Xaa15-Xaa16-Xaa17.

In Formula 3—CDR-H3, if n is 1, then the formula will be as follows:

Xaa1-Xaa2-Xaa3-Xaa4-Xaa5-Xaa6-Xaa7.

In Formula 3—CDR-H3, if n is 2, then the formula will be as follows:

Xaa1-Xaa2-Xaa3-Xaa4-Xaa5-Xaa6-Xaa7-Xaa8.

In Formula 3—CDR-H3, if n is 3, then the formula will be as follows:

Xaa1-Xaa2-Xaa3-Xaa4-Xaa5-Xaa6-Xaa7-Xaa8-
    Xaa9.

In Formula 3—CDR-H3, if n is 4, then the formula will be as follows:

Xaa1-Xaa2-Xaa3-Xaa4-Xaa5-Xaa6-Xaa7-Xaa8-
    Xaa9-Xaa10.

In Formula 3—CDR-H3, if n is 5, then the formula will be as follows:

Xaa1-Xaa2-Xaa3-Xaa4-Xaa5-Xaa6-Xaa7-Xaa8-
    Xaa9-Xaa10-Xaa11.

In Formula 3—CDR-H3, if n is 6, then the formula will be as follows:

Xaa1-Xaa2-Xaa3-Xaa4-Xaa5-Xaa6-Xaa7-Xaa8-
    Xaa9-Xaa10-Xaa11-Xaa12.

In Formula 3—CDR-H3, if n is 7, then the formula will be as follows:

Xaa1-Xaa2-Xaa3-Xaa4-Xaa5-Xaa6-Xaa7-Xaa8-
    Xaa9-Xaa10-Xaa11-Xaa12-Xaa13.

In Formula 3—CDR-H3, if n is 8, then the formula will be as follows:

Xaa1-Xaa2-Xaa3-Xaa4-Xaa5-Xaa6-Xaa7-Xaa8-
    Xaa9-Xaa10-Xaa11-Xaa12-Xaa13-Xaa14.

In Formula 3—CDR-H3, if n is 9, then the formula will be as follows:

Xaa1-Xaa2-Xaa3-Xaa4-Xaa5-Xaa6-Xaa7-Xaa8-Xaa9-Xaa10-Xaa11-Xaa12-Xaa13-Xaa14-Xaa15.

In Formula 3—CDR-H3, if n is 10, then the formula will be as follows:

Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16.

In Formula 3—CDR-H3, if n is 11, then the formula will be as follows:

Xaa1-Xaa2-Xaa3-Xaa4-Xaa5-Xaa6-Xaa7-Xaa8-Xaa9-Xaa10-Xaa11-Xaa12-Xaa13-Xaa14-Xaa15-Xaa16-Xaa17.

c. Antibody Preparation/Production

Antibodies may be prepared by any of a variety of techniques. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980)), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human RGMa) and the other heavy and light chain are specific for an antigen other than human RGMa by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with RGMa or a fragment and/or variant thereof. For example, any of SEQ ID NO:65, SEQ ID NO:66, SEQ ID NO:74, a fragment of SEQ ID NO:65, SEQ ID NO:66 or SEQ ID NO:74, or a variant of SEQ ID NO:65, SEQ ID NO:66 SEQ ID NO:74 may be used to immunize the animal. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site which retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region. A polypeptide comprising a single CDR, (e.g., a CDR1, CDR2 or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) Bioinvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) Microbiol. Immunol. 41:901-907; Sandhu et al. (1996) Crit. Rev. Biotechnol. 16:95-118; Eren et al. (1998) Immunol. 93:154-161) that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994)).

An affinity matured antibody may be produced by any one of a number of procedures that are known in the art. For example, see Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); Hawkins et al, J. Mol. Biol., 226: 889-896 (1992). Selective mutation at selective mutagenesis positions and at contact or hypermutation positions with an activity enhancing amino acid residue is described in U.S. Pat. No. 6,914,128 B1.

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., Adv. Exp. Med. Biol. (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al. (1995) Protein Eng. 8(10):1057-1062. Briefly, these antibodies comprise a pair of tandem Fd segments (VH- CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (1314 yttrium-90 (90Y), bismuth-212 (212Bi), bismuth-213 (213Bi), technetium-99m (99 mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies can be sequenced and replicated by recombinant or synthetic means. They also can be further sequenced down to the linear sequence of nucleotides that encode them. Accordingly, this invention provides these polynucleotides, alone or in combination with a carrier, vector or host cell as described above, that encode a sequence of an antibody of this invention.

Antibody production via the use of hybridoma technology, the selected lymphocyte antibody method (SLAM), transgenic animals, and recombinant antibody libraries is described in more detail below.

(1) Anti-RGMa Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, second edition, (Cold Spring Harbor Laboratory Press, Cold Spring Harbor, 1988); Hammerling, et al., In Monoclonal Antibodies and T-Cell Hybridomas, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In an embodiment, the present invention provides methods of generating monoclonal antibodies as well as antibodies produced by the method. The method may comprise culturing a hybridoma cell secreting an antibody of the invention wherein, preferably, the hybridoma is generated by fusing splenocytes isolated from an animal, e.g., a rat or a mouse, immunized with RGMa with myeloma cells and then screening the hybridomas resulting from the fusion for hybridoma clones that secrete an antibody able to bind a polypeptide of the invention. Briefly, rats can be immunized with an RGMa antigen. In a preferred embodiment, the RGMa antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with an RGMa antigen, antibodies and/or antibody-producing cells may be obtained from the animal. An anti-RGMa antibody-containing serum is obtained from the animal by bleeding or sacrificing the animal. The serum may be used as it is obtained from the animal, an immunoglobulin fraction may be obtained from the serum, or the anti-RGMa antibodies may be purified from the serum. Serum or immunoglobulins obtained in this manner are polyclonal, thus having a heterogeneous array of properties.

Once an immune response is detected, e.g., antibodies specific for the antigen RGMa are detected in the rat serum, the rat spleen is harvested and splenocytes isolated. The splenocytes are then fused by well-known techniques to any suitable myeloma cells, for example cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding RGMa. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using RGMa, or a portion thereof, or a cell expressing RGMa. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-RGMa antibody-producing hybridomas are selected, cloned, and further screened for desirable characteristics, including robust hybridoma growth, high antibody production, and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-RGMa antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce two identical Fab fragments) or pepsin (to produce a F(ab')$_2$ fragment). A F(ab')2 fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, a F(ab')2 fragment is still capable of crosslinking antigen molecules like the parent IgG molecule.

(2) Anti-RGMa Monoclonal Antibodies Using SLAM.

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., Proc. Natl. Acad. Sci. USA, 93: 7843-7848 (1996). In this method, single cells secreting antibodies of interest, e.g., lymphocytes derived from any one of the immunized animals are screened using an antigen-specific hemolytic plaque assay, wherein the antigen RGMa, a subunit of RGMa, or a fragment thereof, is coupled to sheep red blood cells using a linker, such as biotin, and used to identify single cells that secrete antibodies with specificity for RGMa. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to RGMa. The amplified immunoglobulin sequences further can be manipulated in vitro, such as by in vitro affinity maturation method. See, for example, PCT Publication No. WO 97/29131 and PCT Publication No. WO 00/56772.

(3) Anti-RGMa Monoclonal Antibodies Using Transgenic Animals.

In another embodiment of the invention, antibodies are produced by immunizing a non-human animal comprising some, or all, of the human immunoglobulin locus with a RGMa antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., Nature Genetics, 7: 13-21 (1994) and U.S. Pat. Nos. 5,916,771; 5,939,598; 5,985,615; 5,998,209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., Nature Genetics, 15: 146-156 (1997), Green and Jakobovits, J. Exp. Med., 188: 483-495 (1998), the disclosures of which are hereby incorporated by reference.

(4) Anti-RGMa Monoclonal Antibodies Using Recombinant Antibody Libraries.

In vitro methods also can be used to make the antibodies of the invention, wherein an antibody library is screened to identify an antibody having the desired RGMa-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., Bio/Technology, 9: 1369-1372 (1991); Hay et al., Hum. Antibod. Hybridomas, 3: 81-85 (1992); Huse et al., Science, 246: 1275-1281 (1989); McCafferty et al., Nature, 348: 552-554 (1990); Griffiths et al., EMBO J., 12: 725-734 (1993); Hawkins et al., J. Mol. Biol., 226: 889-896 (1992); Clackson et al., Nature, 352: 624-628 (1991); Gram et al., Proc. Natl. Acad. Sci. USA, 89: 3576-3580 (1992); Garrard et al., Bio/Technology, 9: 1373-1377 (1991); Hoogenboom et al., Nucl. Acids Res., 19: 4133-4137 (1991); Barbas et al., Proc. Natl. Acad. Sci. USA, 88: 7978-7982 (1991); US Patent Application Publication No. 2003/0186374; and PCT Publication No. WO 97/29131, the contents of each of which are incorporated herein by reference.

The recombinant antibody library may be from a subject immunized with RGMa, or a portion of RGMa. Alternatively, the recombinant antibody library may be from a naive subject, i.e., one who has not been immunized with RGMa, such as a human antibody library from a human subject who has not been immunized with human RGMa. Antibodies of the invention are selected by screening the recombinant antibody library with the peptide comprising human RGMa to thereby select those antibodies that recognize RGMa. Methods for conducting such screening and selection are well known in the art, such as described in the references in the preceding paragraph. To select antibodies of the invention having particular binding affinities for RGMa, such as those that dissociate from human RGMa with a particular $K_{off}$ rate constant, the art-known method of surface plasmon resonance can be used to select antibodies having the desired $K_{off}$ rate constant. To select antibodies of the invention having a particular neutralizing activity for hRGMa, such as those with a particular $IC_{50}$, standard methods known in the art for assessing the inhibition of RGMa activity may be used.

In one aspect, the invention pertains to an isolated antibody, or an antigen-binding portion thereof, that binds human RGMa. Preferably, the antibody is a neutralizing antibody. In various embodiments, the antibody is a recombinant antibody or a monoclonal antibody.

For example, antibodies of the present invention can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies of the present invention include those disclosed in Brinkmann et al., J. Immunol. Methods, 182: 41-50 (1995); Ames et al., J. Immunol. Methods, 184:177-186 (1995); Kettleborough et al., Eur. J. Immunol., 24: 952-958 (1994); Persic et al., Gene, 187: 9-18 (1997); Burton et al., Advances in Immunology, 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., BioTechniques, 12(6): 864-869 (1992); Sawai et al., Am. J. Reprod. Immunol., 34: 26-34 (1995); and Better et al., Science, 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., Proc. Natl. Acad. Sci. USA, 90: 7995-7999 (1993); and Skerra et al., Science, 240: 1038-1041 (1988).

Alternative to screening of recombinant antibody libraries by phage display, other methodologies known in the art for screening large combinatorial libraries can be applied to the identification of antibodies of the invention. One type of alternative expression system is one in which the recombinant antibody library is expressed as RNA-protein fusions, as described in PCT Publication No. WO 98/31700 (Szostak and Roberts), and in Roberts and Szostak, Proc. Natl. Acad. Sci. USA, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology, is PROfusion display technology.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in U.S. Pat. No. 6,699,658 (Wittrup et al.) incorporated herein by reference.

d. Production of Recombinant RGMa Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human RGMa) and the other heavy and light chain are specific for an antigen other than human RGMa by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

(a) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816,567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present invention can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for RGMa and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for RGMa, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libararies via PROfusion and/or yeast related technologies. See Examples provided below. It is also possible to produce transgenic animals (e.g. mice that are capable, upon immunization, of producing a full repertoire of human antibodies in the absence of endogenous immunoglobulin production. For example, the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922, 845; 6,017,517; 6,096,311; 6,111,166; 6,270,765; 6,303,755; 6,365,116; 6,410,690; 6,682,928; and 6,984,720, the contents each of which are herein incorporated by reference.

3. Pharmaceutical Compositions

The antibody may be a component in a pharmaceutical composition. The pharmaceutical composition may also contain a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which activity of a targeted RGMa is detrimental. In a further embodiment, the prophylactic or therapeutic agents are known to be useful for, or have been, or are currently being used in the prevention, treatment, management, or amelioration of a disorder, or one or more symptoms thereof. In accordance with these embodiments, the composition may further comprise of a carrier, diluent or excipient.

The antibodies of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody.

In a further embodiment, the pharmaceutical composition comprises at least one additional therapeutic agent for treating a disorder as disclosed herein.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO97/32572; WO97/44013; WO98/31346; and WO99/66903, each of which is incorporated herein by reference in their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the antibodies of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the antibody can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO99/15154; and PCT Publication No. WO99/20253. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a particular embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention. See, e.g., U.S. Pat. No. 4,526,938, PCT publication WO91/05548, PCT publication WO96/20698, Ning et al., 1996, "Intratumoral Radioimmunotherapy of a Human Colon Cancer Xenograft Using a Sustained-Release Gel," Radiotherapy & Oncology 39:179-189; Song et al., 1995, "Antibody Mediated Lung Targeting of Long- Circulating Emulsions," PDA Journal of Pharmaceutical Science & Technology 50:372-397; Cleek et al., 1997, "Biodegradable Polymeric Carriers for a bFGF Antibody for Cardiovascular Application," Pro. Int'l. Symp. Control. Rel. Bioact. Mater. 24:853-854; and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p- hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the antibodies, or pharmaceutical compositions, of the invention is packaged in a hermetically sealed container such as an ampoule or sachette indicating the quantity of the antibody. In one embodiment, one or more of the antibodies, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the antibodies or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions of the invention should be stored at between 2° C. and 8° C. in its original container and the antibodies, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions of the invention is supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The antibodies of the invention can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies of the invention prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (See International Appln. Publication No. WO 04/078140 and U.S. Patent Appln. Publication No. US2006104968, incorporated herein by reference.)

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Compositions can be in the form of injectable or infusible solutions, such as compositions similar to those used for passive immunization of humans with other antibodies. In one embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., a binding protein, e.g. an antibody, of the present invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, methods of preparation comprise vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies of the present invention can be administered by a variety of methods known in the art. For many therapeutic applications, the route/mode of administration may be subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody of the invention may be orally administered, for example, with an inert diluent or an assimilable edible carrier. The antibody (and other ingredients, if desired) may also be enclosed in a hard or soft shell gelatin capsule, compressed into tablets, or incorporated directly into the subject's diet. For oral therapeutic administration, the antibody may be incorporated with excipients and used in the form of ingestible tablets, buccal tablets, troches, capsules, elixirs, suspensions, syrups, wafers, and the like. To administer an antibody of the invention by other than parenteral administration, it may be necessary to coat the antibody with, or co-administer the antibody with, a material to prevent its inactivation.

Supplementary active compounds can also be incorporated into the compositions. In certain embodiments, an antibody of the invention is coformulated with and/or coadministered with one or more additional therapeutic agents that are useful for treating disorders or diseases described herein. For example, an anti-RGMa antibody of the invention may be coformulated and/or coadministered with one or more additional antibodies that bind other targets (e.g., antibodies that bind other soluble antigens or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody of the invention is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990). Detailed description of various methods of gene therapy are disclosed in US20050042664 A1 which is incorporated herein by reference.

Antibodies of the invention can be used alone or in combination to treat diseases or conditions associated with neurite degeneration, such as multiple sclerosis, Alzheimer's disease, Down syndrome, dementia, Parkinson's disease, a traumatic injury to the central nervous system, or any other disease or condition associated with RGMa.

It should be understood that the antibodies of the invention can be used alone or in combination with one or more additional agents, e.g., a therapeutic agent (for example, a small molecule or biologic), said additional agent being selected by the skilled artisan for its intended purpose. For example, the additional therapeutic agent may be an immunosuppressant or an agent that treats one or more symptoms associated with multiple sclerosis. The additional drug may be a beta interferon. Beta interferons, such as Avonex, Betaseron, Extavia and Rebif, may slow the rate at which multiple sclerosis symptoms worsen over time. The additional agent may be Glatiramer (Copaxone), which may block the immune system's attack on myelin. The additional agent may be Fingolimod (Gilenya), which may trap immune cells in lymph nodes. The additional agent may be Natalizumab (Tysabri), which may interfere with the movement of potentially damaging immune cells from the bloodstream to the brain and spinal cord. The additional drug may be Mitoxantrone (Novantrone), which is an immunosuppressant drug.

The additional therapeutic agent can be a "cognitive enhancing drug," which is a drug that improves impaired human cognitive abilities of the brain (namely, thinking, learning, and memory). Cognitive enhancing drugs work by altering the availability of neurochemicals (e.g., neurotransmitters, enzymes, and hormones), by improving oxygen supply, by stimulating nerve growth, or by inhibiting nerve damage. Examples of cognitive enhancing drugs include a compound that increases the activity of acetylcholine such as, but not limited to, an acetylcholine receptor agonist (e.g., a nicotinic α-7 receptor agonist or allosteric modulator, an α4β2 nicotinic receptor agonist or allosteric modulators), an acetylcholinesterase inhibitor (e.g., donepezil, rivastigmine, and galantamine), a butyrylcholinesterase inhibitor, an N-methyl-D-aspartate (NMDA) receptor antagonist (e.g., memantine), an activity-dependent neuroprotective protein (ADNP) agonist, a serotonin 5-HT 1A receptor agonist (e.g., xaliproden), a 5-HT4 receptor agonist, a 5-HT6 receptor antagonist, a serotonin 1A receptor antagonist, a histamine H3 receptor antagonist, a calpain inhibitor, a vascular endothelial growth factor (VEGF) protein or agonist, a trophic growth factor, an anti-apoptotic compound, an AMPA-type glutamate receptor activator, a L-type or N-type calcium channel blocker or modulator, a potassium channel blocker, a hypoxia inducible factor (HIF) activator, a HIF prolyl 4-hydroxylase inhibitor, an anti-inflammatory agent, an inhibitor of amyloid Aβ peptide or amyloid plaque, an inhibitor of tau hyperphosphorylation, a phosphodiesterase 5 inhibitor (e.g., tadalafil, sildenafil), a phosphodiesterase 4 inhibitor, a monoamine oxidase inhibitor, or pharmaceutically acceptable salt thereof. Specific examples of such cognitive enhancing drugs include, but are not limited to, cholinesterase inhibitors such as donepezil (Aricept®), rivastigmine (Exelon®), galanthamine (Reminyl®), N-methyl-D-aspartate antagonists such as memantine (Namenda®). At least one cognitive enhancing drug can be administered simultaneously with the antibodies of the present invention or sequentially with the antibodies of the present invention (and in any order) including those agents currently recognized, or in the future being recognized, as useful to treat the disease or condition being treated by an antibody of the present invention). Additionally, it is believed that the combinations described herein may have additive or synergistic effects when used in the above described treatment. The additional agent also can be an agent that imparts a beneficial attribute to the therapeutic composition, e.g., an agent that affects the viscosity of the composition.

It should further be understood that the combinations are those combinations useful for their intended purpose. The agents set forth above are for illustrative purposes and not intended to be limiting. The combinations can comprise an antibody and at least one additional agent selected from the lists below. The combination can also include more than one additional agent, e.g., two or three additional agents if the combination is such that the formed composition can perform its intended function.

The pharmaceutical compositions may include a "therapeutically effective amount" or a "prophylactically effective amount" of an antibody. A "therapeutically effective amount" refers to an amount effective, at dosages and for periods of time necessary, to achieve the desired therapeutic result. A therapeutically effective amount of the antibody may be determined by a person skilled in the art and may vary according to factors such as the disease state, age, sex, and weight of the individual, and the ability of the antibody to elicit a desired response in the individual. A therapeutically effective amount is also one in which toxic or detrimental effects, if any, of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of the antibody is a dose of between 0.1 and 200 mg/kg, for example between 0.1 and 10 mg/kg. The therapeutically or prophylactically effective amount of the antibody may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated. Further, the antibody dose may be determined by a person skilled in the art and may vary according to factors such as the disease state, age, sex, and weight of the individual, and the ability of the antibody to elicit a desired response in the individual. The dose is also one in which toxic or detrimental effects, if any, of the antibody are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

4. Method of Treating, Preventing, Modulating or Attenuating a Disease Associated With Neurite Degeneration In any subject, an assessment may be made as to whether the subject has a neurite degenerative disorder. The assessment may indicate an appropriate course of therapy, such as preventative therapy, maintenance therapy, or modulative therapy. Accordingly, provided herein is a method of treating, preventing, modulating, or attenuating a disease/disorder of neurite degeneration. The antibody may be administered to a subject in need thereof. The antibody may be administered in a therapeutically effective amount.

In general, the dosage of administered antibodies will vary depending upon such factors as the patient's age, weight, height, sex, general medical condition and previous medical history. Typically, it is desirable to provide the recipient with a dosage of antibody component, immunoconjugate or fusion protein which is in the range of from about 1 pg/kg to 10 mg/kg (amount of agent/body weight of patient), although a lower or higher dosage also may be administered as circumstances dictate. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 0.5-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Administration of antibodies to a patient can be intravenous, intraarterial, intraperitoneal, intramuscular, subcutaneous, intrapleural, intrathecal, intraocular, intravitreal, by perfusion through a regional catheter, or by direct intralesional injection. When administering therapeutic proteins by injection, the administration may be by continuous infusion or by single or multiple boluses. Intravenous injection provides a useful mode of administration due to the thoroughness of the circulation in rapidly distributing antibodies. The antibody may be administered orally, for example, with an inert diluent or an assimilable edible carrier. The antibody and other ingredients, if desired, may be enclosed in a hard or soft shell gelatin capsule, compressed into tablets, buccal tablets, troches, capsules, elixirs, suspensions, syrups, wafers, and the like.

Anti-RGMa antibodies may be administered at low protein doses, such as 20 milligrams to 2 grams protein per dose, given once, or repeatedly, parenterally. Alternatively, the antibodies may be administered in doses of 20 to 1000 milligrams protein per dose, or 20 to 500 milligrams protein per dose, or 20 to 100 milligrams protein per dose.

The antibodies may be administered alone or they may be conjugated to liposomes, and can be formulated according to known methods to prepare pharmaceutically useful compositions, whereby the antibodies are combined in a mixture with a pharmaceutically acceptable carrier. A "pharmaceutically acceptable carrier" may be tolerated by a recipient patient. Sterile phosphate-buffered saline is one example of a pharmaceutically acceptable carrier. Other suitable carriers are well known to those in the art. See, for example, REMINGTON'S PHARMACEUTICAL SCIENCES, 19th Ed. (1995).

For purposes of therapy, antibodies are administered to a patient in a therapeutically effective amount in a pharmaceutically acceptable carrier. A "therapeutically effective amount" is one that is physiologically significant. The antibody is physiologically significant if its presence results in a detectable change in the physiology of a recipient patient. In the present context, the antibody may be physiologically significant if its presence results in, for example, decreased interferon-γ (INF-γ), interleukin-2 (IL-2), IL-4 and/or IL-17 secretion from $CD4^+$ T cells. An agent is physiologically significant if its presence results in, for example, reduced proliferative responses and/or pro-inflammatory cytokine expression in peripheral blood mononuclear cells (PBMCs).

Additional treatment methods may be employed to control the duration of action of an antibody in a therapeutic application. Control release preparations can be prepared through the use of polymers to complex or adsorb the antibody. For example, biocompatible polymers include matrices of poly (ethylene-co-vinyl acetate) and matrices of a polyanhydride copolymer of a stearic acid dimer and sebacic acid. Sherwood et al., Bio/Technology 10:1446 (1992). The rate of release of an antibody from such a matrix depends upon the molecular weight of the protein, the amount of antibody within the matrix, and the size of dispersed particles. Saltzman et al., Biophys. J. 55:163 (1989); Sherwood et al., supra. Other solid dosage forms are described in REMINGTON'S PHARMACEUTICAL SCIENCES, 19th ed. (1995).

a. Neurite Degenerative Disorders/Diseases

The neurite disorder/disease may be any disease or disorder in which there is neurite damage and compromised synaptic function. This damage and compromised function may result from nerves lacking sufficient myelination and/or axon transection. The neurite degenerative disorder or disease may be multiple sclerosis, Alzheimer's disease, Parkinson's disease, amyotrophic lateral sclerosis and other motoneuron diseases, huntington's disease, Tay-Sachs disease, Niemann-Pick disease, Gaucher's disease, Hurler's syndrome, idiopathic inflammatory demyelinating diseases, vitamin B 12 deficiency, central pontine myelinolysis, tabes dorsalis, transverse myelitis, Devic's disease, progressive multifocal leukoencephalopathy, optic neuritis and other retinopathies associated with neurite degeneration, such as glaucoma, diabetic neuropathy and age-dependent macular degeneration, traumatic injury to the central nervous system, or leukodystrophies for example. The neurite degenerative disorder or disease may result from nerve fibers lacking sufficient wrapping of layers of tissue composed of a fat (lipoprotein) called myelin. These layers form the myelin sheath. The myelin sheath may enable electrical impulses to be conducted along the nerve fiber with speed and accuracy. When the myelin sheath is damaged or is missing, nerves do not conduct electrical impulses normally. Sometimes, as a result of the damaged or missing myelin sheath, the nerve fibers may also be damaged.

Young infants may normally lack mature myelin sheaths. As a result, their movements are jerky, uncoordinated, and awkward. As myelin sheaths develop, movements become smoother, more purposeful, and more coordinated. However, myelin sheaths do not develop normally in children with certain diseases, such as Tay-Sachs disease, Niemann-Pick disease, Gaucher's disease, and Hurler's syndrome.

In adults, the myelin sheath can be destroyed by stroke, inflammation, immune disorders, metabolic disorders, and nutritional deficiencies (such as a lack of vitamin B 12). Poisons, drugs (such as the antibiotic ethambutol), and excessive use of alcohol can damage or destroy the myelin sheath. If the sheath is able to repair and regenerate itself, normal nerve function may return. However, if the sheath is severely damaged, the underlying nerve fiber can die. Because nerve fibers in the central nervous system (brain and spinal cord) rarely regenerate, such damage is irreversible.

Some neurite degenerative disorders that cause demyelination affect mainly the central nervous system. Others affect mainly nerves in other parts of the body. Neurite degenerative disorders that cause demyelination in the central nervous system and have no known cause are called primary demyelinating disorders. Multiple sclerosis is the most common of these disorders.

(1) Multiple Sclerosis

The clinical course of MS may be divided into four major categories (or subtypes): relapsing remitting (RRMS), secondary progressive (SPMS), primary progressive (PMS) and progressive relapsing (PRMS). Patients who have clinical relapses every few months or years with intervening periods of clinically stability define RRMS. RRMS may be twice more common in females than males in the second or third decade of life. In contrast to RRMS, patients with SPMS display progressive deterioration between relapses. RRMS patients may convert to SPMS over time characterized by a gradual decline in neurological function. Approximately 15% of MS patients have PPMS characterized by late onset and an unrelenting deterioration of neurological function from disease onset. Benign MS is arbitrarily defined as those RRMS patients who after more than 15 years following initial diagnosis are still mobile and show only mild deficits (Expanded Disability Status Scale [EDSS]). Typically, these patients show little or no progression after their initial attack and require no therapeutic intervention; however, it is not possible to diagnose this form of MS until 5 years from MS onset.

(2) Parkinson's Disease

Parkinson's disease is widespread throughout the Western hemisphere and was first reported by physician James Parkinson in 1817. Parkinson's disease may be first detected as a tremor in a limb, and may ultimately progress to include three other manifestations: (i) rigidity, which is characterized by "cog wheel" like movement and "lead pipe" rigidity; (ii) bradykinesia or slowness in movement, and (iii) postural instability associated with a stooped stance and an impaired gait. These altered movements are features of a motor dysfunction, but in addition there can also be a mental impairment in as many as 40% of all Parkinson's patients.

Parkinson's disease may be caused by a deficient state of levodopamine in the brain. More specifically, levodopamine may induce dyskinesis in Parkinson's patients and result of denervation of the substantia nigra. To date, medical science has not found a substrate that would allow an injectable form of levodopa to reach the brain and successfully cross the blood brain barrier. The current dopamine replacement therapy is aimed at either direct replacement or mimicking the action at the dopamine receptor sites in the brain. While the levodopa therapy may create some beneficial changes initially, those changes may wane over time, and produce other problems such as severe sleep disturbance, dyskinesias, and constant nausea. Medical approaches to Parkinson's disease include surgical destruction of the tissue of the brain and the insertion of microelectrodes (deep brain electrical stimulation) to affected portions of the brain. The insertion of electrodes has the advantage of being reversible. These interventions, however, are generally transient and neither produces a permanent change in the Parkinsonian state nor reverses the effects of the disease.

Parkinson's disease may be a multifactor, neurodegenerative disorder, which evolves due to excessive oxidation. The substantia nigra is susceptible to oxidative damage which supports this theory of the formation of Parkinson's disease. Abnormalities of the oxidative phosphorylation impair the mitochondria of the substantia nigra, and intensify free radical generation.

(3) Injury from Reactive Oxygen Species (Free Radicals)

Reactive oxygen species (ROS) may attack several types of tissues and chronic exposure to ROS may attenuate various biological functions and increase the risk of several types of serious disorders, including neurite degenerative disorders and diseases. ROS can attack neurons and induce cell death. For example, treatment of neurons with low concentrations of hydrogen peroxide may induce neurite injury by influencing detrimental changes in neurite morphology, sometimes called neurite beading. Neurite beading may be one of the early events of neuronal degeneration prior to induction of death of hydrogen peroxide-treated neurons.

(4) Alzheimer's Disease

Alzheimer's disease (AD) is the major cause of dementia in the elderly. Although rare genetic forms of AD exist, most patients are classified as having sporadic AD, since no family history is usually identified. Pathologically, AD is characterized by neuronal and synaptic degeneration with an increased number of senile plaques and neurofibrillary tangles compared to non-demented individuals of comparable age.

The senile plaques, characteristic of Alzheimer's disease, are composed of a central core of aggregated beta-amyloid, a breakdown product of amyloid precursor protein (APP). The neurofibrillary tangles are insoluble intracellular thread-like structures made up of a hyperphosphorylated form of a protein called tau, which is associated with microtubules.

Post-mortem slices of brain tissue of victims of Alzheimer's disease exhibit the presence of amyloid in the form of proteinaceous extracellular cores of the neuritic plaques that are characteristic of AD. The amyloid cores of these neuritic plaques are composed of a protein called β-amyloid that is arranged in a predominately beta-pleated sheet configuration. Mori et al., Journal of Biological Chemistry 267: 17082 (1992); Kirschner et al., PNAS 83: 503 (1986). Neuritic plaques are an early and invariant aspect of the disease. Mann et al., J. Neurol. Sci. 89: 169; Mann, Mech. Ageing Dev. 31: 213 (1985); Terry et al., J. Neuropathol. Exp. Neurol 46: 262 (1987).

The initial deposition of Aβ may occur before clinical symptoms are noticeable. The currently recommended "minimum microscopic criteria" for the diagnosis of AD is based on the number of neuritic plaques found in brain. Khachaturian, Arch. Neurol., supra (1985). Unfortunately, assessment of neuritic plaque counts must be delayed until after death.

Amyloid-containing neuritic plaques are a prominent feature of selective areas of the brain in AD as well as Down's Syndrome and in persons homozygous for the apolipoprotein E4 allele who are very likely to develop AD. Corder et al., Science 261: 921 (1993); Divry, P., J. Neurol. Psych. 27: 643-657 (1927); Wisniewski et al., in Zimmerman, H. M. (ed.): PROGRESS IN NEUROPATHOLOGY (Grune and Stratton, N.Y. 1973) pp. 1-26. Brain amyloid is readily demonstrated by staining brain sections with thioflavin S or Congo red. Puchtler et al., J. Histochem. Cytochem. 10: 35 (1962). Congo red stained amyloid is characterized by a dichroic appearance, exhibiting a yellow-green polarization color. The dichroic binding is the result of the beta-pleated sheet structure of the amyloid proteins. Glenner, G. N. Eng. J. Med. 302: 1283 (1980). A detailed discussion of the biochemistry and histochemistry of amyloid can be found in Glenner, N. Eng. J. Med., 302: 1333 (1980).

(5) Traumatic Injury to Central Nervous System

The incidence of traumatic brain injury (TBI) in the United States is conservatively estimated to be more than 2 million persons annually with approximately 500,000 hospitalizations. Of these, about 70,000 to 90,000 head injury survivors are permanently disabled.

Neural pathways in the central nervous system of a subject are at risk if neurons are subjected to mechanical or chemical trauma or to neuropathic degeneration sufficient to put neurons at risk of dying. A host of neuropathies, some of which affect only a subpopulation or a system of neurons in the peripheral or central nervous systems have been identified to date. The neuropathies, which may affect the neurons themselves or the associated glial cells, may result from cellular metabolic dysfunction, infection, exposure to toxic agents, autoimmunity dysfunction, malnutrition or ischemia. In some cases the cellular dysfunction is thought to induce cell death directly. In other cases, the neuropathy may induce sufficient tissue necrosis to stimulate the body's immune/inflammatory system and the mechanisms of the body's immune response to the initial neural injury then destroys the neurons and the pathway defined by these neurons.

b. Subject

The subject may be a mammal, which may be a human. The subject may have, or be at risk of developing a neurite degenerative disorder or disease. The subject may already be undergoing treatment for a neurite degenerative disorder or disease.

5. Method of Diagnosis

Provided herein is a method for determining whether a subject has neurite degenerative disease or disorder. The level of membrane associated RGMa may be measured and compared to a level of RGMa in a control sample. The control sample may be from a normal tissue. An altered level of RGMa as compared to the control may indicate that the subject has a neurite degenerative disease or disorder. For example, an increased level of RGMa, as compared to a normal control, may indicate that the subject has a neurite degenerative disease or disorder. The level of RGMa may be measured using the herein described antibodies.

a. Sample

The sample may be any tissue sample from the subject. The sample may comprise protein from the subject. The sample may be blood serum, plasma, or a tissue biopsy. The sample may be used directly as obtained from the subject or following pretreatment to modify a characteristic of the sample. Pretreatment may include extraction, concentration, inactivation of interfering components, and/or the addition of reagents.

Any cell type, tissue, or bodily fluid may be utilized to obtain a sample. Such cell types, tissues, and fluid may include sections of tissues such as biopsy and autopsy samples, frozen sections taken for histologic purposes, blood, plasma, serum sputum, stool, tears, mucus, saliva, hair, and skin. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g. isolated by another person, at another time, and/or for another purpose). Archival tissues, such as those having treatment or outcome history, may also be used. Protein purification may not be necessary.

b. RGMa Detection

The presence or amount of RGMa present in a body sample may be readily determined by, for example, mass spectrometry, immunoassays or immunohistochemistry (e.g. with sections from tissue biopsies) using the herein described antibodies (monoclonal or polyclonal) or fragments thereof against RGMa. Anti-RGMa antibodies and fragments thereof can be produced as described above. Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety.

(1) Immunoassay

RGMa, and/or peptides thereof, may be analyzed using an immunoassay. The presence or amount of RGMa can be determined using the herein described antibodies and detecting specific binding to RGMa. For example, the antibody, or fragment thereof, may specifically bind to a polypeptide comprising SEQ ID NO:65, or a fragment thereof. The antibody, or fragment thereof, may specifically bind to a polypeptide comprising SEQ ID NO:66, or a fragment thereof.

Any immunoassay may be utilized. The immunoassay may be an enzyme-linked immunoassay (ELISA), radioimmunoassay (RIA), a competitive inhibition assay, such as forward or reverse competitive inhibition assays, a fluorescence polarization assay, or a competitive binding assay, for example. The ELISA may be a sandwich ELISA. Specific immunological binding of the antibody to the RGMa can be detected via direct labels, such as fluorescent or luminescent tags, metals and radionuclides attached to the antibody or via indirect labels, such as alkaline phosphatase or horseradish peroxidase.

The use of immobilized antibodies or fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and then processed quickly through washes and detection steps to generate a measurable signal, such as a colored spot.

(a) Sandwich ELISA

The Sandwich ELISA measures the amount of antigen between two layers of antibodies (i.e. capture and a detection antibody). The RGMa to be measured may contain at least two antigenic sites capable of binding to antibody. Either monoclonal or polyclonal antibodies may be used as the capture and detection antibodies in the sandwich ELISA.

Generally, at least two antibodies are employed to separate and quantify RGMa or RGMa fragment in a test sample. More specifically, the at least two antibodies bind to certain epitopes of RGMa or RGMa fragment forming an immune complex which is referred to as a "sandwich". One or more antibodies can be used to capture the RGMa or RGMa fragment in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, both antibodies binding to their epitope may not be diminished by the binding of any other antibody in the assay to its respective epitope. In other words, antibodies may be selected so that the one or more first antibodies brought into contact with a test sample suspected of containing RGMa or RGMa fragment do not bind to all or part of an epitope recognized by the second or subsequent antibodies, thereby interfering with the ability of the one or more second detection antibodies to bind to the RGMa or RGMa fragment.

The antibodies may be used as a first antibody in said immunoassay. Preferably, the antibody immunospecifically binds to epitopes comprising at least three contiguous (3) amino acids of SEQ ID NOs:65, 66 or 74. In addition to the antibodies of the present invention, said immunoassay may comprise a second antibody that immunospecifically binds to epitopes having an amino acid sequence comprising at least three contiguous (3) amino acids of SEQ ID NO:65, 66 or 74, wherein the contiguous (3) amino acids to which the second antibody binds is different from the contiguous (3) amino acids to which the first antibody binds.

In a preferred embodiment, a test sample suspected of containing RGMa or RGMa fragment can be contacted with at least one first capture antibody (or antibodies) and at least one second detection antibodies either simultaneously or sequentially. In the sandwich assay format, a test sample suspected of containing RGMa or RGMa fragment is first brought into contact with the at least one first capture antibody that specifically binds to a particular epitope under conditions which allow the formation of a first antibody-RGMa complex. If more than one capture antibody is used, a first multiple capture antibody-RGMa complex is formed. In a sandwich assay, the antibodies, preferably, the at least one capture antibody, are used in molar excess amounts of the maximum amount of RGMa or RGMa fragment expected in the test sample. For example, from about 5 µg/ml to about 1 mg/ml of antibody per ml of microparticle coating buffer may be used.

Optionally, prior to contacting the test sample with the at least one first capture antibody, the at least one first capture antibody can be bound to a solid support which facilitates the separation the first antibody-RGMa complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind RGMa or RGMa fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing RGMa or RGMa fragment is brought into contact with the at least one first capture antibody, the test sample is incubated in order to allow for the formation of a first capture antibody (or multiple antibody)-RGMa complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

After formation of the first/multiple capture antibody-RGMa complex, the complex is then contacted with at least one second detection antibody (under conditions which allow for the formation of a first/multiple antibody-RGMa-second antibody complex). If the first antibody-RGMa complex is contacted with more than one detection antibody, then a first/multiple capture antibody-RGMa-multiple antibody detection complex is formed. As with first antibody, when the at least second (and subsequent) antibody is brought into contact with the first antibody-RGMa complex, a period of incubation under conditions similar to those described above is required for the formation of the first/multiple antibody-RGMa-second/multiple antibody complex. Preferably, at least one second antibody contains a detectable label. The detectable label can be bound to the at least one second antibody prior to, simultaneously with or after the formation of the first/multiple antibody-RGMa-second/multiple antibody complex. Any detectable label known in the art can be used.

(b) Forward Competitive Inhibition

In a forward competitive format, an aliquot of labeled RGMa, RGMa fragment or RGMa variant thereof of a known concentration is used to compete with RGMa or RGMa fragment in a test sample for binding to RGMa antibody (such as an antibody of the present invention).

In a forward competition assay, an immobilized antibody (such as an antibody of the present invention) can either be sequentially or simultaneously contacted with the test sample and a labeled RGMa, RGMa fragment or RGMa variant thereof. The RGMa peptide, RGMa fragment or RGMa variant can be labeled with any detectable label, including those detectable labels discussed above in connection with the anti-RGMa antibodies. In this assay, the antibody can be immobilized on to a solid support. Alternatively, the antibody can be coupled to an antibody, such as an antispecies antibody, that has been immobilized on to a solid support, such as a microparticle.

The labeled RGMa peptide, RGMa fragment or RGMa variant, the test sample and the antibody are incubated under conditions similar to those described above in connection with the sandwich assay format. Two different species of antibody-RGMa complexes may then be generated. Specifically, one of the antibody-RGMa complexes generated contains a detectable label while the other antibody-RGMa complex does not contain a detectable label. The antibody-RGMa complex can be, but does not have to be, separated from the remainder of the test sample prior to quantification of the detectable label. Regardless of whether the antibody-RGMa complex is separated from the remainder of the test sample, the amount of detectable label in the antibody-RGMa complex is then quantified. The concentration of RGMa or RGMa fragment in the test sample can then be determined by comparing the quantity of detectable label in the antibody-RGMa complex to a standard curve. The standard curve can be generated using serial dilutions of RGMa or RGMa fragment of known concentration, by mass spectrometry, gravimetrically and by other techniques known in the art.

The antibody-RGMa complex can be separated from the test sample by binding the antibody to a solid support, such as the solid supports discussed above in connection with the sandwich assay format, and then removing the remainder of the test sample from contact with the solid support.

(c) Reverse Competition Assay

In a reverse competition assay, an immobilized RGMa peptide, RGMa fragment or RGMa variant thereof can either be sequentially or simultaneously contacted with a test sample and at least one labeled antibody. Preferably, the antibody specifically binds to an epitope having an amino acid sequence comprising at least three contiguous (3) amino acids of SEQ ID NO:65 or 66. The RGMa peptide, RGMa fragment or RGMa variant can be bound to a solid support, such as the solid supports discussed above in connection with the sandwich assay format. The RGMa peptide fragment may have an amino acid sequence that contains SEQ ID NO:65 or 66.

The immobilized RGMa peptide, RGMa peptide fragment or RGMa variant thereof, test sample and at least one labeled antibody are incubated under conditions similar to those described above in connection with the sandwich assay format. Two different species RGMa-antibody complexes are then generated. Specifically, one of the RGMa-antibody complexes generated is immobilized and contains a detectable label while the other RGMa-antibody complex is not immobilized and contains a detectable label. The non-immobilized RGMa-antibody complex and the remainder of the test sample are removed from the presence of the immobilized RGMa-antibody complex through techniques known in the art, such as washing. Once the non-immobilized RGMa antibody complex is removed, the amount of detectable label in the immobilized RGMa-antibody complex is then quantified. The concentration of RGMa or RGMa fragment in the test sample can then be determined by comparing the quantity of detectable label in the RGMa-complex to a standard curve. The standard curve can be generated using serial dilutions of RGMa or RGMa fragment of known concentration, by mass spectrometry, gravimetrically and by other techniques known in the art.

(d) Fluorescence Polarization

In a fluorescence polarization assay, an antibody or functionally active fragment thereof may first contacted with an unlabeled test sample suspected of containing RGMa or a RGMa fragment thereof to form an unlabeled RGMa-antibody complex. The unlabeled RGMa-antibody complex is then contacted with a fluorescently labeled RGMa, RGMa fragment or RGMa variant thereof. The labeled RGMa, RGMa fragment or RGMa variant competes with any unlabeled RGMa or RGMa fragment in the test sample for binding to the antibody or functionally active fragment thereof. The amount of labeled RGMa-antibody complex formed is determined and the amount of RGMa in the test sample determined via use of a standard curve.

The antibody used in a fluorescence polarization assay specifically binds to an epitope having an amino acid sequence comprising at least three (3) amino acids from SEQ ID NO:65 or SEQ ID NO:66 or SEQ ID NO:74.

The antibody, labeled RGMa peptide, RGMa peptide fragment or RGMa variant thereof and test sample and at least one labeled antibody may be incubated under conditions similar to those described above in connection with the sandwich immunoassay.

Alternatively, an antibody or functionally active fragment thereof may be simultaneously contacted with a fluorescently labeled RGMa, RGMa fragment or RGMa variant thereof and an unlabeled test sample suspected of containing RGMa or RGMa fragment thereof to form both labeled RGMa-antibody complexes and unlabeled RGMa-antibody complexes. The amount of labeled RGMa-antibody complex formed is determined and the amount of RGMa in the test sample determined via use of a standard curve.

Alternatively, an antibody or functionally active fragment thereof is first contacted with a fluorescently labeled RGMa, RGMa fragment or RGMa variant thereof to form a labeled RGMa-antibody complex. The labeled BNP-antibody complex is then contacted with an unlabeled test sample suspected of containing RGMa or an RGMa fragment thereof. Any unlabeled RGMa or RGMa fragment in the test sample competes with the labeled RGMa, RGMa fragment or RGMa variant for binding to the antibody or functionally active fragment thereof. The amount of labeled RGMa-antibody complex formed is determined the amount of RGMa in the test sample determined via use of a standard curve. The antibody used in this immunoassay specifically binds to an epitope having an amino acid sequence comprising at least three contiguous (3) amino acids of SEQ ID NOs:65, 66 or 74.

(e) Mass Spectrometry

Mass spectrometry (MS) analysis may be used alone or in combination with other methods. Other methods include immunoassays and those described above to detect specific polynucleotides. The mass spectrometry method may be used to determine the presence and/or quantity of one or more biomarkers. MS analysis may comprise matrix-assisted laser desorption/ionization (MALDI) time-of-flight (TOF) MS analysis, such as, for example, directed-spot MALDI-TOF or liquid chromatography MALDI-TOF mass spectrometry analysis. In some embodiments, the MS analysis comprises electrospray ionization (ESI) MS, such as liquid chromatography (LC) ESI-MS. Mass analysis can be accomplished using commercially-available spectrometers. Methods for utilizing MS analysis, including MALDI-TOF MS and ESI-MS, to detect the presence and quantity of biomarker peptides in biological samples may be used. See, for example, U.S. Pat. Nos. 6,925,389; 6,989,100; and 6,890,763 for guidance, each of which is incorporated herein by reference.

c. Control

It may be desirable to include a control sample. The control sample may be analyzed concurrently with the sample from the subject as described above. The results obtained from the subject sample can be compared to the results obtained from the control sample. Standard curves may be provided, with which assay results for the biological sample may be compared. Such standard curves present levels of marker as a function of assay units, i.e. fluorescent signal intensity, if a fluorescent label is used. Using samples taken from multiple donors, standard curves can be provided for control levels of the RGMa in normal tissue, as well as for "at-risk" levels of the RGMa in tissue taken from donors, who may have one or more of the characteristics set forth above.

6. KIT

Provided herein is a kit, which may be used for treating or diagnosing a subject. The kit may comprise the antibody and a means for administering the antibody. The kit can further comprise instructions for using the kit and conducting the analysis, monitoring, or treatment.

The kit may also comprise one or more containers, such as vials or bottles, with each container containing a separate reagent. The kit may further comprise written instructions, which may describe how to perform or interpret an analysis, monitoring, treatment, or method described herein.

The present invention has multiple aspects, illustrated by the following non-limiting examples.

EXAMPLES

Example 1

Anti-RGMa Human Monoclonal Antibody Production and Isolation

Using PROfusion mRNA display technology, pooled human spleen, tonsil, PBMC and lymph node antibody libraries were selected through eight rounds against RGMa antigens: 100 nM biotin-labeled human or rat RGMa. PROfusion technology is described in U.S. Patent Application Publication Nos: 20100099103 and 20100105569, the contents each of which are herein incorporated by reference. Selected sc-Fv fragments were reformatted into fully human IgGs. Following screening of IgGs in RGMa-based ELISAs, AE12-1 through AE12-8 were identified as positive binders to human and rat RGMa.

Antibodies AE12-13, AE12-15, AE12-20, AE12-21, AE12-23, and AE12-24 are fully human anti-RGMa antibodies identified from large naïve human scFv yeast libraries selected against human RGMa using standard yeast display technologies. 2 rounds of Magnetic-activated cell sorting (MACS) and 4 rounds of Fluorescence-activated cell sorting (FACS) were performed on the libraries using 100 nM biotinylated human RGMa as the selection antigen. For the last round of sorting, cells were also negatively selected against a human RGMc-Fc antigen. Selected sc-Fv fragments were reformatted into fully human IgGs. Following screening of IgGs in human RGMa ELISA, AE12-13, -15, -20, -21, -23, and -24 were identified as positive binders to human RGMa. AE12-13, AE12-15 and AE12-23 also cross-reacted to human RGMc as evaluated by ELISA.

Example 2

Antibody Characterization

The 8 PROfusion mAbs (AE12-1, AE12-2, AE12-3, AE12-4, AE12-5, AE12-6, AE12-7, and AE12-8), were tested by direct binding ELISAs to examine binding to human RGMa (hRGMa) and rat RGMa and cross-reactivity to hRGMc. hRGMa competition ELISA was employed to test if any of these mAbs would compete h5F9.23 for binding to hRGMa. h5F9.23 is a humanized anti-RGMa lead mAb derived from rat hybridoma and known to bind the N-terminal domain of RGMa. H5F9.23 has the following sequences:

| | | |
|---|---|---|
| VH h5F9.23 | 151 | EVQLVESGGGLVQPGGSLRLSCAASGFTFS NYGMNWIRQAPGKGLEWIGMIYYDSSEKHYA DSVKGRFTISRDNSKNTLYLQMNSLRAEDTAV YYCAKGTTPDYWGQGTMVTVSS |
| VL h5F9.23 | 152 | DVVLTQSPLSLPVTLGQPASISCRSSQSLEY SDGYTFLEWFQQRPGQSPRLLIYEVSNRFSG VPDRFSGSGSGTDFTLKISRVEAEDVGVYY CFQATHDPLTFGQGTKLEIKR |
| VH h5F9.23 CDR-H1 | 153 | NYGMN |
| VH h5F9.23 CDR-H2 | 154 | MIYYDSSEKHYADSVKG |
| VH h5F9.23 CDR-H3 | 155 | GTTPDY |
| VL h5F9.23 CDR-L1 | 156 | RSSQSLEYSDGYTFLE |
| VL h5F9.23 CDR-L2 | 157 | EVSNRFS |
| VL h5F9.23 CDR-L3 | 158 | FQATHDPLT |

Neogenin or BMP-2/BMP-4 competition ELISA was employed to determine if these mAbs would block hRGMa binding to its receptor neogenin or BMP-2/BMP-4.

Based on ELISA data, all 8 PROfusion mAbs bound to human and rat RGMa (Table 3). For RGMc binding in ELISA, 3 mAbs (AE12-6, -7 and -8) showed binding to hRGMc, AE12-4 showed weak binding at high concentrations, and the other 4 mAbs (AE12-1, -2, -3 and -5) showed no binding to hRGMc at concentrations up to 100 nM. In hRGMa competition ELISA, AE12-1, AE12-3 and AE12-6 were able to compete with h5F9.23 in binding to hRGMa, suggesting that the binding epitopes of these 3 mAbs are near or overlap with h5F9.23 epitope. Dot blotting assay with hRGMa fragments showed that AE12-1 and AE12-6 bound the N-terminal fragment, AE12-2 and AE12-4 bound the C-terminal fragment, and the other 4 Abs did not show any detectable binding signal. For blocking hRGMa binding to neogenin in competition ELISA, only AE12-5 and AE12-6 showed blocking activity comparative to or better than h5F9.23, AE12-1 and AE12-4 showed weak inhibition, and AE12-2, -3, -7, and -8 showed no inhibition at concentrations up to 100 nM. In BMP-2/BMP-4 competition ELISA, only AE12-1, AE12-4 and AE12-6 blocked hRGMa binding to BMP-2/BMP-4.

The PROfusion mAbs were further tested in cell-based binding assays for their ability to block hRGMa binding to neuronal cells. In MSD-based cell binding assay in which cells were incubated with biotinylated hRGMa-Fc at room temperature and the hRGMa binding was detected by streptavidin-Sulfo-Tag, only AE12-1 and AE12-6 blocked hRGMa binding to human SH-SY5Y neuronal cells, similar to h5F9.23 (Table 3).

However, in a high content screening (HCS) assay, in which cells were incubated with hRGMa-Fc at 37° C. and the hRGMa binding was detected by Cy3-labeled anti-Fc Ab and calculated with high content fluorescent image analysis, only AE12-6 among PROfusion antibodies showed strong inhibition on RGMa binding to both SH-SY5Y neuronal cells and rat hippocampal primary neurons (Table 3, FIG. 13). Also shown in FIG. 13, AE12-15 and AE12-23, the antibodies derived from naïve human scFv yeast libraries, inhibited hRGMa binding to cells.

The BMP responsive element (BRE) was constructed using overlapping oligos based on the sequence described by Korchynskyi and ten Dijke (J. Biol. Chem. 2002, 277:4883), and cloned into a basic luciferase reporter vector pGL4.27 [luc2P/minP/Hygro] (Promega) to generate a BRE luciferase reporter construct. RGM family members (RGMa, RGMb and RGMc) are coreceptors for BMP signaling. Both RGMa and RGMc BMP reporter assays were established by cotransfection of 293HEK cells with BMP reporter plasmid and RGMa or RGMc expression plasmid, and used to screen mAbs for neutralizing activity towards RGMa and RGMc. In RGMa BMP reporter assay, AE12-1 and AE12-6 neutralized RGMa activity, consistent with data from MSD-based cell binding assay (Table 3). In the RGMc BMP reporter assay, AE12-6 neutralized RGMc activity, whereas AE12-1 did not. Thus, AE12-1 is a neutralizing mAb specific to RGMa.

The PROfusion mAbs were further tested for their ability to neutralize RGMa in a chemotaxis assay with SH-SY5Y neuronal cells. In this assay, RGMa acts as a repulsive molecule to inhibit cell chemotaxis. AE12-1 showed strong neutralizing activity towards hRGMa (Table 3). AE12-4 and AE12-6 showed some neutralizing activity.

AE12-1 was tested in neurite outgrowth assay with human SH-SY5Y neuronal cells. In this assay, RGMa, either full-length or N-terminal fragment, inhibits neurite outgrowth. Consistent with its functional activity in RGMa BMP reporter assay and chemotaxis assay, AE12-1 exhibited strong neutralizing activity towards either full-length hRGMa or N-terminal fragment (Table 3).

BIAcore analysis of AE12-1 on hRGMc and human, cynomolgus (cyno) monkey and rat RGMa demonstrated that AE12-1 did not bind hRGMc but exhibited good cross-reactivity to human, cyno and rat RGMa with comparable affinity. See Table 4.

TABLE 3

| Clone→ | AE12-1 | AE12-2 | AE12-3 | AE12-4 | AE12-5 | AE12-6 | AE12-7 | AE12-8 | h5F9.23 |
|---|---|---|---|---|---|---|---|---|---|
| hRGMa binding (ELISA) | ++ | ++ | ++ | + | + | ++ | + | + | ++ |
| Rat RGMa binding (ELISA) | ++ | ++ | ++ | + | + | ++ | + | + | ++ |
| hRGMc-His ELISA | − | − | − | +/− | − | ++ | + | + | ++ |
| Compete with h5F9.23 for binding to hRGMa (ELISA) | + | − | + | − | − | + | − | − | |
| Mapping hRGMa fragments | N | C | [a]Neg | C | [a]Neg | N | [a]Neg | [a]Neg | N |
| Compete with biot-hRGMa-Fc for binding to neo-His (ELISA) | +/− | − | − | +/− | ++ | +++ | − | − | ++ |
| [b]Block hRGMa-Fc binding to SH-SY5Y cells (MSD) | ++ | − | − | − | − | ++ | − | − | ++ |
| [c]Block hRGMa-Fc binding to SH-SY5Y cells (HCS) | [d](−) | − | − | − | + | +++ | − | − | ++ |
| Compete with FL-RGMa-Fc for binding to BMP-2 (ELISA) | ++ | − | − | ++ | − | ++ | − | − | ++ |
| Compete with FL-RGMa-Fc for binding to BMP-4 (ELISA) | ++ | − | − | ++ | − | ++ | [e]? | − | ++ |
| Neutralize hRGMa in RGMa BMP reporter assay | ++ | − | − | − | − | ++ | − | − | ++ |
| Neutralize hRGMc in RGMc BMP reporter assay | − | − | − | − | − | ++ | − | − | ++ |
| Neuralize hRGMa in Chemotaxis with SH-SY5Y cells | +++ | − | − | [f]+ | − | + | − | − | ++ |
| Neutralize hRGMa in neurite outgrowth assay | ++ | | | | | | | | ++ |

With respect to Table 3, "Neg" corresponds to negative binding with all fragments tested in dot blotting. "[b]MSD" corresponds to using biotinylated hRGMa-Fc complexed with streptavidin-Sulfo-Tag, and incubation with cells at room temperature (RT). "HCS" corresponds to using hRGMa-Fc complexed with Cy3-labeled anti-Fc Ab, and inbation with cells at 37° C. "[d]AE12-1" corresponds to a dramatically enhanced RGMa-Fc binding to cells, in contrast to inhibiting biotin-RGMa-Fc binding to SH-SY5Y cells by MSD. "[e]?" corresponds to data that is inconclusive for AE12-7. "[f]AE12-4"—the concentration of AE12-4 in the chemotaxis assay is inversely correlated with neutralizing activity.

In a BMP-responsive reporter assay in which RGMa or RGMc enhances BMP signaling by interacting with BMPs, an antibody comprising SEQ ID NOs:1 and 5 (AE12-1) blocked RGMa activity but not RGMc activity, consistent with its functional antagonism and binding specificity for RGMa.

FIGS. 13 and 14 illustrate the neutralizing effects of the specified antibodies on RGMa binding to neuronal cells using a live cell binding assay on SH-SY5Y cells and rat hippocampal primary neurons. Fc-tagged RGMa and Cy3-labeled anti-Fc antibodies are complexed at 4° C. for 60 minutes, followed by an incubation of the complex with a blocking antibody at room temperature for 10 minutes. The RGMa- Cy3+ antibody complex is then added to cells together with Hoechsts 33342 for 30 minutes at 37° C. to allow binding onto the cells. The cell are then washed twice in culture medium and fixed with PFH. Cell imaging is performed with the BD Pathway and images analyzed with the Definiens Architect software.

All variants blocked hRGMa binding to SH-SY5Y cells in MSD-based cell binding assay, neutralized RGMa but not RGMc activity in BMP reporter assays, and exhibited high thermal stability and good solubility in preformulation studies.

TABLE 4

| Ab | | AE12-1 | AE12-1-F | AE12-1-H | AE12-1-L | AE12-1-V | AE12-1-I | AE12-1-K | AE12-1-Y |
|---|---|---|---|---|---|---|---|---|---|
| hRGMa binding (ELISA) | | ++ | ++ | ++ | ++ | ++ | +++ | +++ | +++ |
| Cyno RGMa binding (ELISA) | | ++ | +++ | +++ | +++ | +++ | +++ | +++ | +++ |
| hRGMa-His | ka (M-1s-1) | $3.1 \times 10^4$ | $2.7 \times 10^4$ | $3.2 \times 10^4$ | $3.8 \times 10^4$ | $2.5 \times 10^4$ | $3 \times 10^4$ | $3.4 \times 10^4$ | $2.2 \times 10^4$ |
| | kd (s-1) | $2.3 \times 10^{-4}$ | $3.9 \times 10^{-5}$ | $1.2 \times 10^{-4}$ | $2.5 \times 10^{-4}$ | $1.5 \times 10^{-4}$ | $1.3 \times 10^{-4}$ | $3.0 \times 10^{-4}$ | $1.3 \times 10^{-5}$ |
| | Kd (nM) | 7.3 | 1.4 | 3.8 | 6.6 | 5.9 | 4.5 | 8.8 | 0.6 |
| Cyno RGMa-His | ka (M-1s-1) | $1.9 \times 10^5$ | $4.4 \times 10^4$ | $4.7 \times 10^4$ | $6.2 \times 10^4$ | $1.1 \times 10^5$ | $9.9 \times 10^4$ | $5.1 \times 10^4$ | $4 \times 10^4$ |
| | kd (s-1) | $1.7 \times 10^{-3}$ | $2.5 \times 10^{-4}$ | $6.3 \times 10^{-4}$ | $6.7 \times 10^{-4}$ | $9.9 \times 10^{-4}$ | $8.7 \times 10^{-4}$ | $4.7 \times 10^{-4}$ | $2 \times 10^{-4}$ |
| | Kd (nM) | 8.8 | 5.4 | 13.4 | 10.1 | 9.2 | 8.9 | 9.3 | 4.9 |
| Rat RGMa-His | ka (M-1s-1) | $2.6 \times 10^4$ | $2.6 \times 10^4$ | $2.9 \times 10^4$ | $3.2 \times 10^4$ | $2.2 \times 10^5$ | $2.8 \times 10^4$ | $1.6 \times 10^4$ | $1.4 \times 10^4$ |
| | kd (s-1) | $4.8 \times 10^{-4}$ | $1.4 \times 10^{-4}$ | $2.5 \times 10^{-4}$ | $3.9 \times 10^{-4}$ | $3.2 \times 10^{-4}$ | $3.2 \times 10^{-4}$ | $2.8 \times 10^{-4}$ | $6.9 \times 10^{-5}$ |
| | Kd (nM) | 19 | 5.2 | 8.6 | 12 | 15 | 12 | 17 | 5 |
| hRGMc-His | BIAcore binding | − | − | − | − | − | − | − | − |
| Block hRGMa-Fc binding to SH-SY5Y cells (MSD) | | ++ | ++ | ++ | ++ | ++ | ++ | ++ | ++ |
| Neutralize RGMa in BRE luc assay | | ++ | ++ | ++ | ++ | ++ | ++ | ++ | ++ |
| Neutralize RGMc in BRE luc assay | | − | − | − | − | − | − | − | − |
| Tier 1 solubility/stability | | ++ | ++ | ++ | ++ | ++ | ++ | ++ | ++ |

As mentioned above, AE12-6, AE12-15, and AE12-23 blocked binding of RGMa to SH-SY5Y cells and primary neurons. See FIG. 13. In the HCS assay, AE12-1 did not inhibit binding of RGMa on SH-SY5Y cells. See FIG. 14. The highest concentrations of AE12-1 enhanced RGMa-Fc binding to cells, whereas in the lower concentrations the levels were equal to control RGMa binding levels. This is in contrast to inhibiting biotin-RGMa-Fc binding to SH-SY5Y cells by MSD (MSD corresponds to using biotinylated hRGMa-Fc complexed with streptavidin-Sulfo-Tag, and incubation with cells at room temperature). The difference between the MSD and the HCS assay may be due to different assay conditions.

Figure 15A:
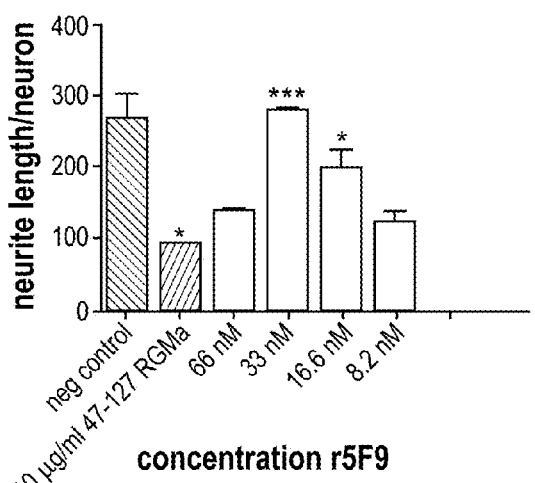
FIGS. 15A-15C show the neutralizing effect of AE12-1 and AE12-6 on RGMa neurite outgrowth repulsion in a neurite outgrowth assay on rat hippocampal primary neurons. r5F9 antibody is used as a control
Figure 15B:
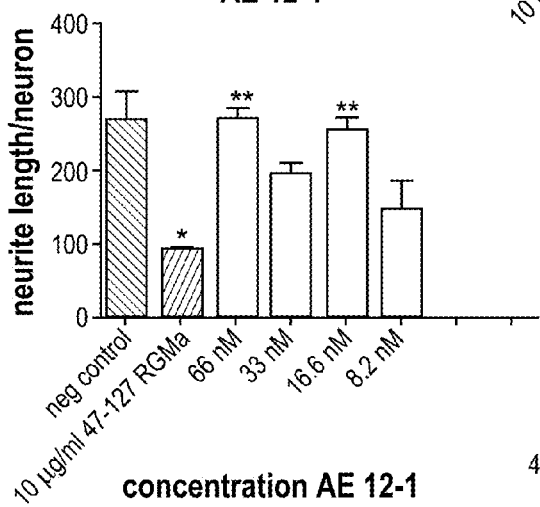
Figure 15C:
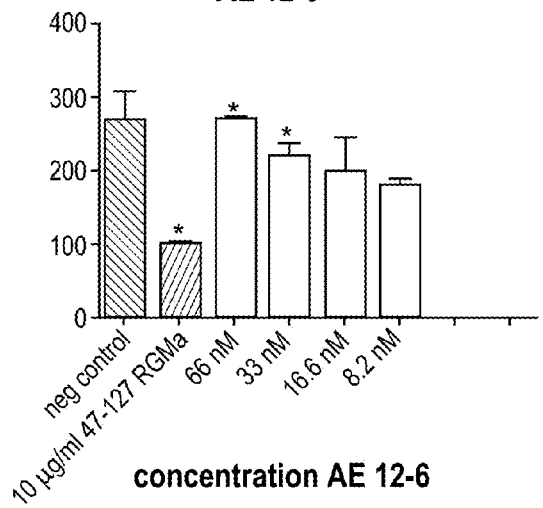

FIG. 15 shows the neutralization effects on RGMa repulsion by r5F9 (control), AE12-1, and AE12-6 in a neurite outgrowth assay. 6500 rat hippocampal primary neurons per well were plated on poly-1-lysine coated 96-well imaging plates. The cells were treated for 24 hours with RGMa fragment 47-127 of SEQ ID NO:65 (SEQ ID NO:139) in combination with anti-RGMa antibodies. The cells were fixed and stained with BIII-tubulin using a neurite outgrowth kit protocol from Millipore. Images were acquired with a BD Pathway and were analyzed with Definiens Architect to measure the neurite outgrowth per neuron.

Example 3

Antibody Variants and Binding Data

Table 4 shows that by substituting for the Cys residue in AE12-1 VL CDR3 (SEQ ID NO:8), one can generate variants having improved affinity to hRGMa. See SEQ ID NOs:67-73. For example, see Table 4, wherein antibody clone AE12-1-Y showed at least a 10-fold increased affinity to hRGMa and AE12-1-F showed a 5-fold increased affinity to hRGMa. Others showed comparable affinity as the parental AE12-1.

Example 4

Neurite Outgrowth

Figure 2:
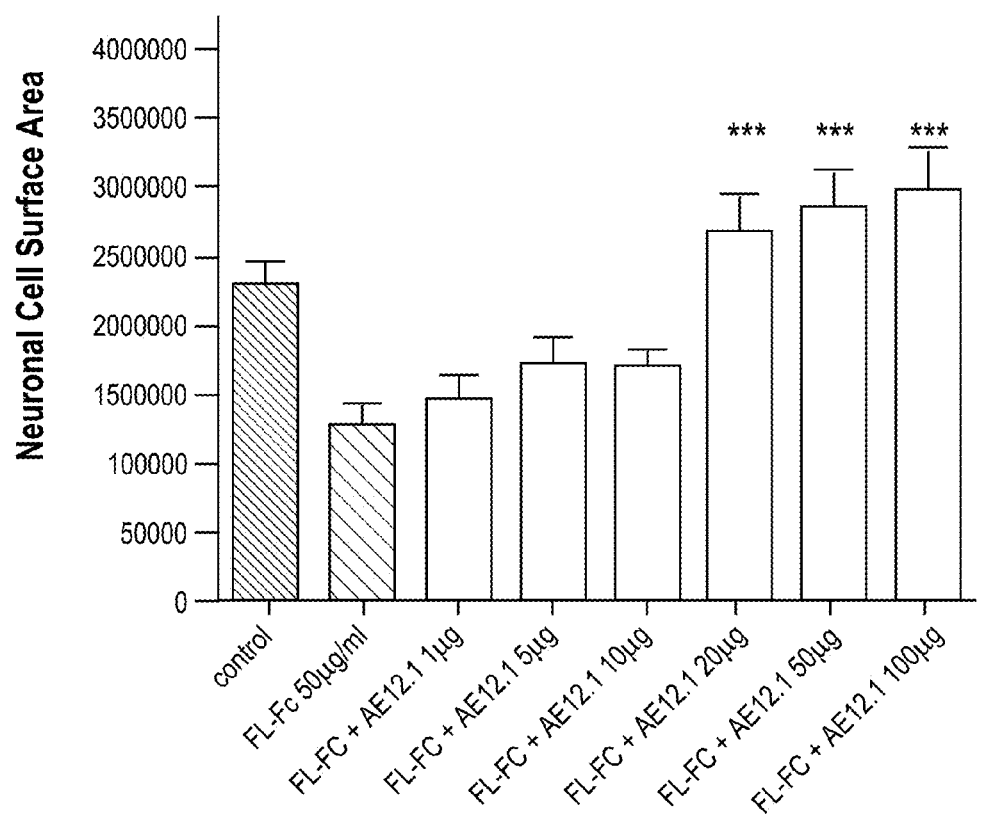
FIG. 2 shows testing results from neurite outgrowth assay using 50 µg/ml of full length hRGMa.

As shown in FIGS. 1, 2 and 15, AE12-1 compeletely neutralized full length hRGMa and a fragment of hRGMa, as shown on SH-SY5Y cells and rat hippocampal primary neurons. This fragment of hRGMa corresponds to amino acids 47-127 of SEQ ID NO:65 as shown here: PCKI LKCNSEF-WSA TSGSHAPASD DTPEFCAALR SYALCTRRTA RTCRGDLAYH SAVHGIEDLM SQHNCSKDGP TSQPRLR (SEQ ID NO:139).

Further neurite outgrowth experiments were performed to assess the effects of AE12-1 as well as AE12-1 variants, wherein the antibody comprises SEQ ID NOs:1 and 5, or 2-4 and 6-8, wherein the Cys residue of SEQ ID NO:8 is substituted for another amino acid, or wherein the Cys residue at position 91 of SEQ ID NO:5 is substituted with another amino acid (i.e. AE12-1-F, AE12-1-H, AE12-1-L, AE12-1-V, AE12-1-I, AE12-1-K, and AE12-1-Y). See FIGS. 9-12, wherein inhibition by the described antibody (24 hours incubation) on neurite outgrowth of SH-SY5Y cells treated with FL hRGMa are shown.

Example 5

In Vivo Studies

Figure 3:
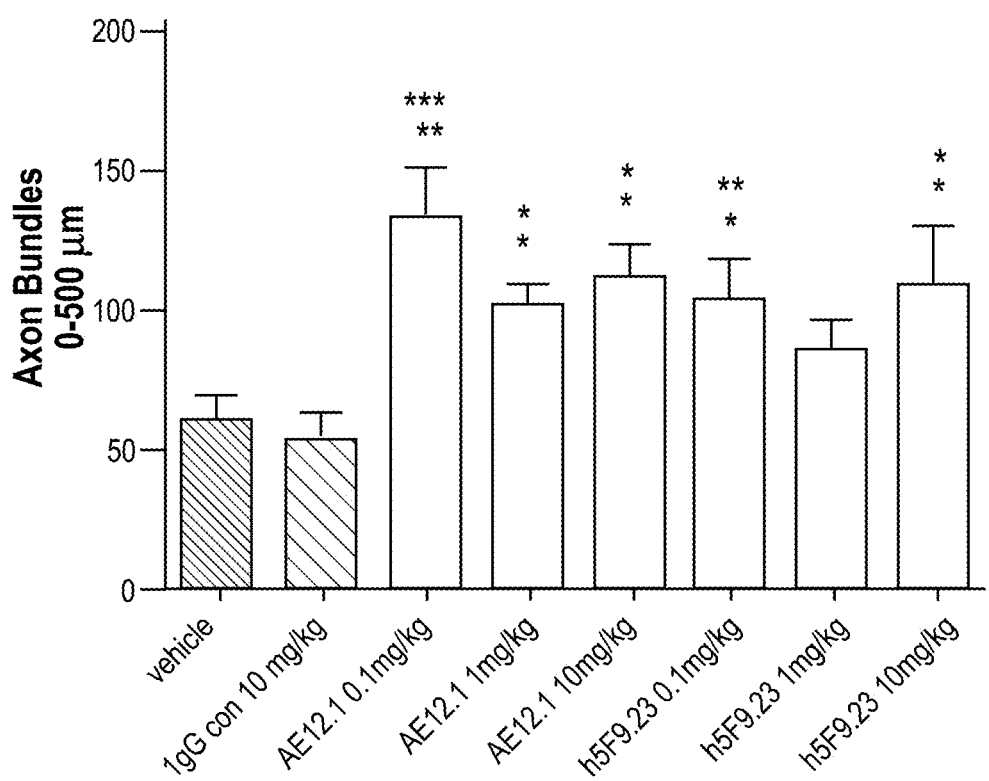
FIG. 3 shows a bar chart that is reflective of the level of in vivo regenerative growth of retinal ganglion cells axons perilesionally (0-500 µm) in the presence of antibody AE12-1.
Figure 4:
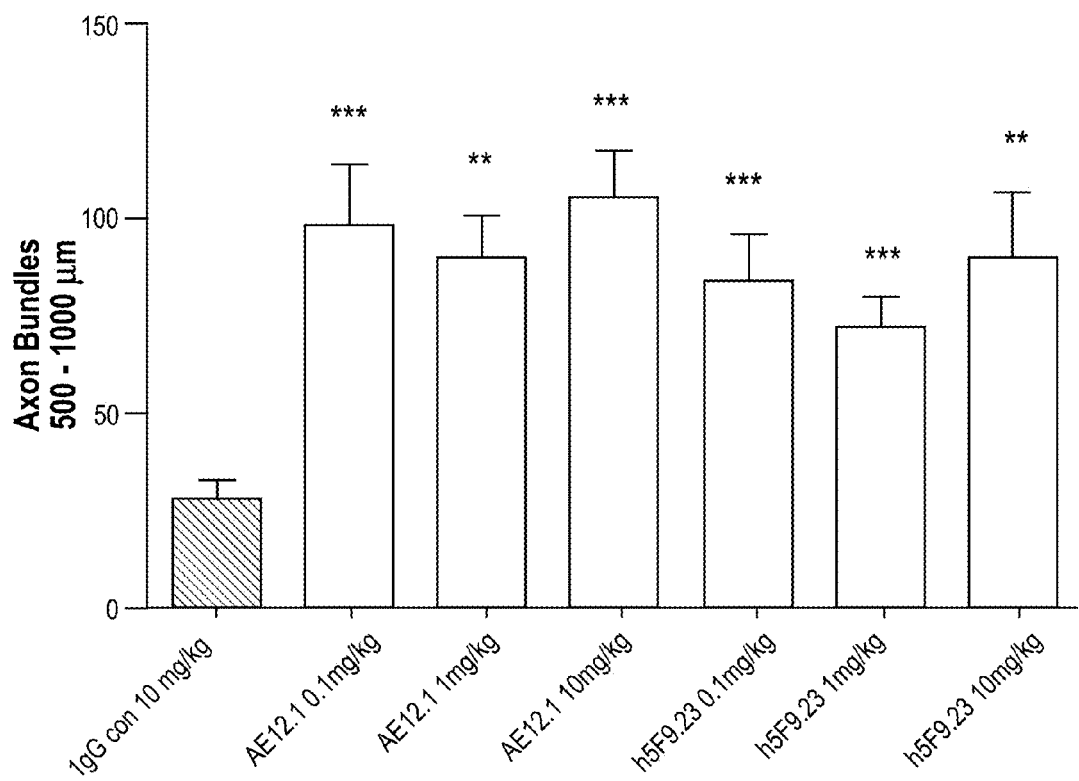
FIG. 4 shows a bar chart that is reflective of the level of in vivo regenerative growth of retinal ganglion cell axons (500-1000 µm) in the presence of antibody AE12-1 in direct comparison with human 5F9.23.

As shown in FIGS. 3 and 4, AE12-1 enhanced regenerative growth of retinal ganglion cell axons perilesionally (0-500 μm) (n=3-5 rats/group). See FIG. 3. Antibody AE12-1 also enhanced regenerative growth of retinal ganglion cell axons into areas further away from the lesion (500-1000 μm) (n=3-5 rats/group).

Example 6

Rat Optic Nerve Crush Experiments

Figure 8A:
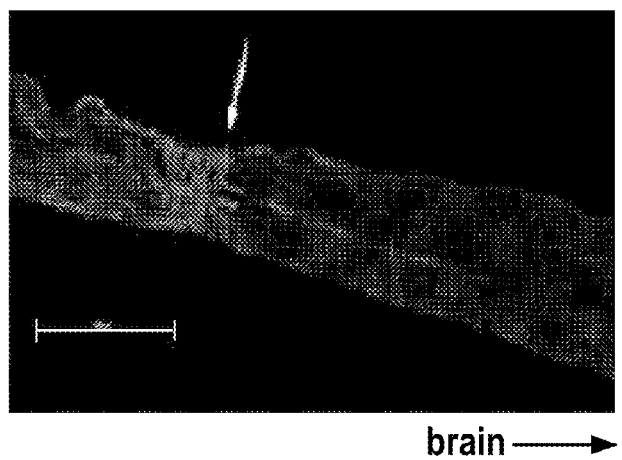
FIGS. 8A-8C show micrographs of nerve lesions in rats treated with a control antibody (hIgG at 10 mg/kg; see FIG. 8A), AE12-1 antibody at 1 mg/kg (see FIG. 8B), or h5F9.23 antibody at 1 mg/kg (see FIG. 8C).
Figure 8B:
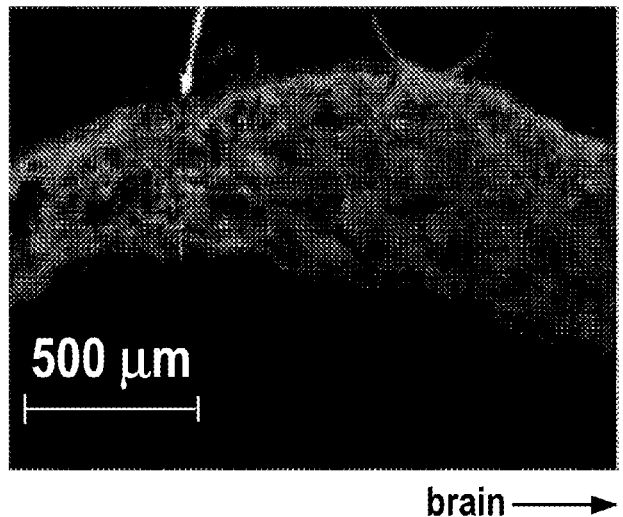
Figure 8C:
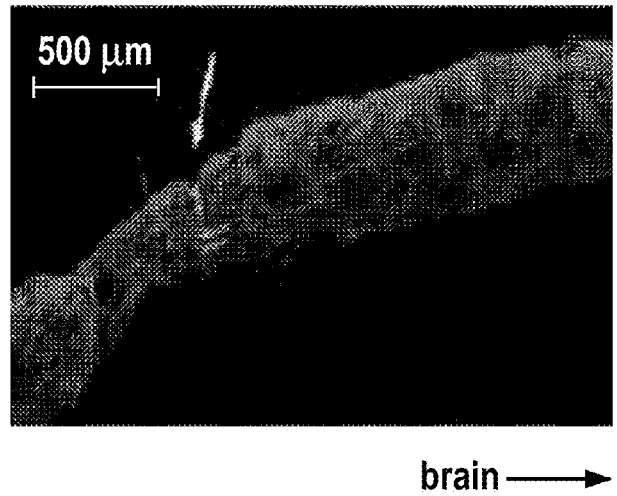
Figure 9A:
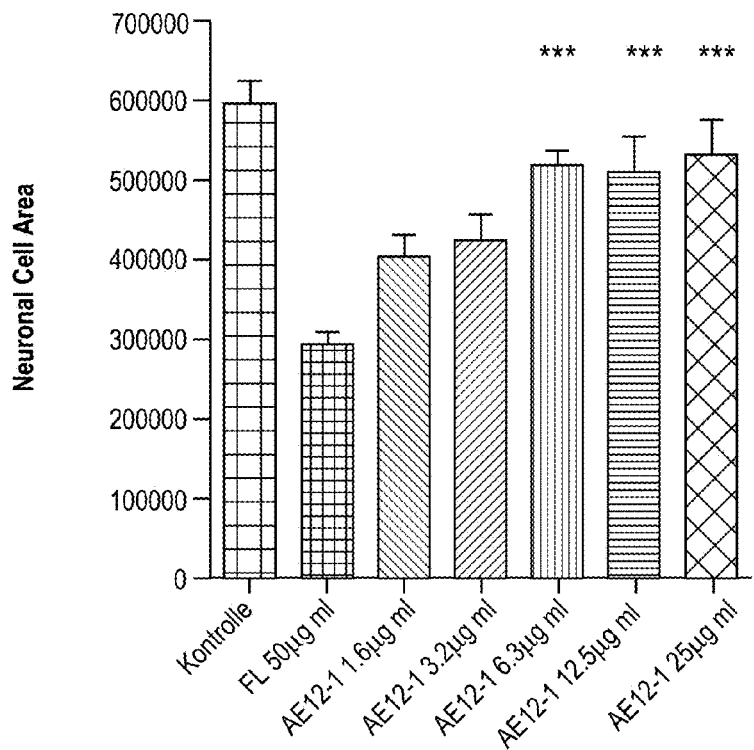
FIGS. 9A-9B show the results of an analysis of neurite outgrowth of SH-SY5Y cells on 96 well plates coated with fibronectin as a substrate after treatment with full length human RGMa and its neutralization by AE12-1 (FIG. 9A) and AE12-1-H (FIG. 9B). Antibody and full length hRGMa were added at the same time and subsequently cultures were incubated for 24 hours.
Figure 9B:
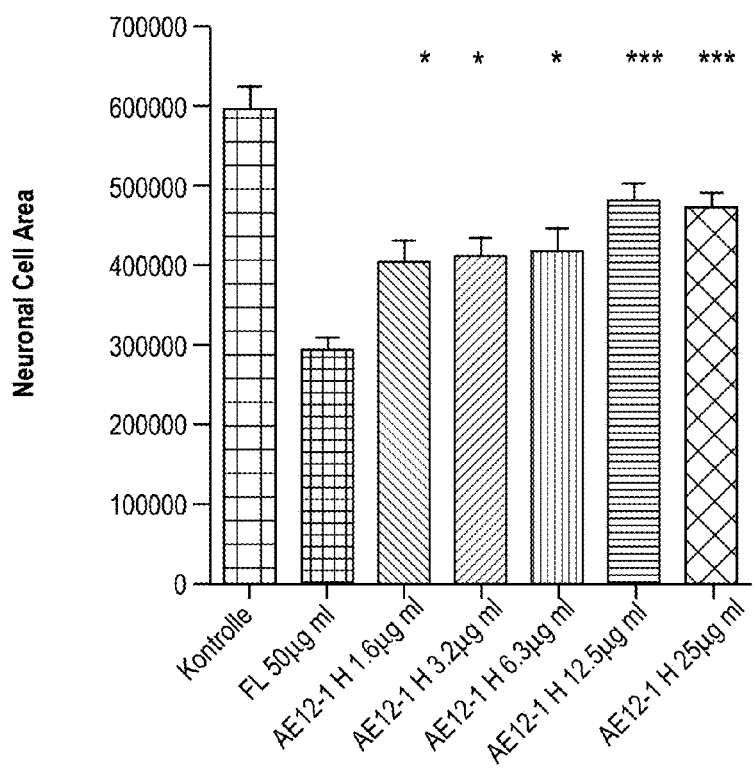
Figure 10A:
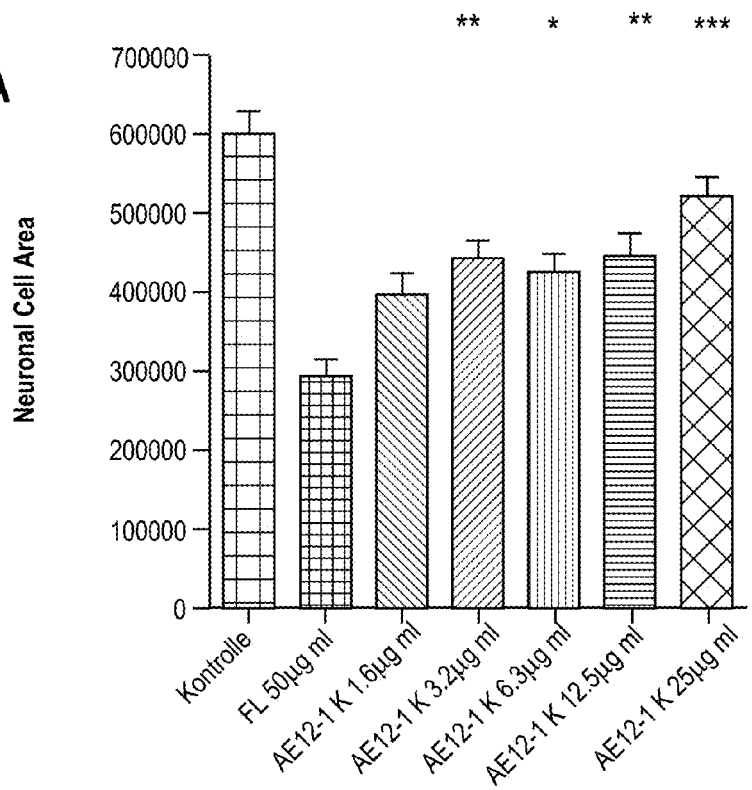
FIGS. 10A-10B show the results of an analysis of neurite outgrowth of SH-SY5Y cells on 96 well plates coated with fibronectin as a substrate after treatment with full length human RGMa and its neutralization by AE12-1-K (FIG.10A) and AE12-1-F (FIG. 10B). Antibody and full length hRGMa were added at the same time and subsequently cultures were incubated for 24 hours.
Figure 10B:
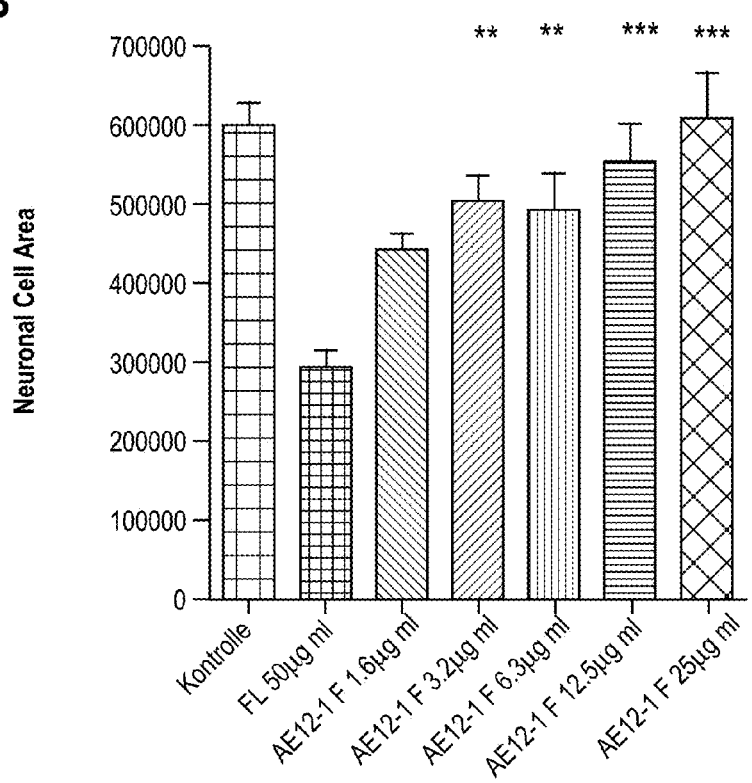
Figure 11A:
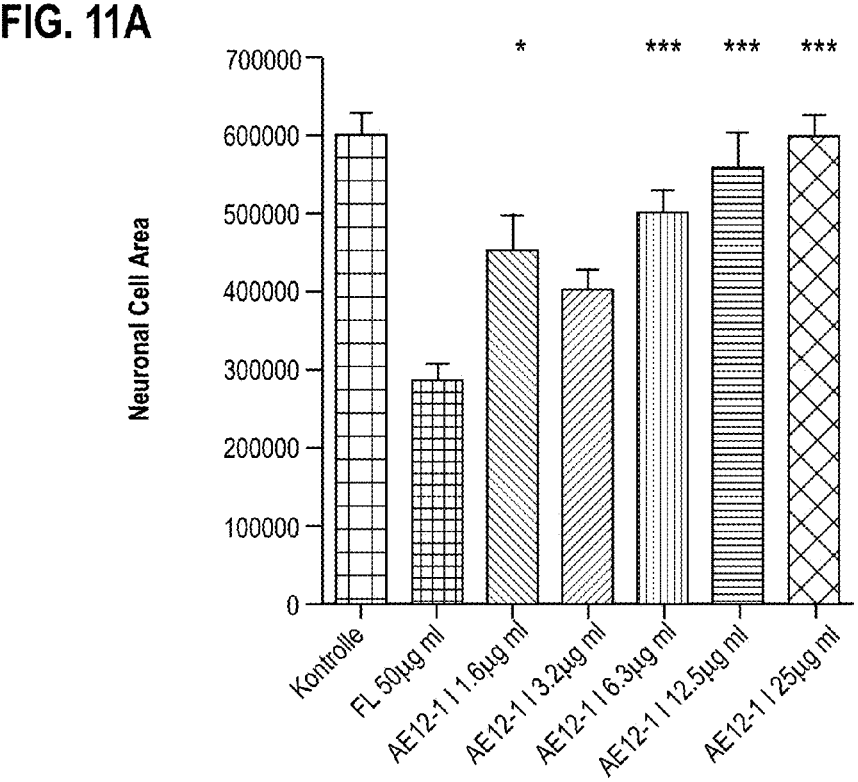
FIGS. 11A-11B show the results of an analysis of neurite outgrowth of SH-SY5Y cells on 96 well plates coated with fibronectin as a substrate after treatment with full length human RGMa and its neutralization by AE-12-1-I (FIG. 11A) and AE-12-L (FIG. 11B). Antibody and full length hRGMa were added at the same time and the cultures were subsequently incubated for 24 hours.
Figure 11B:
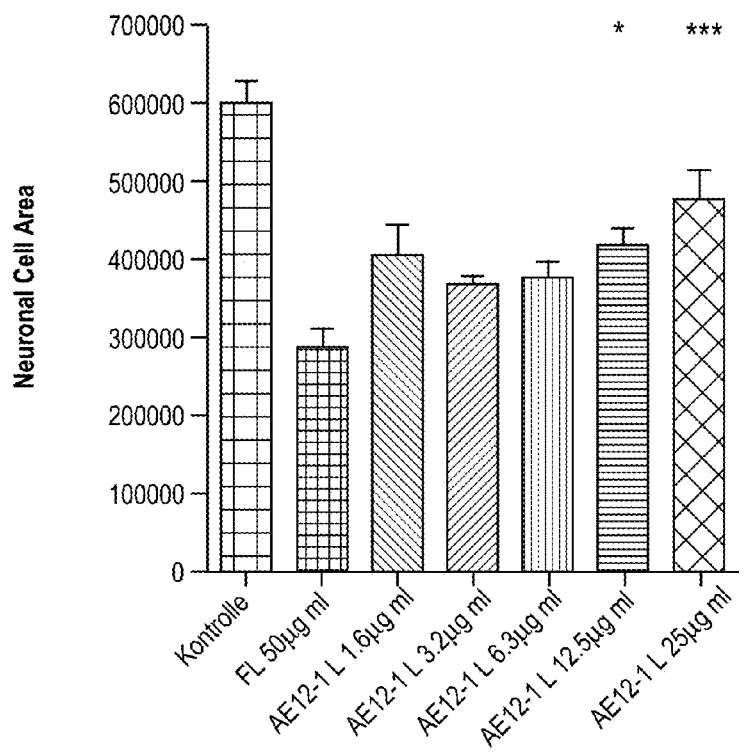
Figure 12A:
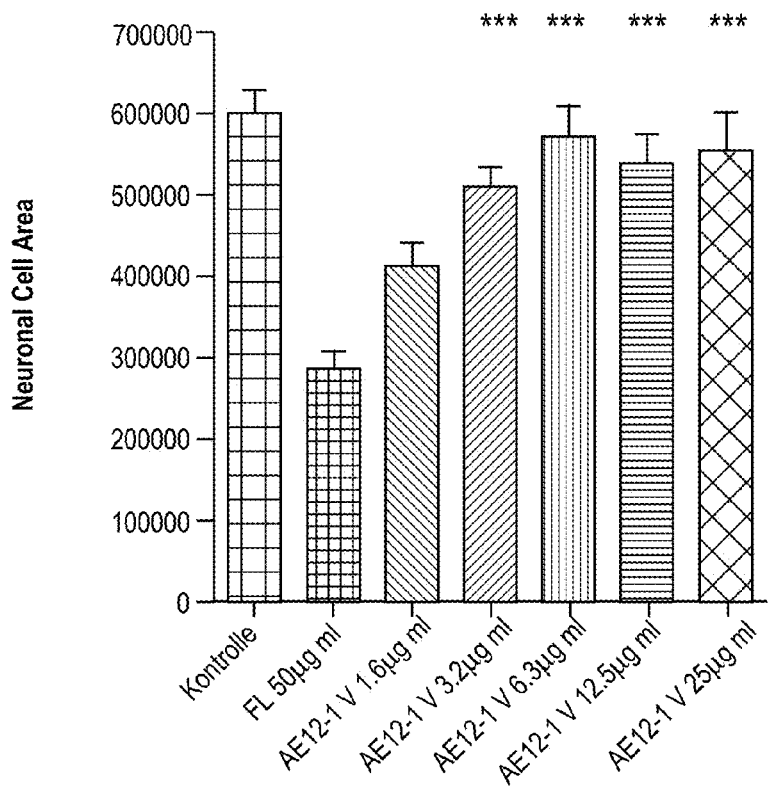
FIGS. 12A-12B show the results of an analysis of neurite outgrowth of SH-SY5Y cells on 96 well plates coated with fibronectin as a substrate after treatment with full length human RGMa and its neutralization by AE12-1-V (FIG. 12A) and AE-12-1-Y (FIG. 12B). Antibody and full length hRGMa were added at the same time and the cultures were subsequently incubated for 24 hours.
Figure 12B:
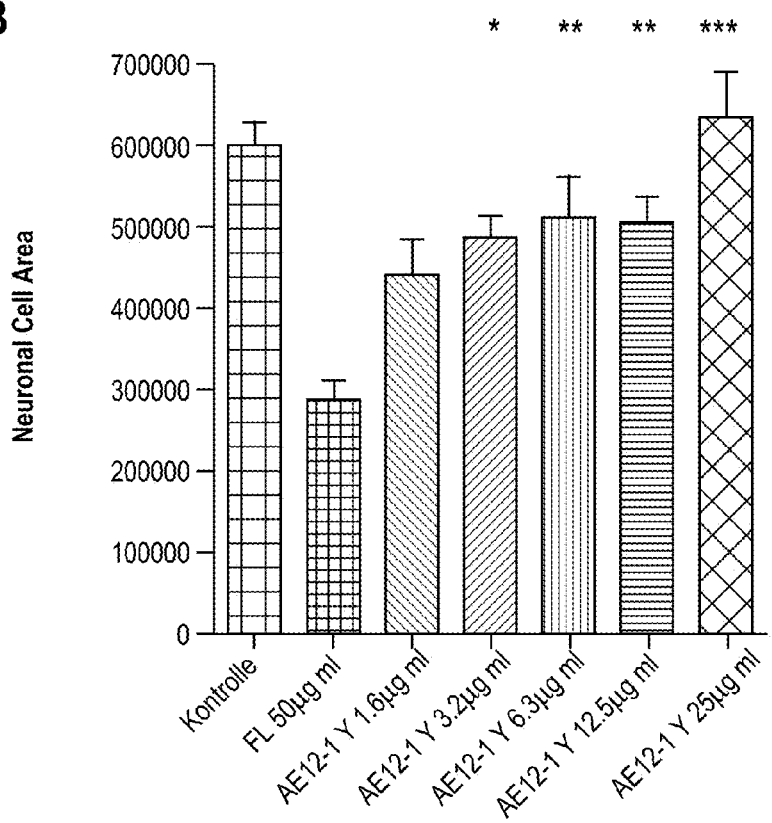
Figure 14A:
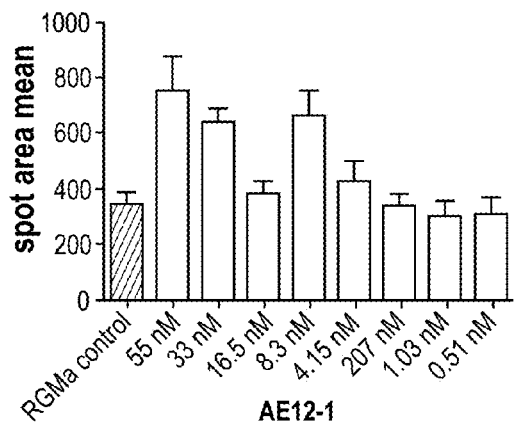
FIGS. 14A-14H show the results of an RGMa binding inhibition assay on SH-SY5Y cells (via High Content Analysis (HCA)) using AE12-1 and the AE12-1 cysteine variants.
Figure 14B:
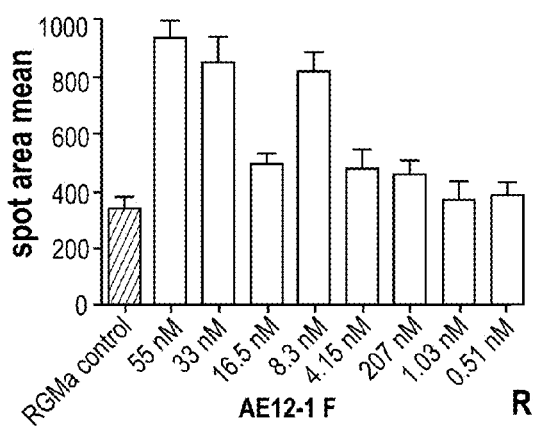
Figure 14C:
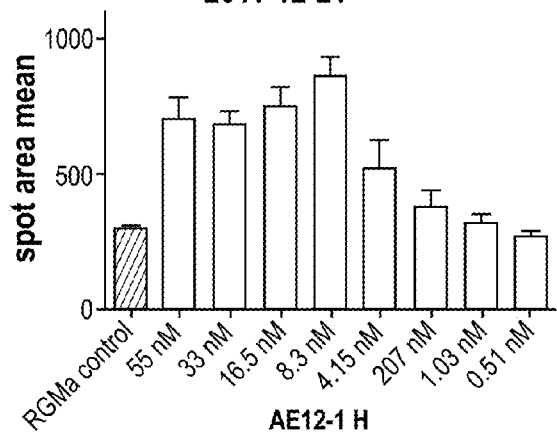
Figure 14D:
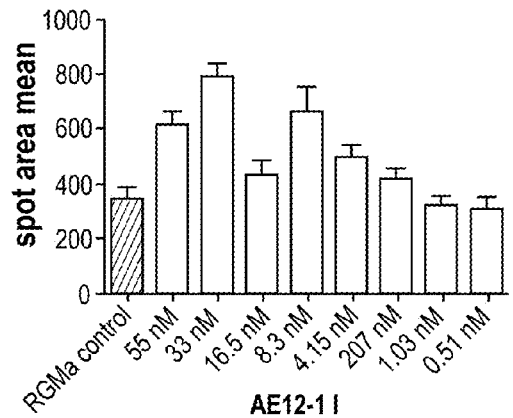
Figure 14E:
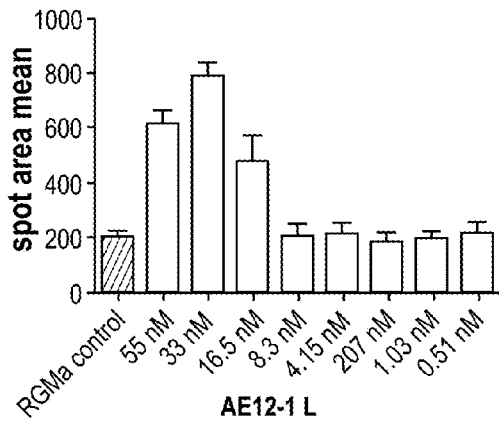
Figure 14F:
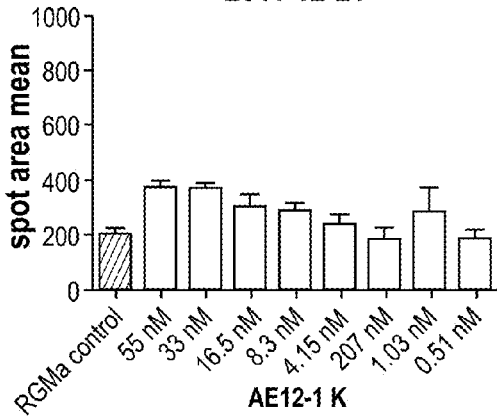
Figure 14G:
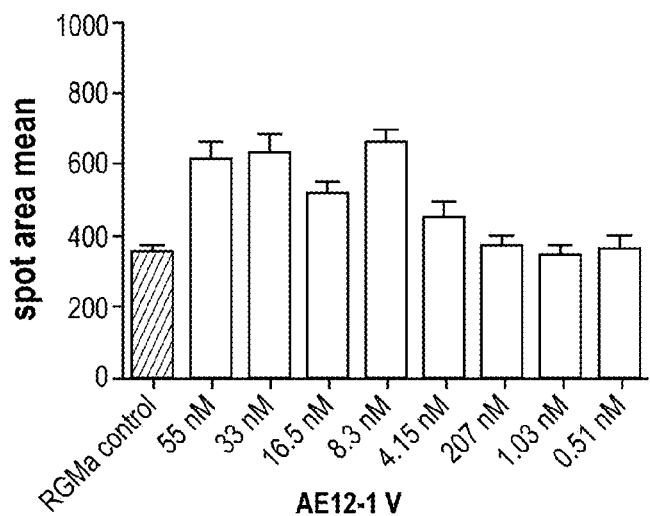
Figure 14H:
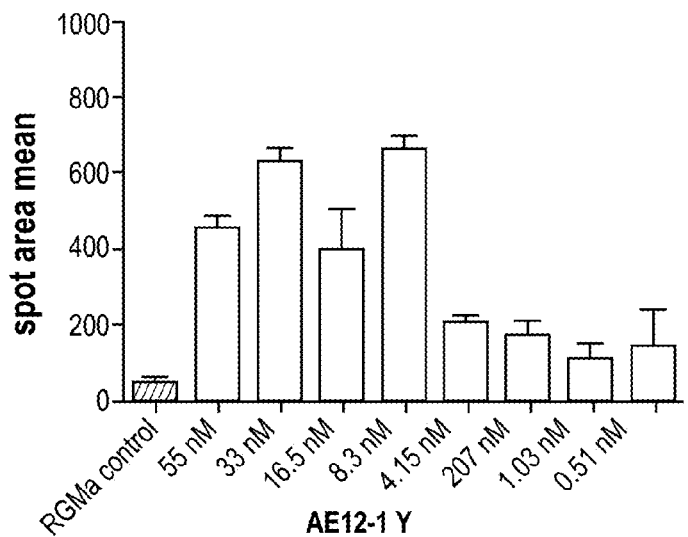

AE12-1 was active in rat optic nerve crush experiments. See FIG. 8. A unilateral optic nerve crush lesion was done in male Wistar rats, 2-4 mm behind the eye. Rats were followed for 6 weeks (8 groups, n=6) and antibodies were administered once per week intravenously at either 10 mg/kg, 1 mg/kg, or 0.1 mg/kg. The hIgG1 control was administered intravenously, once per week at 10 mg/kg (n=6 rats). In AE12-1 treated rats regenerating fibers were able to grow beyond the optic nerve crush lesion, whereas in control antibody hIgG1-treated rats, regenerating fibers accumulate at the lesion due to their inability to overcome the lesions. See FIG. 8.

Example 7

Epitope Mapping of Human RGMa (hRGMa) with Monoclonal Antibody AE12-1

Epitope mapping studies were undertaken for monoclonal antibody AE12-1. Data suggested that the epitope for AE12-1 is located in the N-terminal region of RGMa. Several constructs of hRGMa were employed to attempt to determine the epitope for AE12-1. These constructs included:

pelB-M-[RGMA(47-168)]-6His ("6H is" disclosed as SEQ ID NO: 148) (*E. coli*) produced recombinantly. Antigen is 0.41 mg/mL in ChemTag#16211, S100 buffer, pH8, 25 mM Tris, 100 mM NaCl, 1 mM DTT, 10% (v/v) glycerol. Sequence of this first antigen construct is: MKYLL PTAAA GLLLL AAQPA MAMPC KILKC NSEFW SATSG SHAPA SDDTP EFCAA LRSYA LCTRR TARTC RGDLA YHSAV HGIED LMSQH NCSKD GPTSQ PRLRT LPPAG DSQER SDSPE ICHYE KSFHK HSATP NYTHC GLFGD HHH-HHH (SEQ ID NO:75).

[IgK-leader]-AttB1-[hRGMA(47-422)]-AttB2-MYC-6His ("6H is" disclosed as SEQ ID NO: 148) produced recombinantly, 0.85 mg/ml in PBS. Sequence of this second antigen construct is: METDT LLLWV LLLWV PGSTG DAAQP ARRAR RTKLG TELGS TSPVW WNSAD ITSLY KKAGS PCKIL KCNSE FWSAT SGSHA PASDD TPEFC AALRS YALCT RRTAR TCRGD LAYHS AVHGI EDLMS QHNCS KDGPT SQPRL RTLPP AGDSQ ERSDS PEICH YEKSF HKHSA TPNYT HCGLF GDPHL RTFTD RFQTC KVQGA WPLID NNYLN VQVTN TPVLP GSAAT ATSKL TIIFK FNQEC VDQKV YQAEM DELPA AFVDG SKNGG DKHGA NSLKI TEKVS GQHVE IQAKY IGTTI VVRQV GRYLT FAVRM PEEVV NAVED WDSQG LYLCL RGCPL NQQID FQAFH TNAEG TGARR LAAAS PAPTA PETFP YETAV AKCKE KLPVE DLYYQ ACVFD LLTTG DVNFT LAAYY ALEDV KMLHS NKDKL HLYER TRDLP GNPAF LYKVV ISSTV AAARG GPEQK LISEE DLNSA VDHHH HHH (SEQ ID NO:76).

[IgK-leader]-AttB1-[hRGMA(47-168)]-Xa-[hIgG L Fc (257-481)] (mammalian construct), produced recombinantly, 1.18 mg/mL, in PBS. Sequence of this third antigen construct is: METDT LLLWV LLLWV PGSTG DAAQP ARRAR RTKLP CKILK CNSEF WSATS GSHAP ASDDT PEFCA ALRSY ALCTR RTART CRGDL AYHSA VHGIE DLMSQ HNCSK DGPTS QPRLR TLPPA GDSQE RSDSP EICHY EKSFH KHSAT PNYTH CGLFG DLNSA DIEGR MDPPC PAPEL LGGPS VFLFP PKPKD TLMIS RTPEV TCVVV DVSHE DPEVK FNWYV DGVEV HNAKT KPREE QYNST YRVVS VLTVL HQDWL NGKEY KCKVS NKALP APIEK TISKA KGQPR EPQVY TLPPS REEMT KNQVS LTCLV KGFYP SDIAV EWESN GQPEN NYKTT PPVLD SDGSF FLYSK LTVDK SRWQQ GNVFS CSVMH EALHN HYTQK SLSLS PGK (SEQ ID NO:77).

All of the antigens used contain the amino acid sequence of RGMa (47-168), wherein the numbering used to identify sequence positions correspond to the numbering of the parent protein. The sequence of hRGMa (47-168) is: PCKI LKCNS EFWSA TSGSH APASD DTPEF CAALR SYALC TRRTA RTCRG DLAYH SAVHG IEDLM SQHNC SKDGP TSQPR LRTLP PAGDS QERSD SPEIC HYEKS FHKHS ATPNY THCGL FGD (SEQ ID NO:78).

The buffers used for excising the epitopes were as follows:
Buffer A: 100 mM NaHCO$_3$, 500 mM NaCl, pH 8;
Buffer B: 100 mM NaHCO$_3$, 100 mM NaCl, pH 8;
Buffer C: 100 mM NaOAc, 500 mM NaCl, pH 4; and
Buffer D: 100 mM Tris-HCl, 500 mM NaCl, pH 8.

The monoclonal antibody was immobilized as follows. Twenty milligrams of CNBr-activated Sepharose beads (GE Healthcare, Uppsala Sweden) was weighed into a compact reaction column (USB Corp., Cleveland, Ohio) with a 35 μm frit and washed 3 times with 200 μl of 1 mM HCl, followed by washing 3 times with 200 μl of Buffer A.

Approximately 5-6 nmol of the AE12-1 mAb solution was dialyzed against PBS using a 10,000 MWCO Slide-A-Lyzer mini dialysis unit (Pierce, Rockford, Ill.) for approximately 40 minutes to remove the histidine buffer which would interfere with antibody binding to Sepharose. The dialyzed mAb solution was added to the activated resin and allowed to mix on a rotator (Mix-All Laboratory Tube Mixer, Torrey Pines Scientific, San Marcos, Calif.) for 4 hours at room temperature. After binding, the resin flow-through was collected, and the resin was washed three times with 200 μl Buffer A. The resin was suspended in 200 μl of Buffer D, and rotated at room temperature for 1 hour to block excess binding sites in the resin. The Buffer D solution was flushed out and the resin was washed alternately with 200 μA of Buffer C and Buffer D (low/high pH washing), a total of three times each. The resin was washed three times with 200 μA of Buffer B, to make it ready for coupling with antigen.

Immobilized AE12-1 monoclonal antibody was coupled to hRGMa. Compact reaction columns (CRC) were prepared for the antigen coupling by washing the 35 μm frit of the CRC three times with 200 μA of Buffer B. The resin with the bound antibody was mixed gently to re-suspend the resin homogeneously, and 50 μl of the resin was placed in each prepared CRC. The resin was washed three times with 200 μA Buffer B. Approximately 1.5 nmol of hRGMa antigen was added to the resin with enough Buffer B to make a total volume of at least 200 μl. Prior to antigen coupling, the *E. coli* produced antigen was dialyzed against PBS buffer for approximately 30 minutes using a 3500 MWCO Slide-A-Lyzer mini-dialysis unit to remove DTT from the antigen buffer. The antigen/resin mixture was allowed to mix on a rotator for 4 hours at room temperature. The flow-through (FT) was collected, and the resin was washed three times with 200 μl of Buffer B.

The epitopes were excised using trypsin and endoproteinase Asp-N. The resin containing the immobilized antibody/antigen complex was suspended in 200 μl of Buffer B. A vial with 20 μg of trypsin (Promega, Madison, Wis.) was dissolved in 100 μl of the resuspension buffer (50 mM HOAc), for a concentration of 0.2 μg/μl, and a 2 μg vial of endoproteinase Asp-N (Roche) was dissolved in 50 μl water (0.04 μg/μl). The antigen cleavages were performed with 1:100 ratios (w/w) enzyme:antigen. The reaction proceeded for 4-6 hours with rotation at room temperature.

After digestion, the FT was collected and the resin was washed twice with 200 μl of Buffer B, with collection of each wash separately (Wash 1 and 2), 200 μl of Buffer A (Wash 3), and then 200 μl of Buffer B (Wash 4). The antigen peptides that were bound to the antibody were eluted from the resin with three 200 μl aliquots of 2% formic acid, and each elution was collected separately (Elution 1, 2 and 3). The Elution1 fraction was analyzed by mass spectrometry (LC-MS/MS) to determine the epitope region.

The Elution 1 fractions that were collected after digestion were analyzed by LC-ESI-MS/MS (positive ion) using an Agilent (Santa Clara, Calif.) 1100 capillary HPLC loading pump and 1200 nano-HPLC gradient pump, with a Chip Cube (40 mL enrichment column, 75 μm×43 mm analytical column, C8 ZORBAX chip) interfaced to an Agilent 6510 QTOF MS. Injections of up to 7 μA were used, and MS/MS was performed on the top 3 ions meeting the specified MS signal criteria.

Initial MS analysis of the epitope excison fractions (Elution 1) indicated the presence of large peptide species that could not be matched to expected proteolytic peptides due to the likely presence of disulfide linked peptides. To reduce disulfide bonds, 10 μA aliquots were pH adjusted to pH~8 using diluted NaOH, and reduced in 5 mM dithiothreitol (DTT) at 37° C. for 30 minutes before re-analysis by MS. Some fractions required denaturation to achieve reduction, in which case the aliquot was diluted in an equal volume of 8M guanidine hydrochloride, 100 mM Tris (pH 8) before addition of DTT.

LC-ESI-MS/MS analysis of all Elution 1 fractions of the enzymatic digest of AE12-1 mAb coupled with the various constructs of hRGMa indicated the presence of several large peptide species with molecular weights in the range of 8.5-12 kDa. The masses and fragmentation of the large species were not sufficient to identify the peptides. In order to identify the epitope peptides, reduction of the disulfide bonds was necessary. In all cases, the MS signal intensity of the peptides decreased significantly after reduction, in some cases being undetectable unless reduced in the presence of a denaturant.

After reduction of the Elution 1 fraction with DTT, the fractions were reanalyzed by LC-MS/MS. In the excision experiment using *E. coli* produced hRGMa, most of the peaks observed in the ion chromatogram were single charged species, many related to polymers or other additives. Two peptides were identified as being related to the hRGMa construct used. See FIG. 5. The first was a peptide with a monoisotopic molecular weight of 2420.2 Da. The molecular weight of the peptide and the masses of a few fragments observed in the MS/MS spectra (not shown) are consistent with the sequence PCKILKCNSEFWSATSGSHAPAS (hRGMa 47-69) (SEQ ID NO:79) although the assignment was inconsistent with the enzyme specificity. The second potential epitope peptide with a monoisotopic molecular weight of 2551.2 Da revealed only 2-3 identifiable MS/MS fragments that were consistent with the sequence MPCKILKCNSEFWSATSGSHAPAS (SEQ ID NO:80). The enzyme specificity was not consistent; however, since the molecular weight of the starting antigen did not match the calculated mass of the full sequence, it is possible that the antigen has N-terminal heterogeneity that would account for the apparent inconsistent enzyme specificity.

Figure 6A:
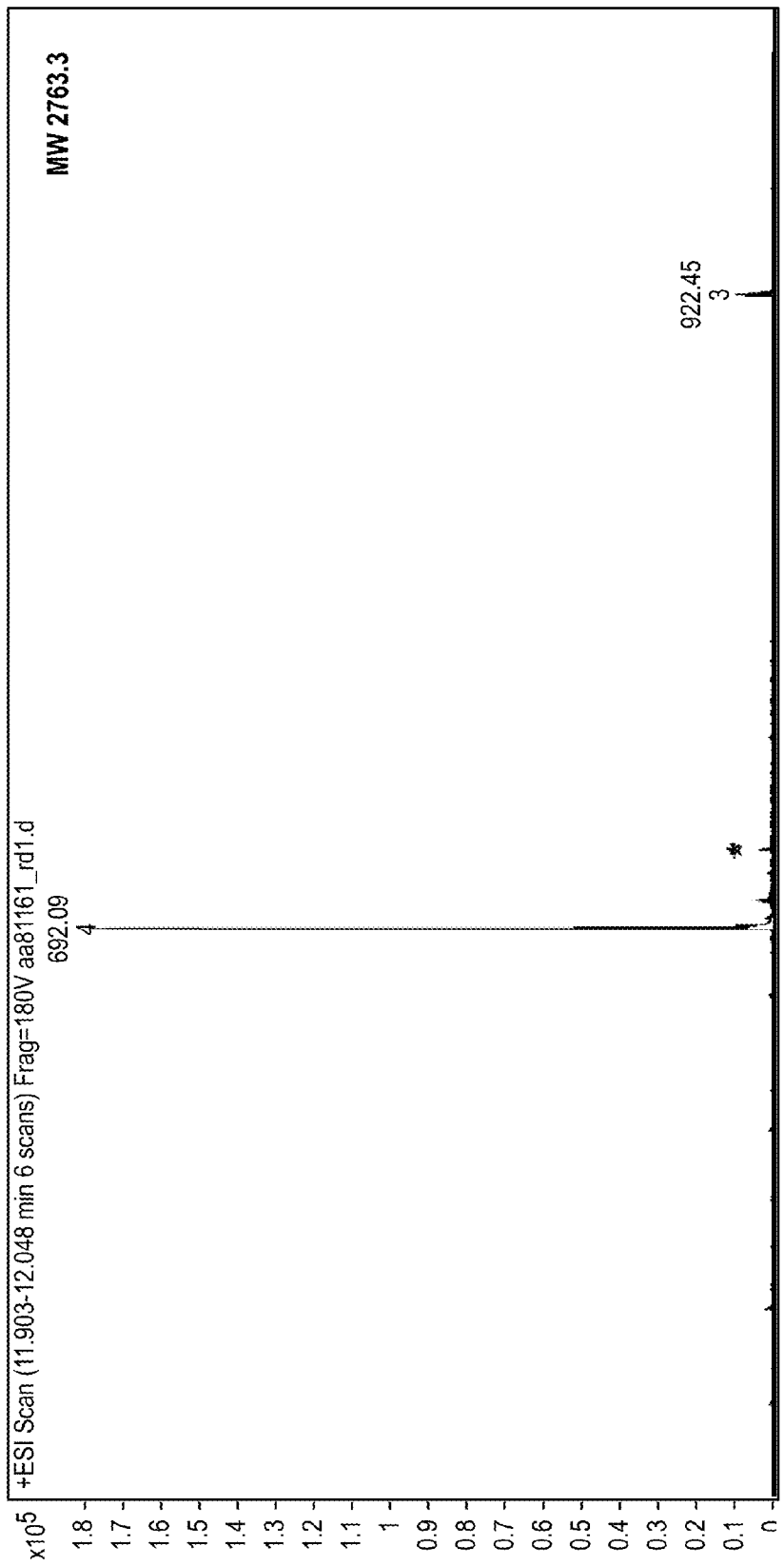
FIGS. 6A-6B show MS (FIG. 6A) and MS/MS (FIG. 6B) spectra from denatured, reduced E1 fraction of hRGMa (MYC construct) with AE12-1 mAb excised with trypsin and Asp-N, confirming the sequence of the excised peptide as KAGSPCKILKCNSEFWSATSGSHAPAS (SEQ ID NO:81).
Figure 6B:
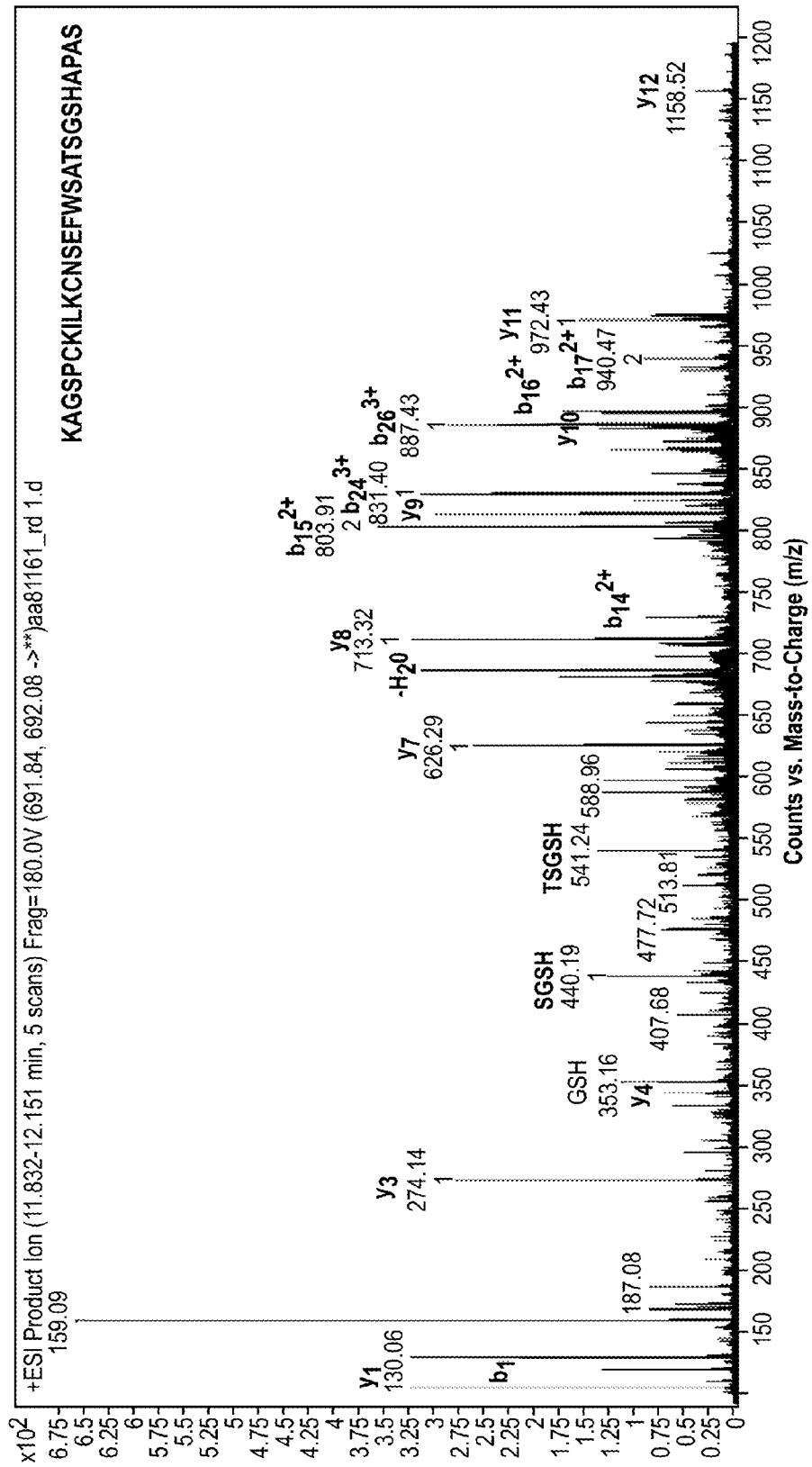
Figure 7A:
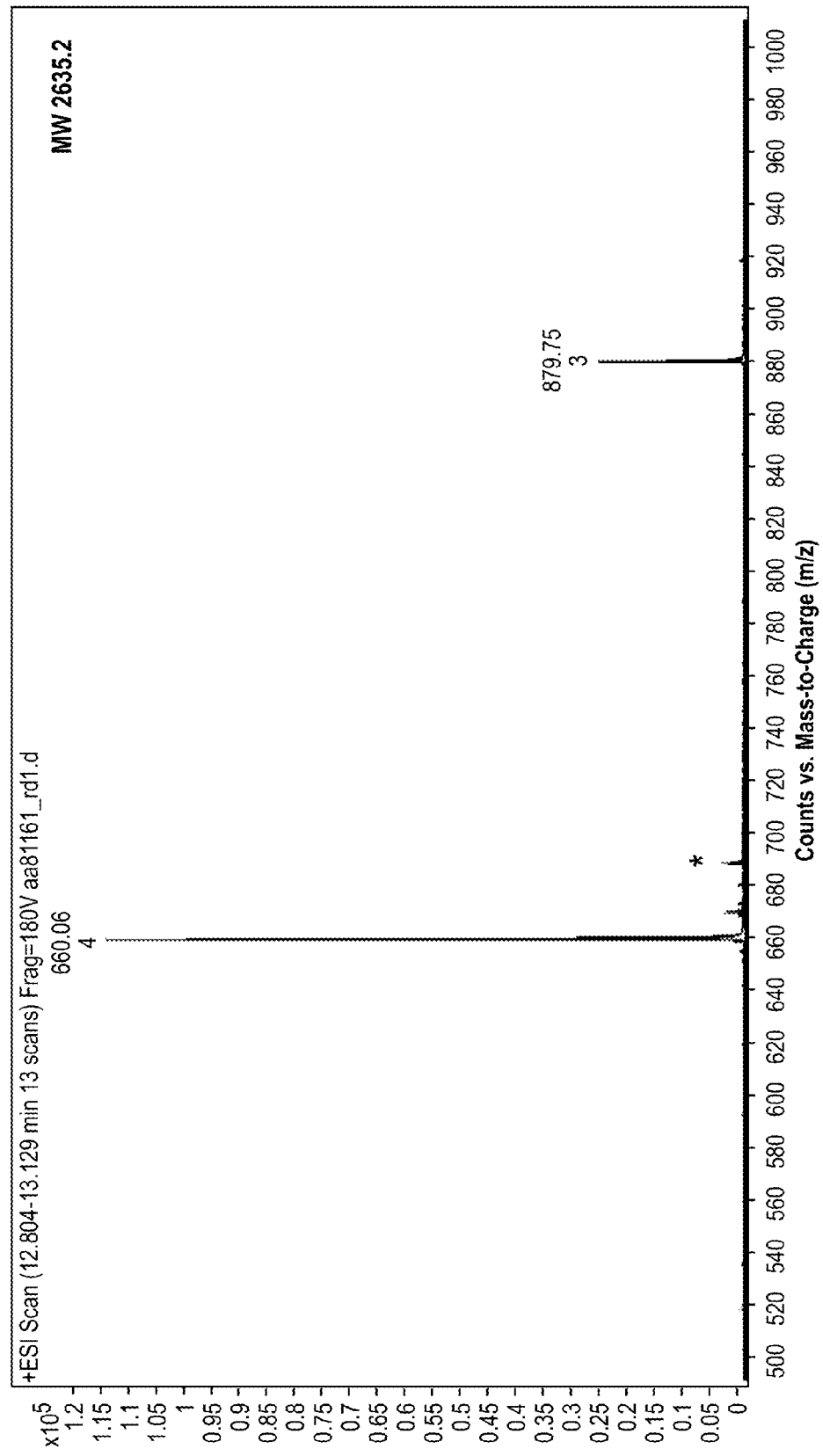
FIGS. 7A-7B show MS (FIG. 7A) and MS/MS (FIG. 7B) spectra from denatured, reduced E1 fraction of hRGMa (MYC construct) with AE12-1 mAb excised with trypsin and Asp-N, confirming the sequence of the excised peptide as AGSPCKILKCNSEFWSATSGSHAPAS (SEQ ID NO:89).
Figure 7B:
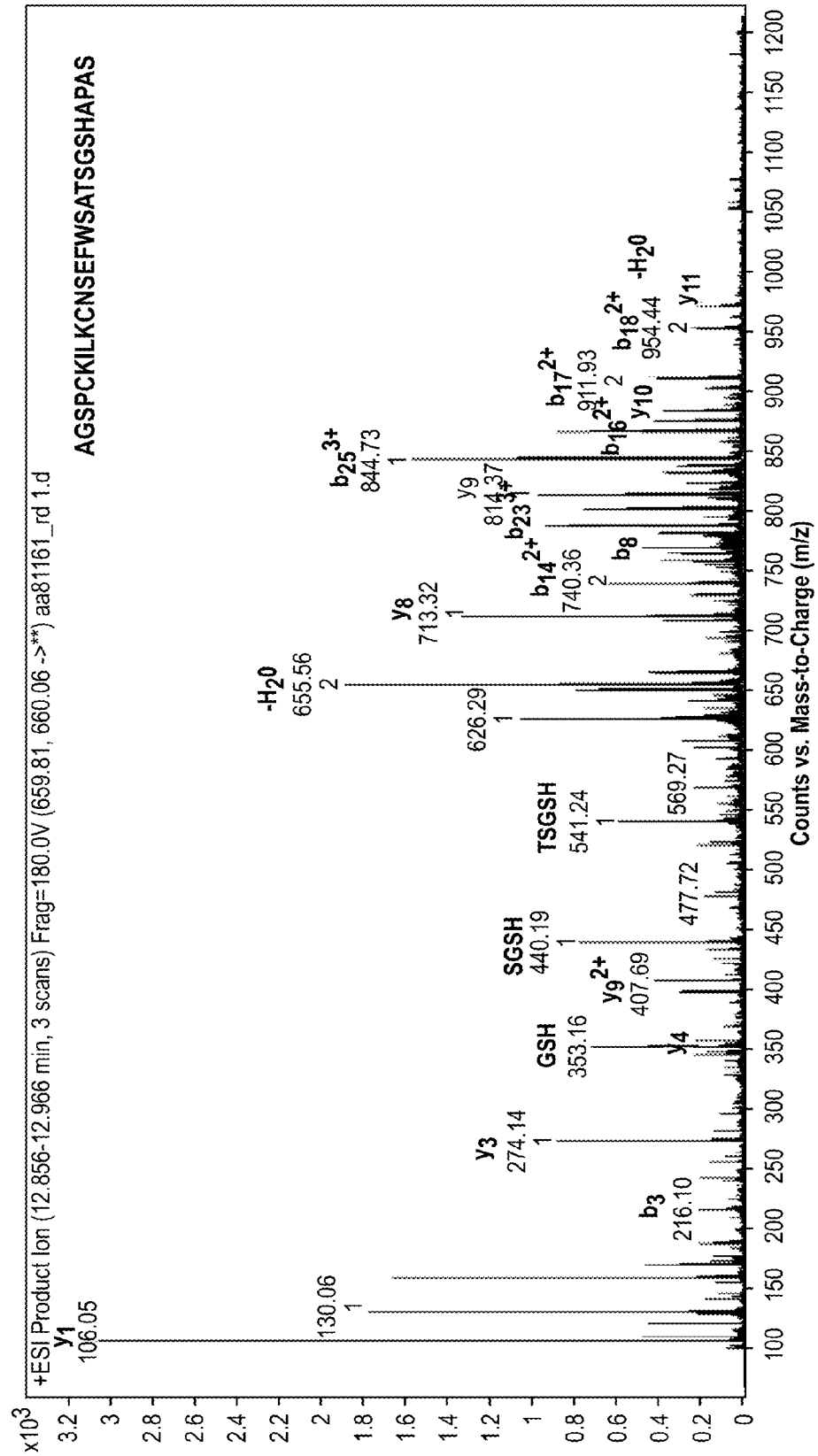

Using the second antigen construct no peptides could be observed in the MS spectrum after DTT reduction. MS analysis after reduction under denaturing conditions did reveal peptides among the singly charged, background ions. Four peptides from the antigen were identified in the denatured and reduced E1 fraction. The first antigen-related peptide had a monoisotopic molecular weight of 2763.3 Da, which, along with the MS/MS fragmentation, was consistent with the sequence KAGSPCKILKCNSEFWSATSGSHAPAS (SEQ ID NO:81) (hRGMa 47-69 with 4 additional N-terminal residues). The spectra associated with this peptide are shown in FIG. 6. A very low intensity peptide signal in the same spectrum (MW 2878.4 Da; +4 at m/z 720.84, marked with an asterisk in FIG. 6) was consistent with the sequence KAGSPCKILKCNSEFWSATSGSHAPPASD (SEQ ID NO:82). A peptide of MW 2635.2, shown in FIG. 7, was consistent with the sequence AGSPCKILKCNSEFWSATSGSHAPPAS (SEQ ID NO:90). An additional peptide at m/z 688.82 (most abundant isotope, +4 charge state), marked with an asterisk in FIG. 7, co-eluted with the MW 2635.2 peptide. The limited MS/MS data obtained on this low intensity component was consistent with the sequence AGSPCKILKCNSEFWSATSGSHAPPASD (SEQ ID NO:83) (MW 2750.3 Da).

The third construct of hRGMa was used to try to confirm the eptiope with AE12-1. In the Elution 1 fraction that was DTT-reduced, very little reduction was observed, but one peptide could be identified as being related to hRGMa antigen and consistent with the results from the other antigen constructs. The peptide was observed at m/z 691.60 (+4 charge state), giving it a monoisotopic molecular weight of 2762.4 Da. Limited MS/MS data obtained for this peptide (not shown) suggests the sequence as TKLPCKILKCNSEFWSATSGSHAPAS (SEQ ID NO:84). Other peptides that were observed in the MS spectrum that could be assigned as being related to the region of hRGMa (47-168) included DSPEICHYEK (SEQ ID NO:85); GDLAYHSAVHGIE (SEQ ID NO:86); DLAYHSAVHGIE (SEQ ID NO:87); and DDTPEFCAALR (SEQ ID NO:88).

In the Elution 1 fractions (trypsin/Asp-N digestion) from the epitope excision experiment of hRGMa bound to AE12-1, the peptide hRGMa (47-69) was identified from three constructs of antigen. The peptide identified as the epitope for hRGMa with AE12-1 is: PCKILKCNSEFWSATSGSHAPAS (hRGMa 47-69) (SEQ ID NO:79).

Example 8

Toxicology Studies

Because iron accumulation in hepatocytes and the decrease of iron in the spleen may result from RGMc neutralization, the toxicokinetics and tolerability of the herein described RGMa-selective monoclonal antibodies were studied. The studies are expected to show that iron accumulation in hepatocytes and iron depletion in the spleen will not occur when the RGMa-selective monoclonal antibodies are administered to Sprague-Dawley rats.

Example 9

RGMa-Selective Monoclonal Antibodies AE12-1 and AE12-1Y, like Humanized Monoclonal Antibody 5F9, Induce Regeneration of Crushed, Damaged Optic Nerve Axons in a Rat Model of Optic Nerve Injury The Optic Nerve Crush (also referred to as "Optic Nerve Injury") model provides an animal model to test various substances that stimulate regeneration of the optic nerve fibers and reduce the massive cell death of retinal ganglion cells.

The experiments were carried out in adult male Wistar rats obtained from Charles River (D) Laboratories (Germany). The animals are kept in single cages on a 12:12 hour light/dark cycle with food and water ad libitum. The optic nerve crush is always performed only at the left eye by minimal anterior surgery as described in P. Monnier et al., *J. Neurosci.*, 31:10494-10505 (2011), the contents of which are herein incorporated by reference, and follows human anterior visual surgical methods. Before and during the operation, the procedure animals are anesthetized by inhalation anesthesia using Sevoflurane (Abbott GmbH Co. & KG, Delkenheim, Germany) and are fixed on the operation table by using jaw clamp and adhesive tape for the limbs. A drop in body temperature is prevented by mounting animals on a heating pad. For anterior crush surgery of the rat optic nerve, the left eye is carefully freed of ligament and connective tissue. As a first step, a microsurgical cut (2-3 mm) of the adjacent tissue in the outer corner of the eye is performed. As a next step, the optic nerve is exposed by using a pair of forceps to move to the side the eye muscles and lacrimal gland, thus sparing it. As a further step, the meninges were longitudinally opened by using microscissors to expose the optic nerve. This results in a higher mobility of the eye and enables lateral rotation of the eye and access to its left optic nerve. The optic nerve is injured approximately 1-3 mm behind the eye, using a pair of forceps set to provide a fixed maximum pressure for 10-20 seconds. Special care is taken not to damage the vascular supply to the eye.

After minimal invasive surgery, the animals are placed on paper towels in the clean cage placed on the warmer to control the body temperature until they start to move. An ointment which contains antibiotic (Gentamytrex, Dr. Mann Pharma) is applied onto the eye to avoid bacterial infection and drying-out of the sclera.

Carprofen (Rimadyl, 5 mg/kg) is applied intraperitoneally for postoperative pain therapy directly after surgery and then twice per day for a 3 day period. The animals are observed and controlled regularly for several hours directly after surgery and in the next 2-4 days to make sure that all the animals survived and recovered from anesthesia and surgery.

The above described modified anterior optic nerve crush approach has significant advantages in comparison with the standard optic nerve crush procedure which originates from the posterior part of the eye. Specifically, in the procedure described herein, no large open wounds are generated which require suturing and the infection risk of the very small wounds is significantly reduced. In addition, as a result of the lower time required for the crush (the above described anterior method is approximately 3 times faster than the posterior method known in the art) animals suffer less and are thus less stressed. Moreover, the amount of pain suffered by the animals is significantly reduced and animals recover at a much rates and much more quickly.

Systemic Administration of Antibodies

Figure 16:
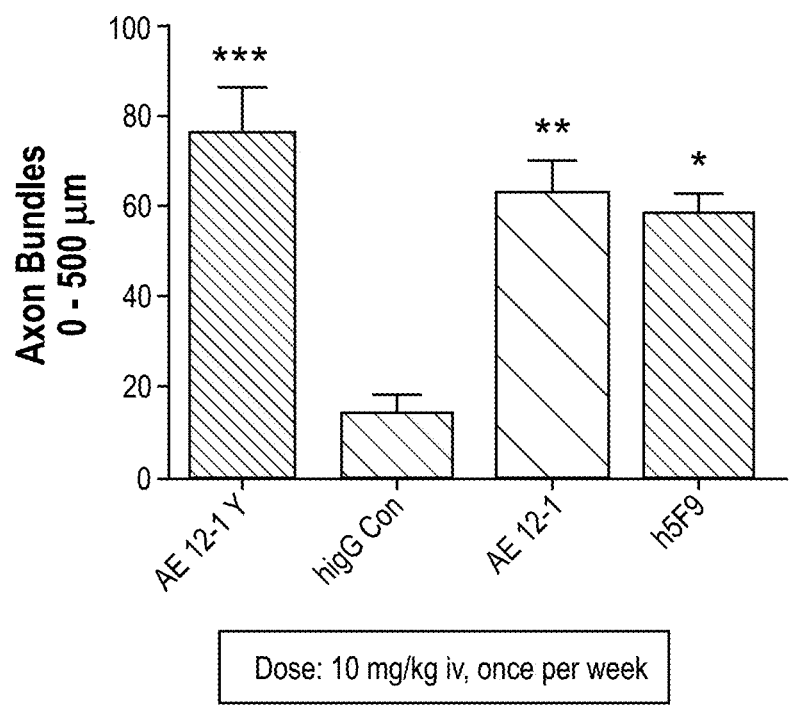
FIG. 16 shows that three (3) RGMa selective monoclonal antibodies, specifically, AE12-1, AE12-1Y and h5F9.23, induce massive regeneration of GAP-43 positive fibers beyond the crush site as described in Example 9. Y-axis=number of axon bundles in the area 0-500 µm beyond crush site. *$p<0.001$: significance versus hIgG, $p<0.01$: significance versus hIgG, *$p<0.05$: significance versus human IgG.

For systemic antibody delivery, male Wistar rats were treated systemically intravenously, (iv) with a humanized RGMa and RGMc-blocking 5F9 antibody (h5F9) (n=8 animals) (humanized antibody 5F9 is described in U.S. Patent Publication No. 2010/0028340, the contents of which are herein incorporated by reference), with an RGMa-selective, human antibody, AE12-1, described herein, and with a closely related RGMa mAb, AE12-1Y, also described herein and with a human isotype control antibody (hIgG) (n=8 animals). Rats were injected once per week intraveneously with 10 mg/kg of antibody given and injections were started immediately after optic nerve crush. All rats received 5 injections and animals were euthanized 6 weeks after crush injury. Experimenters were blinded and tissue isolation, processing, preparation of sections and quantitative analysis was done as described in P. Monnier et al., J. Neurosci., 31:10494-10505 (2011) and Koeberle et al., Neuroscience, 169:495-504 (2010), the contents of each of which are herein incorporated by reference. Composite images of rat optic nerves were prepared, the crush site was identified and GAP-43 positive fibers extending beyond the crush site for 500 µm were counted. As shown in FIG. 16, all three RGMa antibodies -h5F9, AE12-1 and AE12-1Y induced significant regenerative growth beyond the crush site, in contrast to control animals treated with hIgG.

Example 10

RGMa-selective Monoclonal Antibodies AE12-1 and AE12-1Y like Humanized Antibody 5F9, Protect the Retinal Nerve Fiber Layer (RNLF) from Degeneration In order to observe protection of RNLF degeneration, a new laboratory assay method was used. This method is based on explanting and analyzing adult rat retina from the eyes of rats with optic nerve crush and systemically treated with antibody 5F9, AE12-1, AE2-1Y and control antibody, human IgG. This method is an adaptation of the methods described by P. Monnier et al., J. Neurosci., 31:10494-10505 (2011) and Koeberle et al., Neuroscience, 169:495-504 (2010). P. Monnier et al., J. Neurosci., 31:10494-10505 (2011) and Koeberle et al., Neuroscience, 169:495-504 (2010). Adult male Wistar rates obtained from Charles River Laboratories (Germany) were injected once per week intraveneously with 10 mg/kg of antibody given and injections were started immediately after optic nerve crush. All rats received 5 injections and animals were euthanized 6 weeks after crush injury.

Retina Preparation and Immunofluorescent Staining:

Animals were deep anesthetized with Sevoflurane (8%; Abbott GmbH Co. & KG, Delkenheim, Germany), then immediately sacrificed by opening the ribcage and perfused with 4% paraformaldehyde (PFA) solution through the left heart ventricle. The eyes were dissected with the connective tissue adjusted and placed in 4% PFA until preparation of retina takes place.

The preparation of the retina was performed in Hank's Balanced Salt Solution (HBSS, Magnesium- and Calcium-free; Invitrogen, #14170070). The eye was fixed at the connective tissue by tweezers and a round cut was made in sclera just around the cornea. The half-sphere of retina was cut in four points, opened and spread on a gray nitrocellulose membrane (Sartorius, #13006-50-N). If necessary, the membrane with retina on it was allowed to air dry for 5-10 seconds Thereafter, the retina on membrane was placed in 10% neutral phosphate-buffered formaldehyde solution (pH 7.3; Fisher Scientific, #F/1520/21) at +4° C. until immunofluorescent staining was performed. Staining is performed according to the protocol described below.

The retina preparation was washed with TBS, followed by blocking and permeabilization with 5% BSA, 1% Triton X-100 in TBS for 30 minutes and then washed again with TBS. Primary antibodies, namely, monoclonal Ab TUJ-1, a mouse anti-B III Tubulin Ab, AbCam, #ab14545; 1:500 dilution, in TBS, 5% BSA, was added for 1 hour at room temperature in the dark followed by washing with TBS, 0.1% Tween 20. Next, a secondary antibody, namely, Donkey anti-mouse Cy3; Jackson ImmunoResearch (Dianova) 715-165-151, 1:1000 dilution, and Bisbenzimid (50 µg/ml 1:100 dilution in TBS, 5% BSA) were added for 1 hour at room temperature in the dark followed by washing with TBS, 0.1% Tween 20, and the subsequent washing with desalted $H_2O$. The preparation was then mounted with Fluoromount G and stored at +4° C. in the dark.

Quantitative Analysis of the Protective Effect of RGMa Antibodies on the Retinal Nerve Fiber Layer in the Eye (the RNFL)

Using the Axiovision software, randomly selected images (n=12) of each retina were chosen and the number of nerve fibers determined for each image. For these experiments, 5-8 retinae with crushed optic nerves were used for each group: the h5F9 MAb group, the hIgG control MAb group and the AE12.1 and AE12-1Y MAb groups. Data analysis and statistical analysis was performed using the GraphPad prism program.

Figure 17:
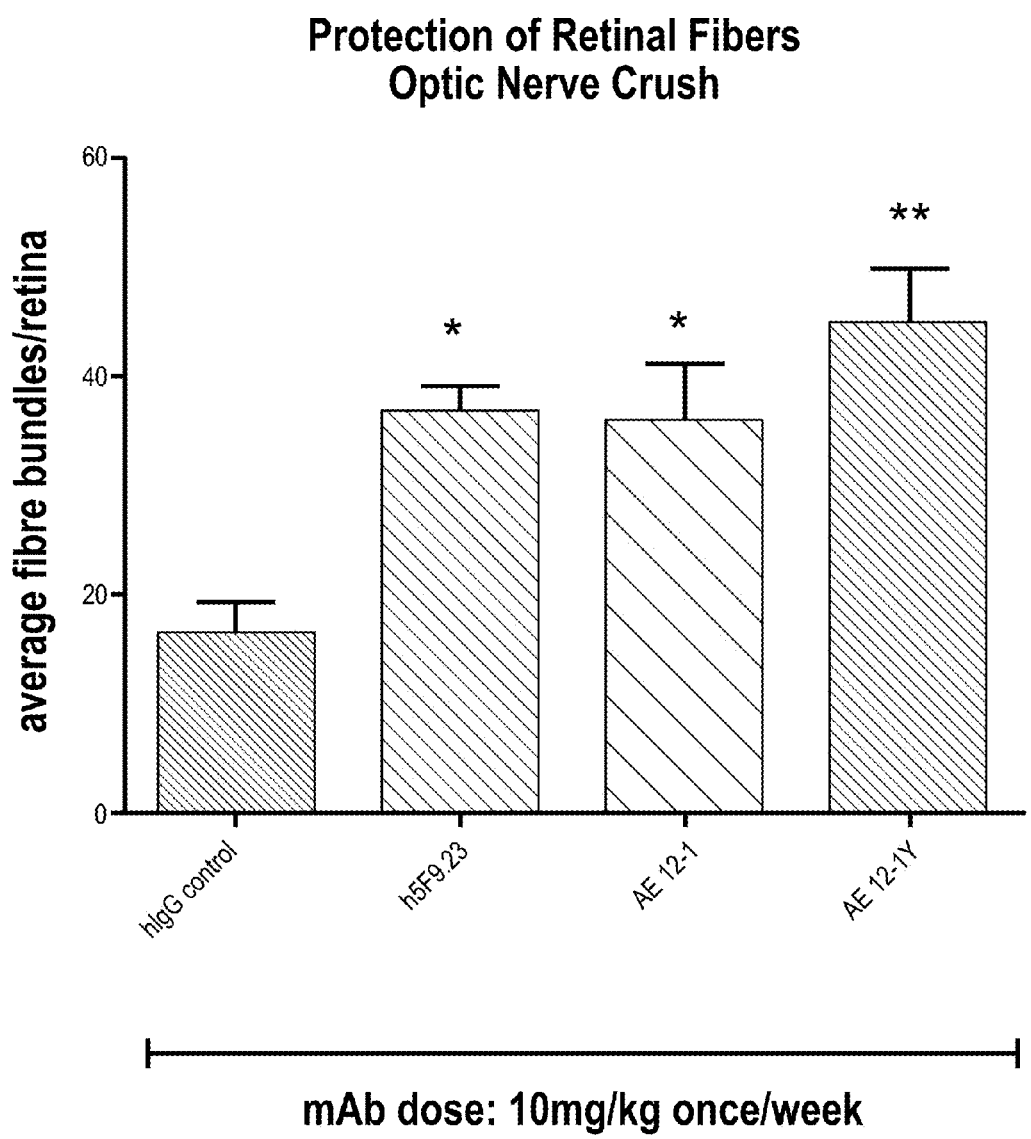
FIG. 17 shows that three (3) RGMa selective monoclonal antibodies, specifically, AE12-1, AE12-1Y and h5F9.23, increase the number of retinal axonal bundles, thereby protecting the retinal nerve fiber layer. Y-axis=number of fiber bundles in the retina as described in Example 10. **$p<0.01$: significance versus hIgG, *$p<0.05$: significance versus hIgG.

The results are illustrated in FIG. 17. Specifically, a significantly higher number of nerve fiber bundles is observed in retinae of animals systemically treated with RGMa antibodies of the present invention when compared to hIgG control antibody treated animals.

Example 11

RGMa Antibodies Accelerate Functional Recovery in a Focal Spinal Experimental Autoimmune Encephalomyelitis (EAE) Model Kerschensteiner et al. (*Am. J. Pathol.* 164: 1455-69, 2004) developed a focal, localized EAE model where large inflammatory lesions are not spread randomly in spinal cord, brain and optic nerve but can be selectively induced in either in the spinal cord or in other brain areas. Using this focal or targeted EAE model, large inflammatory lesions, very similar to MS spinal cord lesions, are induced in the dorsal columns of the spinal cord, affecting the corticospinal tract. In this model, rats are first immunized with the myelin protein MOG. Two to three weeks after immunization, MOG antibody titers were determined and animals with a positive immune response were injected with a cytokine mixture (TNFα 250 ng, IFNg 150 U) locally at thoracical level 8 (T8). Within one week after cytokine injection, the rats developed hindlimb motor defects, tail paralysis and gait disturbances reaching an EAE score of 2.5. Four weeks after cytokine injection, this score improved to an EAE score of 1 (Kerschensteiner et al., *Am. J. Pathol.* 164: 1455-69, 2004).

Female Lewis rats were injected subcutaneously with 75 µA of MOG (75 µg, 1-125 aa, BlueSky Biotech, Worcester, Mass.) dissolved in saline and then emulsified with 75 µA of Incomplete Freund's Adjuvans (IFA, Sigma, #F5506). Right before injection and then every 7-8$^{th}$ day, blood samples were taken from animals to analyze the samples for MOG antibodies.

Two or three weeks after MOG immunization, blood was collected from immunized rats and an ELISA was performed to detect MOG-specific antibodies. Immunization results in induction of MOG antibodies in more than 90% of immunized rats. In this strain however, MOG antibody induction did not result in any disease symptoms. Lewis rats only developed motor deficits after local injection of 2 inflammatory cytokines (TNF a, IFNg) into the thoracical spinal cord at thoracical level 8 (T8).

For cytokine injection, rats were subject to Inhalation anesthesia with Sevoflurane (8%; Abbott GmbH Co. & KG, Delkenheim, Germany) and a laminectomy was performed by a standard procedure. Specifically, the skin on the back of the rat was shaved and disinfected with 70% of ethanol, then the shaved area was wiped with the prodine and a 2-3 cm cut was made with scalpel starting approx. from T3-4 till T11-12. The superficial fat was separated with fine scissors from the muscles and the muscles were cut by the middle line along the spine from one side. The gap between T8 and T9 was located and T8 was cleared from adjacent tissue. A microdrill was used to make a round hole approximately 1-2 mm in diameter in T8 and small tipped forceps were used to remove the periosteum and any bone fragments. Next, the dura mater was removed with micro scissors and a stereotactic injection was done with a very thin glass capillary connected to a 10 µl Hamilton syringe with Luer Tip (LT) and filled in with the mineral oil (Sigma Aldrich).

Using an automatic injector, the capillary was filled with 3 µl of cytokine mixture in PBS or just PBS with traces of Evans blue. A four times (4×) higher dose of TNFα (1000 ng) and the same dose of IFNγ (150 U) was used as reported by Kerschensteiner et al. (2004). The four times higher dose resulted in a significant extension of the recovery process in vehicle or control treated rats.

In the next step, a glass capillary was inserted to a depth of 0.7 mm and 2 µl of the cytokine mixture were injected in the middle of spinal cord at (T8) during a 5 minute-period using an automatic injector. After applying Lidocaine and closing the wound, rats were treated with an analgesic drug Rimadyl (directly after surgery and daily for another 3-4 days). Rats were then placed in a clean page on paper towels and were kept in the warmth until they awoke.

Figure 18:
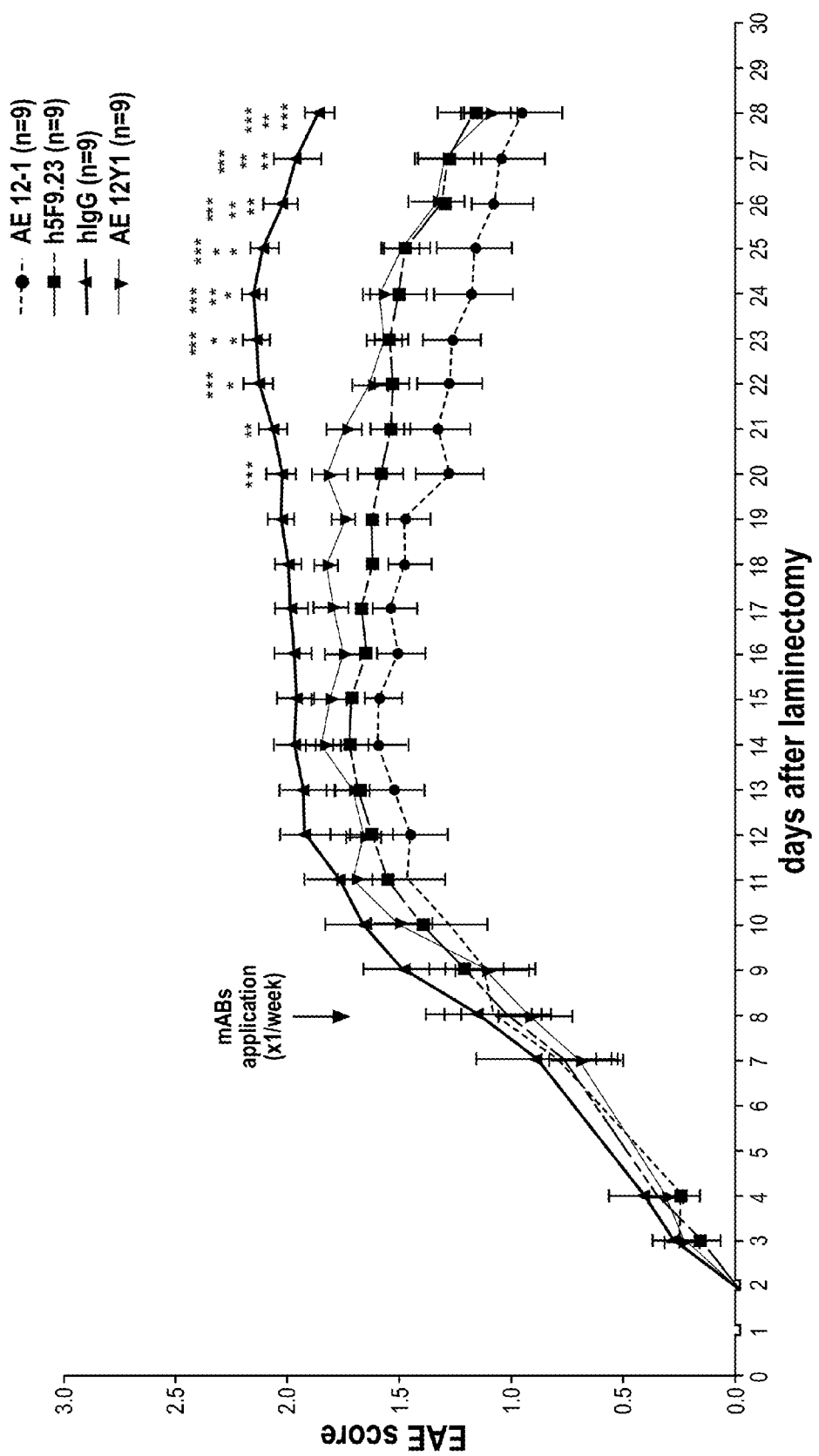
FIG. 18 shows that the RGMa mAbs AE12-1, AE12-1Y and h5F9.23 accelerate functional recovery in the spinal tEAE model as described in Example 11. Antibody treatment (iv) was started approximately one week after cytokine injection and was repeated once per week. Doses given were 10 mg/kg. *$p<0.001$: significance versus hIgG, $p<0.01$: significance versus hIgG, *$p<0.05$: significance versus hIgG.

Rats developed first symptoms within one week after cytokine injection. Antibody treatment was started on day 7 or 8 after cytokine application. A hIgG control antibody and several different RGMa antibodies (namely, AE12-1, AE12-1Y and humanized 5F9.23 (h5f9.23 which is described in U.S. Patent Publication No. 2010/0028340)) were used and rats were treated once per week via the intravenous route. EAE scoring was done daily and scores were documented. Individuals conducting the experiments were blinded for the different treatment groups. After a period of 27-29 days post cytokine administration, the animals were killed, spinal cords were isolated and analyzed for expression of the following proteins: GAP-43 (regeneration marker), CD68 (inflammatory marker for activated microglia cells and macrophages) and MPB (myelin basic protein, a marker for remyelination or preserved myelin tracts). The area of these markers was measured, analyzed and statistically evaluated using one way ANOVA and Bonferroni significance test. As shown in FIG. 18, all three RGMa antibodies accelerated functional recovery in the spinal tEAE model.

Figure 19A:
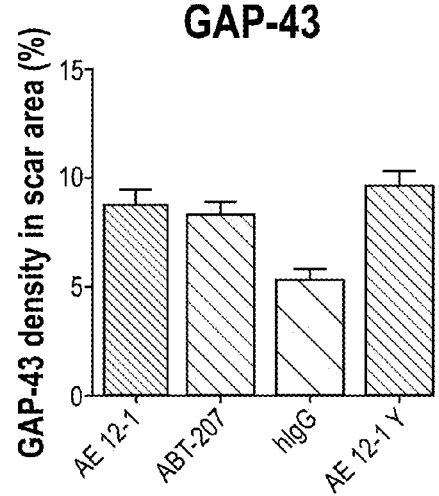
FIGS. 19A-19C show that the RGMa mAbs AE12-1, AE12-1Y and ABT-207 (h5F9.23) increase GAP-43 and MBP area and decrease the inflammatory lesion in direct comparison with the human IgG control antibody as described in Example 11. *$p<0.001$: significance versus hIgG, $p<0.01$: significance versus hIgG, *$p<0.05$: significance versus hIgG.
Figure 19B:
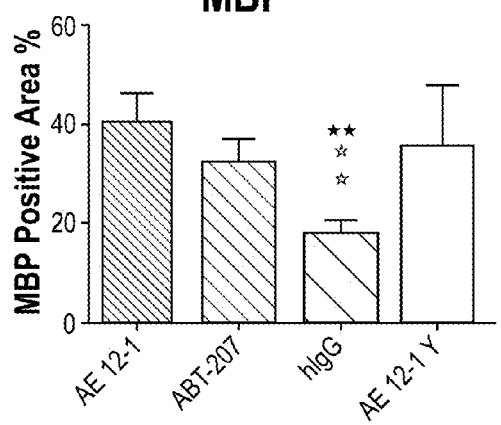
Figure 19C:
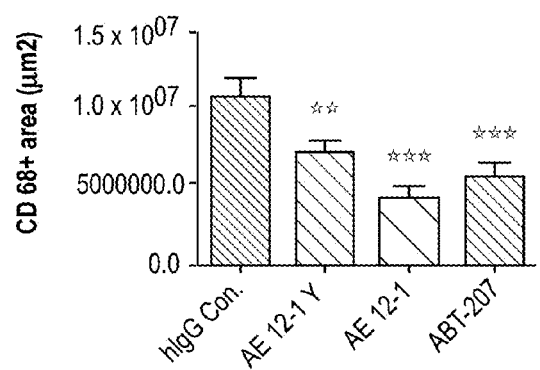

In the spinal tEAE model, all RGMa antibodies showed very similar regeneration- and neuroprotection stimulating activity. The RGMa-selective antibodies AE12-1 and AE12-1Y showed similar activity compared with h5F9.23, which neutralizes both RGMa and RGMc. Neutralization of RGMc does not seem to be required for efficacy. Therefore, to better understand the mechanism of action of all three RGMa mAbs in the focal spinal EAE model, several markers were evaluated in serial sections of spinal cords of antibody treated rats AE12-1Y, AE12-1 and h5F9.23 increased the regeneration area (GAP-43), the remyelination area (myelin basic protein (MBP)) and decreased the inflammatory CD68 (CD68-positive) area around the spinal lesion site (See, FIG. 19).

Figure 20:
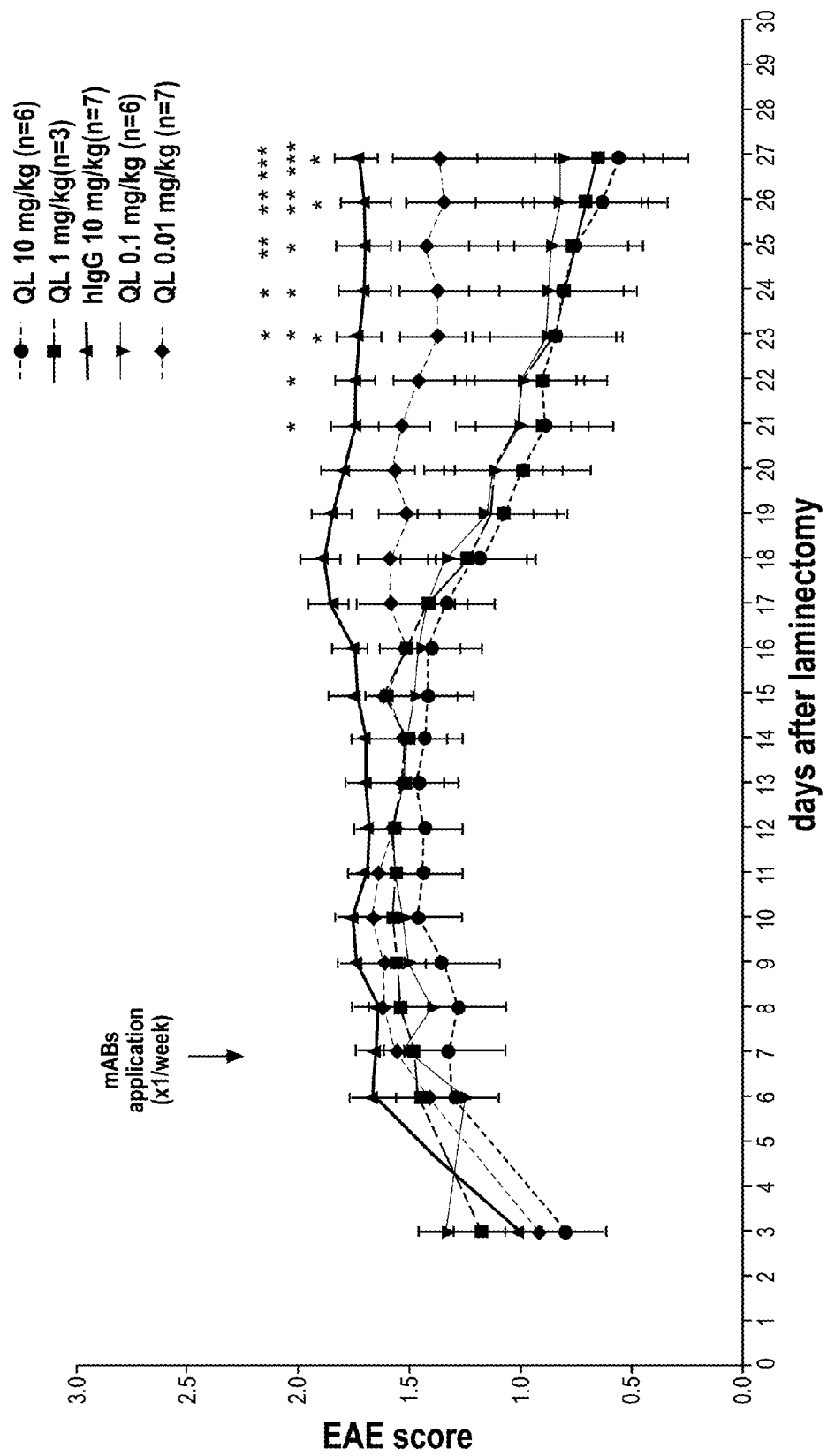
FIG. 20 shows that the RGMa mAb AE12-1Y-QL accelerated functional recovery in the spinal tEAE model at three different doses 0.1; 1 and 10 mg/kg given once per week intravenously as described in Example 11. Antibody treatment (iv) was started approximately one week after cytokine injection and was repeated once per week. *$p<0.001$: significance versus hIgG, $p<0.01$: significance versus hIgG, *$p<0.05$: significance versus hIgG.

The RGMa-selective antibody AE12-1Y-QL was tested to determine what doses of this antibody are active in this spinal tEAE model. Specifically, 4 different antibody doses (namely, (0.01, 0.1, 1, 10 mg/k were given IV systemically once per week to the rats. AE12-1Y-QL showed significant activity at 0.1, 1 and 10 mg/kg (FIG. 20). However, a dose of 0.01 mg/kg did not show efficacy.

We claim:

1. An isolated antibody the antibody comprising:
   (a) a variable heavy domain comprising a complementarity-determining region (CDR) 1 comprising an amino acid sequence as set forth in SEQ ID NO:2, a CDR2 comprising an amino acid sequence as set forth in SEQ ID NO:3, and a CDR3 comprising an amino acid sequence as set forth in SEQ ID NO:4, and a variable light domain comprising a CDR1 comprising an amino acid sequence as set forth in SEQ ID NO:6, a CDR2 comprising an amino acid sequence as set forth in SEQ ID NO:7, and a CDR3 comprising an amino acid sequence as set forth in SEQ ID NO:73; or
   (b) a light chain variable amino acid sequence as set forth in SEQ ID NO:146 and a heavy chain variable amino acid sequence as set forth in SEQ ID NO:147,
wherein the antibody binds to Repulsive Guidance Molecule a (RGMa), wherein the antibody is selected from the group consisting of a human antibody, a monoclonal antibody, an affinity matured, a chimeric antibody and a humanized antibody.

2. The isolated antibody of claim 1, further comprising a constant sequence of SEQ ID NO:143.

3. A pharmaceutical composition comprising the antibody of claim 1.

4. A pharmaceutical composition comprising the antibody of claim 2.

5. The isolated antibody of claim 1, wherein the variable heavy domain comprises the CDR1 comprising the amino acid sequence as set forth in SEQ ID NO:2, the CDR2 comprising the amino acid sequence as set forth in SEQ ID NO:3, and the CDR3 comprising the amino acid sequence as set forth in SEQ ID NO:4, and the variable light domain comprises the CDR1 comprising the amino acid sequence as set forth in SEQ ID NO:6, the CDR2 comprising the amino acid sequence as set forth in SEQ ID NO:7, and the CDR3 comprising the amino acid sequence as set forth in SEQ ID NO:73.

* * * * *

SEQUENCE LISTING

<160> NUMBER OF SEQ ID NOS: 158

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Gly Ile Ser Trp Val Arg Gln Ala Pro Gly Gln Gly Leu Asp Trp Met
        35                  40                  45

Gly Trp Ile Ser Pro Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Ser Gly Pro Tyr Tyr Tyr Met Asp Val Trp Gly Gln
            100                 105                 110

Gly Thr Leu Val Thr Val Ser Ser
        115                 120

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser His Gly Ile Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Ile Ser Pro Tyr Ser Gly Asn Thr Asn Tyr Ala Gln Lys Leu Gln
1               5                   10                  15

Gly

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Gly Ser Gly Pro Tyr Tyr Tyr Met Asp Val

<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Val Gly Asp Ser
            20                  25                  30

Ile Tyr Val Ser Trp Tyr Gln Gln His Pro Gly Lys Ala Pro Lys Leu
        35                  40                  45

Met Leu Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Thr
                85                  90                  95

Asp Thr Leu Phe Gly Gly Gly Thr Lys Val Thr Val Leu
            100                 105

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Gly Thr Ser Ser Ser Val Gly Asp Ser Ile Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Val Thr Lys Arg Pro Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Ser Tyr Ala Gly Thr Asp Thr Leu
1               5

<210> SEQ ID NO 9
<211> LENGTH: 115

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Ser Leu Ser Val Trp Gly Gln Gly Thr Leu Val Thr
            100                 105                 110

Val Ser Ser
        115

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Asp Ile Asn
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Met Asn Pro Asn Ser Gly Asn Thr Gly Tyr Ala Gln Lys Phe Gln
1               5                   10                  15

Gly

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Thr Ser Leu Ser Val
1               5

<210> SEQ ID NO 13
<211> LENGTH: 106
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Lys Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Gly Val
                85                  90                  95

Phe Gly Pro Gly Thr Lys Val Thr Val Leu
            100                 105

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Asp Lys Leu Gly Asp Lys Tyr Ala Cys
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Asp Ser Lys Arg Pro Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ala Trp Asp Ser Ser Thr Gly Val
1               5

<210> SEQ ID NO 17
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 17

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Val Tyr Ser Ser Gly Lys Glu Gly Tyr Tyr Tyr Gly
            100                 105                 110

Met Asp Val Trp Gly Gln Gly Thr Met Val Thr Val Ser Ser
        115                 120                 125
```

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Asp Tyr Ala Met His
1               5
```

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Val Ile Ser Tyr Asp Gly Ser Asn Lys Tyr Tyr Ala Asp Ser Val Lys
1               5                   10                  15

Gly
```

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Glu Arg Val Tyr Ser Ser Gly Lys Glu Gly Tyr Tyr Tyr Gly Met Asp
1               5                   10                  15

Val
```

<210> SEQ ID NO 21
<211> LENGTH: 111
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 21

Gln Ser Gly Leu Thr Gln Pro Pro Ser Val Ser Ala Ala Pro Gly Gln
1               5                   10                  15

Arg Val Thr Ile Ser Cys Thr Gly Ser Gly Ser Asn Ile Gly Ala Gly
            20                  25                  30

Tyr Gly Val His Trp Tyr Gln Gln Leu Pro Ala Thr Ala Pro Lys Ile
        35                  40                  45

Leu Ile Tyr Gly Asp Tyr Asn Arg Pro Ser Gly Val Pro Asp Arg Phe
    50                  55                  60

Ser Gly Ser Arg Ser Gly Thr Ser Ala Ser Leu Thr Ile Thr Gly Leu
65                  70                  75                  80

Gln Ala Glu Asp Glu Ala Asp Tyr Tyr Cys Gln Ser Tyr Asp Asn Ser
                85                  90                  95

Leu Arg Gly Val Leu Phe Gly Gly Gly Thr Lys Leu Thr Val Leu
            100                 105                 110

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Gly Ser Gly Ser Asn Ile Gly Ala Gly Tyr Gly Val His
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Asp Tyr Asn Arg Pro Ser
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Tyr Asp Asn Ser Leu Arg Gly Val Leu
1               5                   10

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Glu Val Gln Leu Val Glu Ser Gly Gly Gly Val Val Gln Pro Gly Thr
1               5                   10                  15

Ser Leu Arg Leu Ser Cys Ala Ala Ser Gly Phe Pro Phe Ser Ser Tyr
            20                  25                  30

Gly Met His Trp Val Arg Gln Ala Pro Gly Lys Gly Leu Glu Trp Val
        35                  40                  45

Ala Ala Ile Ser Gly Asp Gly Ile Leu Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Ser Gly Glu Asp Thr Gly Leu Tyr Tyr Cys
                85                  90                  95

Ala Arg Asn Tyr Asp Asn Ser Leu Asp Tyr Trp Gly Gln Gly Thr Leu
                100                 105                 110

Val Thr Val Ser Ser
        115

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Tyr Gly Met His
1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ile Ser Gly Asp Gly Ile Leu Lys Tyr Tyr Thr Asp Ser Val Lys
1               5                   10                  15

Gly

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Tyr Asp Asn Ser Leu Asp Tyr
1               5

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

```
Gln Pro Val Leu Thr Gln Ser Pro Ser Val Ser Ala Ser Leu Gly Ala
1               5                  10                 15

Ser Val Lys Val Thr Cys Thr Leu Ser Ser Gly His Ser Ala Tyr Ala
            20                  25                 30

Ile Ala Trp His Gln Gln Pro Glu Lys Gly Pro Arg Tyr Leu Met
            35                  40                  45

Lys Val Asn Ser Asp Gly Ser His Asn Lys Gly Asp Gly Val Pro Asp
        50                  55                  60

Arg Phe Ser Gly Ser Ser Gly Ala Glu Arg Tyr Leu Ile Ile Ser
65                  70                  75                  80

Gly Leu Gln Ser Glu Asp Glu Ala Asp Tyr Tyr Cys Gln Thr Trp Gly
                85                  90                  95

Pro Gly Ile Arg Val Phe Gly Gly Gly Thr Lys Leu Thr Val Leu
            100                 105                 110
```

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Thr Leu Ser Ser Gly His Ser Ala Tyr Ala Ile Ala
1               5                   10
```

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Val Asn Ser Asp Gly Ser His Asn Lys Gly Asp
1               5                   10
```

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Gln Thr Trp Gly Pro Gly Ile Arg Val
1               5
```

<210> SEQ ID NO 33
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Glu Val Gln Leu Val Gln Ser Gly Ala Glu Val Lys Lys Pro Gly Ala
1               5                   10                  15

Ser Val Lys Val Ser Cys Lys Val Ser Gly His Ser Leu Ser Glu Leu
            20                  25                  30
```

```
Thr Ile His Trp Val Arg Gln Ala Pro Gly Lys Gly Leu Glu Trp Met
        35                  40                  45

Gly Gly Phe Asp Pro Glu Asp Gly Arg Gly Thr Tyr Ala Pro Asn Phe
50                  55                  60

Arg Gly Arg Val Thr Met Thr Glu Asp Thr Ser Thr Asp Thr Ala Tyr
65                  70                  75                  80

Met Glu Leu Ser Gly Leu Arg Ser Glu Asp Ala Ala Val Tyr Tyr Cys
                85                  90                  95

Ala Thr Leu Leu Gly Glu Tyr Asp Ser Tyr Phe Asp Leu Trp Gly Arg
                100                 105                 110

Gly Thr Leu Val Thr Val Ser Ser
        115                 120

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Leu Thr Ile His
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Phe Asp Pro Glu Asp Gly Arg Gly Thr Tyr Ala Pro Asn Phe Arg
1               5                   10                  15

Gly

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Leu Gly Glu Tyr Asp Ser Tyr Phe Asp Leu
1               5                   10

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Val Val Met Thr Gln Ser Pro Asp Phe Gln Ser Val Thr Pro Glu
1               5                   10                  15

Asp Lys Val Thr Ile Thr Cys Arg Ala Ser Gln Ser Ile Gly Ser Cys
                20                  25                  30
```

```
Leu His Trp Tyr Gln Gln Lys Pro Asp Gln Ser Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Tyr
                85                  90                  95

Thr Phe Gly Gln Gly Thr Lys Leu Glu Ile Lys
            100                 105

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ala Ser Gln Ser Ile Gly Ser Cys Leu His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ala Ser Gln Ser Ile Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Gln Ser Ser Ser Leu Pro Tyr Thr
1               5

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
                20                  25                  30

Asp Ile Ala Trp Val Arg Gln Ala Pro Gly Gln Gly Leu Glu Trp Met
            35                  40                  45

Gly Trp Met Asn Pro Asp Ser Gly Asn Thr Gly Phe Val Gln Lys Phe
```

```
                50                  55                  60
Lys Gly Arg Val Thr Ala Thr Ser Asn Thr Asp Ile Thr Thr Ala Tyr
 65                  70                  75                  80

Met Glu Leu Ser Ser Leu Thr Ser Glu Asp Thr Ala Val Tyr Tyr Cys
                 85                  90                  95

Ala Arg Asp Arg Phe Gly Ser Gly Tyr Asp Leu Asp His Trp Gly Gln
            100                 105                 110

Gly Thr Leu Val Thr Val Ser Ser
        115                 120

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Tyr Asp Ile Ala
 1               5

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Met Asn Pro Asp Ser Gly Asn Thr Gly Phe Val Gln Lys Phe Lys
 1               5                  10                  15

Gly

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Arg Phe Gly Ser Gly Tyr Asp Leu Asp His
 1               5                  10

<210> SEQ ID NO 45
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ser Tyr Glu Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
```

```
                    50                  55                  60
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Gly Ser Ser Asp His
                 85                  90                  95

Tyr Val Phe Gly Thr Gly Thr Lys Val Thr Val Leu
            100                 105

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Asn Asn Ile Gly Ser Lys Ser Val His
 1               5                  10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Asp Ser Asp Arg Pro Ser
 1               5

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Val Trp Gly Ser Ser Ser Asp His Tyr Val
 1               5                  10

<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ser Ser Ser Tyr
                20                  25                  30

Ala Met Thr Trp Val Arg Gln Ala Pro Gly Lys Gly Leu Glu Trp Val
            35                  40                  45

Ser Gly Ile Ser Gly Ser Gly Glu Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Val Glu Asp Thr Ala Ile Tyr Tyr Cys
                85                  90                  95

Ala Arg Gln Gly Tyr Gly Ala His Asp Tyr Trp Gly Gln Gly Thr Leu
            100                 105                 110

Val Thr Val Ser Ser
        115

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Tyr Ala Met Thr
1               5

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ile Ser Gly Ser Gly Glu Ser Thr Tyr Tyr Ala Asp Ser Val Lys
1               5                   10                  15

Gly

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Gly Tyr Gly Ala His Asp Tyr
1               5

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ser Val Leu Thr Gln Pro Pro Ser Ala Ser Gly Thr Pro Gly Gln
1               5                   10                  15

Arg Val Thr Ile Ser Cys Ser Gly Ala Ser Ser Asn Val Gly Ser Asn
            20                  25                  30

Arg Val Asn Trp Tyr Gln Gln Phe Pro Gly Met Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80
```

```
Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Gly Ala Ser Ser Asn Val Gly Ser Asn Arg Val Asn
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Asn Asn Gln Arg Pro Ser
1               5

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ala Trp Asp Asp Ser Leu Asn Gly Tyr Val
1               5                   10

<210> SEQ ID NO 57
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Pro Lys Val Gly Gly Tyr Ser Tyr Gly Tyr Gly Ala
            100                 105                 110
```

```
Leu Gly Tyr Trp Gly Gln Gly Thr Pro Val Thr Val Ser Ser
        115                 120                 125

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Tyr Ala Met His
1               5

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Ile Ser Trp Asp Gly Gly Ser Thr Tyr Tyr Ala Asp Ser Val Lys
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Ile Pro Lys Val Gly Gly Tyr Ser Tyr Gly Tyr Gly Ala Leu Gly
1               5                   10                  15

Tyr

<210> SEQ ID NO 61
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ser Tyr Glu Leu Thr Gln Pro Pro Ser Val Ser Val Ala Pro Gly Gln
1               5                   10                  15

Thr Ala Arg Ile Thr Cys Gly Gly Asn Asn Ile Gly Asp Ile Ser Val
                20                  25                  30

His Trp Tyr Gln Gln Lys Ser Gly Gln Ala Pro Met Leu Val Val His
            35                  40                  45

Asp Asp Ser Asp Arg Pro Ser Gly Ile Pro Glu Arg Phe Ser Gly Ser
        50                  55                  60

Asn Ser Gly Ser Ser Ala Thr Leu Thr Ile Ser Arg Val Glu Ala Gly
65                  70                  75                  80

Asp Glu Ala Asp Tyr His Cys Gln Val Trp Asp Ser Gly Ser Gly His
                85                  90                  95
```

His Val Phe Gly Thr Gly Thr Lys Val Thr Val Leu
            100                 105

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Asn Asn Ile Gly Asp Ile Ser Val His
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Asp Ser Asp Arg Pro Ser
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Val Trp Asp Ser Gly Ser Gly His His Val
1               5                   10

<210> SEQ ID NO 65
<211> LENGTH: 450
<212> TYPE: PRT
<213> ORGANISM: Homo sapiens

<400> SEQUENCE: 65

Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Phe Trp Pro
            20                  25                  30

Thr Leu Ala Phe Leu Leu Cys Ser Phe Pro Ala Ala Thr Ser Pro Cys
        35                  40                  45

Lys Ile Leu Lys Cys Asn Ser Glu Phe Trp Ser Ala Thr Ser Gly Ser
    50                  55                  60

His Ala Pro Ala Ser Asp Asp Thr Pro Glu Phe Cys Ala Ala Leu Arg
65                  70                  75                  80

Ser Tyr Ala Leu Cys Thr Arg Arg Thr Ala Arg Thr Cys Arg Gly Asp
                85                  90                  95

Leu Ala Tyr His Ser Ala Val His Gly Ile Glu Asp Leu Met Ser Gln
            100                 105                 110

His Asn Cys Ser Lys Asp Gly Pro Thr Ser Gln Pro Arg Leu Arg Thr
        115                 120                 125

Leu Pro Pro Ala Gly Asp Ser Gln Glu Arg Ser Asp Ser Pro Glu Ile
    130                 135                 140

Cys His Tyr Glu Lys Ser Phe His Lys His Ser Ala Thr Pro Asn Tyr
145                 150                 155                 160

Thr His Cys Gly Leu Phe Gly Asp Pro His Leu Arg Thr Phe Thr Asp
            165                 170                 175

Arg Phe Gln Thr Cys Lys Val Gln Gly Ala Trp Pro Leu Ile Asp Asn
            180                 185                 190

Asn Tyr Leu Asn Val Gln Val Thr Asn Thr Pro Val Leu Pro Gly Ser
            195                 200                 205

Ala Ala Thr Ala Thr Ser Lys Leu Thr Ile Ile Phe Lys Asn Phe Gln
210                 215                 220

Glu Cys Val Asp Gln Lys Val Tyr Gln Ala Glu Met Asp Glu Leu Pro
225                 230                 235                 240

Ala Ala Phe Val Asp Gly Ser Lys Asn Gly Gly Asp Lys His Gly Ala
            245                 250                 255

Asn Ser Leu Lys Ile Thr Glu Lys Val Ser Gly Gln His Val Glu Ile
            260                 265                 270

Gln Ala Lys Tyr Ile Gly Thr Thr Ile Val Val Arg Gln Val Gly Arg
            275                 280                 285

Tyr Leu Thr Phe Ala Val Arg Met Pro Glu Glu Val Val Asn Ala Val
290                 295                 300

Glu Asp Trp Asp Ser Gln Gly Leu Tyr Leu Cys Leu Arg Gly Cys Pro
305                 310                 315                 320

Leu Asn Gln Gln Ile Asp Phe Gln Ala Phe His Thr Asn Ala Glu Gly
            325                 330                 335

Thr Gly Ala Arg Arg Leu Ala Ala Ala Ser Pro Ala Pro Thr Ala Pro
            340                 345                 350

Glu Thr Phe Pro Tyr Glu Thr Ala Val Ala Lys Cys Lys Glu Lys Leu
            355                 360                 365

Pro Val Glu Asp Leu Tyr Tyr Gln Ala Cys Val Phe Asp Leu Leu Thr
            370                 375                 380

Thr Gly Asp Val Asn Phe Thr Leu Ala Ala Tyr Tyr Ala Leu Glu Asp
385                 390                 395                 400

Val Lys Met Leu His Ser Asn Lys Asp Lys Leu His Leu Tyr Glu Arg
            405                 410                 415

Thr Arg Asp Leu Pro Gly Arg Ala Ala Ala Gly Leu Pro Leu Ala Pro
            420                 425                 430

Arg Pro Leu Leu Gly Ala Leu Val Pro Leu Leu Ala Leu Leu Pro Val
            435                 440                 445

Phe Cys
    450

<210> SEQ ID NO 66
<211> LENGTH: 122
<212> TYPE: PRT
<213> ORGANISM: Homo sapiens

<400> SEQUENCE: 66

Pro Cys Lys Ile Leu Lys Cys Asn Ser Glu Phe Trp Ser Ala Thr Ser
1               5                   10                  15

Gly Ser His Ala Pro Ala Ser Asp Asp Thr Pro Glu Phe Cys Ala Ala
            20                  25                  30

Leu Arg Ser Tyr Ala Leu Cys Thr Arg Arg Thr Ala Arg Thr Cys Arg
            35                  40                  45

Gly Asp Leu Ala Tyr His Ser Ala Val His Gly Ile Glu Asp Leu Met

```
                    50                  55                  60
Ser Gln His Asn Cys Ser Lys Asp Gly Pro Thr Ser Gln Pro Arg Leu
 65                  70                  75                  80

Arg Thr Leu Pro Pro Ala Gly Asp Ser Gln Glu Arg Ser Asp Ser Pro
                 85                  90                  95

Glu Ile Cys His Tyr Glu Lys Ser Phe His Lys His Ser Ala Thr Pro
            100                 105                 110

Asn Tyr Thr His Cys Gly Leu Phe Gly Asp
        115                 120

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe Ser Tyr Ala Gly Thr Asp Thr Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

His Ser Tyr Ala Gly Thr Asp Thr Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Ser Tyr Ala Gly Thr Asp Thr Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Ser Tyr Ala Gly Thr Asp Thr Leu
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 71

Ile Ser Tyr Ala Gly Thr Asp Thr Leu
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Ser Tyr Ala Gly Thr Asp Thr Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Ser Tyr Ala Gly Thr Asp Thr Leu
1               5

<210> SEQ ID NO 74
<211> LENGTH: 23
<212> TYPE: PRT
<213> ORGANISM: Homo sapiens

<400> SEQUENCE: 74

Pro Cys Lys Ile Leu Lys Cys Asn Ser Glu Phe Trp Ser Ala Thr Ser
1               5                   10                  15

Gly Ser His Ala Pro Ala Ser
            20

<210> SEQ ID NO 75
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Lys Tyr Leu Leu Pro Thr Ala Ala Ala Gly Leu Leu Leu Leu Ala
1               5                   10                  15

Ala Gln Pro Ala Met Ala Met Pro Cys Lys Ile Leu Lys Cys Asn Ser
            20                  25                  30

Glu Phe Trp Ser Ala Thr Ser Gly Ser His Ala Pro Ala Ser Asp Asp
        35                  40                  45

Thr Pro Glu Phe Cys Ala Ala Leu Arg Ser Tyr Ala Leu Cys Thr Arg
    50                  55                  60

Arg Thr Ala Arg Thr Cys Arg Gly Asp Leu Ala Tyr His Ser Ala Val
65                  70                  75                  80

His Gly Ile Glu Asp Leu Met Ser Gln His Asn Cys Ser Lys Asp Gly
                85                  90                  95

Pro Thr Ser Gln Pro Arg Leu Arg Thr Leu Pro Pro Ala Gly Asp Ser
            100                 105                 110
```

Gln Glu Arg Ser Asp Ser Pro Glu Ile Cys His Tyr Glu Lys Ser Phe
            115                 120                 125

His Lys His Ser Ala Thr Pro Asn Tyr Thr His Cys Gly Leu Phe Gly
    130                 135                 140

Asp His His His His His
145             150

<210> SEQ ID NO 76
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Glu Thr Asp Thr Leu Leu Leu Trp Val Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Gly Thr Glu Leu Gly Ser Thr Ser Pro Val Trp Trp Asn Ser
            35                  40                  45

Ala Asp Ile Thr Ser Leu Tyr Lys Lys Ala Gly Ser Pro Cys Lys Ile
    50                  55                  60

Leu Lys Cys Asn Ser Glu Phe Trp Ser Ala Thr Ser Gly Ser His Ala
65                  70                  75                  80

Pro Ala Ser Asp Asp Thr Pro Glu Phe Cys Ala Ala Leu Arg Ser Tyr
                85                  90                  95

Ala Leu Cys Thr Arg Arg Thr Ala Arg Thr Cys Arg Gly Asp Leu Ala
            100                 105                 110

Tyr His Ser Ala Val His Gly Ile Glu Asp Leu Met Ser Gln His Asn
            115                 120                 125

Cys Ser Lys Asp Gly Pro Thr Ser Gln Pro Arg Leu Arg Thr Leu Pro
    130                 135                 140

Pro Ala Gly Asp Ser Gln Glu Arg Ser Asp Ser Pro Glu Ile Cys His
145                 150                 155                 160

Tyr Glu Lys Ser Phe His Lys His Ser Ala Thr Pro Asn Tyr Thr His
                165                 170                 175

Cys Gly Leu Phe Gly Asp Pro His Leu Arg Thr Phe Thr Asp Arg Phe
            180                 185                 190

Gln Thr Cys Lys Val Gln Gly Ala Trp Pro Leu Ile Asp Asn Asn Tyr
            195                 200                 205

Leu Asn Val Gln Val Thr Asn Thr Pro Val Leu Pro Gly Ser Ala Ala
    210                 215                 220

Thr Ala Thr Ser Lys Leu Thr Ile Ile Phe Lys Phe Asn Gln Glu Cys
225                 230                 235                 240

Val Asp Gln Lys Val Tyr Gln Ala Glu Met Asp Glu Leu Pro Ala Ala
                245                 250                 255

Phe Val Asp Gly Ser Lys Asn Gly Gly Asp Lys His Gly Ala Asn Ser
            260                 265                 270

Leu Lys Ile Thr Glu Lys Val Ser Gly Gln His Val Glu Ile Gln Ala
            275                 280                 285

Lys Tyr Ile Gly Thr Thr Ile Val Val Arg Gln Val Gly Arg Tyr Leu
    290                 295                 300

Thr Phe Ala Val Arg Met Pro Glu Glu Val Val Asn Ala Val Glu Asp
305                 310                 315                 320

Trp Asp Ser Gln Gly Leu Tyr Leu Cys Leu Arg Gly Cys Pro Leu Asn
            325                 330                 335

Gln Gln Ile Asp Phe Gln Ala Phe His Thr Asn Ala Glu Gly Thr Gly
            340                 345                 350

Ala Arg Arg Leu Ala Ala Ser Pro Ala Pro Thr Ala Pro Glu Thr
            355                 360                 365

Phe Pro Tyr Glu Thr Ala Val Ala Lys Cys Lys Glu Lys Leu Pro Val
370                 375                 380

Glu Asp Leu Tyr Tyr Gln Ala Cys Val Phe Asp Leu Leu Thr Thr Gly
385                 390                 395                 400

Asp Val Asn Phe Thr Leu Ala Ala Tyr Tyr Ala Leu Glu Asp Val Lys
            405                 410                 415

Met Leu His Ser Asn Lys Asp Lys Leu His Leu Tyr Glu Arg Thr Arg
            420                 425                 430

Asp Leu Pro Gly Asn Pro Ala Phe Leu Tyr Lys Val Val Ile Ser Ser
            435                 440                 445

Thr Val Ala Ala Arg Gly Gly Pro Glu Gln Lys Leu Ile Ser Glu
            450                 455                 460

Glu Asp Leu Asn Ser Ala Val Asp His His His His His His
465                 470                 475

<210> SEQ ID NO 77
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Pro Cys Lys Ile Leu Lys Cys Asn Ser Glu Phe Trp Ser Ala
            35                  40                  45

Thr Ser Gly Ser His Ala Pro Ala Ser Asp Asp Thr Pro Glu Phe Cys
50                  55                  60

Ala Ala Leu Arg Ser Tyr Ala Leu Cys Thr Arg Arg Thr Ala Arg Thr
65                  70                  75                  80

Cys Arg Gly Asp Leu Ala Tyr His Ser Ala Val His Gly Ile Glu Asp
                85                  90                  95

Leu Met Ser Gln His Asn Cys Ser Lys Asp Gly Pro Thr Ser Gln Pro
            100                 105                 110

Arg Leu Arg Thr Leu Pro Pro Ala Gly Asp Ser Gln Glu Arg Ser Asp
            115                 120                 125

Ser Pro Glu Ile Cys His Tyr Glu Lys Ser Phe His Lys His Ser Ala
        130                 135                 140

Thr Pro Asn Tyr Thr His Cys Gly Leu Phe Gly Asp Leu Asn Ser Ala
145                 150                 155                 160

Asp Ile Glu Gly Arg Met Asp Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser

```
                195                 200                 205
His Glu Asp Pro Glu Val Lys Phe Asn Trp Tyr Val Asp Gly Val Glu
210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
            245                 250                 255

Gly Lys Glu Tyr Lys Cys Lys Val Ser Asn Lys Ala Leu Pro Ala Pro
        260                 265                 270

Ile Glu Lys Thr Ile Ser Lys Ala Lys Gly Gln Pro Arg Glu Pro Gln
    275                 280                 285

Val Tyr Thr Leu Pro Pro Ser Arg Glu Glu Met Thr Lys Asn Gln Val
290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
            325                 330                 335

Pro Val Leu Asp Ser Asp Gly Ser Phe Phe Leu Tyr Ser Lys Leu Thr
        340                 345                 350

Val Asp Lys Ser Arg Trp Gln Gln Gly Asn Val Phe Ser Cys Ser Val
    355                 360                 365

Met His Glu Ala Leu His Asn His Tyr Thr Gln Lys Ser Leu Ser Leu
370                 375                 380

Ser Pro Gly Lys
385

<210> SEQ ID NO 78
<211> LENGTH: 122
<212> TYPE: PRT
<213> ORGANISM: Homo sapiens

<400> SEQUENCE: 78

Pro Cys Lys Ile Leu Lys Cys Asn Ser Glu Phe Trp Ser Ala Thr Ser
1               5                   10                  15

Gly Ser His Ala Pro Ala Ser Asp Asp Thr Pro Glu Phe Cys Ala Ala
            20                  25                  30

Leu Arg Ser Tyr Ala Leu Cys Thr Arg Arg Thr Ala Arg Thr Cys Arg
        35                  40                  45

Gly Asp Leu Ala Tyr His Ser Ala Val His Gly Ile Glu Asp Leu Met
    50                  55                  60

Ser Gln His Asn Cys Ser Lys Asp Gly Pro Thr Ser Gln Pro Arg Leu
65                  70                  75                  80

Arg Thr Leu Pro Pro Ala Gly Asp Ser Gln Glu Arg Ser Asp Ser Pro
            85                  90                  95

Glu Ile Cys His Tyr Glu Lys Ser Phe His Lys His Ser Ala Thr Pro
        100                 105                 110

Asn Tyr Thr His Cys Gly Leu Phe Gly Asp
    115                 120

<210> SEQ ID NO 79
<211> LENGTH: 23
<212> TYPE: PRT
<213> ORGANISM: Homo sapiens

<400> SEQUENCE: 79

Pro Cys Lys Ile Leu Lys Cys Asn Ser Glu Phe Trp Ser Ala Thr Ser
```

-continued

```
                1               5                  10                  15
Gly Ser His Ala Pro Ala Ser
            20

<210> SEQ ID NO 80
<211> LENGTH: 24
<212> TYPE: PRT
<213> ORGANISM: Homo sapiens

<400> SEQUENCE: 80

Met Pro Cys Lys Ile Leu Lys Cys Asn Ser Glu Phe Trp Ser Ala Thr
1               5                   10                  15

Ser Gly Ser His Ala Pro Ala Ser
            20

<210> SEQ ID NO 81
<211> LENGTH: 27
<212> TYPE: PRT
<213> ORGANISM: Homo sapiens

<400> SEQUENCE: 81

Lys Ala Gly Ser Pro Cys Lys Ile Leu Lys Cys Asn Ser Glu Phe Trp
1               5                   10                  15

Ser Ala Thr Ser Gly Ser His Ala Pro Ala Ser
            20                  25

<210> SEQ ID NO 82
<211> LENGTH: 29
<212> TYPE: PRT
<213> ORGANISM: Homo sapiens

<400> SEQUENCE: 82

Lys Ala Gly Ser Pro Cys Lys Ile Leu Lys Cys Asn Ser Glu Phe Trp
1               5                   10                  15

Ser Ala Thr Ser Gly Ser His Ala Pro Pro Ala Ser Asp
            20                  25

<210> SEQ ID NO 83
<211> LENGTH: 28
<212> TYPE: PRT
<213> ORGANISM: Homo sapiens

<400> SEQUENCE: 83

Ala Gly Ser Pro Cys Lys Ile Leu Lys Cys Asn Ser Glu Phe Trp Ser
1               5                   10                  15

Ala Thr Ser Gly Ser His Ala Pro Pro Ala Ser Asp
            20                  25

<210> SEQ ID NO 84
<211> LENGTH: 26
<212> TYPE: PRT
<213> ORGANISM: Homo sapiens

<400> SEQUENCE: 84

Thr Lys Leu Pro Cys Lys Ile Leu Lys Cys Asn Ser Glu Phe Trp Ser
1               5                   10                  15

Ala Thr Ser Gly Ser His Ala Pro Ala Ser
            20                  25

<210> SEQ ID NO 85
<211> LENGTH: 10
<212> TYPE: PRT
```

```
<213> ORGANISM: Homo sapiens

<400> SEQUENCE: 85

Asp Ser Pro Glu Ile Cys His Tyr Glu Lys
1               5                   10

<210> SEQ ID NO 86
<211> LENGTH: 13
<212> TYPE: PRT
<213> ORGANISM: Homo sapiens

<400> SEQUENCE: 86

Gly Asp Leu Ala Tyr His Ser Ala Val His Gly Ile Glu
1               5                   10

<210> SEQ ID NO 87
<211> LENGTH: 12
<212> TYPE: PRT
<213> ORGANISM: Homo sapiens

<400> SEQUENCE: 87

Asp Leu Ala Tyr His Ser Ala Val His Gly Ile Glu
1               5                   10

<210> SEQ ID NO 88
<211> LENGTH: 11
<212> TYPE: PRT
<213> ORGANISM: Homo sapiens

<400> SEQUENCE: 88

Asp Asp Thr Pro Glu Phe Cys Ala Ala Leu Arg
1               5                   10

<210> SEQ ID NO 89
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Gly Ser Pro Cys Lys Ile Leu Lys Cys Asn Ser Glu Phe Trp Ser
1               5                   10                  15

Ala Thr Ser Gly Ser His Ala Pro Ala Ser
            20                  25

<210> SEQ ID NO 90
<211> LENGTH: 27
<212> TYPE: PRT
<213> ORGANISM: Homo sapiens

<400> SEQUENCE: 90

Ala Gly Ser Pro Cys Lys Ile Leu Lys Cys Asn Ser Glu Phe Trp Ser
1               5                   10                  15

Ala Thr Ser Gly Ser His Ala Pro Pro Ala Ser
            20                  25

<210> SEQ ID NO 91
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 91

```
Glu Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Asp Gly Ala Gly Val Phe Asp Leu Trp Gly Arg Gly Thr Leu
            100                 105                 110

Val Thr Val Ser Ser
        115
```

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

```
Gly Tyr Tyr Trp Ser
1               5
```

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

```
Glu Ile Asn His Ser Gly Ser Thr Asn Tyr Asn Pro Ser Leu Lys Ser
1               5                   10                  15
```

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

```
Asp Asp Gly Ala Gly Val Phe Asp Leu
1               5
```

<210> SEQ ID NO 95
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

```
Asp Ile Gln Leu Thr Gln Ser Pro Ser Ser Leu Ser Ala Ser Val Gly
1               5                   10                  15

Asp Gly Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Phe Phe Thr Leu Thr Ile Asn Asn Leu Gln Pro
65              70                  75                  80

Glu Asp Phe Ala Thr Tyr Tyr Cys Gln Gln Ser Gly Asn Thr Pro Trp
                85                  90                  95

Thr Phe Gly Gln Gly Thr Lys Val Glu Ile Asn Arg
            100                 105
```

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

```
Gln Ala Ser Gln Asp Ile Ser Asn Tyr Leu Asn
1               5                   10
```

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

```
Asp Ala Ser Asn Leu Glu Thr
1               5
```

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

```
Gln Gln Ser Gly Asn Thr Pro Trp Thr
1               5
```

<210> SEQ ID NO 99
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Glu Val Gln Leu Val Gln Ser Gly Ala Glu Val Lys Glu Pro Gly Ala
1               5                   10                  15

Ser Val Lys Val Ser Cys Lys Ala Ser Gly Tyr Thr Phe Thr Asp Tyr
```

```
            20                  25                  30
Tyr Ile Gln Trp Val Arg Gln Ala Pro Gly His Gly Leu Glu Trp Met
        35                  40                  45

Gly Trp Ile Asn Pro Lys Thr Gly Gly Thr Asn Tyr Leu Gln Lys Phe
    50                  55                  60

Gln Gly Arg Val Thr Met Thr Arg Asp Thr Ser Thr Thr Ala Tyr
65                  70                  75                  80

Met Glu Leu Ser Ser Leu Arg Ser Asp Asp Thr Ala Phe Tyr Tyr Cys
                85                  90                  95

Val Arg Glu Asp Met Asn Thr Val Leu Ala Thr Ser Trp Phe Asp Pro
                100                 105                 110

Trp Gly Gln Gly Thr Leu Val Thr Val Ser Ser
            115                 120

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Tyr Tyr Ile Gln
1               5

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Trp Ile Asn Pro Lys Thr Gly Gly Thr Asn Tyr Leu Gln Lys Phe Gln
1               5                   10                  15

Gly

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Glu Asp Met Asn Thr Val Leu Ala Thr Ser Trp Phe Asp Pro
1               5                   10

<210> SEQ ID NO 103
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ser Tyr Glu Leu Thr Gln Pro Pro Ser Val Ser Val Ser Pro Gly Gln
1               5                   10                  15

Thr Ala Arg Ile Thr Cys Ser Gly Asn Gln Leu Gly His Lys Phe Ala
```

```
                20                  25                  30
Ser Trp Tyr Gln Gln Lys Pro Gly Gln Ser Pro Val Val Ile Tyr
                35                  40                  45

Glu Asp Lys Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Val Trp Asp Val Ile Thr Asp His
                85                  90                  95

Tyr Val Phe Gly Thr Gly Thr Lys Val Thr Val Leu Gly
                100                 105

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Gly Asn Gln Leu Gly His Lys Phe Ala Ser
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Asp Lys Lys Arg Pro Ser
1               5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Val Trp Asp Val Ile Thr Asp His Tyr Val
1               5                   10

<210> SEQ ID NO 107
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Gln Ser Gly Ser Glu Val Lys Lys Pro Gly Ala
1               5                   10                  15

Ser Val Lys Leu Ser Cys Lys Thr Ser Gly Tyr Thr Phe Thr Asn Ser
                20                  25                  30

Ala Ile His Trp Val Arg Gln Ala Pro Gly Gln Arg Leu Glu Trp Met
                35                  40                  45
```

```
Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Trp Ala Tyr Cys Gly Gly Asp Cys Tyr Ser Leu Asp Tyr Trp Gly
            100                 105                 110

Gln Gly Thr Leu Val Thr Val Ser Ser
        115                 120

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Ser Ala Ile His
1               5

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Trp Ile Asn Ala Gly Asn Gly Asn Thr Lys Tyr Ser Gln Lys Phe Gln
1               5                   10                  15

Gly

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Tyr Cys Gly Gly Asp Cys Tyr Ser Leu Asp Tyr
1               5                   10

<210> SEQ ID NO 111
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Gln Val Thr Gln Ser Pro Ser Ser Leu Ala Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Arg Pro Gly Lys Ala Pro Lys Leu Leu Ile
        35                  40                  45
```

```
Tyr Asp Ala Ser Asn Leu Glu Thr Gly Val Pro Pro Arg Phe Ser Gly
     50                  55                  60

Asp Gly Ser Gly Thr His Phe Ser Phe Thr Ile Thr Asn Val Gln Pro
 65                  70                  75                  80

Glu Asp Val Gly Thr Tyr Tyr Cys Gln Gln Tyr Asp Ser Leu Pro Leu
                 85                  90                  95

Thr Phe Gly Gln Gly Thr Arg Leu Glu Ile Lys Arg
                100                 105
```

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

```
Gln Ala Ser Gln Asp Ile Ser Asn Tyr Leu Asn
 1               5                  10
```

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Asp Ala Ser Asn Leu Glu Thr
 1               5
```

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

```
Gln Gln Tyr Asp Ser Leu Pro Leu Thr
 1               5
```

<210> SEQ ID NO 115
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Glu Val Gln Leu Leu Glu Ser Gly Gly Asp Leu Val Arg Pro Gly Gly
 1               5                  10                  15

Ser Leu Arg Leu Thr Cys Glu Gly Ser Gly Phe Asn Phe Phe Thr Gln
                20                  25                  30

Thr Ile His Trp Val Arg Gln Ala Pro Gly Lys Gly Leu Glu Trp Val
             35                  40                  45

Ala Ser Ile Ser Ser Asp Ser Asn Tyr Ile Tyr His Ala Asp Ser Leu
     50                  55                  60

Lys Gly Arg Phe Thr Val Ser Arg Asp Asn Ala Gln Asp Ser Val Phe
 65                  70                  75                  80
```

```
Leu Gln Met Asn Ser Leu Arg Val Glu Asp Thr Ala Val Tyr Tyr Cys
                85                  90                  95

Ala Arg Asp Ile Leu Leu Glu Pro Leu Ala Pro His Tyr Tyr Tyr Gly
            100                 105                 110

Leu Asp Val Trp Gly Gln Gly Thr Thr Val Thr Val Ser Ser
        115                 120                 125

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Gln Thr Ile His
1               5

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Ile Ser Ser Asp Ser Asn Tyr Ile Tyr His Ala Asp Ser Leu Lys
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Ile Leu Leu Glu Pro Leu Ala Pro His Tyr Tyr Tyr Gly Leu Asp
1               5                   10                  15

Val

<210> SEQ ID NO 119
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Pro Ile Ser Thr Tyr
            20                  25                  30

Val Asn Trp Tyr Gln Gln Lys Pro Gly Lys Ala Pro Lys Leu Leu Ile
        35                  40                  45

Tyr Asp Ala Ser Thr Leu Glu Ile Gly Val Pro Ser Arg Ile Ser Gly
    50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Phe Pro Leu
                 85                  90                  95

Thr Phe Gly Gly Gly Thr Lys Val Asp Ile Lys Arg
            100                 105
```

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Arg Ala Ser Gln Pro Ile Ser Thr Tyr Val Asn
 1               5                  10
```

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Asp Ala Ser Thr Leu Glu Ile
 1               5
```

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Gln Gln Tyr Asp Asn Phe Pro Leu Thr
 1               5
```

<210> SEQ ID NO 123
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Gly Tyr
                 20                  25                  30

Tyr Trp Ser Trp Ile Arg Gln Ser Pro Gly Lys Gly Leu Glu Trp Ile
             35                  40                  45

Gly Glu Ile Phe His Thr Gly Arg Thr Tyr Tyr Asn Pro Ser Leu Arg
     50                  55                  60

Ser Arg Leu Thr Ile Ser Val Asp Thr Ser Lys Asn Gln Phe Ser Leu
 65                  70                  75                  80

Lys Leu Ser Ser Leu Thr Ala Ala Asp Thr Ala Val Tyr Tyr Cys Ala
                 85                  90                  95
```

Arg Asp Ser Ala Phe Gly Ser Phe Asp Tyr Trp Gly Gln Gly Thr Leu
            100                 105                 110

Val Thr Val Ser Ser
        115

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Tyr Tyr Trp Ser
1               5

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Ile Phe His Thr Gly Arg Thr Tyr Tyr Asn Pro Ser Leu Arg Ser
1               5                   10                  15

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asp Ser Ala Phe Gly Ser Phe Asp Tyr
1               5

<210> SEQ ID NO 127
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Ile Arg Val Thr Gln Ser Pro Ser Ser Leu Ser Ala Ser Val Gly
1               5                   10                  15

Asp Arg Val Thr Ile Thr Cys Gln Ala Asn Glu Asp Ile Ser Ile Tyr
            20                  25                  30

Leu Asn Trp Tyr Gln Gln Arg Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr His Thr Tyr Pro Phe
                85                  90                  95

Thr Phe Gly Gly Gly Thr Lys Val Asp Ile Lys Arg

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Ala Asn Glu Asp Ile Ser Ile Tyr Leu Asn
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Ala Ser Asn Leu Glu Thr
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Gln Tyr His Thr Tyr Pro Phe Thr
1               5

<210> SEQ ID NO 131
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Gln Glu Ser Gly Pro Gly Leu Val Lys Pro Ser Glu
1               5                   10                  15

Thr Leu Ser Leu Thr Cys Asn Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Asn Ile Tyr Tyr Ser Gly Ser Thr Asn Tyr Asn Pro Ser Leu Lys
    50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Ala Leu Asp Phe Trp Ser Gly Gln Tyr Phe Asp Tyr Trp Gly Gln
            100                 105                 110

Gly Thr Leu Val Thr Val Ser Ser
        115                 120

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Tyr Tyr Trp Ser
1               5

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asn Ile Tyr Tyr Ser Gly Ser Thr Asn Tyr Asn Pro Ser Leu Lys Ser
1               5                   10                  15

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Leu Asp Phe Trp Ser Gly Gln Tyr Phe Asp Tyr
1               5                   10

<210> SEQ ID NO 135
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Val Met Thr Gln Thr Pro Ser Ser Leu Ser Ala Ser Val Gly
1               5                   10                  15

Asp Arg Val Thr Ile Thr Cys Gln Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Ser Ile Pro Pro
                85                  90                  95

Thr Phe Gly Pro Gly Thr Arg Leu Glu Ile Lys Arg
            100                 105

<210> SEQ ID NO 136
<211> LENGTH: 11
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 136

Gln Ala Ser Gln Asp Ile Ser Asp Tyr Leu Asn
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Ala Ser Thr Leu Glu Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Gln Ser Tyr Ser Ile Pro Pro Thr
1               5

<210> SEQ ID NO 139
<211> LENGTH: 81
<212> TYPE: PRT
<213> ORGANISM: Homo sapiens

<400> SEQUENCE: 139

Pro Cys Lys Ile Leu Lys Cys Asn Ser Glu Phe Trp Ser Ala Thr Ser
1               5                   10                  15

Gly Ser His Ala Pro Ala Ser Asp Asp Thr Pro Glu Phe Cys Ala Ala
            20                  25                  30

Leu Arg Ser Tyr Ala Leu Cys Thr Arg Arg Thr Ala Arg Thr Cys Arg
        35                  40                  45

Gly Asp Leu Ala Tyr His Ser Ala Val His Gly Ile Glu Asp Leu Met
    50                  55                  60

Ser Gln His Asn Cys Ser Lys Asp Gly Pro Thr Ser Gln Pro Arg Leu
65                  70                  75                  80

Arg

<210> SEQ ID NO 140
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 141
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Ala Ala Gly Gly Pro Ser Val Phe Leu Phe Pro Pro
    115                 120                 125

Lys Pro Lys Asp Gln Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 142
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 142

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys

```
            85                   90                   95
Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Leu His Glu Ala Leu His Asn His Tyr Thr
305                 310                 315                 320

Gln Lys Ser Leu Ser Leu Ser Pro Gly Lys
            325                 330

<210> SEQ ID NO 143
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110
```

```
Pro Ala Pro Glu Ala Ala Gly Gly Pro Ser Val Phe Leu Phe Pro Pro
            115                 120                 125

Lys Pro Lys Asp Gln Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Asn His Tyr Thr
305                 310                 315                 320

Gln Lys Ser Leu Ser Leu Ser Pro Gly Lys
                325                 330

<210> SEQ ID NO 144
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Val Gly Asp Ser
            20                  25                  30

Ile Tyr Val Ser Trp Tyr Gln Gln His Pro Gly Lys Ala Pro Lys Leu
        35                  40                  45

Met Leu Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Val Ser Tyr Ala Gly Thr
                85                  90                  95

Asp Thr Leu Phe Gly Gly Gly Thr Lys Val Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140
```

```
Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Arg
        180                 185                 190

Ser Tyr Ser Cys Gln Val Thr His Glu Gly Ser Thr Val Glu Lys Thr
    195                 200                 205

Val Ala Pro Thr Glu Cys Ser
210                 215

<210> SEQ ID NO 145
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Gly Ile Ser Trp Val Arg Gln Ala Pro Gly Gln Gly Leu Asp Trp Met
        35                  40                  45

Gly Trp Ile Ser Pro Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Ser Gly Pro Tyr Tyr Tyr Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Gln Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
                275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Leu His
            420                 425                 430
Glu Ala Leu His Asn His Tyr Thr Gln Lys Ser Leu Ser Leu Ser Pro
        435                 440                 445
Gly Lys
    450

<210> SEQ ID NO 146
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Ser Ala Leu Thr Gln Pro Arg Ser Val Ser Gly Ser Pro Gly Gln
1               5                   10                  15
Ser Val Thr Ile Ser Cys Thr Gly Thr Ser Ser Val Gly Asp Ser
            20                  25                  30
Ile Tyr Val Ser Trp Tyr Gln Gln His Pro Gly Lys Ala Pro Lys Leu
        35                  40                  45
Met Leu Tyr Asp Val Thr Lys Arg Pro Ser Gly Val Pro Asp Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Tyr Ser Tyr Ala Gly Thr
                85                  90                  95
Asp Thr Leu Phe Gly Gly Gly Thr Lys Val Thr Val Leu Gly Gln Pro
            100                 105                 110
Lys Ala Ala Pro Ser Val Thr Leu Phe Pro Pro Ser Ser Glu Glu Leu
        115                 120                 125
Gln Ala Asn Lys Ala Thr Leu Val Cys Leu Ile Ser Asp Phe Tyr Pro
    130                 135                 140
Gly Ala Val Thr Val Ala Trp Lys Ala Asp Ser Ser Pro Val Lys Ala
145                 150                 155                 160
Gly Val Glu Thr Thr Thr Pro Ser Lys Gln Ser Asn Asn Lys Tyr Ala
                165                 170                 175
```

```
Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 147
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Gly Ile Ser Trp Val Arg Gln Ala Pro Gly Gln Gly Leu Asp Trp Met
        35                  40                  45

Gly Trp Ile Ser Pro Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Ser Gly Pro Tyr Tyr Tyr Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Gln Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Leu His
            420                 425                 430
Glu Ala Leu His Asn His Tyr Thr Gln Lys Ser Leu Ser Leu Ser Pro
        435                 440                 445
Gly Lys
    450

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 148

His His His His His His
1               5

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp Asp Asp Asp Lys
1               5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Asp Asp Asp Asp Lys
1               5

<210> SEQ ID NO 151
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 151

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Ile Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser
        115

<210> SEQ ID NO 152
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Tyr Ser
            20                  25                  30

Asp Gly Tyr Thr Phe Leu Glu Trp Phe Gln Gln Arg Pro Gly Gln Ser
        35                  40                  45

Pro Arg Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110

Arg

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asn Tyr Gly Met Asn
1               5

<210> SEQ ID NO 154
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 154

Met Ile Tyr Tyr Asp Ser Ser Glu Lys His Tyr Ala Asp Ser Val Lys
1               5                   10                  15

Gly

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Thr Thr Pro Asp Tyr
1               5

<210> SEQ ID NO 156
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Arg Ser Ser Gln Ser Leu Glu Tyr Ser Asp Gly Tyr Thr Phe Leu Glu
1               5                   10                  15

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Val Ser Asn Arg Phe Ser
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Phe Gln Ala Thr His Asp Pro Leu Thr
1               5
```